United States Patent [19]

Robl

[11] Patent Number: 5,506,219

[45] Date of Patent: Apr. 9, 1996

[54] PYRIDINE ANCHORS FOR HMG-COA REDUCTASE INHIBITORS

[75] Inventor: Jeffrey A. Robl, Holland, Pa.

[73] Assignee: E. R. Squibb & Sons, Inc., Princeton, N.J.

[21] Appl. No.: 400,629

[22] Filed: Mar. 7, 1995

Related U.S. Application Data

[63] Continuation of Ser. No. 588,800, Sep. 27, 1990, abandoned, which is a continuation-in-part of Ser. No. 485,398, Feb. 26, 1990, abandoned, which is a continuation-in-part of Ser. No. 272,610, Nov. 17, 1988, abandoned, which is a continuation-in-part of Ser. No. 237,349, Aug. 29, 1988, abandoned.

[51] Int. Cl.$^6$ .................. C07F 9/58; C07F 9/60; A01N 43/40; A01N 43/42
[52] U.S. Cl. .................. 514/89; 546/22; 546/23
[58] Field of Search ............... 546/22; 514/89

[56] References Cited

U.S. PATENT DOCUMENTS

| | | | |
|---|---|---|---|
| 3,983,140 | 9/1976 | Endo et al. | 549/292 |
| 4,049,495 | 9/1977 | Endo et al. | 435/125 |
| 4,137,322 | 1/1979 | Endo et al. | 514/400 |
| 4,375,475 | 3/1983 | Willard et al. | 514/460 |
| 4,613,610 | 9/1986 | Wareing | 514/406 |
| 4,647,576 | 3/1987 | Hoefle et al. | 514/422 |
| 4,686,237 | 8/1987 | Anderson | 514/532 |
| 4,761,419 | 8/1988 | Picard et al. | 514/311 |
| 4,804,679 | 2/1989 | Anderson | 514/460 |
| 4,906,624 | 3/1990 | Chucholowski et al. | 514/210 |
| 5,091,386 | 2/1992 | Kessler et al. | 514/277 |
| 5,169,857 | 12/1992 | Angerbauer et al. | 514/344 |
| 5,177,080 | 1/1993 | Angerbauer et al. | 514/277 |

OTHER PUBLICATIONS

*Synthesis and Biological Activity of New HMG–CoA Reductase Inhibitors. 1. Lactones of Pyridine– and Pyrimidine–Substituted 3,5–Dihydroxy–6–heptenoic (–heptanoic) Acids,* G. Beck, et al., J. Med. Chem. 1990, 33: 52–60.
*Hypolipidemic HMG–CoA Reductase Inhibitor,* Drugs of the Future 1994, 19(6): 537–541.
195th Nat.l Meeting of the American Chemical Society, Toronto, Apr. 1988, MED 127.
F. M. Singer et al., Proc. Soc. Exper. Bio. Med., 102, 370 (1959).
F. H. Hulcher, Arch. Biochem. Biophys., 146, 422 (1971).
Brown et al., J. Chem Soc. Perkin I. 1165 (1976).
Tetrahedron Letters, 29, 929, 1988.
Cho, et al., J. Org. Chem. 50, 4227–4230 (1985).

*Primary Examiner*—Alan L. Rotman
*Attorney, Agent, or Firm*—Burton Rodney

[57] ABSTRACT

Compounds which are useful as inhibitors of cholesterol biosynthesis and thus as hypocholesterolemic agents are provided which have a quinoline or a pyridine anchor attached by means of a linker to a binding domain sidechain, which compounds inhibit the enzyme 3-hydroxy-3-methyl-glutaryl-coenzyme A reductase.

22 Claims, No Drawings

PYRIDINE ANCHORS FOR HMG-COA REDUCTASE INHIBITORS

CROSS-REFERENCE TO RELATED APPLICATIONS

This is a continuation of application Ser. No. 07/588,800 filed Sep. 27, 1990, abandoned, which is a continuation-in-part of U.S. patent application Ser. No. 485,398 (filed Feb. 26, 1990), abandoned, which is a continuation-in-part of U.S. patent application Ser. No. 272,610 (filed Nov. 17, 1988), abandoned, which is a continuation-in-part of U.S. patent application Ser. No. 237,349 (filed Aug. 29, 1988), abandoned.

FIELD OF THE INVENTION

The present invention is related to compounds and pharmaceutical compositions useful as hypocholesterolemic and hypolipidemic agents. More particularly, this invention concerns (1) certain inhibitors of the enzyme 3-hydroxy-3-methylglutaryl-coenzyme A reductase (HMG-CoA reductase) that contain a quinoline or pyridine nucleus attached by means of a linker to an HMG-binding domain sidechain, (2) pharmaceutical compositions containing such compounds and (3) a method of lowering blood serum cholesterol levels employing such pharmaceutical compositions.

BRIEF DESCRIPTION OF THE INVENTION

In accordance with the present invention, there are provided certain quinoline- and pyridine-containing compounds that are potent inhibitors of cholesterol biosynthesis by virtue of their ability to inhibit the enzyme 3-hydroxy-3-methyl-glutaryl-coenzyme A reductase (HMG-CoA reductase).

In particular, in its broadest chemical compound aspect, the present invention provides compounds of the formula

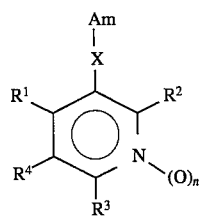

I wherein:
Am is a binding domain sidechain;
X is a linker;
$R^1$ and $R^2$ are the same or different and are each independently selected from
(i) hydrogen,
(ii) alkyl,
(iii) aryl,
(iv) cycloalkyl,
(v) aralkyl,
(vi) aralkoxy,
(vii) alkenyl,
(viii) cycloalkenyl, and
(ix) heterocyclo (e.g., thienyl, benzodioxolyl);
$R^3$ is selected from
(i) hydrogen,
(ii) lower alkyl,
(iii) aryl,
(iv) cycloalkyl,
(v) alkoxy,
(vi) aralkyl,
(vii) aralkoxy,
(viii) alkenyl,
(ix) cycloalkenyl,
(x) halo-substituted alkyl,
(xi) adamantyl, and
(xii) heterocyclo (e.g., thienyl, benzodioxolyl);
$R^4$ is selected from
(i) hydrogen,
(ii) lower alkyl,
(iii) aryl,
(iv) cycloalkyl,
(v) alkoxy,
(vi) aralkyl,
(vii) aralkoxy,
(viii) alkenyl,
(ix) cycloalkenyl,
(x) adamantyl,
(xi) halogen,
(xii) halo-substituted alkyl (e.g., trifluoromethyl), and
(xiii) heterocyclo (e.g., thienyl, benzodioxolyl);
or $R^3$ and $R^4$ taken together can be $-(CH_2)p-$,

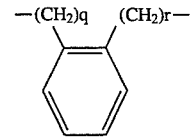

or $(CH=CH)_2$; but when $A_m$ is

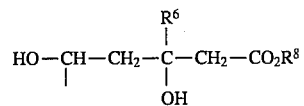

or a δ lactone thereof, $R^3$ and $R^4$ cannot be $(CH=CH)_2$;
$R^6$ is hydrogen or lower alkyl;
$R^8$ is hydrogen, lower alkyl, alkali metal, or alkaline earth metal;
n is 0 or 1;
p is 3, 4 or 5;
q is 0, 1, 2, or 3; and
r is 0, 1, 2, or 3.

In another aspect, the present invention provides pharmaceutical compositions, useful as hypolipidemic or hypocholesterolemic agents comprising a hypolipidemic or hypocholesterolemic amount of a compound in accordance with this invention as set forth above, in combination with a pharmaceutically acceptable carrier.

In another aspect, the present invention provides a method of inhibiting cholesterol biosynthesis in a patient in need of such treatment by administering a pharmaceutical composition in accordance with the present invention as defined above.

DETAILED DESCRIPTION OF THE INVENTION

In accordance with the present invention, there is provided compounds useful in inhibiting the enzyme 3-hydroxy-3-methylglutaryl-coenzyme A (HMG-CoA reductase), which inhibitors are useful as hypocholesterolemic and hypolipidemic agents, and which compounds comprise a quinoline nucleus or pyridine nucleus

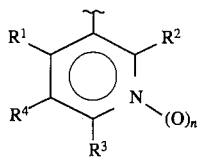
Ia linked by a suitable linker (X) to an HMG-binding domain sidechain (Am) ($R^1$–$R^4$ and n are as defined above).

The quinoline and pyridine nuclei appear to act as hydrophobic anchors of the inhibitor, by binding to a hydrophobic pocket of the reductase enzyme, which results in enhanced inhibitory activity relative to compounds without such an anchor.

Preferred Moieties

In preferred embodiments of the invention, (Am) is an HMG-binding domain sidechain having a dihydroxy or a phosphinic acid function.

A suitable phosphinic (or phosphonic when X is $CH_2$—O—) acid HMG-binding domain sidechain ($A_1$) is

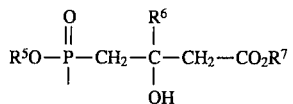

wherein $R^5$ and $R^7$ are independently selected from hydrogen, lower alkyl, alkali metal ion and alkaline earth metal ion; and $R^6$ is hydrogen or lower alkyl. Sidechain $A_1$ is novel and forms an integral part of this invention.

A suitable dihydroxy acid binding domain sidechain ($A_2$) is

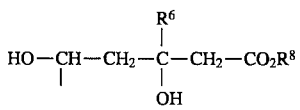

wherein $R^6$ is hydrogen or lower alkyl, $R^8$ is hydrogen or lower alkyl in free acid form or in the form of a physiologically acceptable and hydrolyzable ester or δ lactone thereof (i.e., when $A_2$ is

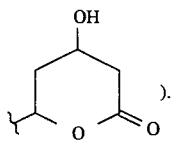

In addition, $R^8$ can be alkali metal ion or alkaline earth metal ion.

A suitable linker (X) is —$(CH_2)_a$—, —CH=CH—, —C≡C—, —$CH_2$O—, wherein O is linked to the phosphorous atom or the aromatic anchor when Am is $A_1$, and wherein O is linked to the aromatic anchor when Am is $A_2$, and wherein "a" is 1, 2, or 3.

Definitions of Terms

The terms "salt" and "salts" refer to basic salts formed with inorganic and organic bases. Such salts include ammonium salts; alkali metal salts, such as lithium, sodium and potassium salts (which are preferred); alkaline earth metal salts, such as calcium and magnesium salts; salts with organic bases, such as amine like salts (e.g., dicyclohexylamine salt, benzathine, N-methyl-D-glucamine, and hydrabamine salts); and salts with amino acids like arginine, lysine and the like; and zwitterions, the so-called "inner salts". Nontoxic, pharmaceutically acceptable salts are preferred, although other salts are also useful, e.g., in isolating or purifying the product.

The term "lower alkyl" or "alkyl" as employed herein alone or as part of another group includes both straight and branched chain hydrocarbons, containing 1 to 12 carbons in the normal chain or the various branched isomers thereof, preferably 1 to 7 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like, as well as such groups including one or more substituents selected from halogen, (such as F, Br, Cl, and I), $CF_3$, aryl, cycloalkyl, alkoxy, hydroxy, alkylamino, alkanoylamino, carbonylamino, nitro, cyano, mercapto, and alkylthio.

The terms "cycloalkyl" and "cycloalkenyl" as employed herein alone or as part of another group includes cyclic hydrocarbon groups containing 3 to 12 carbons, preferably 3 to 8 carbons, which include cyclopropyl, cyclobutyl, cyclobutenyl, cyclopentyl, cyclopentenyl, cyclohexyl, and cyclohexenyl, as well as groups substituted with 1 or 2 halogens, 1 or 2 lower alkyl groups, 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 mercapto groups, and/or 1 or 2 alkylthio groups.

The terms "aryl" or "ar" as employed herein refer to monocyclic or bicyclic aromatic groups containing 6 to 10 carbons in the ring portion, such as phenyl, naphthyl, substituted phenyl or substituted naphthyl, wherein the substituents on either the phenyl or naphthyl may be alkyl, halogen (Cl, Br or F), $CF_3$, 1, 2 or 3 lower alkoxy groups, 1, 2 or 3 aralkyl groups, 1, 2 or 3 hydroxy groups, 1, 2 or 3 phenyl groups, 1, 2 or 3 alkanoyloxy groups, 1, 2 or 3 benzoyloxy groups, 1, 2 or 3 halophenyl groups, 1, 2 or 3 alkyl groups, 1, 2 or 3 alkylamino groups, 1, 2 or 3 alkanoylamino groups, 1, 2 or 3 arylcarbonylamino groups, 1, 2 or 3 amino groups, 1, 2 or 3 nitro groups, 1, 2 or 3 cyano groups, and 1, 2 or 3 thiol groups, with the aryl group preferably containing 3 substituents.

The terms "aralkyl", "aryl-alkyl" or "aryl-lower alkyl" as used herein alone or as part of another group refer to groups having at least one alkyl and at least one aryl group as defined above, such as benzyl, as well as such groups having one or more substituents selected from cycloalkyl, alkylcycloalkyl, amino, oxy, alkoxy, and adamantyl.

The term "alkenyl" by itself or as part of another groups refers to both straight and branched chain groups. Those groups having 2 to 10 carbon atoms are preferred. The term "alkenyl" further includes groups having one or two halo substituents, an alkoxy substituent, an aryl substituent, an alkyl-aryl substituent, a haloaryl substituent, a cycloalkyl substituent, or an alkylcycloalkyl substituent.

The term "alkanoyl" as used herein as part of another group refers to lower alkyl linked to a carbonyl group.

The terms "halogen" or "halo" as used herein refer to chlorine, bromine, fluorine, and iodine, with chlorine and fluorine being preferred.

The term "halo substituted alkyl" refers to alkyl groups in which one or more hydrogens have been replaced by chloro, bromo, or fluoro groups.

The term "heterocyclo" refers to fully saturated or unsaturated, monocyclic or bicyclic, aromatic or nonaromatic hydrocarbon groups having 5 or 6 atoms in each ring and at least one heteroatom. The heterocyclo group has 1 or 2 oxygen atoms, 1 or 2 sulfur atoms, or 1 to 4 nitrogen atoms in the ring. The bicyclic heterocyclo group may comprise a benzene ring, provided that the bicyclic group is attached by way of an available carbon atom in the benzene ring. The heterocyclo group may be substituted with halogen (Cl, Br or F), $CF_3$, 1, 2 or 3 lower alkoxy groups, 1, 2, or 3 aralkyl groups, 1, 2 or 3 hydroxy groups, 1, 2 or 3 phenyl groups, 1, 2 or 3 alkanoyloxy groups, 1, 2 or 3 benzoyloxy groups, 1, 2 or 3 halophenyl groups, 1, 2 or 3 alkyl groups, 1, 2 or 3 alkylamino groups, 1, 2 or 3 alkanoylamino groups, 1, 2 or 3 arylcarbonylamino groups, 1, 2 or 3 amino groups, 1, 2 or 3 nitro groups, 1, 2 or 3 cyano groups, and 1, 2 or 3 thiol groups, with the aryl group preferably containing 3 groups, preferably having 3 substituents. Exemplary heterocyclo groups are 2- and 3-thienyl, 2- and 3-furyl, 2- and 3-pyrrolyl, 2-, 3- and 4-pyridyl, 2-, 4- and 5-imidazolyl, 2- and 3-pyrrolidinyl, 2-, 3- and 4-piperidinyl, 2-, 3- and 4-azepinyl, 4, 5, 6 or 7-indolyl, 4, 5, 6 or 7-isoindolyl, 5, 6, 7 or 8-quinolinyl, 5, 6, 7 or 8-isoquinolinyl, 4, 5, 6 or 7-benzothiazolyl, 4, 5, 6 or 7-benzoxazolyl, 4, 5, 6 or 7-benzimidazolyl, 4, 5, 6 or 7-benzoxadiazolyl, and 4, 5, 6 or 7-benzofurazanyl.

Processes of Preparation

The compounds of the present invention are made generally in the following manner.

The syntheses of aldehyde 5, which is the starting material for compounds of the invention when $R^3$ and $R^4$ taken together can be $(CH=CH)_2$, are shown in Scheme 1. Reaction of anthranilonitrile 1 with an excess of Grignard reagent ($R^1MgBr$) in an aprotic solvent, such as ether ($Et_2O$) or tetrahydrofuran (THF), followed by acidic and basic work-up affords keto-aniline 2. Friedlander condensation of 2 with an appropriately substituted β-keto-ester under acidic conditions (i.e. $H_2SO_4/HOAc/\Delta$, $H_2SO_4/ethanol$ (EtOH)/Δ) provides quinoline 3. Reduction of the ester group in 3 with reducing agents such as $LiAlH_4$ or DIBAL-H in inert solvents such as THF, $Et_2O$, or toluene gives alcohol 4. Oxidants such as Dess-Martin periodinane or oxalyl chloride/dimethylsulfoxide (DMSO)/triethylamine convert compound 4 to aldehyde 5.

SCHEME 1

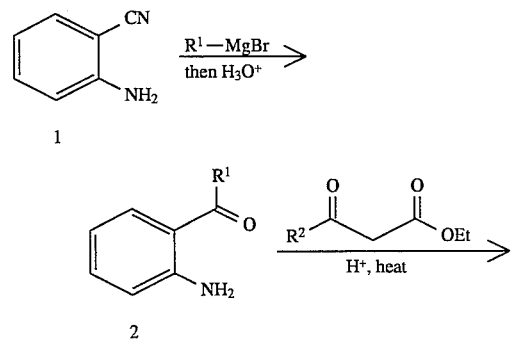

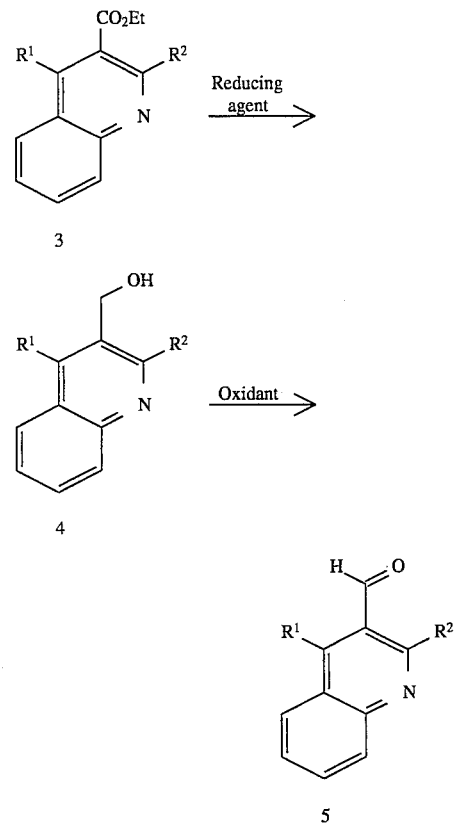

The syntheses of aldehyde 10, which is the starting material for compounds of the invention I wherein $R_3$ and $R_4$ are not $(CH=CH)_2$, are shown in Scheme 2. Condensation of ketone $R^3COCH_2R^4$ with aldehyde $R^1CHO$ under either acidic or basic conditions (i.e. $H_2SO_4/EtOH$ or EtONa/EtOH) provides α,β-unsaturated ketone 6. Michael addition of a β-keto-ester to compound 6 under basic conditions (i.e. EtONa/EtOH, KOBu$^t$/EtOH, NaH/THF) gives 1,5-diketone 7.

Alternatively, compound 7 may be prepared by an additional route. Knoevenagel condensation of an appropriately substituted β-keto-ester with aldehyde $R^1CHO$ (piperidine/HOAc/benzene/heat) provides compound 11. Addition of a ketone enolate, generated by treatment of $R^3COCH_2R^4$ with bases such as LDA, LiTMP, or $LiN(TMS)_2$ in an aprotic solvent such as THF, to compound 11 gives 1,5-diketone 7.

Compound 8 is formed by treatment of compound 7 with $NH_2OH.HCl$ or $NH_4OAc/Cu(OAc)_2$ in hot HOAc. Reduction of the ester group in 8 with a reducing agent such as $LiAlH_4$ or DIBAL-H in inert solvents such as THF, $Et_2O$, or toluene gives alcohol 9. Oxidants such as Dess-Martin periodinane or oxalyl chloride/DMSO/triethylamine convert compound 9 to aldehyde 10.

SCHEME 2

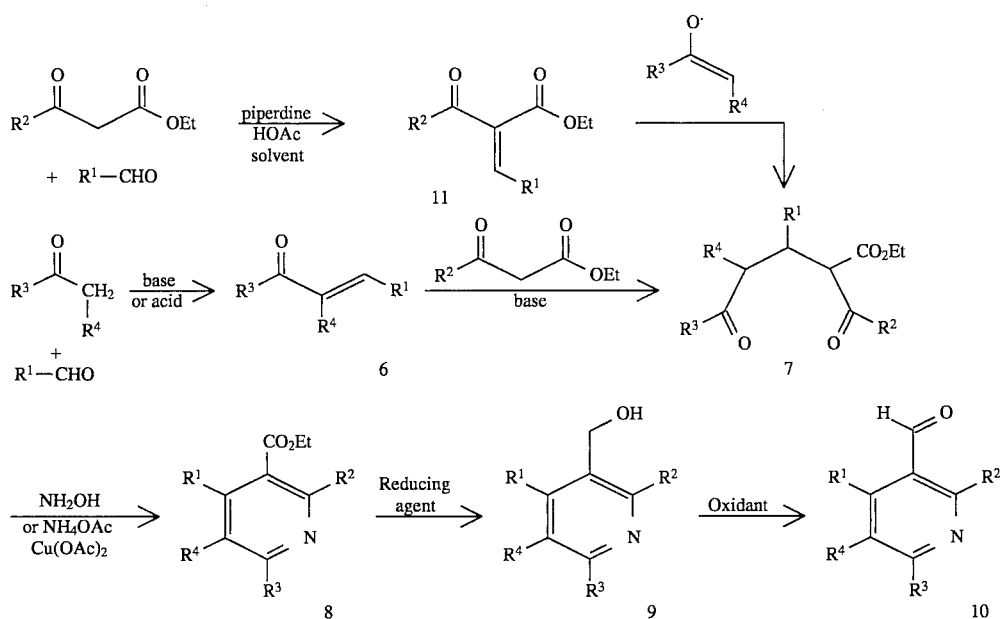

The synthesis of compounds I wherein Am is $A_2$ and X is CH=CH and $CH_2CH_2$ (Compounds 16 and 18) is described in Scheme 3. Reaction of aldehyde 12 with cis-1-ethoxy-2-lithioethylene at low temperatures (−78° C.) in an appropriate solvent such as THF, followed by acidic work-up provides enal 13. Condensation of the dianion of methyl acetoacetate with enal 13 in an aprotic solvent (THF, $Et_2O$) affords compound 14. Compound 15 is obtained via stereoselective reduction of 14 with a trialkylborane and a reducing agent such as $NaBH_4$ in a solvent such as THF containing MeOH and a small amount of catalyst such as $O_2$ or pivalic acid. Compound 15 can be saponified to 16 using aqueous solutions of a metal hydroxide in an appropriate solvent (i.e. MeOH, dioxane). Additionally, 15 may be hydrogenated to 17 in the presence of a suitable cataylst (Pd, Pt, Ru) and solvent (MeOH, EtOAc, EtOH) and then saponified as described above to provide compound 18.

SCHEME 3

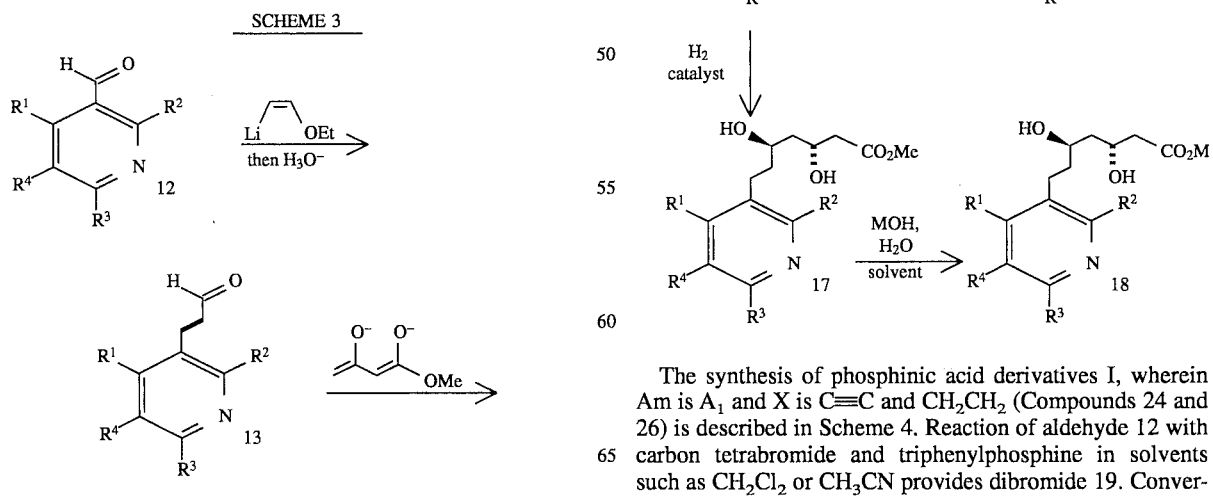

The synthesis of phosphinic acid derivatives I, wherein Am is $A_1$ and X is C≡C and $CH_2CH_2$ (Compounds 24 and 26) is described in Scheme 4. Reaction of aldehyde 12 with carbon tetrabromide and triphenylphosphine in solvents such as $CH_2Cl_2$ or $CH_3CN$ provides dibromide 19. Conversion of 19 to 20 is effected by treatment of 19 with alkyl lithium reagents such as n-BuLi at low temperature (−78° C.) in an aprotic solvent such as THF. Conversely, 20 may be obtained directly from 12 utilizing dimethyl diazomethylphosphonate and KOBut in a solvent such as THF (−78° C. to room temperature). Metallation of 20 (RLi, THF, −78° C.) followed by treatment with the chiral phosphonochloridate 21 affords compound 22 which can subsequently be desilylated (TBAF/HOAc) in an appropriate solvent such as THF to provide 23. Compound 23 can be saponified to 24 using aqueous solutions of a metal hydroxide in an appropriate solvent (i.e., MeOH, dioxane). Additionally, 23 may be hydrogenated to 25 in the presence of a suitable catalyst (Pd, Pt, Ru) and solvent (MeOH, EtOAc, EtOH) and then saponified as above to provide compound 26.

using aqueous solutions of a metal hydroxide in an appropriate solvent (e.g., MeOH, dioxane).

SCHEME 5

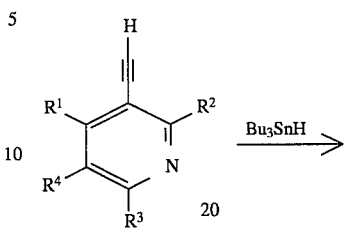

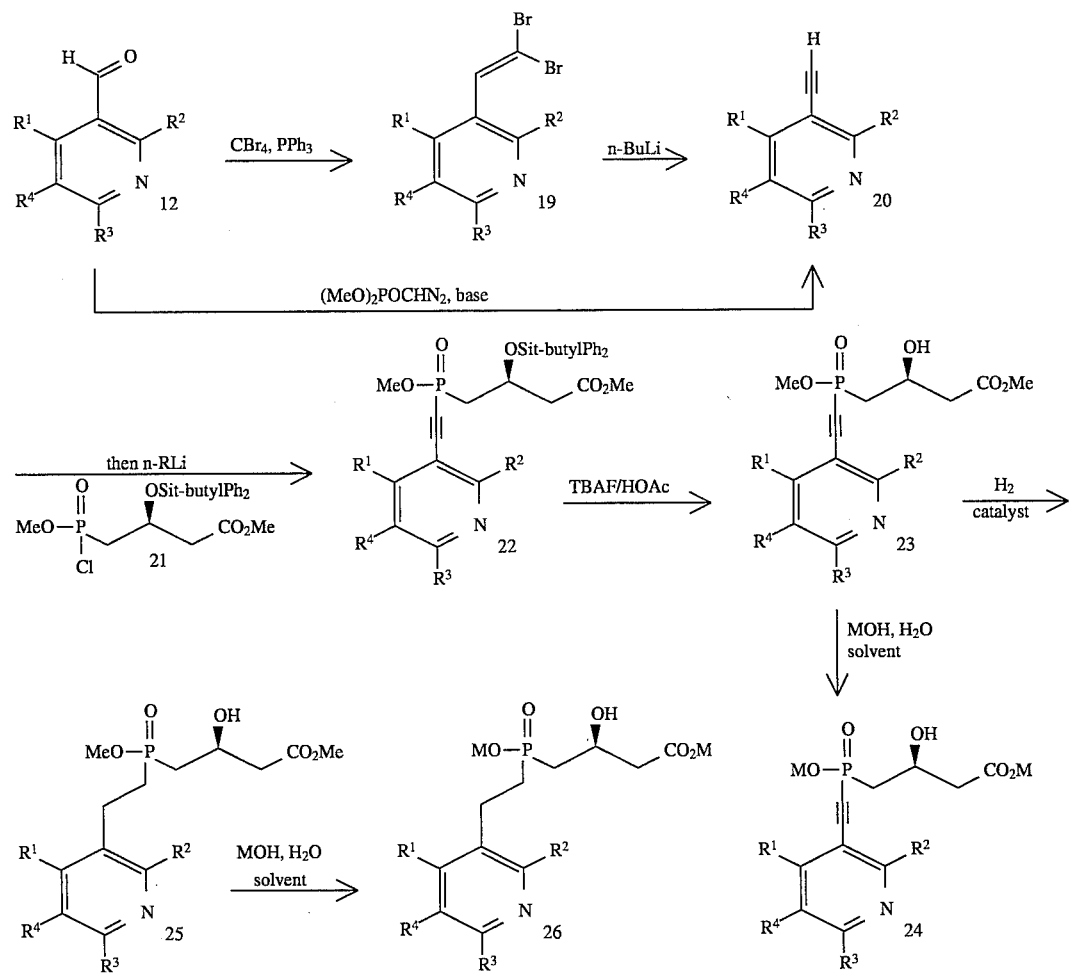

Scheme 5 describes the synthetic route to compounds I where Am is $A_1$ and X is CH=CH (e.g. compound 31. Treatment of acetylene 20 with neat $Bu_3SnH$ in the presence of AIBN at an elevated temperature (i.e. 140° C.) affords trans- vinyl stannane 27. Compound 27 was converted to 28 by iodine treatment of 27 in an appropriate solvent such as $Et_2O$ or $CHCl_3$. Metallation of 28 (t-butylLi) at −78° C. in an aprotic solvent such as THF gives the corresponding vinyl anion, which may be coupled with phosphonochloridate 21 at −100° C. to provide 29. Subsequently 29 may be desilylated (TBAF/HOAc) in an appropriate solvent such as THF to provide 30. Compound 30 can be saponified to 31

-continued
SCHEME 5

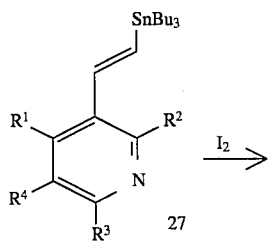

SCHEME 5
-continued

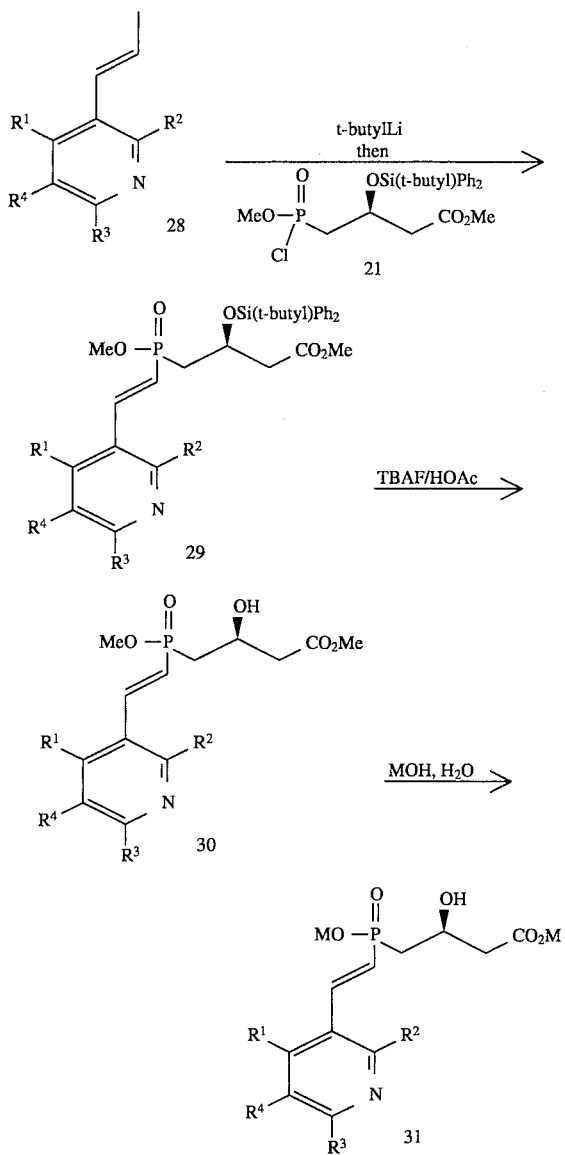

SCHEME 6

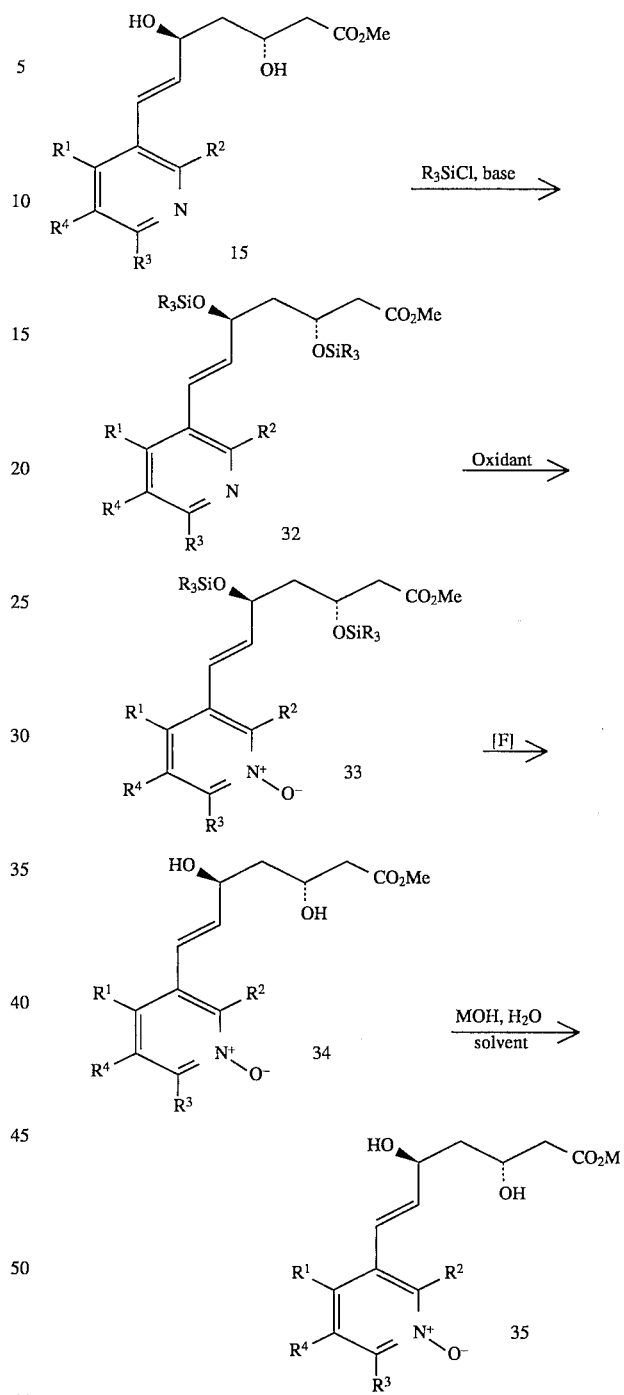

The synthesis of compounds I wherein Am is $A_2$, X is CH=CH and n is 1 (e.g., compound 35) is described in Scheme 6. Bis-silylation of compound 15 with a bulky silylchloride (e.g., ClSi(t-butyl)Ph$_2$, ClSi(t-butyl)Me$_2$, ClSiPh$_3$) in the presence of a suitable base (e.g., TEA, imidazole, pyridine) and solvent (e.g., $CH_2Cl_2$, THF) provides compound 32. Treatment of 32 with oxidants such as m-CPBA or $CF_3CO_3H$ in an appropriate solvent such as $CH_2Cl_2$ or HOAc affords N-oxide 33. Desilylation of 33 (TBAF/HOAc/THF or HF/$CH_3CN$) gives 34, which may be saponified to 35 using aqueous solutions of a metal hydroxide in an appropriate solvent (e.g., MeOH, dioxane).

Additionally, compound 17 may be oxidized and saponified, as described above, to provide compounds I wherein Am is $A_2$, X is $CH_2CH_2$ and n is 1 (e.g., compound 37) as shown in Scheme 7.

SCHEME 7

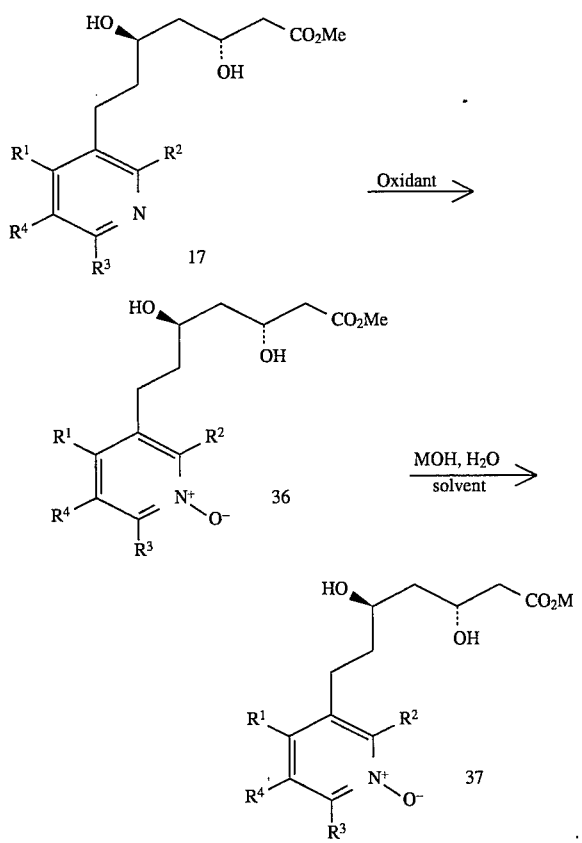

Scheme 8 depicts the chemistry used to synthesize compounds I wherein Am is $A_1$ and n is 1 (e.g., compound 40). Treatment of 38 with oxidants such as m-CPBA or $CF_3CO_3H$ in an appropriate solvent such as $CH_2Cl_2$ or HOAc affords N-oxide 39. Compound 39 may be saponified to 40 using aqueous solutions of a metal hydroxide in an appropriate solvent (i.e. MeOH, dioxane).

SCHEME 8

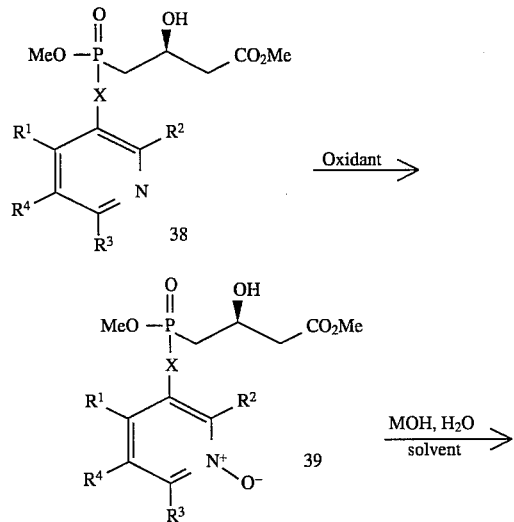

-continued
SCHEME 8

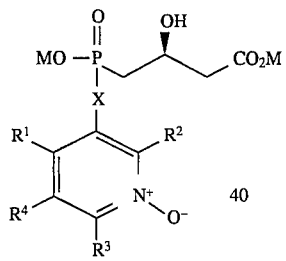

Reaction scheme 9 shows a preferred method for preparing the preferred quinolinealdehyde 5, which can be used as described in schemes 3 and 4 to prepare a corresponding compound of formula I. Reagent 42 (wherein M is lithium or magnesium halide) is reacted with anthranilonitrile 41 to form ketoaniline 43. Acylation of ketoaniline 43 with ethylmalonyl chloride affords amide 44 ("Et" refers to ethyl). Ethanolic sodium ethoxide is used to cause Knoevenagel condensation of amide 44 to form quinoline ester 45. A reducing agent (e.g., lithium aluminum hydride) converts quinoline ester 45 to quinolinolmethanol 46. An oxidizing agent (e.g., manganese dioxide) converts compound 46 to aldehyde 47. Triflation of aldehyde 47 (e.g., with trifluoromethanesulfonic anhydride) affords aldehyde 48. Stannane 49 is prepared by reaction of the corresponding lithium or Grignard reagent with tri-n-alkyltin chloride in diethy ether at −78° C. Aldehyde 48 and stannane 49 undergo palladium-catalyzed coupling to form 2,4-substituted 3-quinolinealdehyde 5. All reactions is scheme 9 take place under argon atmosphere.

SCHEME 9

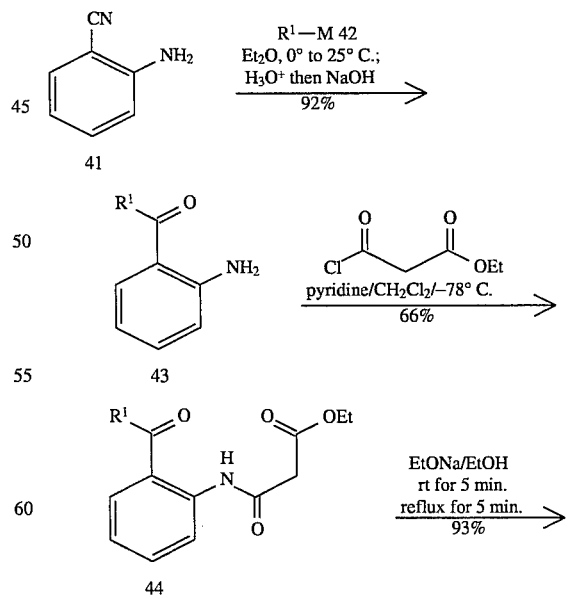

15
-continued
SCHEME 9

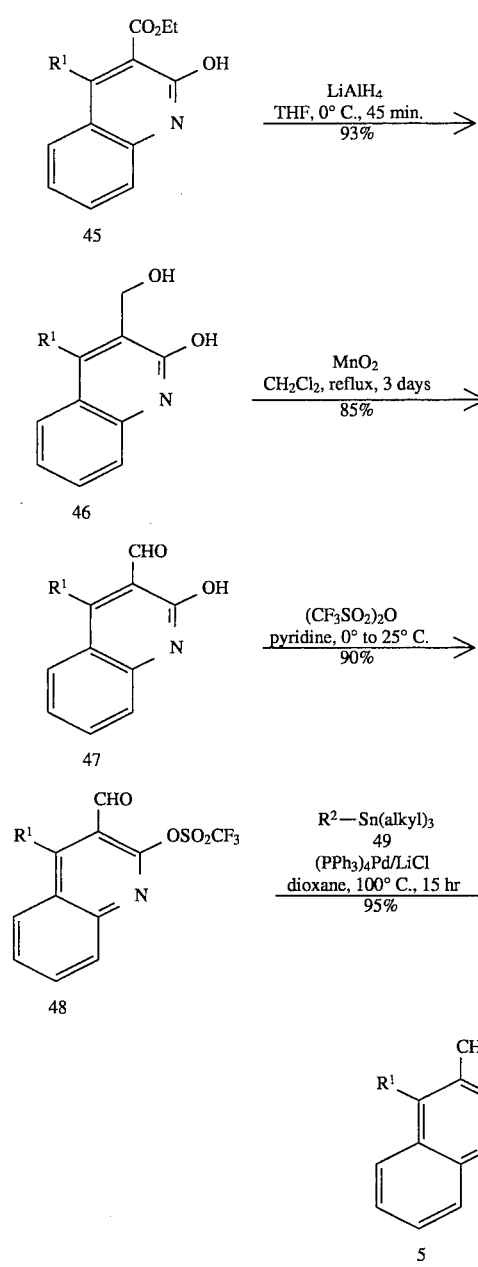

16
SCHEME 10

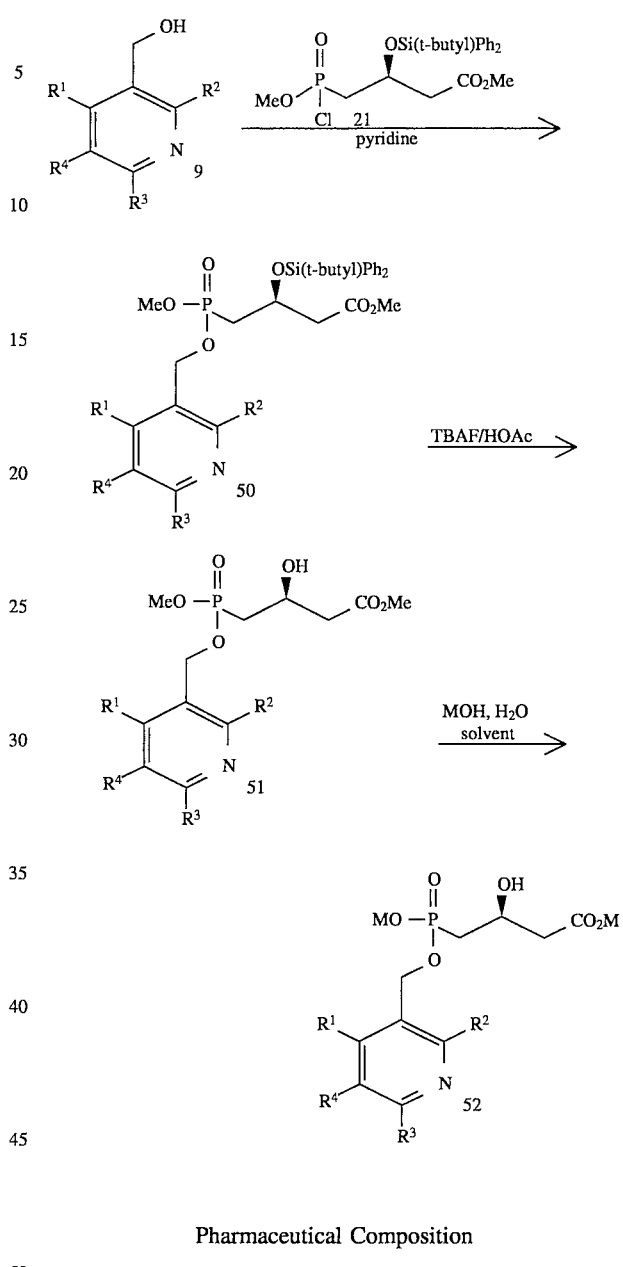

Scheme 10 describes the synthetic route to compounds I wherein Am is $A_1$ and X is $CH_2O$ (e.g. compound 52). Reaction of alcohol 9 with phosphonochloridate 21 in a solvent such as pyridine affords phosphonate 50. Compound 50 may be desilylated (HOAc/TBAF) in THF to give compound 51. Saponification of 51 using aqueous solutions of a metal hydroxide in an organic solvent (e.g., MeOH, dioxane) provides compound 52. Further reaction conditions are described in Example 99.

Pharmaceutical Composition

A further aspect of the present invention is a pharmaceutical composition consisting of at least one of the compounds of the present invention in association with a pharmaceutical vehicle or diluent. The pharmaceutical composition can be formulated employing conventional solid or liquid vehicles of diluents and pharmaceutical additives of a type appropriate to the mode of desired administration. The compounds can be administered by an oral route, for example, in the form of tablets, capsules, granules or powders, or they can be administered by a parenteral route in the form of injectable preparations, such dosage forms containing from 1 to 2000 mg of active compound per dosage, for use in the treatment. The dose to be administered depends on the unitary dose, the symptoms, and the age and the body weight of the patient.

Use and Utility

The compounds of the present invention can be administered in a similar manner as known compounds suggested for use in inhibiting cholesterol biosynthesis, such as lovastatin, in mammalian species such as humans, dogs, cats and the like. Thus, the compounds of the invention may be administered in an amount from about 4 to 2000 mg in a single dose or in the form of individual doses from 1 to 4 times per day, preferably 4 to 200 mg in divided dosages of 1 to 100 mg, suitably 0.5 to 50 mg 2 to 4 times daily or in sustained release form.

Compounds containing dihydroxy acid HMG-CoA binding domain side chains are prepared as racemic mixtures (3S*, 5R*) and may later be resolved to obtain the 3S, 5R isomer, which is preferred.

Phosphorus-containing HMG-CoA binding domain sidechains may be prepared as racemic mixtures and may later be resolved to obtain the S-isomer, which is preferred. However, these compounds may be prepared directly in the form of their S-isomers as described herein and in the working examples set out hereinafter.

The compounds of the invention are inhibitors of 3-hydroxy-3-methyl-glutaryl coenzyme A (HMG-CoA) reductase and thus are useful in inhibiting cholesterol biosynthesis as demonstrated by the following tests.

1) Rat Hepatic HMG-CoA Reductase

Rat hepatic HMG-CoA reductase activity is measured using a modification of the method described by Edwards (Edwards, P. A., et al., J. Lipid Res. 20:40, 1979). Rat hepatic microsomes are used as a source of enzyme, and the enzyme activity is determined by measuring the conversion of the $^{14}$C-HMG-CoA substrate to $^{14}$C-mevalonic acid.

a. Preparation of Microsomes

Livers are removed from 2–4 cholestyramine-fed, decapitated, Sprague Dawley rats, and homogenized in phosphate buffer A (potassium phosphate, 0.04M, pH 7.2; KCl, 0.05M; sucrose, 0.1M; EDTA, 0.03M; aprotinin, 500 KI units/ml). The homogenate is spun at 16,000 × g for 15 minutes at 4° C. The supernatant is removed and recentrifuged under the same conditions a second time. The second 16,000× g supernatant is spun at 100,000× g for 70 minutes at 4° C. Pelleted microsomes are resuspended in a minimum volume of buffer A (3–5 ml per liver), and homogenized in a glass/glass homogenizer. Dithiothreitol is added (10 mM), and the preparation is aliquoted, quick frozen in acetone/dry ice, and stored at –80° C. The specific activity of the first microsomal preparation was 0.68 nmole mevalonic acid/mg protein/minute.

b. Enzyme Assay

The reductase is assayed in 0.25 ml which contains the following components at the indicated final concentrations:

| | |
|---|---|
| 0.04 M | Potassium phosphate, pH 7.0 |
| 0.05 M | KCl |
| 0.10 M | Sucrose |
| 0.03 M | EDTA |
| 0.01 m | Dithiothreitol |
| 3.5 mM | NaCl |
| 1% | Dimethylsulfoxide |
| 50–200 μg | Microsomal protein |
| 100 μM | $^{14}$C-[DL]HMG-CoA (0.05 μCi, 30–60 mCi/mmole) |
| 2.7 mM | NADPH (nicotinamide adenine dinucleotide phosphate) |

Reaction mixtures are incubated at 37° C. Under the conditions described, enzyme activity increases linearly up to 300 μg microsomal protein per reaction mixture, and is linear with respect to incubation time up to 30 minutes. The standard incubation time chosen for drug studies is 20 minutes, which results in 12–15% conversion of HMG-CoA substrate to the mevalonic acid product. [DL-]HMG-CoA substrate is used at 100 μM, twice the concentration needed to saturate the enzyme under the conditions described. NADPH is used in excess at a level 2.7 times the concentration required to achieve maximum enzyme velocity.

Standardized assays for the evaluation of inhibitors are conducted according to the following procedure. Microsomal enzyme is incubated in the presence of NADPH at 37° C. for 15 minutes. DMSO vehicle with or without test compound is added, and the mixture is further incubated for 15 minutes at 37° C. The enzyme assay is initiated by adding $^{14}$C-HMG-CoA substrate. After 20 minutes of incubation at 37° C., the reaction is stopped by the addition of 25 μl of 33% KOH. $^3$H-mevalonic acid (0.05 μCi) is added, and the reaction mixture is allowed to stand at room temperature for 30 minutes. Fifty μl of 5N HCl is added to lactonize the mevalonic acid. Bromophenol blue is added as a pH indicator to monitor an adequate drop in pH. Lactonization is allowed to proceed for 30 minutes at room temperature. Reaction mixtures are centrifuged for 15 minutes at 2800 rpm. The supernatants are layered onto 2 grams AG 1-X8 anion exchange resin (Biorad, formate form) poured in 0.7 cm (id) glass columns, and eluted with 2.0 ml $H_2O$. The first 0.5 ml is discarded, and the next 1.5 ml is collected and counted for both tritium and carbon 14 in 10.0 ml Opti-fluor scintillation fluid. Results are calculated as nmoles mevalonic acid produced per 20 minutes, and are corrected to 100% recovery of tritium. Drug effects are expressed as $I_{50}$ values (concentration of drug producing 50% inhibition of enzyme activity) derived from composite dose response data with the 95% confidence interval indicated.

Conversion of drugs in lactone form to their sodium salts is accomplished by solubilizing the lactone in DMSO, adding a 10-fold molar excess of NaOH, and allowing the mixture to stand at room temperature for 15 minutes. The mixture is then partially neutralized (pH 7.5–8.0) using 1N HCl, and diluted into the enzyme reaction mixture.

2) Cholesterol Synthesis in Freshly Isolated Rat Hepatocytes

Compounds which demonstrate activity as inhibitors of HMG-CoA reductase are evaluated for their ability to inhibit $^{14}$C-acetate incorporation into cholesterol in freshly isolated rat hepatocyte suspensions using methods originally described by Capuzzi et al., (Capuzzi, D. M. and Margolis, S., Lipids, 6:602, 1971).

a. Isolation of Rat Hepatocytes

Sprague Dawley rats (180–220 grams) are anesthetized with Nembutal (50 mg/kg). The abdomen is opened and the first branch of the portal vein is tied closed. Heparin (100–200 units) is injected directly into the abdominal vena cava. A single closing suture is placed on the distal section of the portal vein, and the portal vein is canulated between the suture and the first branching vein. The liver is perfused at a rate of 20 ml/minute with prewarmed (37° C.), oxygenated buffer A (HBSS without calcium or magnesium containing 0.5 mM EDTA) after severing the vena cava to allow drainage of the effluent. The liver is additionally perfused with 200 ml of prewarmed buffer B (HBSS containing 0.05% bacterial collagenase). Following perfusion with buffer B, the liver is excised and decapsulated in 60 ml Waymouth's medium allowing free cells to disperse into the medium. Hepatocytes are isolated by low speed centrifugation for 3 minutes at 50× g at room temperature. Pelleted hepatocytes are washed once in Waymouth's medium, counted and assayed for viability by trypan blue exclusion. These hepatocyte enriched cell suspensions routinely show 70–90% viability.

b. $^{14}$C-Acetate Incorporation into Cholesterol

Hepatocytes are resuspended at 5×10$^6$ cells per 2.0 ml in incubation medium (IM) [0.02M Tris-HCl (ph 7.4), 0.1M KCl, 3.3 mM sodium citrate, 6.7 mM nicotinamide, 0.23 mM NADP, 1.7 mM glucose-6-phosphate].

Test compounds are routinely dissolved in DMSO or DMSO:H$_2$O (1:3) and added to the IM. Final DMSO concentration in the IM is ≦ 1.0%, and has no significant effect on cholesterol synthesis.

Incubation is initiated by adding $^{14}$C-acetate (58 mCi/mmol, 2 μci/ml), and placing the cell suspensions (2.0 ml) in 35 mm tissue culture dishes, at 37° C. for 2.0 hours. Following incubation, cell suspensions are transferred to glass centrifuge tubes and spun at 50× g for 3 minutes at room temperature. Cell pellets are resuspended and lysed in 1.0 ml H$_2$O, and placed in an ice bath.

Lipids are extracted essentially as described by Bligh, E. G. and W. J. Dyer, Can. J. Biochem. and Physiol., 37:911, 1959. The lower organic phase is removed and dried under a stream of nitrogen, and the residue resuspended in (100 μl) chloroform:methanol (2:1). The total sample is spotted on silica gel (LK6D) thin-layer plates and developed in hexane:ethyl ether:acetic acid (75:25:1). Plates are scanned and counted using a BioScan automated scanning system. Radiolabel in the cholesterol peak (RF 0.28) is determined and expressed at total counts per peak and as a percent of the label in the total lipid extract. Cholesterol peaks in control cultures routinely contain 800–1000 cpm, and are 9–20% of the label present in the total lipid extract; results compatable with Capuzzi, et al., indicating 9% of extracted label in cholesterol.

Drug effects (% inhibition of cholesterol synthesis) are determined by comparing % of label in cholesterol for control and drug treated cultures. Dose response curves are constructed from composite data from two or more studies, and results are expressed as I$_{10}$ values with a 95% confidence interval.

3) Cholesterol Synthesis in Human Skin Fibroblasts

Compound selectivity favoring greater inhibitory activity in hepatic tissue would be an attribute for a cholesterol synthesis inhibitor. Therefore, in addition to evaluating cholesterol synthesis inhibitors in hepatocytes, these compounds are also tested for their activity as inhibitors of cholesterol synthesis in cultured fibroblasts.

a. Human Skin Fibroblast Cultures

Human skin fibroblasts (passage 7-27) are grown in Eagles' minimal essential medium (EM) containing 10% fetal calf serum. For each experiment, stock cultures are trypsinized to disperse the cell monolayer, counted, and plated in 35 mm tissue culture wells (5×10$^5$ cells/2.0 ml). Cultures are incubated for 18 hours at 37° C. in 5% CO$_2$/95% humidified room air. Cholesterol biosynthetic enzymes are induced by removing the serum containing medium, washing the cell monolayers, and adding 1.0 ml of EM containing 1.0% fatty acid free bovine serum albumin, and incubating the cultures an additional 24 hours.

b. $^{14}$C-Acetate Incorporation into Cholesterol

Induced fibroblast cultures are washed with EMEM$_{100}$ (Earle's minimal essential medium). Test compounds are dissolved in DMSO or DMSO:EM (1:3) (final DMSO concentration in cell cultures ≦ 1.0%), added to the cultures, and the cultures preincubated for 30 minutes at 37° C. in 5% CO$_2$/95% humidified room air. Following preincubation with drugs, [1-$^{14}$C]Na acetate (2.0 μCi/ml, 58 mCi/mmole) is added, and the cultures reincubated for 4 hours. After incubation, the culture medium is removed, and the cell monolayer (200 μg cell protein per culture) is scraped into 1.0 ml of H$_2$O. Lipids in the lysed cell suspension are extracted into chloroform:methanol as described for hepatocyte suspensions. The organic phase is dried under nitrogen, and the residue resuspended in chloroform:methanol (2:1) (100 μl), and the total sample spotted on silica gel (LK6D) thin-layer plates, and analyzed as described for hepatocytes.

Inhibition of cholesterol synthesis is determined by comparing the percentage of label in the cholesterol peak from control and drug-treated cultures. Results are expressed as I$_{50}$ values, and are derived from composite dose response curves from two or more experiments. A 95% confidence interval for the I$_{50}$ value is also calculated from the composite dose response curves.

The following working Examples represent preferred embodiments of the present invention. Unless otherwise indicated, all temperatures are expressed in degrees Centigrade.

Example 1

(3R*, 5S*, 6E)-7-[4-(4-Fluorophenyl)-2-(1-methylethyl)-6-phenyl-3-pyridinyl]-3,5-dihydroxy-6-heptenoic acid, monolithium salt

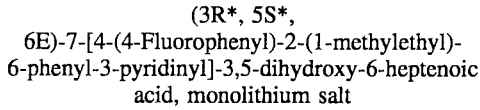

A. (E)-3-(4-fluorophenyl)-1-phenyl-2-propen-1-one

A mixture of acetophenone (7.02 gm, 58.4 mmol), p-fluorobenzaldehyde (7.24 gm, 58.4 mmol) and concentrated H$_2$SO$_4$ (10 ml) in glacial HOAc (116 ml) was stirred at room temperature for 2 days. The solution was poured into H$_2$O (250 ml) and neutralized with 10% NaOH (200 ml). The aqueous layer was extracted once with Et$_2$O and the Et$_2$O layer was washed successively with H$_2$O, saturated NaHCO$_3$ (2×) and brine, then dried (MgSO$_4$). Filtration and removal of the solvent afforded a yellow solid which was recrystallized from hot hexane to give (E)-3-(4-fluorophenyl)-1 -phenyl-2-propen-1-one (7.94 gm, 60%) as light yellow needles.

m.p. 86°–88° C. TLC: R$_f$ 0.36 (20% EtOAc in hexane)

B. β-(4-fluorophenyl)-α-(2-methyl-1 -oxopropyl)-δ-oxobenzenepentanoic acid, ethyl ester To a mixture of (E)-3-(4-fluorophenyl)-1 -phenyl-2-propen-1-one (4.59 gm, 20.3 mmol) and ethyl isobutyrylacetate (3.86 gm, 24.4 mmol) in absolute EtOH (100 ml) was added a solution of EtONa in EtOH. The EtONa solution was prepared by dissolving Na metal (50 mg, 2.2 mmol) in EtOH (10 ml). After stirring at room temperature for 3 hours, additional ethyl isobutyrylacetate (1.0 gm, 6.3 mmol) was added. Stirring continued for an additional 2 hours. The mixture was poured into a separatory funnel containing Et$_2$O and saturated NH$_4$Cl. The phases were shaken and separated. The aqueous layer was extracted once with EtOAc and the combined organic layers were washed with brine and dried (Na$_2$SO$_4$). Filtration and removal of the solvent gave a solid/liquid mixture. Crystallization of the residue from hot hexane/EtOAc gave β-(4-fluorophenyl)-α-(2-methyl-1-oxopropyl)-δ-oxobenzenepentanoic acid, ethyl ester (5.91 gm, ~ 95% one diastereomer) as colorless needles. The mother liquor was stripped and recrystallized from hot hexane to afford additional product, giving a total of 7.21 gm (92%) β-(4 -fluorophenyl)-α-(2-methyl-1-oxopropyl)-δ -oxobenzenepentanoic acid, ethyl ester as a 7:3:1 mixture of diastereomers.

m.p. (1st crop) 119.2°–120.8° C. TLC: $R_f$ 0.22 and 0.18 (20% EtOAc in hexane)

C. 4-(4-fluorophenyl)-2-(1-methylethyl)-6-phenyl-3-pyridinecarboxylic acid, ethyl ester A mixture of β-(4-fluorophenyl)-α-(2-methyl-1-oxopropyl)-δ-oxobenzenepentanoic acid, ethyl ester (7.92 gm, 20.6 mmol) and hydroxylamine hydrochloride (4.32 gm, 62.2 mmol) in glacial HOAc (100 ml) was refluxed for 2.5 hours. The reaction was cooled to room temperature and poured into an ice cold solution of concentrated $NH_4OH$ (140 ml) in $H_2O$ (400 ml). The resulting mixture was extracted twice with $Et_2O$ and the combined ethereal layers were washed with brine, dried ($Na_2SO_4$), filtered and stripped to yield a gummy orange-red oil. Flash chromatography of the oil (Merck $SiO_2$, 7% EtOAc in hexane) gave 4-(4-fluorophenyl)-2-(1-methylethyl)- 6-phenyl-3-pyridinecarboxylic acid, ethyl ester (4.88 gm, 65%) as a near colorless gum.

TLC: $R_f$ 0.47 (20% EtOAc in hexane)

D. 4-(4-fluorophenyl)-2-(1-methylethyl)- 6-phenyl-3-pyridinemethanol

A slurry of $LiAlH_4$ (775 mg, 20.4 mmol) in dry $Et_2O$ (70 ml) at 0° C. was treated with a solution of 4-(4-fluorophenyl)-2-(1-methylethyl)- 6-phenyl-3-pyridinecarboxylic acid, ethyl ester (4.80 gm, 13.2 mmol) in $Et_2O$ (5 ml). After 2.5 hours, the reaction was quenched and diluted with $H_2O$ and the aqueous layer was extracted twice with $Et_2O$ and once with EtOAc. The combined organic layers were washed with $H_2O$ and brine, then dried ($Na_2SO_4$), filtered and stripped. The resulting solid was dissolved in hot EtOAc and directly chromatographed (flash, Merck $SiO_2$, 20% EtOAc in hexane) to give crude 4-(4-fluorophenyl)-2-(1-methylethyl)-6-phenyl-3-pyridinemethanol. Recrystallization from hot hexane/EtOAc gave 4-(4-fluorophenyl)-2-(1-methylethyl)-6-phenyl-3-pyridinemethanol (3.30 gm) as a white solid. The mother liquor was stripped and recrystallized again to give an additional 230 mg of product (total 3.53 gm, 84%).

m.p. 167.2°–167.8° C. TLC: $R_f$ 0.26 (20% EtOAc in hexane)

E. 4-(4-fluorophenyl)-2-(1-methylethyl)- 6-phenyl-3-pyridinecarboxaldehyde

A solution of Dess-Martin periodinane (1.54 gm, 3.63 mmol) in dry $CH_2Cl_2$ (17 ml) was treated with t-butanol (267 mg, 3.60 mmol) and stirred for 15 minutes at room temperature. A solution of 4-(4-fluorophenyl)-2-(1-methylethyl)-6-phenyl-3-pyridinemethanol (895 mg, 2.78 mmol) in $CH_2Cl_2$ (12 ml) was then added and stirring was continued 30 minutes, after which time the mixture was quenched by the addition of $Et_2O$ (70 ml) and 1N NaOH (35 ml). The biphasic mixture was stirred for 10 minutes and the layers were separated. The organic layer was washed with 1N NaOH, $H_2O$ and brine, then dried ($Na_2SO_4$), filtered and stripped. The solid residue was chromatographed (Flash, Merck $SiO_2$, 10% EtOAc in hexane) to afford pure 4-(4-fluorophenyl)- 2-(1-methylethyl)-6-phenyl-3-pyridinecarboxaldehyde (782 mg, 88%) as a white solid. Analytically pure material was obtained by recrystallization of the solid from a minimum amount of hot hexane.

m.p. 105°–107° C. TLC: $R_f$ 0.50 (20% EtOAc in hexane)

F. (E)-3-[4-(4-fluorophenyl)-2-(1-methylethyl)- 6-phenyl-3-pyridinyl]-2-propenal n-BuLi (1.6M in hexanes, 1.52 ml, 2.43 mmol) was added to a solution of cis-1-ethoxy-2-(tri-n-butylstannyl)ethylene (961 mg, 2.66 mmol) in dry THF (7.5 ml) at −78° C. The mixture was stirred for 1 hour, then treated with a solution of 4-(4-fluorophenyl)-2-(1-methylethyl)-6-phenyl-3-pyridinecarboxaldehyde (708 mg, 2.22 mmol) in THF (3.5 ml). One hour after the addition, the reaction was immersed in an ice bath, stirred for 5 minutes, then the mixture was quenched with $H_2O$ (8 ml) and 10% HCl (8 ml). The solution was stirred at room temperature for 2 hours, then basicified with 10% NaOH (10 ml) and extracted twice with $Et_2O$. The combined $Et_2O$ layers were washed with $H_2O$ and brine, dried ($Na_2SO_4$), then filtered and stripped to give a yellow oil. Chromatographic purification of the oil (Flash, Merck $SiO_2$, 10% EtOAc in hexane) gave (E)-3-[4-(4-fluorophenyl)-2-(1-methylethyl)-6-phenyl-3-pyridinyl]-2-propenal (665 mg, 87%) as a white solid. Recrystallization from hot hexane gave analytically pure material (580 mg).

m.p. 113.8°–114.4° C. TLC: $R_f$ 0.35 (20% EtOAc in hexane)

G. (E)-7-[4-(4-fluorophenyl)-2-(1-methylethyl)- 6-phenyl-3-pyridinyl]-5-hydroxy- 3-oxo-6-heptenoic acid, methyl ester Methyl acetoacetate (272 mg, 2.34 mmol) was added dropwise to a slurry of NaH (60% in mineral oil, 93.7 mg, 23.4 mmol) in dry THF (5.5 ml) at 0° C. After 15 minutes, the solution was treated with n-BuLi (1.6M in hexanes, 1.11 ml, 1.78 mmol) and stirred an additional 15 minutes. (E)-3-[4 -(4-fluorophenyl)-2-(1-methylethyl)-6-phenyl-3-pyridinyl] -2-propenal (560 mg, 1.62 mmol) in THF (3.0 ml) was added, resulting in an orange solution. After 25 minutes, the solution was poured into a biphasic mixture $Et_2O$ (30 ml), 1N HCl (4.5 ml) and $H_2O$ (16 ml). The aqueous phase was neutralized with saturated $NaHCO_3$ and the layers were separated. The aqueous layer was extracted again with $Et_2O$ and the combined $Et_2O$ layers were washed with brine and dried ($Na_2SO_4$). Filtration and solvent removal afforded an oil which was chromatographed (Flash, Merck $SiO_2$, 30% EtOAc in hexane) to give (E)-7-[4-(4-fluorophenyl)-2-(1-methylethyl)-6-phenyl-3-pyridinyl]-5-hydroxy-3-oxo-6-heptenoic acid, methyl ester (387 mg, 52%) as a light yellow oil.

TLC: $R_f$ 0.31 (40% EtOAc in hexane)

H. (3R, 5S, 6E)-7-[4-(4-fluorophenyl)-2-(1-methylethyl)-6-phenyl-3-pyridinyl]-3,5-dihydroxy-6-heptenoic acid, methyl ester A solution of (E)-7-[4-(4-fluorophenyl)-2-(1-methylethyl)-6-phenyl-3-pyridinyl]-5-hydroxy-3-oxo-6-heptenoic acid, methyl ester (357 mg, 0.77 mmol) in THF (12 ml) was treated with triethylborane (1.0M in THF, 1.62 ml, 1.62 mmol). Twenty five milliliters of air was bubbled through the solution and the mixture was stirred at room temperature for 30 minutes. The solution was cooled to −78° C. and treated with $NaBH_4$ (29.4 mg, 0.78 mmol) followed by dropwise addition of dry methanol (1.90 ml). After stirring at −78° C. for 1.5 hours, the mixture was quenched with 30% $H_2O_2$ (3.5 ml) in $H_2O$ (11 ml). The mixture was kept at −78° C. for 15 minutes, then warmed to room temperature and stirred for 30 minutes. The solution was poured into 50% saturated $NaHCO_3$ and extracted with $Et_2O$ (3×). The $Et_2O$ extracts were combined, washed with $H_2O$, saturated $NaHCO_3$ and brine, then dried ($Na_2SO_4$). Filtration and removal of the solvent gave a yellow oil which was chromatographed (Flash, Merck $SiO_2$, 40% EtOAc in hexane) to afford (3R, 5S, 6E)-7-[4-(4-fluorophenyl)- 2-(1-methylethyl)-6-phenyl-3-pyridinyl] -3,5-dihydroxy-6-heptenoic acid, methyl ester (320 mg, 89%) as a colorless oily foam.

TLC: $R_f$ 0.17 (40% EtOAc in hexane)

I. (3R*, 5S*, 6E)-7-[4-Fluorophenyl)-2 -(1-methyl-ethyl)-6-phenyl-3-pyridinyl] -3,5-dihydroxy-6-heptenoic acid, monolithium salt A solution of (3R, 5S, 6E)-7-[4-(4-fluorophenyl)- 2-(1-methylethyl)-6-phenyl-3-pyridinyl] -3,5-dihydroxy-6-heptenoic acid, methyl ester (290 mg, 0.625 mmol) in dioxane (4.0 ml) and H$_2$O (4.0 ml) was treated with 1N LiOH (0.75 ml) at room temperature. After 20 minutes, the solvent was evaporated and the residue was chromatographed on HP-20 (25 mm×90 mm column) eluting in succession with H$_2$O (150 ml), 25% CH$_3$CN in H$_2$O (100 ml) and 50% CH$_3$CN in H$_2$O (200 ml). The desired fractions were pooled and evaporated and the residue was taken up in H$_2$O and lyophilized to give (3R*, 5S*, 6E)-7-[4-Fluorophenyl)-2-(1-methyl-ethyl)-6 -phenyl-3-pyridinyl]-3,5-dihydroxy-6-heptenoic acid, monolithium salt (265 mg, 91%) as a white solid.

TLC: R$_f$ 0.50 (8:1:1, CH$_2$Cl$_2$:HOAc:MeOH)

Example 2

(3R*, 5S*, 6E)-7-[4-(4-Fluorophenyl)-2-methyl-6 -phenyl-3-pyridinyl] -3,5-dihydroxy-6-heptenoic acid, monolithium salt A. α-acetyl-β-(4-fluorophenyl)-δ-oxobenzenepentanoic acid, ethyl ester To a mixture of (E)-3-(4-fluorophenyl)-1-phenyl-2-propen-1-one (4.62 gm, 20.4 mmol) (the preparation of which is described in Example 1 and ethyl acetoacetate (5.32 gm, 40.9 mmol) in absolute EtOH (100 ml) was added a solution of EtONa in EtOH. The EtONa solution was prepared by dissolving Na metal (65 mg, 2.8 mmol) in EtOH (10 ml). A precipitate formed after 4 hours of stirring. After 6 hours, the reaction was diluted with a solution of HOAc (170 mg) in H$_2$O (100 ml), stirred for 5 minutes, then filtered. The solid was washed with H$_2$O and dried overnight in vacuo to afford α-acetyl-β-(4-fluorophenyl)-δ-oxobenzenepentanoic acid, ethyl ester (6.12 gm) in ~ 60–65% purity. This material was used directly in the next reaction.

TLC: R$_f$ 0.15 (20% EtOAc in hexane)

B. 4-(4-fluorophenyl)-2-methyl-6-phenyl-3 -pyridinecarboxylic acid, ethyl ester

A mixture of α-acetyl-β-(4-fluorophenyl)-δ -oxobenzenepentanoic acid, ethyl ester (6.12 gm) and hydroxylamine hydrochloride (3.61 gm, 52 mmol) in glacial HOAc (83 ml) was refluxed for 1 hour. The reaction was cooled to room temperature and poured into an ice cold solution of concentrated NH$_4$OH (115 ml) in H$_2$O (300 ml). The resulting mixture was extracted twice with Et$_2$O and the combined Et$_2$O layers were washed with brine, dried (Na$_2$SO$_4$), filtered and stripped to yield a dark gummy residue. The residue was chromatographed (Flash, Merck SiO$_2$, 8% EtOAc in hexane) to give 4-(4-fluorophenyl)-2-methyl-6-phenyl-3-pyridinecarboxylic acid, ethyl ester which was rechromatographed (8% EtOAc in hexane) to afford pyridine 4-(4-fluorophenyl)-2-methyl-6-phenyl-3 -pyridinecarboxylic acid, ethyl ester (1.652 gm, 24% from (E)-3-(4-fluorophenyl)-1-phenyl-2-propen- 1-one) in >90% purity.

TLC: R$_f$ 0.35 (20% EtOAc in hexane)

C. 4-(4-fluorophenyl)-2-methyl-6-phenyl- 3-pyridinemethanol

A slurry of LiAlH$_4$ (305 mg, 8.04 mmol) in dry Et$_2$O (30 ml) at 0° C. treated with a solution of 4-(4-fluorophenyl)-2-methyl-6-phenyl-3-pyridinecarboxylic acid, ethyl ester (1.587 gm, 4.73 mmol) in Et$_2$O (4 ml). After 50 minutes, the reaction was quenched and diluted with H$_2$O and the solution was adjusted to neutral pH with 10% HCl. EtOAc was added to dissolve suspended product into the Et$_2$O layer and the mixture was subsequently extracted three times with EtOAc. The combined organic layers were washed with H$_2$O and brine, then dried (Na$_2$SO$_4$), filtered and stripped to give a yellow solid. Recrystallization of the solid from hot hexane/acetone afforded 4-(4-fluorophenyl)-2 -methyl-6-phenyl-3-pyridinemethanol (916 mg) as a white solid. An additional 283 mg of 4 -(4-fluorophenyl)-2-methyl-6-phenyl-3-pyridinemethanol was obtained by evaporation of the mother liquor followed by recrystallization of the residue from hot hexane/EtOAc, giving a total of 1.199 gm (86%) product.

m.p. 181°–183° C. TLC: R$_f$ 0.29 (40% EtOAc in hexane)

D. 4-(4-fluorophenyl)-2-methyl-6-phenyl- 3-pyridinecarboxaldehyde

A solution of Dess-Martin periodinane (1.04 gm, 2.45 mmol) in dry CH$_2$Cl$_2$ (12 ml) was treated with t-butanol (182 mg, 2.46 mmol) and stirred at room temperature for 15 minutes. A slurry of 4-(4-fluorophenyl)-2-methyl-6-phenyl-3-pyridinemethanol (555 mg, 1.89 mmol) in CH$_2$Cl$_2$ (10 ml) and CH$_3$CN (2 ml) was then added and stirring was continued for 25 minutes. The mixture was diluted with Et$_2$O (50 ml) and poured into 1N NaOH (25 ml) and stirred for 5 minutes. The phases were separated and the organic layer was washed successively with 1N NaOH, H$_2$O, and brine, then dried (Na$_2$SO$_4$). Filtration and removal of the solvent afforded a solid. The solid was dissolved in hot hexane/EtOAc and the resulting solution was cooled to 0° C., filtered and stripped to give a residue which was chromatographed (Flash, Merck SiO$_2$, 20% EtOAc in hexane). 4-(4-fluorophenyl)-2 -methyl-6-phenyl-3-pyridinecarboxaldehyde was obtained as a white solid (458 mg, 83%). Analytically pure material was obtained by recrystallization from hot hexane.

m.p. 119.5°–120.5° C. TLC: R$_f$ 0.37 (20% EtOAc in hexane)

E. (E)-3-[4-(4-fluorophenyl)-2-methyl-6 -phenyl-3-pyridinyl]-2-Propenal n-BuLi (1.6M in hexanes, 1.52 ml, 2.43 mmol) was added to a solution of cis-1-ethoxy-2 -(tri-n-butylstannyl) ethylene (1.06 gm, 2.94 mmol) in dry THF (7.5 ml) at −78° C. The mixture was stirred for 1¼ hours, then cooled to −100° C. (liquid N$_2$/methanol) and treated with a solution of 4-(4-fluorophenyl)-2-methyl-6-phenyl-3-pyridinecarboxaldehyde (707 mg, 2.43 mmol) in THF (3.0 ml). Forty-five minutes after the addition, the temperature was raised to −78° C. and the mixture was stirred for an additional 50 minutes. The solution was then stirred in an ice bath for 5 minutes and subsequently quenched with H$_2$O (8 ml) and 10% HCl (8 ml). After stirring at room temperature for 1.5 hours, the mixture was made basic with 10% NaOH (10 ml) and extracted twice with Et$_2$O. The combined Et$_2$O layers were washed with H$_2$O and brine, dried (Na$_2$SO$_4$), filtered and stripped to yield a solid. The solid was washed with cold Et$_2$O. The Et$_2$O washings were stripped and triturated with cold hexane to give additional solid, which was pooled with the above solid to give 586 mg (76%) (E)-3-[4-(4-fluorophenyl)-2 -methyl-6-phenyl-3-pyridinyl]-2-propenal. Analytically pure material was obtained by recrystallization from hot hexane/EtOAc.

m.p. 160.5°–163° C. TLC: R$_f$ 0.17 (20% EtOAc in hexane)

F. (E)-7-[4-(4-fluorophenyl)-2-methyl-6 -phenyl-3-pyridinyl]-5-hydroxy-3-oxo- 6-heptenoic acid, methyl ester Methyl acetoacetate (324 mg, 2.79 mmol) was added dropwise to a slurry of NaH (60% in mineral oil, 111.7 mg, 2.79 mmol) in dry THF (7 ml) at 0° C. After 15 minutes, n-BuLi (1.5M in hexanes, 1.46 ml, 2.19 mmol) was added and the mixture was stirred an additional 15 minutes. Addition of a solution of (E)-3-[4-(4-fluorophenyl)-2-methyl- 6-phenyl-3-pyridinyl]-2-propenal (633 mg, 1.99 mmol) in THF (7 ml) to the reaction mixture resulted in the formation of a bright red solution. Twenty minutes after the addition, the solution was poured into a biphasic mixture of Et$_2$O (40 ml) and 1N HCl (5.5 ml) in H$_2$O (20 ml). The aqueous layer was made basic with saturated NaHCO$_3$ and the phases were separated. The aqueous layer was extracted again with Et$_2$O, neutralized with 1N HCl and extracted once more. The combined Et$_2$O layers were washed with brine, dried (Na$_2$SO$_4$), filtered and stripped to yield an oil. Flash chromatography (Merck SiO$_2$, 1:1 EtOAc:hexane) afforded (E)-7-[4-(4-fluorophenyl)- 2-methyl-6-phenyl-3-pyridinyl]-5-hydroxy-3-oxo-6 -heptenoic acid, methyl ester (251 mg, 29%) as a yellow oil TLC: R$_f$ 0.16 (40% EtOAc in hexane)

G. (3R*, 5S*, 6E)-7-[4-(4-fluorophenyl)- 2-methyl-6-phenyl-3-pyridinyl]-3,5 -dihydroxy-6-heptenoic acid, methyl ester A solution of (E)-7-[4-(4-fluorophenyl)-2 -methyl-6-phenyl-3-pyridinyl]-5-hydroxy-3-oxo-6 -heptenoic acid, methyl ester (235 mg, 0.54 mmol) in THF (8 ml) was treated with triethylborane (1.0 M in THF, 1.13 ml, 1.13 mmol). Twenty milliliters of air was bubbled through the solution and the mixture was stirred at room temperature for 25 minutes. The solution was cooled to −78° C. and treated with NaBH$_4$ (20.7 mg, 0.55 mmol) followed by dropwise addition of dry methanol (1.25 ml). After stirring at −78° C. for 1.5 hours, the mixture was quenched with 30% H$_2$O$_2$ (3.5 ml) in H$_2$O (8 ml). The mixture was kept at −78° C. for 15 minutes, then warmed to room temperature and stirred for 30 minutes. The solution was poured into 50% saturated NaHCO$_3$ and extracted with Et$_2$O (3×). The combined Et$_2$O extracts were washed with H$_2$O, saturated NaHCO$_3$ and brine, then dried (Na$_2$SO$_4$), filtered and stripped. Purification of the resulting oil (Flash, Merck SiO$_2$, 70% EtOAc/30% hexane) gave (3R*, 5S*, 6E)-7-[4-(4 -fluorophenyl)-2-methyl-6-phenyl-3-pyridinyl]-3,5 -dihydroxy-6-heptenoic acid, methyl ester (188 mg, 80%) as a colorless oily foam.

TLC: R$_f$ 0.17 (60% EtOAc/40% hexane)

H. (3R*, 5S*, 6E)-7-[4-(4-Fluorophenyl))-2 -methyl-6-phenyl-3-pyridinyl]-3,5-dihydroxy- 6-heptenoic acid, monolithium salt A solution of (3R*, 5S*, 6E)-7-[4-(4-fluorophenyl)-2-methyl-6-phenyl-3-pyridinyl]-3,5-dihydroxy- 6-heptenoic acid, methyl ester (186 mg, 0.47 mmol) in dioxane (3.0 ml) and H$_2$O (3.0 ml) was treated with 1N LiOH (0.51 ml) at room temperature. After 25 minutes, the solvent was evaporated and the residue was chromatographed on HP-20 (25 mm× 90 mm column) eluting in succession with H$_2$O (150 ml), 25% CH$_3$CN in H$_2$O (100 ml), and 50% CH$_3$CN in H$_2$O (200 ml). The desired fractions were pooled and evaporated and the residue was taken up in H$_2$O and lyophilized to give (3R*, 5S*, 6E)-7-[4-(4 -Fluorophenyl)-2-methyl-6-phenyl-3-pyridinyl]-3,5 -dihydroxy-6-heptenoic acid, monolithium salt (174 mg, 93%) as a white solid.

TLC: R$_f$ 0.29 (8:1:1, CH$_2$Cl$_2$:HOAc:MeOH)

Example 3

(3R*, 5S*, 6E)-7-[2-(4-Fluorophenyl)-4-(1-methylethyl)-6-phenyl-3-pyridinyl]-3,5-dihydroxy- 6-heptenoic acid, monolithium salt A. 3-hydroxy-4-methyl-1-phenyl-1-pentanone Acetophenone (11.433 gm, 95 mmol) was added dropwise over a five minute period to a solution of lithium bis(trimethylsilyl)amide (1.0M in THF, 100 ml, 100 mmol) in THF (50 ml) kept at −78° C. After 30 minutes, isobutyraldehyde (6.87 gm, 95 mmol) was added dropwise and stirring was continued for an additional hour. The mixture was quenched with saturated NH$_4$Cl (100 ml), warmed to room temperature, diluted with H$_2$O and extracted 2× with Et$_2$O. The combined Et$_2$O extracts were washed with brine, dried (Na$_2$SO$_4$), filtered and stripped to yield an oil. The oil was distilled (P= 1.5 mm) and the fraction boiling between 120°–124° C. was chromatographed (flash, Merck SiO$_2$, 15% EtOAc in hexane) to give the desired 3 -hydroxy-4-methyl-1-phenyl-1-pentanone as a colorless liquid (9.13 gm, 50%)

TLC: R$_f$ 0.20 (20% EtOAc in hexane)

B. (E)-4-methyl-1-phenyl-2-penten-1-one

A mixture of 3-hydroxy-4-methyl-1-phenyl- 1-pentanone (8.400 gm, 43.7 mmol) and p-toluenesulfonic acid (820 mg, 4.3 mmol) in benzene (210 ml) was refluxed in a Dean-Stark apparatus for 10 minutes. The solution was cooled, diluted with Et$_2$O, and washed with saturated NaHCO$_3$ and brine. Filtration and removal of the solvent afforded a yellow oil which was subsequently distilled (P= 2.0 mm, 97°–100° C.) to give the (E)-4-methyl-1-phenyl-2-penten-1-one (6.94 gm) as a colorless liquid. $^1$H-NMR analysis showed the distillate to be 78% the desired product and 22% the β, δ-unsaturated isomer. The material was used directly for the next reaction.

TLC: R$_f$ 0.35 (10% EtOAc in hexane)

C. α-(4-fluorobenzoyl)-β-(1-methylethyl)-δ -oxobenzenepentanoic, ethyl ester

A mixture of (E)-4-methyl-1-phenyl-2-penten- 1-one (6.32 gm crude, 4.93 gm pure, 28.3 mmol) and ethyl 4-fluorobenzoyl acetate (5.95 gm, 28.3 mmol) in EtOH (120 ml) was treated with a solution of EtONa (3.3 mmol) in EtOH (10 ml) at room temperature. After stirring 3.5 hours, the solution was treated with 73 mg of MeONa. Stirring was continued for an additional 3 hours. The solution was quenched with saturated NH$_4$Cl (80 ml), diluted with H$_2$O, and extracted 3× with Et$_2$O. The combined Et$_2$O extracts were washed with brine and subsequently dried (Na$_2$SO$_4$), filtered and stripped to give a yellow residue. The residue was purified by flash chromatography (Merck SiO$_2$, 50×260 mm column, 3% acetone in hexane) to give a diastereomeric mixture of the α-(4-fluorobenzoyl)-β -(1-methylethyl)-δ-oxobenzene-pentanoic, ethyl ester as a viscous oil (6.99 gm, 64%).

TLC: R$_f$ 0.04 (5% acetone in hexane)

D. 2-(4-fluorophenyl))-4-(1-methylethyl)- 6-phenyl-3-pyridinecarboxylic acid, ethyl ester A mixture of α-(4-fluorobenzoyl)-β-(1 -methylethyl)-δ-oxobenzenepentanoic, ethyl ester (6.967 gm, 18.12 mmol) and hydroxylamine hydrochloride (3.778 gm, 54.4 mmol) in glacial HOAc (82 ml) was refluxed under argon for 2 hours. The cooled solution was added to an ice cold mixture of concentrated NH$_4$OH (120 ml) in H$_2$O (200 ml). The resulting mixture was extracted twice with Et$_2$O and the combined Et$_2$O extracts were washed with brine, dried (Na$_2$SO$_4$), filtered and stripped to yield a orange-red oil. Chromatographic purification of the oil (flash, Merck SiO$_2$, 3% EtOAc in hexane) gave 2-(4-fluorophenyl)- 4-(1-methylethyl)-6-phenyl-3-pyridinecarboxylic acid, ethyl ester as a colorless viscous oil (3.482 gm, 53%)

TLC: R$_f$ 0.39 (10% EtOAc in hexane)

E. 2-(4-fluorophenyl)-4-(1-methylethyl)-6-phenyl-3-pyridinemethanol

To a slurry of LiAlH$_4$ (1.457 gm, 38.4 mmol) in dry THF at 0° C. was added a solution of 2-(4 -fluorophenyl)-4-(1-methylethyl)-6-phenyl-3 -pyridinecarboxylic acid, ethyl ester (3.37 gm, 9.27 mmol) in THF (7 ml). After 4.5 hours, the flask was charged with an additional 0.88 gm LiAlH$_4$ and stirring was continued for 2 more hours. The mixture was quenched with H$_2$O and diluted with H$_2$O and EtOAc. The phases were shaken and separated, and the aqueous layer was extracted again with EtOAc and Et$_2$O. The pooled organic layers were washed with H$_2$O and brine, then dried (Na$_2$SO$_4$), filtered and stripped to give a white solid. The solid was recrystallized from hot EtOAc/hexane to afford 2-(4-fluorophenyl)-4 -(1-methylethyl)-6-phenyl-3-pyridinemethanol as white crystals. The mother liquor was stripped and recrystallized again from hot EtOAc/hexane to give a total of 2.684 gm (90%) desired product.

m.p. 172.5°–173.5° C. TLC: R$_f$ 0.17 (20% EtOAc in hexane)

F. 2-(4-fluorophenyl)-4-(1-methylethyl)- 6-phenyl-3-pyridinecarboxaldehyde t-Butanol (175 mg, 2.35 mmol) was added to a stirring solution of Dess-Martin periodinane (1.005 gm, 2.37 mmol) in dry CH$_3$CN (15 ml). After 15 minutes, a solution of 2-(4-fluorophenyl)-4 -(1-methylethyl)-6-phenyl-3-pyridinemethanol (582 mg, 1.81 mmol) in CH$_3$CN (9 ml) and CH$_2$Cl$_2$ (3 ml) was added to the mixture and stirring was continued for 40 minutes. The mixture was diluted with Et$_2$O and quenched with 1N NaOH (25 ml). After 25 minutes of rapid mixing, the biphasic mixture was separated and the aqueous layer was extracted with Et$_2$O. The combined organic layers were washed in succession with 1N NaOH, H$_2$O, and brine, then dried (Na$_2$SO$_4$), filtered and stripped to yield a solid residue. The residue was chromatographed (Merck SiO$_2$, 30% hexane in CH$_2$Cl$_2$) to give 2-(4-fluorophenyl)-4-(1-methylethyl)-6-phenyl-3 -pyridinecarboxaldehyde as a white solid (532 mg, 92%). An analytical sample was obtained by recrystallization from a minimum amount of hot hexane.

m.p. 115.5°–117.0° C. TLC: R$_f$ 0.43 (20% EtOAc in hexane)

G. (E)-3-[2-(4-fluorophenyl)-4-(1-methylethyl)- 6-phenyl-3-pyridinyl]-2-propenal n-BuLi (1.6M in hexane, 554 ul, 0.83 mmol) was added to a solution of cis-1-ethoxy-2-(tri-n-butylstannyl)ethylene (333 mg, 0.92 mmol) in dry THF (4 ml) at −78° C. The mixture was stirred at −78° C. for one hour, then cooled to −100° C. (liquid N$_2$/MeOH) and treated with a solution of 2-(4-fluorophenyl)- 4-(1-methylethyl)-6-phenyl-3-pyridinecarboxaldehyde (221 mg, 0.69 mmol) in THF (2 ml). One hour after the addition, the temperature was raised to −78° C. and the solution was stirred for an additional one hour. TLC analysis indicated that the reaction was incomplete so an additional amount of the vinyl anion reagent (generated from 317 mg vinyl tin reagent, 370 ul of 1.6M n-BuLi and 4 ml THF) was added via canula at −78° C. the resulting solution stirred an additional 45 minutes. The mixture was warmed to 0° C., stirred for 15 minutes, then quenched with H$_2$O (6 ml) and 10% HCl (6 ml). After one hour of vigorous mixing, the solution was made basic with 10% NaOH (12 ml) and extracted twice with Et$_2$O. The combined Et$_2$O layers were washed with H$_2$O and brine, dried (Na$_2$SO$_4$), filtered and stripped to yield a yellow oil. Chromatographic purification (flash, Merck SiO$_2$, 40% hexane in CH$_2$Cl$_2$ followed by straight CH$_2$Cl$_2$ afforded (E)-3-[2-(4-fluorophenyl)-4-(1-methylethyl)- 6-phenyl-3-pyridinyl] -2-propenal (141 mg, 59%) as a light yellow foam.

TLC: R$_f$ 0.24 (20% EtOAc in hexane)

H. (E)-7-[2-(4-fluorophenyl)-4-(1-methylethyl)- 6-phenyl-3-pyridinyl]-5-hydroxy- 3-oxo-6-heptenoic acid, methyl ester Methyl acetoacetate (160 mg, 1.38 mmol) was dropwise to a slurry of NaH (60% in mineral oil, 55.1 mg, 1.38 mmol) in dry THF (3.5 ml) at 0° C. After 15 minutes, n-BuLi (1.5M in hexane, 830 ul, 1.25 mmol) was added and the mixture was stirred an additional 15 minutes. The bright yellow solution was cooled to −78° C. and treated with a solution of (E)-3-[2-(4-fluorophenyl)-4-(1-methylethyl)- 6-phenyl-3-pyridinyl]-2-propenal (317 mg, 0.92 mmol) in THF (2 ml). Stirring continued for 20 minutes, after which time the reaction was warmed to 0° C. and stirred for an additional 20 minutes. The yellow-orange solution was then added to a biphasic mixture of 1N HCl (3 ml), H$_2$O (15 ml), and Et$_2$O (30 ml). The aqueous layer was made slightly basic with saturated NaHCO$_3$ and the phases were separated. The aqueous layer was diluted with saturated NH$_4$Cl and was extracted with Et$_2$O once again. The combined organic layers were washed with brine and dried (Na$_2$SO$_4$). Filtration and removal of the solvent afforded an oil which was chromatographed (flash, Merck SiO$_2$, 35% EtOAc in hexane) to give (E)-7-[2-(4-fluorophenyl)- 4-(1-methylethyl)-6-phenyl-3-pyridinyl]-5 -hydroxy-3-oxo-6-heptenoic acid, methyl ester as an oily solid (187 mg, 44%).

TLC: R$_f$ 0.21 (40% EtOAc in hexane)

I. (3R*, 5S*, 6E)-7-[2-(4-fluorophenyl)- 4-(1-methylethyl)-6-phenyl-3 -pyridinyl]-3,5-dihydroxy-6-heptenoic acid, methyl ester A solution of (E)-7-[2-(4-fluorophenyl)- 4-(1-methylethyl)-6-phenyl-3-pyridinyl]-5 -hydroxy-3-oxo-6-heptenoic acid, methyl ester (182 mg, 0.39 mmol) in THF (5.5 ml) was treated with triethylborane (1.0N in THF, 830 ul, 0.83 mmol). Twenty milliliters of air was bubbled through the solution and the mixture was stirred at room temperature for 30 minutes. The solution was cooled to −78° C. and treated with NaBH$_4$ (15.0 mg, 0.40 mmol) followed by dropwise addition of dry methanol (0.9 ml). After stirring at −78° C. for 1.75 hours, the mixture was quenched with 30% H$_2$O$_2$ (2.8 ml) in H$_2$O (6 ml). The mixture was kept at −78° C. for 15 minutes, then warmed to room temperature and stirred for 45 minutes. The solution was poured into 50% saturated NaHCO$_3$ and extracted with Et$_2$O (2×). The combined Et$_2$O extracts were washed with saturated NaHCO$_3$, H$_2$O, and brine, then dried (Na$_2$ SO$_4$), filtered and stripped. Purification of the resulting oil (flash, Merck SiO$_2$, 50% EtOAc in hexane) gave (3R*, 5S*, 6E)-7-[2-(4-fluorophenyl)-4-(1-methylethyl)- 6-phenyl-3-pyridinyl] -3,5-dihydroxy-6 -heptenoic acid, methyl ester (157 mg, 86%) as a colorless oily foam.

TLC: R$_f$ 0.27 (60% EtOAc/40% hexane)

J. (3R*, 5S*, 6E)-7-[2-(4-Fluorophenyl)-4-(1 -methylethyl)-6-phenyl-3-pyridinyl] -3,5 -dihydroxy-6-heptenoic acid, monolithium salt A solution of (3R*, 5S*, 6E)-7-[2-(4-fluorophenyl)- 4-(1-methylethyl)-6-phenyl-3-pyridinyl] -3,5-dihydroxy-6-heptenoic acid, methyl ester (152 mg, 0.33 mmol) in dioxane (3 ml) and H$_2$O (3 ml) was treated with 1N LiOH (360 ul) at room temperature. After 30 minutes, the solvent was evaporated and the residue was chromatographed on HP-20 eluting in succession with H$_2$O (150 ml), 25% CH$_3$CN in H$_2$O (100 ml), and 50% CH$_3$CN in H$_2$O (200 ml). The desired fractions were pooled and evaporated and the residue was taken up in H$_2$O and lyophilized to give (3R*, 5S*, 6E)-7- [2-(4-Fluorophenyl)-4-(1-methylethyl)- 6-phenyl-3-pyridinyl]-3,5-dihydroxy- 6-heptenoic acid, monolithium salt (147 mg, 94%) as a white solid.

TLC: R$_f$ 0.22 (20:1:1, CH$_2$Cl$_2$:HOAc:MeOH)

Example 4

(S)-4-[ [ [4-(4-Fluorophenyl)-2-(1-methylethyl)-6 -phenyl-3-pyridinyl] ethynyl] hydroxyphosphinyl] -3 -hydroxybutanoic acid, dilithium salt A. 3-(2,2-dibromoethenyl)-4-(4-fluorophenyl)- 2-(1-methylethyl)-6-phenylpyridine A solution of carbon tetrabromide (2.204 gm, 6.65 mmol) in CH$_2$Cl$_2$ (8 ml) was added over a 12 minute period to a cold (−12° C.) solution of 4-(4-fluorophenyl)-2-(1-methylethyl)-6-phenyl- 3-pyridinecarboxaldehyde (1.415 gm, 4.43 mmol) (the preparation of which is described in Example 1) and triphenylphosphine (3.488 gm, 13.3 mmol) in $CH_2Cl_2$ (25 ml). After the addition was complete, the cooling bath was removed and the mixture was stirred for 20 minutes. The solution was quenched with saturated $NaHCO_3$ and extracted 3× with $CH_2Cl_2$. The combined organic layers were washed with saturated $NaHCO_3$, dried ($Na_2SO_4$), filtered and stripped to give a yellow oil. The oil was chromatographed (flash, Merck $SiO_2$, 40% $CH_2Cl_2$ in hexane) to give 3-(2,2-dibromoethenyl)-4-(4 -fluorophenyl)-2-(1-methylethyl)-6-phenylpyridine as a colorless foam (2.152 gm, 100%).

TLC: $R_f$ 0.53 (20% EtOAc in hexane)

B. 3-ethynyl-4-(4-fluorophenyl)-2-(1 -methylethyl)-6-phenylpyridine

A solution of 3-(2,2-dibromoethenyl)-4 -(4-fluorophenyl)-2-(1-methylethyl)-6-phenylpyridine (2.105 gm, 4.43 mmol) in dry THF (23 ml) was cooled to −78° C. and treated with n-BuLi (1.5M in hexane, 5.95 ml, 8.93 mmol) over a 4 minute period. After stirring at −78° C. for 1.25 hours, the deep purple solution was quenched with saturated $NH_4Cl$, warmed to room temperature, diluted with $H_2O$, and extracted 2× with $Et_2O$. The combined $Et_2O$ extracts were washed with brine, dried ($Na_2SO_4$), filtered and stripped to give a yellow solid. The solid was recrystallized from a minimum amount of hot hexane to afford analytically 3-ethynyl-4-(4-fluorophenyl)- 2-(1-methylethyl)-6-phenylpyridine as white needles. The mother liquor was stripped and recrystallized again from hot hexane to give additional product (total yield 1.199 gm, 86%)

TLC: $R_f$ 0.31 (20% $CH_2Cl_2$ in hexane)

C. (S)-3-[[(1,1-dimethylethyl)diphenylsilyl] oxy]-4-[[[4-(4-fluorophenyl)-2 -(1-methylethyl)-6-phenyl-3-pyridinyl] ethynyl]methoxyphosphinyl]butanoic acid, methyl ester (S)-4-(Hydroxymethoxyphosphinyl)-3 -[[(1,1-dimethylethyl)diphenylsilyl]oxy]butanoic acid, methyl ester, dicyclohexylamine (1:1) salt (4.501 gm, 7.123 mmol) was partitioned between EtOAc and 5% $KHSO_4$. The EtOAc layer was washed 3× with 5% $KHSO_4$, then with brine, then dried ($Na_2SO_4$), filtered and stripped to give a colorless oil (phosphinic acid monomethyl ester). The oil was dissolved in dry $CH_2Cl_2$ (15 ml) and treated with N,N-diethyltrimethylsilylamine (2.70 ml, 2.07 gm, 14.25 mmol). After stirring at room temperature for one hour, the solvent was removed in vacuo and the residue was azeotroped with dry benzene (20 ml). The residue was re-dissolved in dry $CH_2Cl_2$ (15 ml), cooled to −12° C. and treated with 2 drops DMF and oxalyl chloride (700 ul, 1.018 gm, 8.02 mmol). After 15 minutes, the solution was warmed to room temperature and stirred for an additional 45 minutes. The solvent was stripped and the yellow residue (phosphinylchloridate) was azeotroped with benzene (20 ml) and dried in vacuo (oil pump) for 30 minutes.

Meanwhile, a solution of acetylene 3 (1.321 gm, 4.19 mmol) in THF (10 ml) at −78° C. was treated with n-BuLi (1.5M in hexane, 2.8 ml, 4.2 mmol) and the resulting deep green mixture was stirred for 30 minutes. The acetylenic anion solution was added dropwise via canula over a 20 minute period to a −78° C. solution of the phosphinylchloridate in THF (9 ml). The resulting yellow-brown mixture was stirred at −78° C. for 40 minutes, then quenched with 50% saturated $NH_4Cl$. The solution was warmed to room temperature, diluted with $H_2O$, and poured into saturated $NaHCO_3$. The aqueous phase was extracted 3× with $Et_2O$. The combined $Et_2O$ layers were washed with brine, dried ($Na_2SO_4$), filtered and stripped. The residue was chromatographed (flash, Merck $SiO_2$, 30% EtOAc in hexane) to afford (S)-3-[ [ (1,1-dimethylethyl)diphenylsilyl] oxy] -4-[ [ [ 4-(4-fluorophenyl)-2-(1-methylethyl)-6 -phenyl-3-pyridinyl] ethynyl]methoxyphosphinyl] butanoic acid, methyl ester as a colorless foam (2.316 gm, 74%).

TLC: $R_f$ 0.30 (40% EtOAc in hexane)

D. (S)-4-[[[4-(4-fluorophenyl)-2-(1-methylethyl)- 6-phenyl-3-pyridinyl]-ethynyl] methoxy-phosphinyl]-3-hydroxybutanoic acid, methyl ester A mixture of (S)-3-[[(1,1-dimethylethyl)diphenylsilyl] oxy]-4-[[[4-(4-fluorophenyl)-2-(1 -methylethyl)-6-phenyl-3-pyridinyl]ethynyl]methoxyphosphinyl] butanoic acid, methyl ester (800 mg, 1.07 mmol), tetra-n-butylammonium fluoride (1.0M in THF, 3.21 ml, 3.21 mmol), and HOAc (325 mg, 5.41 mmol) in THF (12 ml) was stirred at room temperature for 17 hours. The solution was cooled to 0° C., diluted with $H_2O$, and extracted twice with EtOAc. The pooled EtOAc layers were washed with saturated $NaHCO_3$ and brine. The organic layer was then washed twice 5% $KHSO_4$, then with $H_2O$ and brine. Drying ($Na_2SO_4$), followed by filtration and removal of the solvent afforded a yellow oil. The oil was dissolved in $Et_2O$ (10 ml) and treated with excess diazomethane for 20 minutes. The excess diazomethane was destroyed by the addition of HOAc and the solvent was removed in vacuo. The residue was chromatographed (flash, Merck $SiO_2$, 50× 70 mm column 35% acetone in hexane (650 ml) followed by 1:1 acetone:hexane) to afford (S)-4-[[[4-(4-fluorophenyl)-2-(1-methylethyl)-6-phenyl-3-pyridinyl]-ethynyl]methoxyphosphinyl] -3-hydroxybutanoic acid, methyl ester (463 mg, 85%) as a colorless foam.

TLC: $R_f$ 0.38 (1:1 acetone:hexane)

E. (S)-4-[ [ [ 4-(4-Fluorophenyl)-2-(1-methylethyl)- 6-phenyl-3-pyridinyl]ethynyl] hydroxyphosphinyl] -3-hydroxybutanoic acid, dilithium salt A solution of (S)-4-[[[4-(4-fluorophenyl)-2 -(1-methylethyl)-6-phenyl-3-pyridinyl]-ethynyl]methoxyphosphinyl] -3-hydroxybutanoic acid, methyl ester (446 mg, 0.875 mmol) in dioxane (7 ml) was treated with 1N LiOH (2.63 ml, 2.63 mmol) at room temperature and the mixture was subsequently heated at 55° C. under argon for one hour. The solvent was evaporated and the residue was chromatographed on HP-20 eluting in succession with $H_2O$ (200 ml), 25% MeOH in $H_2O$ (100 ml), 50% MeOH in $H_2O$ (200 ml), and 50% $CH_3CN$ in $H_2O$ (100 ml). The desired fractions were pooled and evaporated and the residue was taken up in $H_2O$ and lyophilized to give (S)-4-[[[4-(4 -Fluorophenyl)-2-(1-methylethyl)-6-phenyl-3-pyridinyl] ethynyl] hydroxyphosphinyl] -3-hydroxybutanoic acid, dilithium salt (416 mg, 94%) as a white solid.

TLC: $R_f$ 0.46 (7:2:1,i-PrOH,$NH_4OH$,$H_2O$)

Example 5

(S)-4-[ [ [ 2-(4-Fluorophenyl)-4-(1-methylethyl)-3 -quinolinyl]ethynyl]hydroxyphosphinyl]-3- hydroxybutanoic acid, dilithium salt A. 1-(2-aminophenyl)-2-methyl-1-propanone A solution of anthranilonitrile (8.507 gm, 72 mmol) in dry $Et_2O$ (20 ml) was added to i-propylmagnesium chloride (2.0M in $Et_2O$, 100 ml, 200 mmol) in dry $Et_2O$ (30 ml) at 0° C. over a 15 minute period. After the addition was complete, the mixture was warmed to room temperature and stirred for 4.5 hours. The solution was cooled to 0° C., quenched with 10% HCl (150 ml), then stirred for 25 minutes. The aqueous layer was made basic with solid NaOH (25 gm) and then extracted with Et$_2$O (3×). The combined Et$_2$O extracts were washed with brine, then dried (Na$_2$SO$_4$), filtered and stripped to give a yellow oil. Flash Chromatography of the oil (Merck SiO$_2$, 15% EtOAc in hexane) afforded 1-(2-aminophenyl)-2-methyl-1-propanone (10.916 gm, 93%) as a golden yellow oil.

TLC: R$_f$ 0.32 (20% EtOAc in hexane)

B. 2-(4-fluorophenyl)-4-(1-methylethyl)-3-quinoline-carboxylic acid, ethyl ester A mixture of 1-(2-aminophenyl)-2-methyl-1-propanone (5.526 gm, 33.9 mmol), ethyl p-fluorobenzoylacetate (7.12 gm, 33.9 mmol) and concentrated H$_2$SO$_4$ (0.34 ml) in glacial HOAc (34 ml) was refluxed for 22 hours. The reaction mixture was cooled to room temperature and poured into an ice-cold solution of concentrated NH$_4$OH (48 ml) in H$_2$O (120 ml). The resulting mixture was extracted twice with Et$_2$O and the combined Et$_2$O layers were washed with H$_2$O and brine, then dried (Na$_2$SO$_4$), filtered and stripped to yield a cloudy brown oil. Flash chromatography (Merck SiO$_2$, 10% EtOAc in hexane) afforded impure 2-(4-fluorophenyl)-4-(1-methylethyl)-3-quinoline-carboxylic acid, ethyl ester as an oil. Most of the volatile impurities were distilled off under an oil pump vacuum (bath temp. 85° C.), leaving a yellow oil (5.096 gm) which was 77% by weight 2-(4-fluorophenyl)-4-(1-methylethyl)-3-quinolinecarboxylic acid, ethyl ester (34% effective yield).

TLC: R$_f$ 0.36 (20% EtOAc in hexane)

C. 2-(4-fluorophenyl)-4-(1-methylethyl)-3-quinolinemethanol

A solution of ester 2-(4-fluorophenyl)-4-(1-methylethyl)-3-quinoline-carboxylic acid, ethyl ester (5.00 gm crude, 3.85 gm pure, 114 mmol) in dry Et$_2$O (5 ml) was added to a slurry of LiAlH$_4$ (1.41 gm, 37.1 mmol) in Et$_2$O (70 ml) at 0° C. After 6.5 hours, the solution was quenched and diluted with H$_2$O and the aqueous layer was extracted with Et$_2$O (3×). The combined Et$_2$O extracts were washed with brine, then dried (Na$_2$SO$_4$), filtered and stripped to yield a semi-solid yellow residue. The residue was crystallized from hot hexane/EtOAc to give 2-(4-fluorophenyl)-4-(1-methylethyl)-3-quinolinemethanol as white needles. The mother liquor was stripped, dissolved in CH$_2$Cl$_2$ (50 ml) and treated with N-chlorosuccinamide (700 mg). After 15 minutes, the solution was concentrated, diluted with Et$_2$O and washed first with saturated NaHCO$_3$, then with a solution of Na$_2$SO$_3$ in saturated NaHCO$_3$. The solvent was removed and the residue was chromatographed (flash, Merck SiO$_2$, 30% EtOAc in hexane) to give additional 2-(4-fluorophenyl)-4-(1-methylethyl)-3-quinoline-methanol as an impure orange semi-solid. Recrystallization from hot hexane/EtOAc gave the desired product as white needles. The pooled solids were recrystallized once again to give analytically pure 2-(4-fluorophenyl)-4-(1-methylethyl)-3-quinolinemethanol (1.17 gm, 35%).

m.p. 208°–210° C. TLC: R$_f$ 0.42 (40% EtOAc in hexane)

D. 2-(4-fluorophenyl)-4-(1-methylethyl)-3-quinolinecarboxaldehyde

Dess-Martin periodinane (1.002 gm, 2.36 mmol) was dissolved in dry CH$_2$Cl$_2$ (11 ml), treated with t-butanol (175 mg, 2.36 mmol) and the resulting mixture was stirred at room temperature for 15 minutes. A slurry of 2-(4-fluorophenyl)-4-(1-methylethyl)-3-quinolinemethanol (505 mg, 1.71 mmol) in CH$_2$Cl$_2$ (8 ml) was then added. After 1.5 hours, the solution was diluted with Et$_2$O and 1N NaOH (25 ml), then stirred an additional 10 minutes. The aqueous layer was separated and extracted once with Et$_2$O. The combined Et$_2$O layers were washed with saturated NaHCO$_3$ and brine, then dried (Na$_2$SO$_4$), filtered and stripped to give an oil. Chromatographic purification (Flash, Merck SiO$_2$, 20% EtOAc in hexane) afforded aldehyde 2-(4-fluorophenyl)-4-(1-methylethyl)-3-quinolinecarboxaldehyde (430 mg, 86%) as a colorless oil which solidified in the freezer.

TLC: R$_f$ 0.40 (20% EtOAc in hexane)

E. 3-(2,2-dibromoethenyl)-2-(4-fluorophenyl)-4-(1-methylethyl)quinoline

A solution of carbon tetrabromide (2.958 gm, 8.92 mmol) in CH$_2$Cl$_2$ (10 ml) was added over a 15 minute period to a cold (−10° C.) solution of 2-(4-fluorophenyl)-4-(1-methylethyl)-3-quinolinecarboxaldehyde (1.744 gm, 5.95 mmol) (the preparation of which is described in Example 2) and triphenylphosphine (4.680 gm, 17.84 mmol) in CH$_2$Cl$_2$ (34 ml). After the addition was complete, the mixture was stirred for 20 minutes then quenched with saturated NaHCO$_3$ and extracted 3× with CH$_2$Cl$_2$. The combined organic layers were washed with brine, dried (Na$_2$SO$_4$), filtered and stripped to give a yellow-orange oil. The oil was chromatographed (flash, Merck SiO$_2$, 30% CH$_2$Cl$_2$ in hexane followed by 1:1 CH$_2$Cl$_2$ in hexane followed by straight CH$_2$Cl$_2$) to give 3-(2,2-dibromoethenyl)-2-(4-fluorophenyl)-4-(1-methylethyl)quinoline as a colorless foam (2.572 gm, 96%)

TLC: R$_f$ 0.37 (20% EtOAc in hexane)

F. 3-ethynyl-2-(4-fluorophenyl)-4-(1-methylethyl)quinoline

A solution of 3-(2,2-dibromoethenyl)-2-(4-fluorophenyl)-4-(1-methylethyl)quinoline (2.563 gm, 5.71 mmol) in dry THF (30 ml) was cooled to −78° C. and treated with n-BuLi (1.5M in hexane, 8.0 ml, 12 mmol) over a 5 minute period. After stirring at −78° C. for 1.25 hours, the brown solution was quenched with saturated NH$_4$Cl, warmed to room temperature, diluted with H$_2$O, and extracted 2× with Et$_2$O. The combined Et$_2$O extracts were washed with brine, dried (Na$_2$SO$_4$), filtered and stripped to give a yellow solid. The solid was recrystallized from hot hexane to afford analytically pure 3-ethynyl-2-(4-fluorophenyl)-4-(1-methylethyl)quinoline as off-white crystals (1.205 gm, 73%).

TLC: R$_f$ 0.44 (20% CH$_2$Cl$_2$ in hexane)

G. (S)-3-[ [ (1,1-dimethylethyl)diphenylsilyl] -oxy] -4-[ [ [2-(4-fluorophenyl)- 4-(1-methylethyl)-3-quinolinyl] ethynyl] methoxyphosphinyl] butanoic acid, methyl ester (S)-4-(Hydroxymethoxyphosphinyl)-3-[ [ (1,1-dimethylethyl)diphenylsilyl] oxy]butanoic acid, methyl ester, dicyclohexylamine (1:1) salt (4.501 gm, 7.123 mmol) (4.390 gm, 6.95 mmol) was partitioned between EtOAc and 5% KHSO$_4$. The EtOAc layer was washed 3× with 5% KHSO$_4$, then with brine, then dried (Na$_2$SO$_4$), filtered and stripped to give a colorless oil (phosphinic acid monomethyl ester). The oil was dissolved in dry CH$_2$Cl$_2$ (12 ml) and treated with N,N-diethyltrimethylsilylamine (2.70 ml, 2.07 gm, 14.25 mmol). After stirring at room temperature for 1.75 hours, the solvent was removed in vacuo and the residue was azeotroped with dry benzene (20 ml). The residue was dissolved in dry CH$_2$Cl$_2$ (12 ml), cooled to −10° C. and treated with 2 drops DMF and oxalyl chloride (670 ul). After 15 minutes, the solution was warmed to room temperature and stirred for an additional 50 minutes. The solvent was then stripped and the yellow residue (phosphinylchloridate) was azeotroped with benzene (20 ml) and dried in vacuo (oil pump) for 30 minutes.

Meanwhile, a solution of 3-ethynyl-2-(4-fluorophenyl)-4-(1-methylethyl)quinoline (1.180 gm, 4.08 mmol) in THF (10 ml) at −78° C. was treated with n-BuLi (1.5M in hexane, 2.75 ml, 4.13 mmol) and the resulting brown mixture was stirred for 30 minutes. The acetylenic anion solution was added dropwise via canula over a 15 minute period to a −78° C. solution of the phosphinylchloridate in THF (9 ml). The resulting yellow-brown mixture was stirred at −78° C. for 45 minutes, then quenched with 50% saturated NH$_4$Cl. The solution was warmed to room temperature, diluted with H$_2$O, and poured into saturated NaHCO$_3$. The aqueous phase was extracted 2× with Et$_2$O. The combined Et$_2$O layers were washed with brine, dried (Na$_2$SO$_4$), filtered and stripped. The cloudy brown residue was chromatographed (flash, Merck SiO$_2$, 40% EtOAc in hexane followed by 1:1 EtOAc:hexane) to afford (S)-3-[[(1,1-dimethylethyl)diphenylsilyl]oxy] -4-[[[2-(4-fluorophenyl)-4-(1-methylethyl)-3 -quinolinyl]ethynyl]methoxyphosphinyl]butanoic acid, methyl ester as a colorless foam (1.898 gm, 64%).

TLC: R$_f$ 0.14 (40% EtOAc in hexane)

H. (S)-4-[[[2-(4-fluorophenyl)-4-(1-methylethyl)- 3-quinolinyl]ethynyl]methoxyphosphinyl] -3-hydroxybutanoic acid, methyl ester A mixture of (S)-3-[ [ (1,1-dimethylethyl)diphenylsilyl] oxy]-4-[ [ [ 2-(4-fluorophenyl)-4-(1 -methylethyl)-3-quinolinyl]ethynyl] methoxyphosphinyl] butanoic acid, methyl ester (729 mg, 0.997 mmol), tetra-n-butylammonium fluoride (1.0M in THF, 3.0 ml, 3.0 mmol), and HOAc (304 mg, 5.06 mmol) in THF (12 ml) was stirred at room temperature for 20 hours. The solution was cooled to 0° C., quenched with 5% KHSO$_4$, and extracted twice with EtOAc. The pooled EtOAc layers were washed twice with 5% KHSO$_4$ and once with brine. The combined aqueous layers were back-extracted 3× with EtOAc and pooled with the initial EtOAc extracts. Drying (Na$_2$SO$_4$), followed by filtration and removal of the solvent afforded a yellow oil. The oil was dissolved in Et$_2$O and EtOAc and treated with excess diazomethane for 30 minutes. The excess diazomethane was destroyed by the addition of HOAc and solvent was removed in vacuo. The residue was chromatographed (flash, Merck SiO$_2$, 40% acetone in hexane) to afford (S)-4-[ [ [ 2-(4-fluorophenyl)-4-(1-methylethyl)- 3-quinolinyl]ethynyl]-methoxyphosphinyl]-3 -hydroxybutanoic acid, methyl ester (349 mg, 72%) as a white oily foam.

TLC: R$_f$ 0.38 (1:1 acetone:hexane)

I. (S)-4-[[[2-(4-Fluorophenyl)-4-(1-methylethyl)- 3-quinolinyl]ethynyl]hydroxyphosphinyl] -3-hydroxybutanoic acid, dilithium salt A solution of (S)-4-[[[2-(4-fluorophenyl)-4 -(1-methylethyl)-3-quinolinyl]ethynyl]-methoxyphosphinyl] -3-hydroxybutanoic acid, methyl ester (333 mg, 0.689 mmol) in dioxane (5.5 ml) was treated with 1N LiOH (2.08 ml, 2.08 mmol) at room temperature and the mixture was subsequently heated at 55° C. under argon for one hour. The solvent was evaporated and the residue was chromatographed on HP-20 eluting in succession with H$_2$O (200 ml), 25% MeOH in H$_2$O (100 ml), and 50% MeOH in H$_2$O (250 ml). The desired fractions were pooled and evaporated and the residue was taken up in H$_2$O and lyophilized to give (S)-4-[[[2-(4-fluorophenyl)-4 -(1-methylethyl)-3-quinolinyl]ethynyl]hydroxyphosphinyl] -3-hydroxybutanoic acid, dilithium salt (314 mg, 92%) as a white solid.

TLC: R$_f$ 0.46 (7:2:1, i-PrOH, NH$_4$OH, H$_2$O)

Example 6

(S)-4-[ [2-[4-[ 4-Fluorophenyl)-2-(1-methylethyl)- 6-phenyl-3-pyridinyl]ethyl]hydroxyphosphinyl]-3 -hydroxybutanoic acid, dilithium salt A. [3S,4(Z)]-3-[[(1,1-dimethylethyl)diphenylsilyl] oxy]-4-[[2-[4-(4-fluorophenyl)- 2-(1-methylethyl)-6-phenyl)-3 -pyridinyl]ethenyl]methoxyphosphinyl] butanoic acid, methyl ester and (S)-3-[[1,1-dimethylethyl)diphenylsilyl] oxy]-4-[[2-[4-(4-fluorophenyl)-2-(1-methylethyl)- 6-phenyl)-3-pyrindinyl]ethyl] methoxyphosphinyl]butanoic acid, methyl ester (S)-3-[[(1,1-dimethylethyl)diphenylsilyl] oxy]-4-[[[4-(4-fluorophenyl)-2-(1-methylethyl)-6 -phenyl)-3-pyridinyl] ethynyl]methoxyphosphinyl]butanoic acid, methyl ester (1.016 gm, 1.36 mmol) (the preparation of which is described in Example 4) was dissolved in MeOH (20 ml) and the mixture was purged with argon. Platinum on carbon (5% pt/C, 316 mg) was then added and the mixture was hydrogenated in a Parr apparatus at 40 psi for 16 hours. The solution was filtered through Celite and the filtrate was stripped and chromatographed (flash, Merck SiO$_2$, 20% acetone in hexane) to give the [3S,4(Z)]-3-[[(1,1-dimethylethyl)diphenylsilyl] oxy]-4-[[2-[4-(4-fluorophenyl)-2-(1 -methylethyl)- 6-phenyl)-3-pyridinyl]ethenyl]methoxyphosphinyl]butanoic acid, methyl ester (795 mg, 78%) as a colorless foam. In addition, the desired (S)-3 -[[1,1-dimethylethyl)diphenylsilyl]oxy]-4 -[[2-[4-(4-fluorophenyl)-2-(1-methylethyl)-6 -phenyl)-3-pyrindinyl]ethyl]methoxyphosphinyl] butanoic acid, methyl ester was also obtained (95 mg, 9%) as a colorless oil.

[3S,4(Z)]-3-[[(1,1-dimethylethyl)diphenylsilyl] oxy]-4-[ [2-[4-(4-fluorophenyl)-2-(1-methylethyl)- 6-phenyl)-3-pyridinyl]ethenyl]methoxyphosphinyl] butanoic acid, methyl ester (781 mg, 1.04 mmol) was dissolved in MeOH, and the solution was treated with 5% Pt/C (386 mg) and hydrogenated at 40 psi in a Parr apparatus for 4 days. Filtration and removal of the solvent afforded a residue which was chromatographed (flash, Merck SiO$_2$, 20% acetone in hexane) to give the desired saturated (S)-3-[[1,1-dimethylethyl)diphenylsilyl]oxy]-4 -[[2-[4-(4-fluorophenyl)-2-(1-methylethyl)-6 -phenyl)-3-pyrindinyl]ethyl]methoxyphosphinyl] butanoic acid, methyl ester (144 mg, 18%) along with unreacted [3S,4(Z)]-3-[[(1,1-dimethylethyl)diphenylsilyl] -oxy]-4-[[2-[4-(4-fluorophenyl)-2 -(1-methylethyl)-6-phenyl)-3-pyridinyl]ethenyl] methoxyphosphinyl]butanoic acid, methyl ester (546 mg). [3S,4(Z)]-3-[[(1,1-dimethylethyl)diphenylsilyl] oxy]-4-[[2-[4-(4-fluorophenyl)-2-(1-methylethyl)- 6-phenyl)-3-pyridinyl]ethenyl]methoxyphosphinyl] butanoic acid, methyl ester:

TLC: R$_f$ 0.16 (20% acetone in hexane)

(S)-3-[[1,1-dimethylethyl)diphenylsilyl]oxy]-4 -[[2-[4-(4-fluorophenyl)-2-(1-methylethyl)-6 -phenyl)-3-pyrindinyl]ethyl]methoxyphosphinyl] butanoic acid, methyl ester:

TLC: R$_f$ 0.09 (20% acetone in hexane)

B. (S)-4-[[2-[4-(4-fluorophenyl)-2 -(1-methylethyl)-6-phenyl-3-pyridinyl] ethyl]methoxyphosphinyl]-3-hydroxybutanoic acid, methyl ester A mixture of (S)-3-[[1,1-dimethylethyl)diphenylsilyl] oxy]-4-[[2-[4-(4-fluorophenyl)-2 -(1-methylethyl)-6-phenyl)-3-pyrindinyl]ethyl] methoxyphosphinyl]butanoic acid, methyl ester (278 mg, 0.37 mmol), tetra-n-butylammonium fluoride (1.0M in THF, 1.1 ml, 1.1 mmol), and HOAc (111 mg, 1.85 mmol) in THF (4 ml) was stirred at room temperature for 18 hours. The solution was quenched with cold H$_2$O and extracted twice with EtOAc. The pooled EtOAc layers were washed with saturated NaHCO$_3$ and brine. Drying (Na$_2$SO$_4$), followed by filtration and removal of the solvent afforded an oil. The oil was chromatographed (flash, Merck SiO$_2$, 50% acetone in hexane followed by 70% acetone in hexane) to afford (S)-4-[[2-[4-(4-fluorophenyl)-2-(1-methylethyl)- 6-phenyl-3-pyridinyl]ethyl]methoxyphosphinyl]-3 -hydroxybutanoic acid, methyl ester (168 mg, 88%) as a colorless foam.

TLC: R$_f$ 0.18 (1:1 acetone:hexane)

C. (S)-4-[[2-[4-[4-Fluorophenyl)-2-(1-methylethyl)-6-phenyl-3-pyridinyl] ethyl]hydroxyphosphinyl]-3-hydroxybutanoic acid, dilithium salt A solution of (S)-4-[[2-[4-(4-fluorophenyl)- 2-(1-methylethyl)-6-phenyl-3-pyridinyl]-ethyl] methoxyphosphinyl] -3-hydroxybutanoic acid, methyl ester (177 mg, 0.345 mmol) of dioxane (3.5 ml) was treated with 1N LiOH (1.05 ml, 1.05 mmol) at room temperature and the mixture was subsequently heated at 57° C. under argon for 1.3 hours. The solvent was evaporated and the residue was chromatographed on HP-20 eluting in succession with $H_2O$ (300 ml), 25% MeOH in $H_2O$ (100 ml), and 50% MeOH in $H_2O$ (250 ml). The desired fractions were pooled and evaporated and the residue was taken up in $H_2O$ and lyophilized to give (S)-4-[[2-[4-[4-Fluorophenyl)- 2-(1-methylethyl)-6-phenyl-3-pyridinyl] ethyl] hydroxyphosphinyl] -3-hydroxybutanoic acid, dilithium salt (156 mg, 85%) as a white solid.

TLC: $R_f$ 0.40 (7:2:1, i-PrOH, $NH_4OH$, $H_2O$)

Example 7

(S,E)-4-[[2-[4-(4-Fluorophenyl)-2-(1-methylethyl)-6-phenyl-3-pyridinyl] ethenyl] hydroxyphosphinyl] -3-hydroxybutanoic acid, dilithium salt A. (E)-4-(4-Fluorophenyl)-3-(2-iodoethenyl)- 2-(1-methylethyl)-6-phenylpyridine A mixture of 3-Ethynyl-4-(4-fluorophenyl)- 2-(1-methylethyl)-6-phenylpyridine (1.500 gm, 4.76 mmol) (The preparation of which is described in example 4) and 14 mg of AIBN in tri-n-butylstannyl hydride ($Bu_3SnH$) (1.90 ml) was rapidly heated to 120° C. After 4 minutes of heating, the mixture was treated with additional $Bu_3SnH$ (0.4 ml) and the temperature of the reaction was raised to 130° C. Approximately 14 mg of AIBN was added to the reaction mixture 0.5, 1.5 and 2.5 hours after heating was initiated. After 4 hours, the mixture was cooled to room temperature, diluted with $Et_2O$ (40 ml) and treated with solid $I_2$ (1.92 gm, 7.56 mmol). The dark reaction mixture was stirred for 1.5 hours, then quenched with 10% $Na_2SO_3$ in saturated $NaHCO_3$. The layers were shaken and separated. The ethereal layer was washed with brine, dried ($Na_2SO_4$), filtered and stripped to yield a yellow oil. Flash chromatography (Merck $SiO_2$, 1% EtOAc in hexane followed by 1.5% EtOAc in hexane afforded (E)-4-(4-Fluorophenyl)-3-(2-iodoethenyl)- 2-(1-methylethyl)-6-phenylpyridine as a solid. Recrystallization of the solid from hot hexane gave 1.438 gm (E)-4-(4-Fluorophenyl)-3-(2 -iodoethenyl)-2-(1-methylethyl)-6-phenylpyridine. An additional 0.19 gm of compound was obtained from the mother liquor to give a total of 1.628 gm (77%) product.

m.p. 111.0°–112.3° C. TLC: $R_f$ 0.28 (2% EtOAC in hexane)

B. (S,E)-3-[[(1,1-Dimethylethyl)diphenylsilyl] oxy]-4-[[2-[4-(4-fluorophenyl)-2 -(1-methylethyl)-6-phenyl-3-pyridinyl] ethenyl]methoxyphosphinyl]butanoic acid, methyl ester (S)-4-(Hydroxymethoxyphosphinyl)-3 -[[(1,1-dimethylethyl)diphenylsilyl]oxy]butanoic acid, methyl ester, dicyclohexylamine (1:1) salt (2.000 gm, 3.17 mmol), the preparation of which is described at the end of this example 7, was partitioned between EtOAc and 5% $KHSO_4$. The EtOAc layer was washed 3× with 5% $KHSO_4$, then with brine, then dried ($Na_2SO_4$), filtered and stripped to give a colorless oil (phosphinic acid monomethyl ester). The oil was dissolved in dry $CH_2Cl_2$ (7 ml) and treated with N,N-diethyltrimethylsilylamine (1.20 ml, 0.92 gm, 6.33 mmol). After stirring at room temperature for one hour, the solvent was removed in vacuo and the residue was azeotroped with dry benzene (10 ml). The residue was dissolved in dry $CH_2Cl_2$ (7 ml), cooled to 10° C. and treated with 1 drop DMF and oxalyl chloride (320 ul). After 15 minutes, the solution was warmed to room temperature and stirred for an additional 50 minutes. The solvent was then stripped and the yellow residue (phosphinylchloridate) was azeotroped with benezene (20 ml) and dried in in vacuo (oil pump) for 30 minutes.

Meanwhile, a solution of (E)-4-(4-Fluorophenyl)- 3-(2-iodoethenyl)-2-(1-methylethyl)-6 -phenylpyridine (827 mg, 1.86 mmol) in THF (2 ml) was added over a 2 minute period to a −78° C. solution of t-butyllithium (1.7M in pentane, 2.20 ml 3.74 mmol) in THF (7 ml). The resulting deep red solution was stirred for 25 minutes then cooled to −100° C. The vinyl anion solution was added over a 30 second period to a −100° C. solution of the phosphinylchloridate in THF (9 ml). The resulting orange mixture was stirred at −100° C. for 5 minutes and at −78° C. for 30 minutes, then quenched with 50% saturated $NH_4Cl$. The solution was warmed to room temperature, diluted with $H_2O$, and poured into saturated $NaHCO_3$. The aqueous phase was extracted 2× with $Et_2O$. The combined $Et_2O$ layers were washed with brine, dried ($Na_2SO_4$), filtered and stripped. The resulting yellow oil was chromatographed (flash, Merck $SiO_2$, 15% acetone in hexane followed by 20% acetone in hexane) to afford (S,E)-3-[[(1,1-Dimethylethyl)diphenylsilyl]oxy] -4-[[2-[4-(4-fluorophenyl)-2-(1-methylethyl)-6 -phenyl-3-pyridinyl]ethenyl] methoxyphosphinyl] butanoic acid, methyl ester as an off-white foam (826 mg, 59%).

TLC: $R_f$ 0.28 (20% acetone in hexane)

C. (S,E)-4-[[2-[4-(4-Fluorophenyl)-2-(1 -methylethyl)-6-phenyl-3-pyridinyl] ethenyl]methoxyphosphinyl]-3-hydroxybutanoic acid, methyl ester A solution of (S,E)-3-[[(1,1-Dimethylethyl)diphenylsilyl] oxy]-4-[[2-[4-(4-fluorophenyl)-2-(1 -methylethyl)-6-phenyl-3-pyridinyl]ethenyl]methoxyphosphinyl] butanoic acid, methyl ester (826 mg, 1.10 mmol) in THF (10 ml) was treated with HOAc (320 ul, 336 mg, 5.6 mmol) and tetra-n-butylammonium fluoride (1.0M in THF, 3.3 ml, 3.3 mmol). After stirring at room temperature for 22 hours, the solution was poured into saturated $NaHCO_3$ and extracted with EtOAc. The EtOAc extract was washed with brine, dried ($Na_2SO_4$), filtered, and stripped to give an oil which was subsequently chromatographed (flash, Merck $SiO_2$, 30% acetone in hexane followed by 50% acetone in hexane). (S,E)-4-[[2-[4-(4 -Fluorophenyl)-2-(1-methylethyl)-6-phenyl-3 -pyridinyl]ethenyl]methoxyphosphinyl]-3-hydroxybutanoic acid, methyl ester (497 mg, 88%) was obtained as a white oily foam.

TLC: $R_f$ 0.40 (1:1 acetone:hexane)

D. (S,E)-4-[[2-[4-(4-Fluorophenyl)-2-(1 -methethyl)-6-phenyl-3-pyridinyl]ethenyl] hydroxyphosphinyl]-3-hydroxybutanoic acid, dilithium salt A solution of (S,E)-4-[[2-[4-(4-Fluorophenyl)- 2-(1-methylethyl)-6-phenyl-3-pyridinyl]ethenyl] methoxyphosphinyl]-3-hydroxybutanoic acid, methyl ester (474 mg, 0.93 mmol) in dioxane (5 ml) was treated with 1N LiOH (3.0 ml, 3.0 mmol) at room temperature and the mixture was subsequently heated at 55° C. under argon for 1.5 hours. The solvent was evaporated and the residue was chromatographed on HP-20 eluting in succession with $H_2O$ (200 ml), 25% MeOH in $H_2O$ (100 ml), and 50% MeOH in $H_2O$ (200 ml). The desired fractions were pooled and evaporated and the residue was taken up in $H_2O$ and lyophilized to give (S,E)-4-[[2-[4-(4-Fluorophenyl)- 2-(1-methethyl)-6-phenyl-3-pyridinyl] ethenyl]hydroxyphosphinyl]-3-hydroxybutanoic acid, dilithium salt (431 mg, 89%) as a white solid.

TLC: $R_f$ 0.48 (7:2:1, i-PrOH, $NH_4OH$, $H_2O$)

(S)-4-(Hydroxymethoxyphosphinyl)-3-[ [ (1,1 -dimethylethyl)diphenylsilyl]oxy]butanoic acid, methyl ester, dicyclohexylamine (1:1) salt (1) (S)-4-Bromo-3-hydroxybutanoic acid, methyl ester (1)(a) [R-(R*,R*)]-2,3,4-trihydroxybutanoic acid, calcium salt, hydrate Ref. Carbohydrate Research 72, pp. 301–304 (1979).

Calcium carbonate (50 g) was added to a solution of D-isoascorbic acid (44.0 g, 250 mmol) in $H_2O$ (625 ml), the suspension cooled to 0° C. (ice bath) and treated portionwise with 30% $H_2O_2$ (100 ml). The mixture was stirred at 30°–40° C. (oil bath) for 30 minutes. Darco (10 g) was added and the black suspension heated on a steam bath until evolution of $O_2$ ceased. The suspension was filtered through Celite, evaporated in vacuo (bath temperature 40° C.). The residue was taken up in $H_2O$ (50 ml), warmed on a steam bath and $CH_3OH$ was added until the solution was turbid. The gummy precipitated solid was collected by filtration and air dried to give 30.836 g (75.2%) of desired calcium salt as a powdery white solid.

TLC: (7:2:1) iPrOH-$NH_4OH$-$H_2O$, Rf= 0.19, PMA.

(1)(b) [ S-(R*,S*)] -2,4-Dibromo-3 -hydroxybutanoic acid, methyl ester

Ref. Bock, K. et al., Acta Scandinavica (B) 37, pp. 341–344 (1983).

Part (1)(a) calcium salt (30 g) was dissolved in 30–32% HBr in acetic acid (210 ml) and stirred at room temperature for 24 hours. Methanol (990 ml) was then added to the brown solution and it was stirred overnight. The mixture was evaporated to an orange oil, taken up in $CH_3OH$ (75 ml), refluxed for 2.0 hours and evaporated. The residue was partitioned between EtOAc (100 ml) and $H_2O$, the organic phase washed with $H_2O$ (2×) and brine then dried over anhydrous $Na_2SO_4$ and evaporated to give 22.83 g (90.5%) of crude dibromide as a light orange oil.

TLC: (1:1) EtOAc-Hex, Rf= 0.69, UV & PMA.

(1)(c) (S)-4-Bromo-3-hydroxybutanoic acid, methyl ester

Ref. the same as for preparation of (1)(b).

An argon-purged solution of the dibromide (20.80 g, 75.4 mmol) and anhydrous NaOAc (21.0 g) in EtOAc (370 ml) and glacial HOAc (37 ml) was treated with 1.30 g of 5% Pd/C and the black suspension stirred under $H_2$ (1 atm) while monitoring $H_2$ uptake. After 2.0 hours $H_2$ uptake was complete, the mixture was filtered through Celite, the filtrate washed with saturated $NaHCO_3$ and brine then dried over anhydrous $MgSO_4$ and evaporated to give crude dibromoester as a brown oil. The crude oil was combined with another batch (starting from 36.77 g of the dibromide) and vacuum distilled to give 25.77 g (61.3%) of desired title bromoester as a clear oil with b.p.= 79°–80° C. (1.0 mm Hg).

TLC: (1:1) EtOAc-Hex, Rf= 0.44, PMA. Anal Calcd for $C_5H_9O_3Br$: C, 30.48; H, 4.60; Br, 40.56 Found: C, 29.76; H, 4.50; Br, 39.86

(2) (S)-4-Bromo-3-[ [ (1,1-dimethylethyl)diphenylsilyl] oxy]butanoic acid, methyl ester A solution of part (1)(c) bromohydrin (4.0 g, 20.4 mmol), imidazole (6.94 g, 5.0 eg.), and 4-dimethylamino pyridine (4-DMAP) (12 mg, 0.005 eg.) in dry DMF (40 ml) was treated with t-butyldiphenylsilyl chloride (5.84 ml, 1.1 eg.) and the homogeneous mixture stirred overnight under argon at room temperature. The mixture was partitioned between 5% $KHSO_4$ and EtOAc, the organic phase washed with $H_2O$ and brine, dried over anhydrous $Na_2SO_4$ and evaporated to give 9.32 g (100%) of crude silyl ether as a clear, viscous oil.

TLC: (3:1) Hex-EtOAc, Rf silyl ether= 0.75, U.V. and PMA.

(3) (S)-4-Iodo-3-[[(1,1-dimethylethyl)diphenylsilyl] oxy] butanoic acid, methyl ester A solution of the crude Part 2 bromide (9.32 g, 201 mole) in methyl ethyl ketone (60 ml, dried over 4 Å sieves) was treated with sodium iodide (15.06 g, 100.5 mole, 5.0 eq.) and the yellow suspension refluxed for 5.0 hours under argon. The mixture was cooled, diluted with EtOAc, filtered, the filtrate washed with dilute $NaHSO_3$ (until colorless) and brine then dried over anhydrous $Na_2SO_4$ and evaporated in vacuo to give 10.17 g of a yellow oil. The crude oil was purified by flash chromatography on silica gel (600 g) eluting with (3:1) Hexane-$CH_2Cl_2$. Product fractions were combined and evaporated to give 7.691 g (74.2%, overall yield for both steps) of desired title iodide as a clear, colorless, viscous oil.

TLC: (3:1) Hex-EtOAc, product. Rf= 0.75, U.V. and PMA. (Note: product iodide co-spots with starting bromide).

(4) (S)-4-Diisopropyloxyphosphinyl)-3 -[ [ (1,1-dimethylethyl)diphenylsilyl] oxy]-butanoic acid, methyl ester The Part (3) iodide (45.1 mmol., 21.70 g) was stirred under high vacuum for 30 minutes. Freshly distilled triisopropyl phosphite (0.451 mol., 93.92 g, 113.37 ml.) was added in one portion and the reaction mixture was stirred under argon and heated in a 155° C. oil bath for 16.5 hours. The mixture was then cooled to room temperature. Excess triisopropyl phosphite and volatile reaction products were removed by short path distillation (10 mm Hg) followed by Kugelrohr distillation (0.50 mm Hg, 100° C., 8 hours). The product was further purified via flash chromatography (95 mm diam. column, 6"/Merck silica gel, 6/3/1 Hexane/acetone/toluene eluent, 2"/min flow rate, 50 ml fractions) to afford 17.68 g (33.96 mmol, 75% yield) of the title isopropylphosphonate as a clear viscous oil.

TLC: Silica gel Rf=0.32 (6:3:1 Hexane/acetone toluene) $^1$HNMR: (270 $MH_z$, $CDCl_3$) δ 7.70-7.65 (m,4H) 7.45-7.35 (m,6H) 4.57-4.44 (m,3H) 3.59 (s,3H) 2.94 and 2.88 (2xd, 1H J=3.7 Hz) 2.65 and 2.60 (2xd, 1H J=7.4 Hz) 2.24-1.87 (Series of m, 2H) 1.19 and 1.12 (2xd, 12H J=6.3 Hz) 1.01 (s, 9H)

(5) (S)-4-(Hydroxymethoxyphosphinyl)-3 -[ [ (1-dimethylethyl)diphenylsilyl] oxy]butanoic acid, methyl ester, dicyclohexylamine (1:1) salt The Part (4) isopropyl phosphonate (30.5 mmol, 10.66 g) was stirred under argon, at room temperature, in 80 ml of dry $CH_2Cl_2$. This solution was treated dropwise (5 min) with bis-trimethylsilyltrifluoroacetamide (BSTFA) (32.8 mmol, 8.44 g, 8.71 ml), followed by dropwise addition (10 min) of trimethylsilylbromide (TMSBr) (51.3 mmol), 7.84 g, 6.75 ml). After stirring at room temperature for 20 hours, the reaction mixture was quenched with 200 ml of 5% aqueous $KHSO_4$ and stirred vigorously for 15 minutes. The aqueous layer was extracted 3 times with ethylacetate. The organic extracts were combined, washed once with brine, dried over $Na_2SO_4$ and concentrated in vacuo. The residue was azeotroped 2 times with 50 ml of toluene. The precipitate which formed was suspended in toluene and filtered. The filtrate was concentrated and the azeotrope/filter process repeated. The resulting filtrate was evaporated in vacuo and then pumped under high vacuum for 5 hours. The resulting viscous clear oil was stirred under argon, at room temperature, in 50 ml of dry pyridine. This solution was treated in one portion with dicyclohexylcarbodiimide (DCC) (22.6 mmol, 4.65 g), followed by addition of methanol (41.0 mmol, 1.31 g, 1.67 ml). After stirring at room temperature for 20 hours, the reaction mixture was filtered through a Celite pad in a sintered glass funnel. The Celite was washed with ethyl acetate and the combined filtrates were evaporated in vacuo. The residue was redissolved in ethyl acetate and washed 2 times with 5% aqueous $KHSO_4$ and once with brine. The organic extract was dried over $Na_2SO_4$, filtered, the filtrate concentrated and azeotroped 2 times with toluene, suspended in toluene and filtered. The resulting filtrate was again concentrated, azeotroped, filtered and the filtrate evaporated in vacuo and place under high vacuum for 6 hours to afford the phosphonate monoester as a clear viscous oil (10.2 g, >100% yield). TLC: silica gel $R_f$=0.50 (7:2:1 nPrOH/NH$_4$OH/H$_2$O). The phosphonate monoester [1.21 g was pumped under high vacuum for 4 hours, affording 1.16 g (2.57 mmol)] was dissolved in 10 ml of dry ethyl ether and treated dropwise with dicyclohexylamine (2.65 mmol, 0.481 g, 0.528 ml). The resulting homogeneous solution sat at room temperature for 7 hours resulting in significant crystal formation. The mixture was stored at −20° C. for 16 hours and then warmed to room temperature and filtered. The crystals were washed with cold, dry ethyl ether and then pumped under high vacuum over $P_2O_5$ for 18 hours. The crystals were subsequently pumped under high vacuum at 45° C. for 4 hours, affording 1.25 g (1.98 mmol, 77% yield) of the title dicyclohexylamine salt as a white powdery solid, m.p. 155°–156° C.

TLC: Silica gel $R_f$=0.57 (20% MeOH/CH$_2$Cl$_2$) $^1$H NMR: (270 MH$_2$, CDCl$_3$) 7.71-7.65 (m, 4H) 7.40-7.32 (m, 6H) 4.02 (m, 1H) 3.52 (s, 3H) 3.28 and 3.22 (m, 1H) 3.11 (d, 3H J=11 Hz) 2.77-2.64 (m, 2H) 2.62-2.56 (m, 1H) 1.92-1.08 (Series of m, 22H) 1.00 (S, 9H) Mass Spec: (FAB) 632 (M&H)$^+$ IR: (KBr) 3466-3457 (broad) 3046, 3016, 2997, 2937, 2858, 2836, 2798, 2721, 2704, 2633, 2533, 2447, 1736, 1449, 1435, 1426, 1379, 1243, 1231, 1191, 1107, 1074, 1061, 1051, 820 CM-1 Anal Calcd for $C_{22}H_{31}O_6PSi \cdot C_{12}H_{23}N$: C,64.63; H,8.61; N,2.22 Found: C, 64.51; H, 8.49; N, 2.18

Example 8

(S)-4-[ [ [ 4-(4-Fluorophenyl)-2-(1-methylethyl)- 3-quinolinyl]ethynyl]hydroxyphosphinyl] - 3-hydroxybutanoic acid, dilithium salt A. 2-Aminophenyl 4-fluorophenyl methanone A dry 500 ml 3-neck flask fitted with a reflux condenser and an addition funnel was charged with Mg turnings (2.80 gm, 0.115 mol) and dry Et$_2$O (35 ml). A solution of 1-bromo- 4-fluorobenzene (18.5 gm, 0.106 mol) in Et$_2$O (20 ml) was added to the addition funnel and approximately 15% of this solution was added to the Mg/Et$_2$O mixture. Once the exothermic reaction had begun (ultrasound was required), the aryl bromide solution was added at such a rate as to maintain a gentle reflux. After the addition was complete, the mixture was refluxed for an additional 30 minutes, then cooled to 0° C. Dropwise addition of a solution of 2-aminobenzonitrile (5.00 gm, 0.042 mol) in dry Et$_2$O (20 ml) over a 10 minute period resulted in the formation of a thick yellow slurry. The resulting mixture was warmed to room temperature and stirred overnight. The solution was then cooled to 0° C. and cautiously quenched with 10% HCl (50 ml). After stirring for 5 minutes, the solution was made basic with 10% NaOH (70 ml) and the aqueous layer was extracted three times with Et$_2$O. The combined Et$_2$O layers were pooled, washed with brine, dried (Na$_2$SO$_4$), filtered and stripped to yield an orange oil. The oil was chromatographed (Flash, Merck SiO$_2$, 25% EtOAc in hexane) to give impure 2-aminophenyl 4-fluorophenyl methanone (~1 gm) and the corresponding impure imine (~5.8 gm, Rf 0.28 in 30% EtOAc in hexane). The imine was stirred with 10% HCl (100 ml) and silica gel (750 mg) for 45 minutes. The mixture was then basicified with NaOH pellets (14 gm) and the aqueous layer was extracted twice with Et$_2$O. The combined Et$_2$O layers were washed with brine, dried (Na$_2$SO$_4$), filtered and stripped to yield a solid. This solid was pooled with impure 2-aminophenyl 4-fluorophenyl methanone from above and recrystallized in hot EtOH/H$_2$O to give analytically pure 2-aminophenyl 4-fluorophenyl methanone as yellow crystals (3.28 gm, 36%).

m.p. 125.2°–127.4° C. TLC: $R_f$ 0.41 (30% EtOAc in hexane)

B. 4-(Fluorophenyl)-2-(1-methylethyl)- 3-quinolinecarboxylic acid, ethyl ester

A mixture of 2-aminophenyl 4-fluorophenyl methanone (3.051 gm, 14 mmol), ethyl isobutrylacetate (2.24 gm, 14 mmol) and concentrated H$_2$SO$_4$ (0.14 ml) in glacial HOAc (14 ml) was refluxed for 4 hours. The reaction mixture was cooled to room temperature and poured into an ice cold solution of concentrated NH$_4$OH (21 ml) in H$_2$O (60 ml). The resulting mixture was extracted twice with Et$_2$O and the combined Et$_2$O extracts were washed with H$_2$O and brine, then dried (Na$_2$SO$_4$), filtered and stripped to yield an orange oil. Flash chromatography of the oil (Merck SiO$_2$, 10% EtOAc in hexane) afforded quinoline 4-(Fluorophenyl)-2- (1-methylethyl)- 3-quinolinecarboxylic acid, ethyl ester (3.212 gm, 68%) as a light yellow oil which slowly solidified overnight under vacuum.

m.p. 65.4°–69.0° C. TLC: $R_f$ 0.46 (20% EtOAc in hexane)

C. 4-(4-Fluorophenyl)-2-(1-methylethyl)- 3-quinolinemethanol

A solution of 4-(Fluorophenyl)-2-(1-methylethyl)- 3-quinolinecarboxylic acid, ethyl ester (3.018 gm, 8.94 mmol) in Et$_2$O (5 ml) was added to a slurry of LiAlH$_4$ (689 mg, 18.0 mmol) in Et$_2$O (22 mol) at 0° C. After 2.5 hours, the solution was quenched and diluted with H$_2$O and the aqueous layer was extracted three times with Et$_2$O. The combined Et$_2$O extracts were washed with brine, dried (Na$_2$SO$_4$), filtered and stripped. The resulting oil was triturated with 30% EtOAc in hexane to obtain a white solid. The solid was collected and the filtrate was concentrated and triturated with hexane to obtain additional solid. The pooled solids were recrystallized from hot hexane/EtOAc to give analytically pure 4-(4-fluorophenyl)-2 -(1-methylethyl)-3-quinolinemethanol as white crystals (1.516 gm). The mother liquor was stripped and recrystallized again from hot hexane/EtOAc, giving a total of 2.039 gm (77%) 4-(4-fluorophenyl)-2 -(1-methylethyl)-3-quinolinemethanol.

m.p. 132.5°–134° C. TLC: $R_f$ 0.22 (20% EtOAc in hexane)

D. 4-(4-fluorophenyl)-2-(1-methylethyl)- 3-quinolinecarboxaldehyde

Dess-Martin periodinane (1.018 gm, 2.40 mmol) was dissolved in dry CH$_2$Cl$_2$ (12 ml), treated with t-butanol (178 mg, 2.40 mmol) and the resulting mixture was stirred at room temperature for 15 minutes. A solution of 4-(4-fluorophenyl)-2 -(1-methylethyl)-3-quinolinemethanol (539 mg, 1.82 mmol) in CH$_2$Cl$_2$ (8 ml) was then added. After 25 minutes, the solution was then diluted with Et$_2$O (40 ml) and 1N NaOH (25 ml), then stirred an additional 5 minutes. The phases were separated and the aqueous layer was extracted with Et$_2$O. The combined organic layers were washed with saturated NaHCO$_3$ and brine, then dried (Na$_2$SO$_4$), filtered and stripped to give a yellow solid. Flash chromatography (Merck SiO$_2$, 40% EtOAc in hexane) gave 4-(4-fluorophenyl)-2-(1-methylethyl)-3 -quinolinecarboxaldehyde (491 mg, 92%) as a white solid. Analytically pure material was obtained by recrystallization from hot hexane.

m.p. 120.4°–122.2° C. TLC: $R_f$ 0.47 (20% EtOAc in hexane)

E. 3-(2,2-Dibromoethenyl)-4-(4-fluorophenyl)- 2-(1-methylethyl)quinoline

A solution of carbon tetrabromide (12.620 gm, 38.0 mmol) in $CH_2Cl_2$ (20 ml) was added over a 10 minute period to a cold (−10° C.) solution of 4-(4-Fluorophenyl)-2-(1-methylethyl)-3-quinolinecarboxaldehyde (7.394 gm, 25.2 mmol) and triphenylphosphine (19.86 gm, 75.7 mmol) in $CH_2Cl_2$ (140 ml). After the addition was complete, the mixture was stirred for 20 minutes then quenched with saturated $NaHCO_3$ and extracted 2× with $CH_2Cl_2$. The combined organic layers were washed with brine, dried ($Na_2SO_4$), filtered and concentrated to 50 ml. The residue was triturated with $Et_2O$ and the precipitated triphenylphosphine oxide was removed by filtration. The filtrate was stripped and the residue was chromatographed (flash, Merck $SiO_2$, 10% EtOAc in hexane) to give 3-(2,2-Dibromoethenyl)-4-(4-fluorophenyl)-2-(1 -methylethyl)quinoline as a light yellow foamy oil (11.556 gm, 102% theory).

TLC: $R_f$ 0.50 (20% EtOAc in hexane)

F. 3-Ethynyl-4-(4-fluorophenyl)-2-(1 -methylethyl)quinoline

A solution of 3-(2,2-Dibromoethenyl)-4-(4 -fluorophenyl)-2-(1-methylethyl)quinoline (25.2 mmol) in dry THF (140 ml) was cooled to −78° C. and treated with n-BuLi (1.6M in hexane, 33 ml, 52.8 mmol) over a 1 minute period. After stirring at −78° C. for one hour, the dark brown solution was quenched with saturated $NH_4Cl$, warmed to room temperature, diluted with $H_2O$, and extracted with $Et_2O$. The $Et_2O$ extract was washed with brine, dried ($Na_2SO_4$), filtered and stripped to give a yellow oil. The oil was boiled in hot hexane and cooled (−15° C.) to afford 3-Ethynyl-4-(4-fluorophenyl)-2 -(1-methylethyl)-quinoline (5.198 gm) as yellow crystals. The mother liquor was stripped and chromatographed (flash, Merck $SiO_2$, 4% EtOAc in hexane) to afford additional product which was recrystallized from hot hexane. A total of 6.793 gm (93%) of 3-Ethynyl-4-(4-fluorophenyl)-2-(1 -methylethyl)quinoline was obtained.

TLC: $R_f$ 0.49 (10% EtOAc in hexane)

G. (S)-3-[ [ (1,1-Dimethylethyl)diphenylsilyl] oxy] -4-[ [ [ 4-(4-fluorophenyl)-2 -(1-methylethyl)-3-quinolinyl] ] ethynyl] methoxyphosphinyl]butanoic acid, methyl ester (S)-4-(Hydroxymethoxyphosphinyl)-3 -[[(1,1-dimethylethyl)diphenylsilyl]oxy]butanoic acid, methyl ester, dicyclohexylamine (1:1) salt (4.501 gm, 7.123 mmol) (4.458 gm, 7.05 mmol) the preparation of which is described at the end of example 7, was partitioned between EtOAc and 5% $KHSO_4$, filtered and stripped to give a colorless oil (phosphinic acid monomethyl ester). The oil was dissolved in dry $CH_2Cl_2$ (15 ml) and treated with N,N-diethyltrimethylsilylamine (2.70 ml, 2.07 gm, 14.25 mmol). After stirring at room temperature for one hour, the solvent was removed in vacuo and the residue was azeotroped with dry benzene (15 ml). The residue was dissolved in dry $CH_2Cl_2$ (15 ml), cooled to −10° C. and treated with 2 drops DMF and oxalyl chloride (677 ul). After 15 minutes, the solution was warmed to room temperature and stirred for an additional 50 minutes. The solvent was then stripped and the yellow residue (phosphinylchloridate) was azeotroped with benzene (15 ml) and dried in vacuo (oil pump) for 30 minutes.

Meanwhile, a solution of 3-Ethynyl-4-(4 -fluorophenyl)-2-(1-methylethyl)quinoline (1.200 gm, 4.15 mmol) in THF (10 ml) at −78° C. was treated with n-BuLi (1.6M in hexane, 2.85 ml, 4.56 mmol) and the resulting clear brown mixture was stirred for 30 minutes. The acetylenic anion solution was added dropwise via canula over a one minute period to a −78° C. solution of the phosphinylchloridate in THF (12 ml). The resulting yellow-brown mixture was stirred at −78° C. for 30 minutes, then quenched with 50% saturated $NH_4Cl$. The solution was warmed to room temperature, diluted with $H_2O$, and poured into saturated $NaHCO_3$. The aqueous phase was extracted 2× with $Et_2O$. The combined $Et_2O$ layers were washed with brine, dried ($Na_2SO_4$), filtered and stripped. The residue was chromatographed (flash, Merck $SiO_2$, 40% EtOAc in hexane followed by 1:1 EtOAc:hexane) to afford (S)-3-[[(1,1 -Dimethylethyl)diphenylsilyl]oxy]-4-[[[4-(4 -fluorophenyl)-2-(1-methylethyl)-3-quinolinyl] ethynyl]methoxyphosphinyl]-butanoic acid, methyl ester as a colorless foam (1.800 gm, 60%).

TLC: $R_f$ 0.24 (40% EtOAc in hexane)

H. (S)-4-[[[4-(4-Fluorophenyl)-2-(1-methylethyl)- 3-quinolinyl]ethynyl]-methoxyphosphinyl] -3-hydroxybutanoic acid, methyl ester A mixture of (S)-3-[[(1,1-Dimethylethyl)diphenylsilyl] oxy]-4-[[[4-(4-fluorophenyl)-2-(1 -methylethyl)-3-quinolinyl]ethynyl]methoxyphosphinyl]butanoic acid, methyl ester (1.041 gm, 1.44 mmol), tetra-n-butylammonium fluoride (1.0M in THF, 5.7 ml, 5.7 mmol), and HOAc (525 mg, 8.73 mmol) in THF (14 ml) was stirred at room temperature for 18 hours. The solution was partitioned between 5% $KHSO_4$ and EtOAc. The layers were shaken and separated and the EtOAc layer was washed again with 5% $KHSO_4$. The pooled aqueous washings were back-extracted twice with EtOAc. The combined EtOAc layers were washed with brine and dried ($Na_2SO_4$). Filtration and removal the solvent afforded an oil. The oil was dissolved in cold (0° C.) 1:1 $Et_2O$:MeOH and treated with excess diazomethane for 30 minutes. The excess diazomethane was destroyed by the addition of HOAc and the solvent was removed in vacuo. The residue was chromatographed (flash, Merck $SiO_2$, 40% acetone in hexane followed by 1:1 actone:hexane) to afford (S)-4-[[[4-(4-Fluorophenyl)- 2-(1-methylethyl)-3-quinolinyl]ethynyl]-methoxyphosphinyl] -3-hydroxybutanoic acid, methyl ester (612 mg, 91%) as an oil.

TLC: $R_f$ 0.38 (1:1 acetone:hexane)

I. (S)-4-[[[4-(4-Fluorophenyl)-2-(1-methylethyl)- 3-quinolinyl]ethynyl]hydroxyphosphinyl] -3-hydroxybutanoic acid, dilithium salt A solution of (S)-4-[[[4-(4-Fluorophenyl)-2 -(1-methylethyl)-3-quinolinyl]ethynyl]-methoxyphosphinyl] -3-hydroxybutanoic acid, methyl ester (285 mg, 0.59 mmol) in dioxane (4.0 ml) was treated with 1N LiOH (2.05 ml, 2.05 mmol) at room temperature and the mixture was subsequently heated at 55° C. under argon for 1.5 hours. The solvent was evaporated and the residue was chromatographed on HP-20 eluting in succession with $H_2O$ (200 ml), 25% MeOH in $H_2O$ (100 ml), and 50% MeOH in $H_2O$ (200 ml). The desired fractions were pooled and evaporated and the residue was taken up in $H_2O$ and lyophilized to give (S)-4-[[[4-(4-Fluorophenyl)- 2-(1-methyl-ethyl)-3-quinolinyl]ethynyl]hydroxyphosphinyl] -3-hydroxybutanoic acid, dilithium salt (243 mg, 84%) as a white solid.

TLC: $R_f$ 0.41 (7:2:1, i-PrOH, $NH_4OH$, $H_2O$)

Example 9

(S)-4-[ [ [ 4-(4-Fluorophenyl)-2-(1-methylethyl)- 3-quinolinyl] ethynyl] hydroxyphosphinyl] -3-hydroxybutanoic acid, N-oxide, dilithium salt A. (S)-4-[[[4-(4-Fluorophenyl)-2-(1-methylethyl)- 3-quinolinyl]ethynyl]-methoxyphosphinyl] -3-hydroxybutanoic acid, methyl ester. 1-oxide A solution of (S)-4-[[[4-(4-Fluorophenyl)-2 -(1-methylethyl)-3-quinolinyl]ethynyl]-methoxyphosphinyl] -3-hydroxybutanoic acid, methyl ester (332 mg, 0.67 mmol) (the preparation of which is described in Example 8) and m-CPBA (80–85%, 585 mg) in dry $CH_2Cl_2$ (18 ml) was stirred at room temperature for 16 hours. Additional m-CPBA (277 mg) was added and stirring was continued for 2 hours. The mixture was diluted with Et$_2$O and washed with 50 ml saturated NaHCO$_3$ containing 2.05 gm Na$_2$SO$_3$. The organic layer was subsequently washed with brine, dried (Na$_2$SO$_4$), filtered and stripped to yield an orange-brown residue. The residue was chromatographed (flash, Merck SiO$_2$, 40% hexane in acetone followed by 30% hexane in acetone) giving (S)-4-[[[4-(4-Fluorophenyl)-2-(1-methylethyl)-3 -quinolinyl]ethynyl]-methoxyphosphinyl]-3-hydroxybutanoic acid, methyl ester. 1-oxide. (226 mg, 68%) as a viscous yellow oil.

TLC: R$_f$ 0.18 (1:1 acetone:hexane)

B. (S)-4-[ [ [4-(4-Fluorophenyl)-2-(1-methylethyl)-3-quinolinyl]ethynyl]hydroxyphosphinyl] -3-hydroxybutanoic acid, N-oxide dilithium salt A solution of (S)-4-[[[4-(4-Fluorophenyl)-2 -(1-methylethyl)-3-quinolinyl]ethynyl]-methoxyphosphinyl] -3-hydroxybutanoic acid, methyl ester. 1-oxide. (220 mg, 0.44 mmol) in dioxane (3.0 ml) was treated with 1N LiOH (1.9 ml, 1.9 mmol) at room temperature and the mixture was subsequently heated at 55° C. under argon for 1 hour. The solvent was evaporated and the residue was chromatographed on HP-20 eluting in succession with H$_2$O (200 ml), 25% MeOH in H$_2$O (100 ml), and 50% MeOH in H$_2$O (200 ml). The desired fractions were pooled and evaporated and the residue was taken up in H$_2$O and lyophilized to give (S)-4-[[[4-(4-Fluorophenyl)-2-(1-methylethyl)- 3-quinolinyl]ethynyl]hydroxyphosphinyl]-3 -hydroxybutanoic acid, N-oxide, dilithium salt (196 mg, 85%) as a dense yellow solid.

TLC: R$_f$ 0.43 (7:2:1, i-PrOH, NH$_4$OH, H$_2$O)

Example 10

[3S,4(E)]-4-[ [2-[2-(4-Fluorophenyl)-4 -(1-methylethyl)-3-quinolinyl]ethenyl]hydroxyphosphinyl] -3-hydroxybutanoic acid, dilithium salt A. (E)-2-(4-Fluorophenyl)-3-(2-iodoethenyl)- 4-(1-methylethyl)quinoline A mixture of 3-Ethynyl-2-(4-fluorophenyl)-4 -(1-methylethyl)-quinoline (1.000 gm, 3.64 mmol) (the preparation of which is described in Example 5) and AIBN (13 mg) in 140 ml of tri-n-butylstannyl hydride was rapidly heated to 110° C. After 5 minutes of heating, the mixture was treated with additional Bu$_3$SnH (0.4 ml) and the temperature of the reaction was raised to 130° C. Approximately 10 mg of AIBN was added to the reaction mixture every 0.5 hours. After 4.5 hours, the mixture was cooled to room temperature, diluted with Et$_2$O (25 ml) and treated with solid I$_2$ (3.08 gm, 12.2 mmol). The dark reaction mixture was stirred for 1 hour, then quenched with 10% Na$_2$SO$_3$ in saturated NaHCO$_3$. The layers were shaken and separated. The ethereal layer was washed with brine, dried (Na$_2$SO$_4$), filtered and stripped to yield a yellow oil which was triturated with cold hexane to give a precipitate. Recrystallization of the solid from hot hexane gave 1.438 gm (E)-2-(4-Fluorophenyl)- 3-(2-iodoethenyl)-4-(1-methylethyl)quinoline (917 mg, 64%) as light yellow crystals.

m.p. 145°–147° C. TLC: R$_f$ 0.15 (6% EtOAC in hexane)

B. (S,E)-3-[ [ (1,1-Dimethylethyl)diphenylsilyl] -4-[ [2-[2-(4-fluorophenyl)-4-(1 -methylethyl)-3-quinolinyl]ethenyl]methoxyphosphinyl]butanoic acid, methyl ester (S)-4-(Hydroxymethoxyphosphinyl)-3 -[[(1,1-dimethylethyl)diphenylsilyl]oxy]butanoic acid, methyl ester, dicyclohexylamine (1:1) salt (4.501 gm, 7.123 mmol) (1.548 gm, 2.45 mmol), the preparation of which is described at the end of example 7, was partitioned between EtOAc and 5% KHSO$_4$. The EtOAc layer was washed 3× with 5% KHSO$_4$, then with brine, then dried (Na$_2$SO$_4$), filtered and stripped to give a colorless oil (phosphinic acid monomethyl ester). The oil was dissolved in dry CH$_2$Cl$_2$ (10 ml) and treated with N,N-diethyltrimethylsilylamine (930 ul, 713 gm, 4.91 mmol). After stirring at room temperature for one hour, the solvent was removed in vacuo and the residue was azeotroped with dry benzene (10 ml). The residue was dissolved in dry CH$_2$Cl$_2$ (10 ml), cooled to −10° C. and treated with 2 drops DMF and oxalyl chloride (235 ul). After 15 minutes, the solution was warmed to room temperature and stirred for an additional 50 minutes. The solvent was then stripped and the yellow residue (phosphinylchloridate) was azeotroped with benzene (20 ml) and dried in vacuo (oil pump) for 30 minutes.

Meanwhile, a solution of (E)-2-(4-Fluorophenyl)- 3-(2-iodoethenyl)-4-(1-methylethyl)quinoline (600 mg, 1.44 mmol) in THF (2 ml) was added over a 2 minute period to a −78° C. solution of t-butyllithium (1.7M in pentane, 1.78 ml, 3.03 mmol) in THF (7 ml). The resulting green-brown solution was stirred for 20 minutes then cooled to −100° C. The vinyl anion solution was added over a 30 second period to a −100° C. solution of the phosphinylchloridate in THF (10 ml). The resulting orange mixture was stirred at −100° C. for 10 minutes and at −78° C. for 20 minutes, then quenched with 50% saturated NH$_4$Cl. The solution was warmed to room temperature, diluted with H$_2$O, poured into saturated NaHCO$_3$. The aqueous phase was extracted 2× with Et$_2$O. The combined Et$_2$O layers were washed with brine, dried (Na$_2$SO$_4$), filtered and stripped. The resulting yellow oil was chromatographed (flash, Merck SiO$_2$, 20% acetone in hexane followed by 30% acetone in hexane) to afford (S,E)-3-[[(1,1-Dimethylethyl)diphenylsilyl] -4-[[2-[2-(4-fluorophenyl)- 4-(1-methylethyl)-3-quinolinyl]ethenyl]methoxyphosphinyl] butanoic acid, methyl ester as a white foam (561 mg, 54%).

TLC: R$_f$ 0.31 (1:2 acetone:hexane)

C. (S,E)-4-[ [2-[2-(4-Fluorophenyl)-4 -(1-methylethyl)-3-quinolinyl]-ethenyl] methoxyphosphinyl]-3-hydroxybutanoic acid, methyl ester A solution of (S,E)-3-[ [ (1,1-Dimethylethyl)diphenylsilyl] -4-[ [ 2-[ 2-(4-fluorophenyl)-4-(1 -methylethyl)-3-quinolinyl]ethenyl]methoxyphosphinyl] butanoic acid, methyl ester (542 mg, 0.749 mmol) in THF (10 ml) was treated with HOAc (215 ul, 226 mg, 3.76 mmol) and tetra-n-butylammonium fluoride (1.0M in THF, 2.25 ml, 2.25 mmol). After stirring at room temperature for 22 hours, the solution was poured into saturated NaHCO$_3$ and extracted with EtOAc. The EtOAc extract was washed with brine, dried (Na$_2$ SO$_4$), filtered and stripped to give an oil which was subsequently chromatographed (flash, Merck, SiO$_2$, 1:1 acetone:hexane followed by 20% hexane in acetone). (S,E)-4-[ [2-[2-(4-Fluorophenyl)-4-(1-methylethyl)- 3-quinolinyl] -ethenyl] methoxyphosphinyl] -3-hydroxybutanoic acid, methyl ester (265 mg, 73%) was obtained as a white foam.

TLC: R$_f$ 0.28 (1:1 acetone:hexane)

D. [3S,4(E)]-4-[[2-[2-(4-Fluorophenyl)-4 -(1-methylethyl)-3-quinolinyl]ethenyl] hydroxyphosphinyl]-3-hydroxybutanoic acid, dilithium salt A solution of (S,E)-4-[[2-[2-(4-Fluorophenyl)- 4-(1-methyl-ethyl)-3-quinolinyl]-ethenyl]methoxyphosphinyl] -3-hydroxybutanoic acid, methyl ester (255 mg, 0.525 mmol) in dioxane (3 ml) was treated with 1N LiOH (1.90 ml, 1.90 mmol) at room temperature and the mixture was subsequently heated at 55° C. under argon for 1.25 hours.

The solvent was evaporated and the residue was chromatographed on HP-20, eluting in succession with H$_2$O (200 ml), 25% MeOH in H$_2$O (100 ml), and 50% MeOH in H$_2$O (200 ml). The desired fractions were pooled and evaporated and the residue was taken up in H$_2$O and lyophilized to give [3S,4(E)]-4-[[2-[2-(4-Fluorophenyl)- 4-(1-methylethyl)-3-quinolinyl]ethenyl] hydroxy-phosphinyl]-3-hydroxybutanoic acid, dilithium salt (232 mg, 89%) as a white solid.

TLC: R$_f$ 0.40 (7:2:1, i-PrOH, NH$_4$OH, H$_2$O).

Example 11

[3S,4(E)]-4-[
[2-[4-(4-Fluorophenyl)-2-(1-methylethyl)-
3-quinolinyl]ethenyl]hydroxy-phosphinyl]
-3-hydroxybutanoic acid, dilithium salt a. (E)-4-(4-Fluorophenyl)-3-(2-iodoethenyl)- 2-(1-methylethyl)quinoline A mixture of 3-Ethynyl-4-(4-fluorophenyl)-2 -(1-methylethyl)quinoline (1.500 gm, 5.18 mmol) (the preparation of which is described in Example 8) and AIBN (15 mg) in tri-n-butylstannyl hydride (2.1 ml) was rapidly heated to 120° C. After 3 minutes of heating, the mixture was treated with additional Bu$_3$SnH (0.6 ml) and the temperature of the reaction was raised to 130° C. Approximately 15 mg of AIBN was added to the reaction mixture of 0.5, 1, and 2 hours after heating was initiated. After 2.5 hours, the mixture was cooled to room temperature, diluted with Et$_2$O (30 ml) and treated with solid I$_2$ (3.86 gm, 15.2 mmol). The dark reaction mixture was stirred for 1 hour, then quenched with 10% Na$_2$SO$_3$ in saturated NaHCO$_3$. The layers were shaken and separated. The ethereal layer was washed with brine, dried (Na$_2$SO$_4$), filtered and stripped to yield a liquid/solid residue. The residue was chromatographed (flash, Merck SiO$_2$, 4% EtOAc in hexane) to give slightly impure (E)-4-(4-Fluorophenyl)- 3-(2-iodoethenyl)-2-(1-methylethyl)quinoline as a solid. Recrystallization of the solid from hot hexane gave (E)-4-(4-Fluorophenyl)- 3-(2-iodoethenyl)-2-(1-methylethyl)quinoline (1.725 gm, 80%) as light yellow crystals.

m.p. 129.4°–131° C. TLC: R$_f$ 0.22 (4% EtOAc in hexane)

B. (S,E)-3-[ [ (1,1-Dimethylethyl)diphenylsilyl] -oxy]-4-[ [2-[4-(4-fluorophenyl)- 2-(1-methylethyl)-3-quinolinyl]ethenyl] methoxyphosphinyl]butanoic acid, methyl ester (S)-4-(Hydroxymethoxyphosphinyl)-3 -[[(1,1-dimethylethyl)diphenylsilyl]oxy]butanoic acid, methyl ester, dicyclohexylamine (1:1) salt (4.501 gm, 7.123 mmol) (3.86 gm, 6.11 mmol) the preparation of which is described at the end of example 7, was partitioned between EtOAc and 5% KHSO$_4$. The EtOAc layer was washed 3× with 5% KHSO$_4$ and then with brine, then dried (Na$_2$SO$_4$), filtered and stripped to give a colorless oil (phosphinic acid monomethyl ester). The oil was dissolved in dry CH$_2$Cl$_2$ (15 ml) and treated with N,N-diethyltrimethylsilylamine (2.32 ml, 1.78 gm, 12.2 mmol). After stirring at room temperature for one hour, the solvent was removed in vacuo and the residue was azeotroped with dry benzene (20 ml). The residue was dissolved in dry CH$_2$Cl$_2$ (15 ml), cooled to −10° C. and treated with 2 drops DMF and oxalyl chloride (590 ul, 858 mg, 6.76 mmol). After 15 minutes, the solution was warmed to room temperature and stirred for an additional 50 minutes. The solvent was then stripped and the yellow residue (phosphinylchloridate) was azeotroped with benzene (20 ml) and dried in vacuo (oil pump) for 30 minutes.

Meanwhile, a solution of (E)-4-(4-Fluorophenyl)- 3-(2-iodoethenyl)-2-(1-methylethyl)quinoline (1.500 mg, 3.59 mmol) in THF (3 ml) was added over a 3 minute period to a −78° C. solution of t-butyllithium (1.7M in pentane, 4.40 ml, 7.48 mmol) in THF (10 ml). The resulting deep green solution was stirred for 20 minutes then cooled to −100° C. The vinyl anion solution was added over a one minute period to a −100° C. solution of the phosphinylchloridate in THF (15 ml). The resulting mixture was stirred at −100° C. for 10 minutes and at −78° C. for 20 minutes, then quenched with 50% saturated NH$_4$Cl. The solution was warmed to room temperature, diluted with H$_2$O, and poured into saturated NaHCO$_3$. The aqueous phase was extracted 2× with Et$_2$O. The combined Et$_2$O layers were washed with brine, dried (Na$_2$SO$_4$), filtered and stripped. The resulting yellow oil was chromatographed (flash, Merck SiO$_2$, 40% EtOAc in hexane followed by 1:1 EtOAc:hexane) to afford (S,E)-3-[[(1,1-Dimethylethyl)diphenylsilyl]oxy] -4-[[2-[4-(4-fluorophenyl)-2-(1-methylethyl)- 3-quinolinyl]ethenyl]methoxyphosphinyl]butanoic acid, methyl ester as an off-white foam (1.615 gm, 62%).

TLC: R$_f$ 0.28 (1:1 EtOAc:hexane)

C. (S,E)-4-[ [ 2-[ 4-(4-Fluorophenyl)-2-(1 -methylethyl)-3-quinolinyl]-ethenyl] methoxyphosphinyl]-3-hydroxybutanoic acid, methyl ester A solution of (S,E)-3-[[(1,1-Dimethylethyl)diphenylsilyl]] -oxy] -4-[ [ 2-[ 4-(4-fluorophenyl)-2-(1 -methylethyl)-3-quinolinyl]ethenyl]methoxyphosphinyl]butanoic acid, methyl ester (1.136 gm, 1.57 mmol) in THF (14 ml) was treated with HOAc (450 ul, 472 mg, 7.9 mmol) and tetra-n-butylammonium fluoride (1.0M in THF, 5.40 ml, 5.40 mmol). After stirring at room temperature for 18 hours, the solution was poured into saturated NaHCO$_3$ and extracted with EtOAc. The EtOAc extract was washed with brine, dried (Na$_2$SO$_4$), filtered, and stripped to give an oil which was subsequently chromatographed (flash, Merck SiO$_2$, 1:1 acetone:hexane). (S,E)-4-[[2-[4-(4-Fluorophenyl)-2-(1-methylethyl)- 3-quinolinyl]-ethenyl]methoxyphosphinyl] -3-hydroxybutanoic acid, methyl ester (709 mg, 93%) was obtained as a colorless oil.

TLC: R$_f$ 0.32 (1:1 acetone:hexane)

D. [3S,4(E)]-4-[ [2-[4-(4-Fluorophenyl)-2 -(1-methylethyl)-3-quinolinyl]ethenyl] hydroxyphosphinyl]-3-hydroxybutanoic acid, dilithium salt A solution of (S,E)-4-[ [2-[4-(4-Fluorophenyl)- 2-(1-methylethyl)-3-quinolinyl]-ethenyl]methoxyphosphinyl] -3-hydroxybutanoic acid, methyl ester (240 mg, 0.496 mmol) in dioxane (3 ml) was treated with 1N LiOH (1.70 ml, 1.70 mmol) at room temperature and the mixture was subsequently heated at 55° C. under argon for 1.5 hours., The solvent was evaporated and the residue was chromatographed on HP-20 on HP-20 eluting in succession with H$_2$O (200 ml), 25% MeOH in H$_2$O (100 ml), and 50% MeOH in H$_2$O (200 ml). The desired fractions were pooled and evaporated and the residue was taken up in H$_2$O and lyophilized to give [3S,4(E)]-4-[[2-[4-(4-Fluorophenyl)- 2-(1-methylethyl)-3-quinolinyl]ethenyl] hydroxyphosphinyl]-3-hydroxybutanoic acid, dilithium salt (210 mg, 86%) as a white solid.

TLC: R$_f$ 0.36 (7:2:1, i-PrOH, NH$_4$OH, H$_2$O)

Example 12

(S)-4-[ [ [ 2-(4-Fluorophenyl)-4-(1-methyl-ethyl)-
3-quinolinyl] ethynyl] hydroxyphosphinyl] -3
-hydroxybutanoic acid, 1-oxide, dilithium salt A. (S)-4-[ [ [ 2-(4-Fluorophenyl)-4-(1-methylethyl)-
3-quinolinyl]ethynyl]methoxyphosphinyl] -3-hydroxybutanoic acid, methyl ester. 1-oxide A solution of (S)-4-[[[2-(4-Fluorophenyl)-4 -(1-methylethyl)-3-quinolinyl]ethynyl]methoxyphosphinyl] -3-hydroxybutanoic acid, methyl ester (486 mg, 1.00 mmol) (the preparation of which is described in Example 5) and m-CPBA (80–85%, 846 mg) in dry $CH_2Cl_2$ (20 ml) was stirred at room temperature for 15 hours. The mixture was diluted with $Et_2O$ and washed with 70 ml saturated $NaHCO_3$ containing 4.0 gm $Na_2SO_3$. The organic layer was subsequently washed with brine, dried ($Na_2SO_4$), filtered and stripped to yield a yellow oil. The oil was chromatographed (flash, Merck $SiO_2$, 30% hexane in acetone) giving (S)-4-[ [[2-(4 -Fluorophenyl)-4-(1-methylethyl)-3-quinolinyl] ethynyl]methoxyphosphinyl]-3-hydroxybutanoic acid, methyl ester. 1-oxide (404 mg, 81%) as a light yellow oily foam.

TLC: $R_f$ 0.15 (1:1 acetone:hexane)

B. (S)-4-[[[2-(4-Fluorophenyl)-4-(1-methylethyl)- 3-quinolinyl]ethynyl]hydroxyphosphinyl] -3-hydroxybutanoic acid, 1-oxide, dilithium salt A solution of (S)-4-[[[2-(4-Fluorophenyl)-4-(1 -methylethyl)-3-quinolinyl]ethynyl]methoxyphosphinyl] -3-hydroxybutanoic acid, methyl ester. 1-oxide (395 mg, 0.79 mmol) in dioxane (5.0 ml) was treated with 1N LiOH (3.0 ml, 3.0 mmol) at room temperature and the mixture was subsequently heated at 55° C. under argon for 1.25 hours. The solvent was evaporated and the residue was chromatographed on HP-20 eluting in succession with $H_2O$ (200 ml), 25% MeOH in $H_2O$ (100 ml), and 50% MeOH in $H_2O$ (200 ml). The desired fractions were pooled and evaporated and the residue was taken up in $H_2O$ and lyophilized to give (S)-4-[[[2-(4-Fluorophenyl)-4-(1-methyl-ethyl)- 3-quinolinyl]ethynyl]hydroxyphosphinyl]-3-hydroxybutanoic acid, 1-oxide, dilithium salt (333 mg, 81%) as a dense yellow solid.

TLC: $R_f$ 0.33 (7:2:1, i-PrOH, $NH_4OH$, $H_2O$)

Example 13

[3S,4(E)]-4-[
[2-[4-(4-Fluorophenyl)-2-(1-methylethyl)-
3-quinolinyl] ethenyl] hydroxyphosphinyl] -3
-hydroxybutanoic acid, 1-oxide, dilithium salt A. (S,E)-4-[[2-[4-(4-Fluorophenyl)-2-(1 -methylethyl)-3-quinolinyl]ethenyl] methoxyphosphinyl]-3-hydroxybutanoic acid, methyl ester. 1-oxide A solution of (S,E)-4-[[2-[4-(4-Fluorophenyl)- 2-(1-methylethyl)-3-quinolinyl]ethenyl]methoxyphosphinyl] -3-hydroxybutanoic acid, methyl ester (438 mg, 0.906 mmol) (the preparation of which is described in Example 11) and m-CPBA (80–85%, 755 mg) in dry $CH_2Cl_2$ (16 ml) was stirred at room temperature for 2 hours. Additional m-CPBA (285 mg) was added and stirring was continued for another 2.5 hours. The mixture was diluted with EtOAc and washed with 75 ml saturated $NaHCO_3$ containing 5.0 gm $Na_2SO_3$. The organic layer was subsequently washed with brine, dried ($Na_2SO_4$), filtered and stripped to yield an orange-brown residue. The residue was chromatographed (flash, Merck $SiO_2$, 30% hexane in acetone followed by 100% acetone) giving (S,E)-4 -[[2-[4-(4-Fluorophenyl)-2-(1-methylethyl)- 3-quinolinyl]ethenyl]methoxyphosphinyl]-3-hydroxybutanoic acid, methyl ester. 1-oxide (298 mg, 66%) as a yellow gum.

TLC: $R_f$ 0.12 (1:1 acetone:hexane)

B. [3S, 4(E)]-4-[ [2-[4-(4-Fluorophenyl)-2 -(1-methylethyl)-3-quinolinyl] ethenyl] hydroxyphosphinyl] -3-hydroxybutanoic acid, 1-oxide, dilithium salt A solution of (S,E)-4-[ [2-[4-(4-Fluorophenyl)-2 -(1-methylethyl)-3-quinolinyl] ethenyl] methoxyphosphinyl] -3-hydroxybutanoic acid, methyl ester. 1-oxide (282 mg, 0.56 mmol) in dioxane (4.0 ml) was treated with 1N LiOH (1.8 ml, 1.8 mmol) at room temperature and the mixture was subsequently heated at 55° C. under argon for 1.5 hours. The solvent was evaporated and the residue was chromatographed on HP-20 eluting in succession with $H_2O$ (200 ml), 25% MeOH in $H_2O$ (100 ml), and 50% MeOH in $H_2O$ (200 ml). The desired fractions were pooled and evaporated and the residue was taken up in $H_2O$ and lyophilized to give [3S, 4(E)]-4-[[2-[4-(4-Fluorophenyl)-2-(1 -methylethyl)-3-quinolinyl]ethenyl]hydroxyphosphinyl]- 3-hydroxybutanoic acid, 1-oxide, dilithium salt (260 mg, 88%) as a dense pale yellow solid.

TLC: $R_f$ 0.37 (7:2:1, i-PrOH, $NH_4OH$, $H_2O$)

Example 14

(S)-4-[ [ [ 2-(4-Fluorophenyl)-4-(1-methylethyl)-
6-phenyl-3-pyridinyl] ethynyl] hydroxyphosphinyl]
-3-hydroxybutanoic acid, dilithium salt A. 3-(2,2-Dibromoethenyl)-2-(4-fluorophenyl)- 4-(1-methylethyl)-6-phenylpyridine A solution of carbon tetrabromide (2.866 gm, 8.64 mmol) in $CH_2Cl_2$ (8 ml) was added over a 10 minute period to a cold (−10° C.) solution of 2-(4-Fluorophenyl)-4-(1-methylethyl)-6-phenyl-3 -pyridinecarboxaldehyde (1.840 gm, 5.76 mmol) (the preparation of which is described in Example 3) and triphenylphosphine (4.590 gm, 17.5 mmol) in $CH_2Cl_2$ (30 ml). After the addition was complete, the cooling bath was removed and the mixture was stirred for 20 minutes. The solution was quenched with saturated $NaHCO_3$ and extracted 2× with $CH_2Cl_2$. The combined organic layers were washed with saturated $NaHCO_3$, dried ($Na_2SO_4$), filtered and concentrated. The concentrate was chromatographed (flash, Merck, $SiO_2$, 1:1 $CH_2Cl_2$: hexane) to give 3-(2,2-Dibromoethenyl)-2-(4-fluorophenyl)- 4-(1-methylethyl)-6-phenylpyridine as a white solid (2.701 gm, 99%).

m.p. 124°–126° C. TLC: $R_f$ 0.28 (1:1 $CH_2 Cl_2$:hexane)

B. 3-Ethynyl-2-(4-fluorophenyl)-4-(1-methylethyl)- 6-phenylpyridine

A solution of 3-(2,2-Dibromoethenyl)-2-(4fluorophenyl)- 4-(1-methylethyl)-6-phenylpyridine (2.677 gm, 5.63 mmol) in dry THF (25 ml) was cooled to −78° C. and treated with n-BuLi (1.6M in hexane, 7.75 ml, 12.4 mmol) over a 1 minute period. After stirring at −78° C. for one hours, the deep green solution was quenched with saturated $NH_4Cl$, warmed to room temperature, diluted with $H_2O$, and extracted once with $Et_2O$. The $Et_2O$ extract was washed with brine, dried ($Na_2SO_4$), filtered and stripped to give a yellow solid. The solid was recrystallized from a minimum amount of hot hexane to afford analytically pure 3-Ethynyl-2-(4-fluorophenyl)-4 -(1-methylethyl)-6-phenylpyridine as yellow crystals (1.572 gm, 89%).

m.p. 121°–123.5° C. TLC: $R_f$ 0.33 (5% EtOAc in hexane)

C. (S)-3-[[1,1-Dimethylethyl)diphenylsilyl] oxy]-4-[[[2-(4-fluorophenyl)-4-(1-methylethyl)- 6-phenyl-3-pyridinyl] ethynyl]-methoxyphosphinyl] butanoic acid, methyl ester (S)-4-(Hydroxymethoxyphosphinyl)-3 -[[[(1,1-dimethylethyl)diphenylsilyl]oxy]butanoic acid, methyl ester, dicyclohexylamine (1:1) salt (4.501 gm, 7.123 mmol) (2.018 gm, 3.19 mmol) the preparation of which is described at the end of example 7, was partitioned between EtOAc and 5% $KHSO_4$. The EtOAc layer was washed 3× with $KHSO_4$, then with brine, then dried ($Na_2SO_4$), filtered and stripped to give a colorless oil (phosphinic acid monomethyl ester). The oil was dissolved in dry $CH_2Cl_2$ (10 ml) and treated with N,N-diethyltrimethylsilylamine (1.22 ml, 0.94 gm, 6.44 mmol). After stirring at room temperature for one hour, the solvent was removed in vacuo and the residue was azeotroped with dry benzene (10 ml). The residue was redissolved in dry $CH_2Cl_2$ (10 ml), cooled to $-12°$ C. and treated with 2 drops DMF and oxalyl chloride (307 ul, 447 mg, 3.52 mmol). After 15 minutes, the solution was warmed to room temperature and stirred for an additional 45 minutes. The solvent was stripped and the yellow residue (phosphinylchloridate) was azeotroped with benzene (20 ml) and dried in vacuo (oil pump) for 30 minutes.

Meanwhile, a solution of 3-Ethynyl-2-(4 -fluorophenyl)-4-(1-methylethyl)-6-phenylpyridine (599 mg, 1.9 mmol) in THF (8 ml) at $-78°$ C. was treated with n-BuLi (1.6M in hexane, 1.30 ml, 2.08 mmol) and the resulting clear green mixture was stirred for 30 minutes. The acetylenic anion solution was added dropwise via canula over a 2 minute period to a $-78°$ C. solution of the phosphinylchloridate in THF (12 ml). The resulting yellow-brown mixture was stirred at $-78°$ C. for 35 minutes, then quenched with 50% saturated $NH_4Cl$. The solution was warmed to room temperature, diluted with $H_2O$, and poured into saturated $NaHCO_3$. The aqueous phase was extracted once with $Et_2O$. The $Et_2O$ extract was washed with brine, dried ($Na_2SO_4$), filtered and stripped. The residual oil was chromatographed (flash, Merck $SiO_2$, 1:1 EtOAc:hexane) to afford (S)-3-[[1, 1-Dimethylethyl)diphenylsilyl]oxy]-4 -[[[2-(4-fluorophenyl)-4-(1-methylethyl)-6-phenyl- 3-pyridinyl]ethynyl]methoxyphosphinyl]butanoic acid, methyl ester as a yellow-white foam (773 mg, 55%).

TLC: $R_f$ 0.18 (40% EtOAc in hexane)

D. (S)-4-[[[2-(4-Fluorophenyl)-4-(1-methylethyl)- 6-phenyl-3-pyridinyl]ethynyl] methoxyphosphinyl]-3-hydroxybutanoic acid, methyl ester A mixture of (S)-3-[[1,1-Dimethylethyl)diphenylsilyl]oxy]-4-[[[2-(4-fluorophenyl)-4-(1-methylethyl)- 6-phenyl-3-pyridinyl]ethynyl]methoxyphosphinyl] butanoic acid, methyl ester (750 mg, 1.00 mmol) tetra-n-butylammonium fluoride (1.0M in THF, 3.50 mmol), and HOAc (330 mg, 5.50 mmol) in THF (12 ml) was stirred at room temperature for 15 hours. The solution was partitioned between 5% $KHSO_4$ and EtOAc. The layers were shaken and separated and the EtOAc layer was washed again with 5% $KHSO_4$. The pooled aqueous washings were back-extracted twice with EtOAc. The combined EtOAc layers were washed with brine and dried ($Na_2SO_4$). Filtration and removal the solvent afforded a yellow oil. The oil was dissolved in $Et_2O$ and treated with excess diazomethane for 20 minutes. The excess diazomethane was destroyed by the addition of HOAc and the solvent was removed in vacuo. The residue was chromatographed (flash, Merck $SiO_2$, 40% acetone in hexane followed by 1:1 acetone:hexane) to afford (S)-4-[[[2-(4-Fluorophenyl)-4-(1-methylethyl)- 6-phenyl-3-pyridinyl] ethynyl]methoxyphosphinyl] -3-hydroxybutanoic acid, methyl ester (446 mg, 88%) as a colorless oil.

TLC: $R_f$ 0.34 (1:1 acetone:hexane)

E. (S)-4-[ [ [ 2-(4-Fluorophenyl)-4-(1-methylethyl)- 6-phenyl -3-pyridinyl] ethynyl] hydroxyphosphinyl] -3-hydroxybutanoic acid, dilithium salt A solution of (S)-4-[[[2-(4-Fluorophenyl)-4 -(1-methylethyl)-6-phenyl-3-pyridinyl]ethynyl]methoxyphosphinyl] -3-hydroxybutanoic acid, methyl ester (436 mg, 0.86 mmol) in dioxane (5 ml) was treated with 1N LiOH (2.6 ml, 2.6 mmol) at room temperature and the mixture was subsequently heated at 55° C. under argon for 1.5 hours. The solvent was evaporated and the residue was chromatographed on HP-20 eluting in succession with $H_2O$ (200 ml), 25% MeOH in $H_2O$ (100 ml), 50% MeOH in $H_2O$ (250 ml). The desired fractions were pooled and evaporated and the residue was taken up in $H_2O$ and lyophilized to give (S)-4-[[[2-(4-Fluorophenyl)-4-(1-methylethyl) -6-phenyl-3-pyridinyl]ethynyl]hydroxyphosphinyl] -3-hydroxybutanoic acid, dilithium salt (369 mg, 84%) as a white solid.

TLC: $R_f$ 0.57 (7:2:1, i-PrOH, $NH_4OH$, $H_2O$)

Example 15

[3S,4(E)]-4-[ [2-[2-(4-Fluorophenyl)-4 -(1-methylethyl)-6-phenyl-3-pyridinyl] ethenyl] hydroxyphosphinyl] -3-hydroxybutanoic acid, dilithium salt A. (E)-2-(4-Fluorophenyl)-3-(2-iodoethenyl)- 4-(1-methylethyl)-6-phenyl-pyridine A mixture of 3-Ethynyl-2-(4-fluorophenyl)-4-(1 -methylethyl)-6-phenylpyridine (700 mg, 2.22 mmol) (the preparation of which is described in Example 14)and AIBN (11 mg) in tri-n-butylstannyl hydride (1.40 ml) was rapidly heated to 120° C. After 5 minutes of heating, the temperature of the reaction was raised to 140° C. and approximately 12 mg of AIBN was added to the reaction mixture every 0.5 hour thereafter. After 2.5 hours, the mixture was cooled to room temperature, diluted with $Et_2O$ (20 ml) and treated with solid $I_2$ (2.00 gm, 7.9 mmol). The dark reaction mixture was stirred for one hour, then quenched with 60 ml saturated $NaHCO_3$ containing 4 gm $Na_2SO_3$. The layers were shaken and separated. The ethereal layer was washed with brine, dried ($Na_2SO_4$), filtered and stripped to yield a yellow oil. The oil was chromatographed twice (Merck $SiO_2$, 5% EtOAc in hexane (1st) then 3% EtOAc in hexane (2nd)) to (E)-2-(4-Fluorophenyl)-3-(2-iodoethenyl)-4-(1 -methylethyl)-6-phenyl-pyridine as a foam which solidified (671 mg). Recrystallization of the solid from hot hexane gave 482 mg of (E)-2-(4 -Fluorophenyl)-3-(2-iodoethenyl)-4-(1-methylethyl)- 6-phenyl-pyridine. An additional 100 mg of 2 was obtained from the mother liquor to give a total of 582 mg (59%) product.

m.p. 110°–111° C. TLC: $R_f$ 0.39 (10% EtOAC in hexane)

B. (S,E)-3-[[1,1-Dimethylethyl)diphenylsilyl] oxy]-4-[[2-[2-(4-fluorophenyl)-4-(1-methylethyl)-6-phenyl-3-pyridinyl] ethenyl]methoxyphosphinyl]butanoic acid, methyl ester (S)-4-(Hydroxymethoxyphosphinyl)-3 -[[(1,1-dimethylethyl)diphenylsilyl]oxy]butanoic acid, methyl ester, dicyclohexylamine (1:1) salt (4.501 gm, 7.123 mmol) (1.211 gm, 1.92 mmol) the preparation of which is described at the end of example 7, was partitioned between EtOAc and 5% $KHSO_4$. The EtOAc layer was washed 3× with 5% $KHSO_4$, then with brine, then dried ($Na_2SO_4$), filtered and stripped to give a colorless oil (phosphinic acid monomethyl ester). The oil was dissolved in dry $CH_2Cl_2$ (10 ml) and treated with N,N-diethyltrimethylsilylamine (727 ul, 558 mg, 3.84 mmol). After stirring at room temperature for one hour, the solvent was removed in vacuo and the residue was azeotroped with dry benzene (10 ml). The residue was dissolved in dry $CH_2Cl_2$ (10 ml) cooled to $-10°$ C. and treated with 2 drops DMF and oxalyl chloride (184 ul, 268 mg, 2.11 mmol). After 15 minutes, the solution was warmed to room temperature and stirred for an additional 50 minutes. The solvent was then stripped and the yellow residue (phosphinylchloridate) was azeotroped with benzene (10 ml) and dried in vacuo (oil pump) for 30 minutes.

Meanwhile, a solution of (E)-2-(4-Fluorophenyl)- 3-(2-iodoethenyl)-4-(1-methylethyl)-6-phenyl-pyridine (502 mg, 1.13 mmol) in THF (2 ml) was added over a 2 minute period to a $-78°$ C. solution of t-butyllithium (1.7M in pentane, 1.46 ml, 2.48 mmol) in THF (6 ml). The mixture was stirred for 20 minutes then cooled to −100° C. The vinyl anion solution was added over a one minute period to a −100° C. solution of the phosphinylchloridate in THF (10 ml). The resulting mixture was stirred at −100° C. for 30 minutes and at −78° C. for 30 minutes, then quenched with 50% saturated NH₄Cl. The solution was warmed to room temperature, diluted with H₂O, and poured into saturated NaHCO₃. The aqueous phase was extracted 2× with Et₂O. The combined Et₂O layers were washed with brine, dried (Na₂SO₄), filtered and stripped. The resulting yellow oil was chromatographed (flash, Merck SiO₂, 15% acetone in hexane followed by 20% acetone in hexane) to afford (S,E)-3-[[1,1-Dimethylethyl)diphenylsilyl] oxy]-4-[[2-[2-(4-fluorophenyl)-4 -(1-methylethyl)-6-phenyl-3-pyridinyl] ethenyl] methoxyphosphinyl]butanoic acid, methyl ester as an off-white foam (256 mg, 30%).

TLC: $R_f$ 0.29 (1:2 acetone:hexane)

C. (S,E)-4-[[2-[2-(4-Fluorophenyl)-4-(1 -methylethyl)-6-phenyl-3-pyridinyl] ethenyl]methoxyphosphinyl]butanoic acid, methyl ester A solution of (S,E)-3-[[1,1-Dimethylethyl)diphenylsilyl] oxy]-4-[[2-[2-(4-fluorophenyl)-4 -(1-methylethyl)-6-phenyl-3-pyridinyl]ethenyl]methoxyphosphinyl] butanoic acid, methyl ester (241 mg, 0.321 mmol) in THF (7 ml) was treated with HOAc (92 ul, 96 mg, 1.61 mmol) and tetra-n-butylammonium fluoride (1.0M in THF, 963 ul, 0.963 mmol). After stirring at room temperature for 18 hours, the solution was poured into saturated NaHCO₃ and extracted with EtOAc. The EtOAc extract was washed with brine, dried, (Na₂SO₄), filtered, and stripped to give an oil which was subsequently chromatographed (flash, Merck SiO₂, 1:1 acetone:hexane followed 100% acetone). (S,E)-4-[[2-[2-(4-Fluorophenyl)-4-(1 -methylethyl)-6-phenyl-3-pyridinyl] ethenyl] methoxyphosphinyl]butanoic acid, methyl ester (124 mg, 76%) was obtained as a colorless oil.

TLC: $R_f$ 0.29 (1:1 acetone:hexane)

D. [3S,4(E)]-4-[[2-[2-(4-Fluorophenyl)-4 -(1-methylethyl)-6-phenyl-3-pyridinyl] ethenyl]-hydroxyphosphinyl]-3-hydroxybutanoic acid, dilithium salt A solution of (S,E)-4-[[2-[2-(4-Fluorophenyl)- 4-(1-methylethyl)-6-phenyl-3-pyridinyl]ethenyl]methoxyphosphinyl] butanoic acid, methyl ester (120 mg, 0.234 mmol) in dioxane (2 ml) was treated with 1N LiOH (0.9 ml, 0.9 mmol) at room temperature and the mixture was subsequently heated at 55° C. under argon for 1.5 hours. The solvent was evaporated and the residue was chromatographed on HP-20 eluting in succession in H₂O (150 ml), 25% MeOH in H₂O (75 ml) and 50% MeOH in H₂O (200 ml). The desired fractions were pooled evaporated and the residue was taken up in H₂O and lyophilized to give [3S,4(E)]-4-[[2-[2-(4-Fluorophenyl)-4 -(1-methylethyl)-6-phenyl-3-pyridinyl] ethenyl] hydroxyphosphinyl]-3-hydroxybutanoic acid, dilithium salt (108 mg, 86%) as a white solid.

TLC: $R_f$ 0.52 (7:2:1, i-PrOH, NH₄OH, H₂O)

Examples 16 to 51

Following the procedures as outlined heretofore and as described in the previous working examples, the following additional compounds may be prepared.

Examples of Structure 1 where Am= $A_1$, X= C≡C

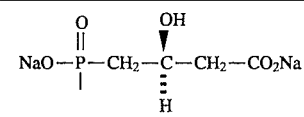

| Ex. # | Structure 1 |
|---|---|
| 16 | 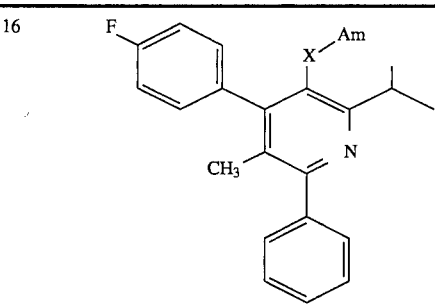 |
| 17 | 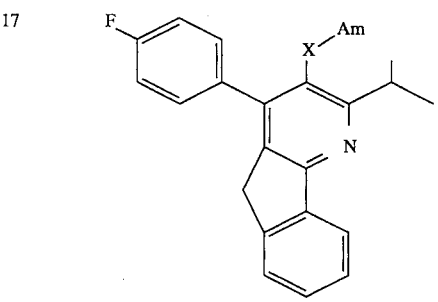 |
| 18 | 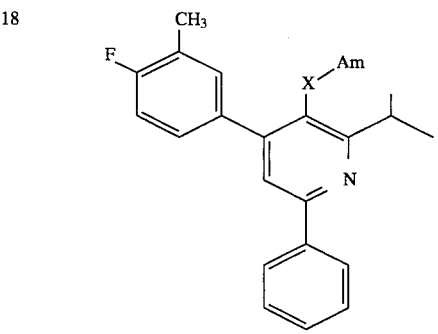 |
| 19 | 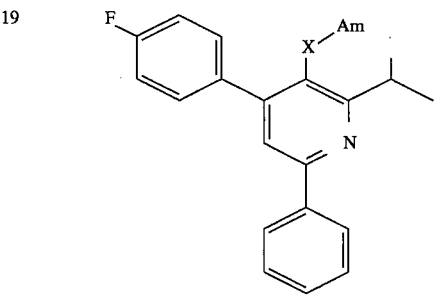 |

53
-continued
| A1 |
|---|
| NaO—P(=O)(O⁻)—CH₂—C(OH)(H)—CH₂—CO₂Na |
| Ex. # | Structure 1 |
|---|---|
| 20 | 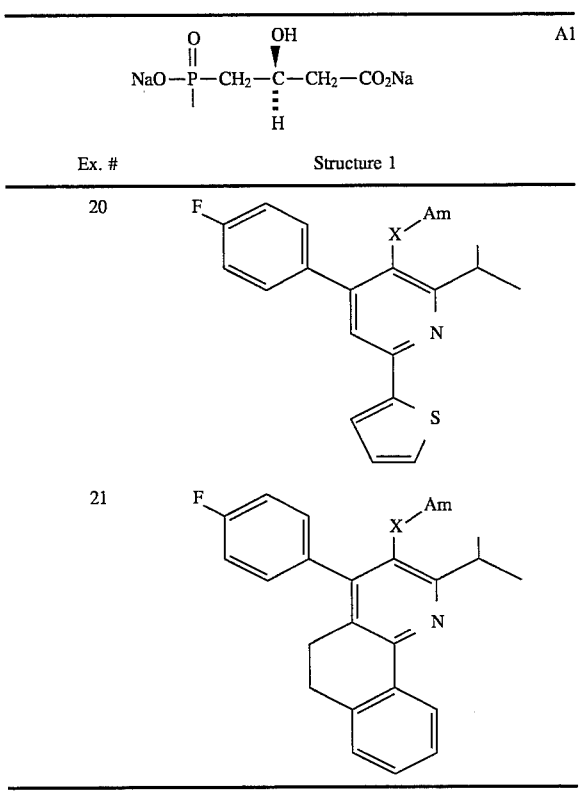 |
| 21 | |
Examples of Structure 1 where Am= A₁, X=C≡C
| A1 |
|---|
| NaO—P(=O)(O⁻)—CH₂—C(OH)(H)—CH₂—CO₂Na |
| Ex. # | Structure 1 |
|---|---|
| 22 | 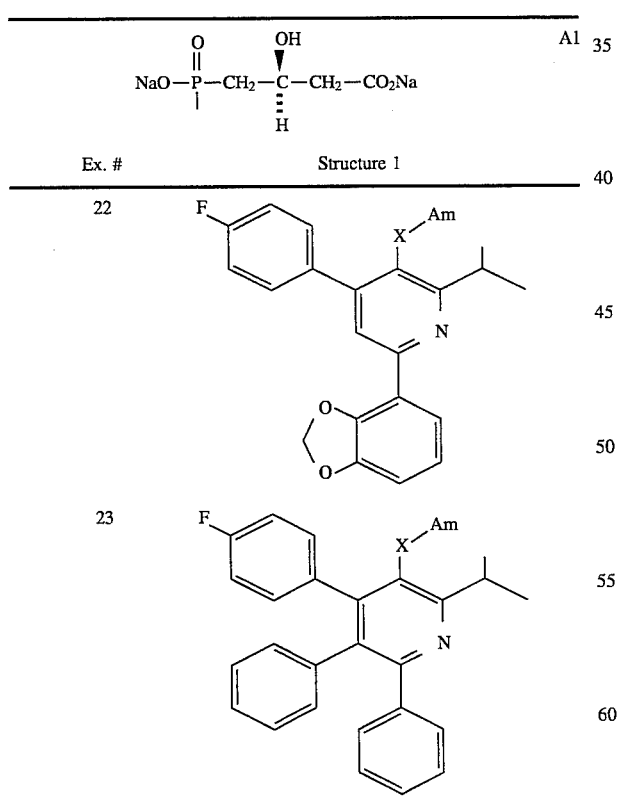 |
| 23 | |
54
-continued
| A1 |
|---|
| NaO—P(=O)(O⁻)—CH₂—C(OH)(H)—CH₂—CO₂Na |
| Ex. # | Structure 1 |
|---|---|
| 24 | 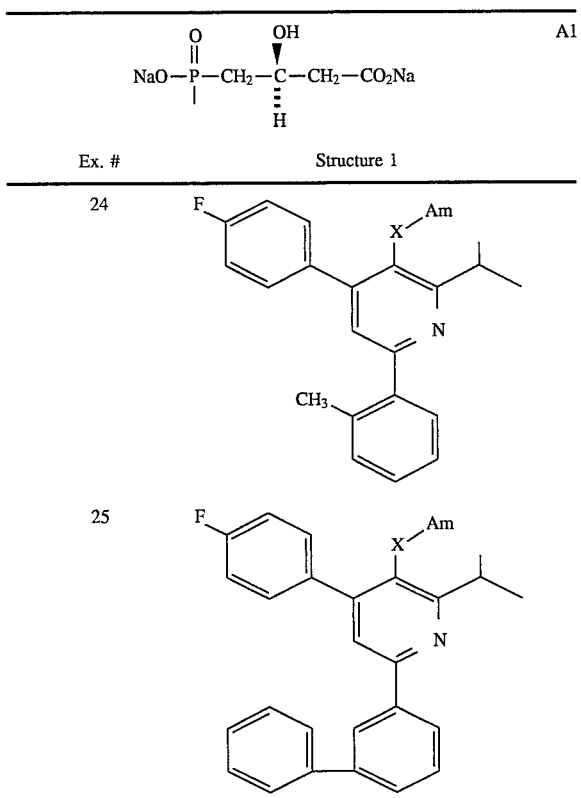 |
| 25 | |
| 26 | 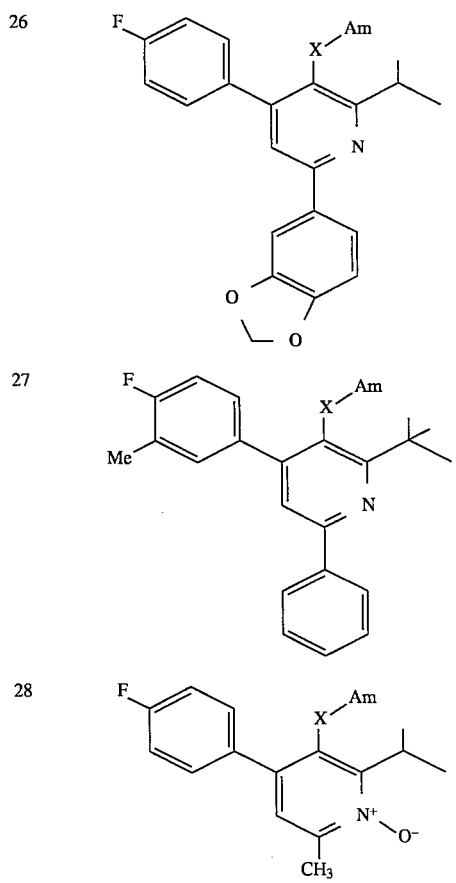 |
| 27 | |
| 28 | |

5,506,219

55
-continued $$NaO-\underset{\underset{O}{\|}}{P}-CH_2-\underset{\underset{H}{|}}{\overset{OH}{C}}-CH_2-CO_2Na \qquad A1$$

| Ex. # | Structure 1 |
|---|---|
| 29 | (4-fluorophenyl) / (2-methylphenyl) pyridine with tert-butyl and X–Am substituents |

Examples of Structure 1 where Am= A₁, X= C≡C $$NaO-\underset{\underset{O}{\|}}{P}-CH_2-\underset{\underset{H}{|}}{\overset{OH}{C}}-CH_2-CO_2Na \qquad A1$$

| Ex. # | Structure 1 |
|---|---|
| 30 | 4-fluorophenyl diene with phenyl pyridine N-oxide, isopropyl, and X–Am |
| 31 | 4-fluorophenyl diene fused with cyclopentane-imine, isopropyl, and X–Am |
| 32 | 4-fluorophenyl diene fused with cyclohexane-imine, isopropyl, and X–Am |

56
-continued $$NaO-\underset{\underset{O}{\|}}{P}-CH_2-\underset{\underset{H}{|}}{\overset{OH}{C}}-CH_2-CO_2Na \qquad A1$$

| Ex. # | Structure 1 |
|---|---|
| 33 | (4-fluoro-3-methylphenyl) diene with phenyl pyridine N-oxide, isopropyl, and X–Am |
| 34 | 4-fluorophenyl quinoline with tert-butyl and X–Am |
| 35 | (4-fluoro-3-methylphenyl) quinoline with isopropyl and X–Am |
| 36 | (3,5-dimethylphenyl) pyridine with isopropyl, phenyl, and X–Am |
| 37 | 4-fluorophenyl bipyridine with isopropyl and X–Am |

Examples of Structure 1 where Am= $A_1$, X=C≡C
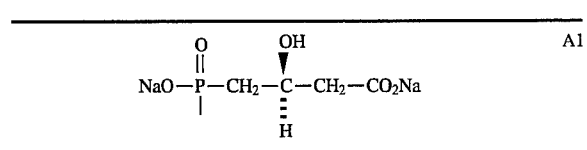
| Ex. # | Structure 1 |
|---|---|
| 38 | 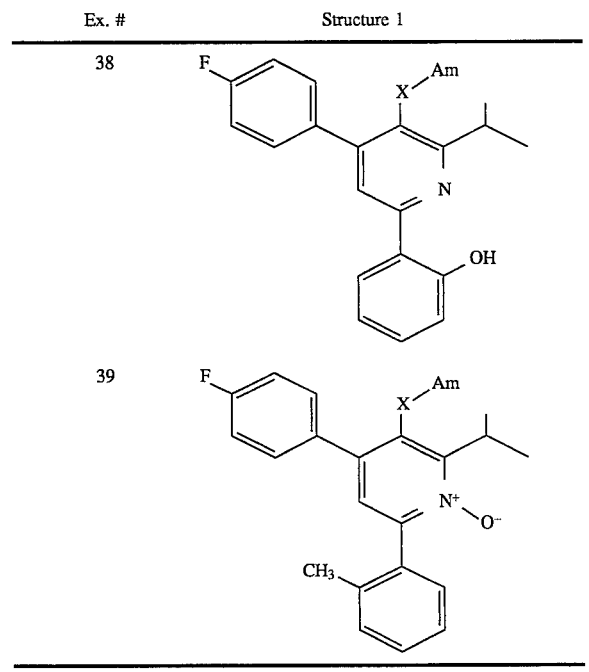 |
| 39 | |
Examples of Structure 1 where Am=$A_2$, X=CH=CH(E)
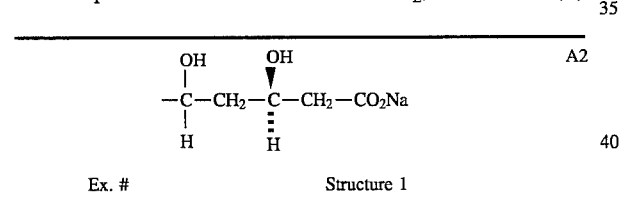
| Ex. # | Structure 1 |
|---|---|
| 40 | 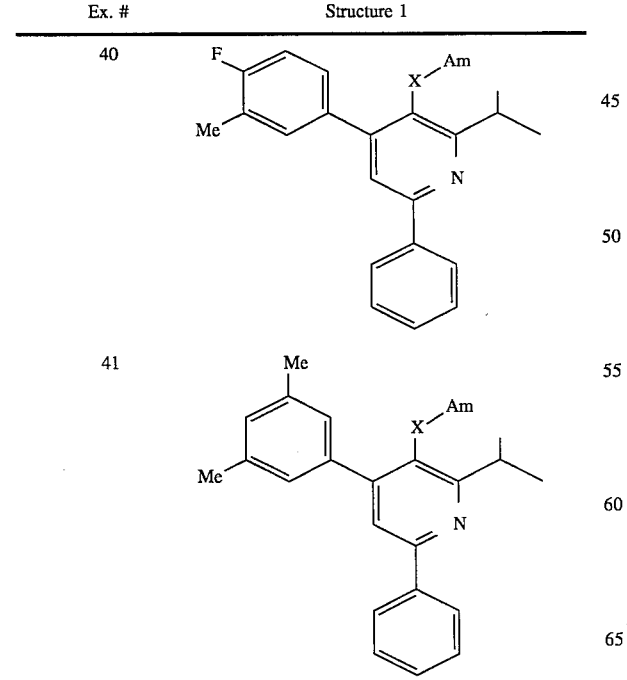 |
| 41 | |
-continued
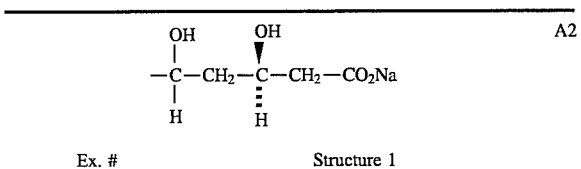
| Ex. # | Structure 1 |
|---|---|
| 42 | 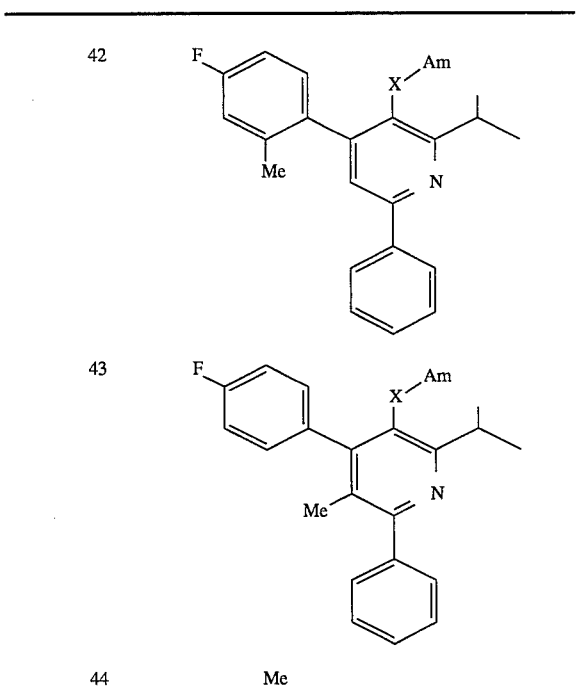 |
| 43 | |
| 44 | |
| 45 | 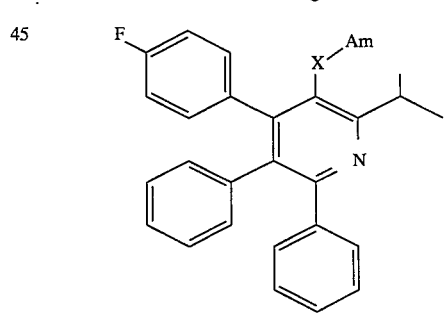 |

| | A2 |
|---|---|
| $\begin{array}{c} \text{OH} \quad \text{OH} \\ | \quad \blacktriangledown \\ -\text{C}-\text{CH}_2-\text{C}-\text{CH}_2-\text{CO}_2\text{Na} \\ | \quad \vdots \\ \text{H} \quad \text{H} \end{array}$ | |

| Ex. # | Structure 1 |
|---|---|
| 46 | *[structure: 4-fluorophenyl and isopropyl substituted pyridine fused to indene, with X-Am group]* |
| 47 | *[structure: 4-fluorophenyl and isopropyl substituted pyridine fused to dihydronaphthalene, with X-Am group]* |

Examples of Structure 1 where Am= A$_2$, X= CH=CH(E)

| | A2 |
|---|---|
| $\begin{array}{c} \text{OH} \quad \text{OH} \\ | \quad \blacktriangledown \\ -\text{C}-\text{CH}_2-\text{C}-\text{CH}_2-\text{CO}_2\text{Na} \\ | \quad \vdots \\ \text{H} \quad \text{H} \end{array}$ | |

| Ex. # | Structure 1 |
|---|---|
| 48 | *[structure: 4-(4-fluorophenyl)-2-isopropyl-6-phenylpyridine with X-Am]* |
| 49 | *[structure: 4-(4-fluoro-3-methylphenyl)-2-isopropyl-pyridine N-oxide with phenyl, X-Am]* |

| | A2 |
|---|---|
| $\begin{array}{c} \text{OH} \quad \text{OH} \\ | \quad \blacktriangledown \\ -\text{C}-\text{CH}_2-\text{C}-\text{CH}_2-\text{CO}_2\text{Na} \\ | \quad \vdots \\ \text{H} \quad \text{H} \end{array}$ | |

| Ex. # | Structure 1 |
|---|---|
| 50 | *[structure: 4-(4-fluorophenyl)-2-isopropyl-5-methyl-6-phenyl pyridine N-oxide, X-Am]* |
| 51 | *[structure: 4-(4-fluorophenyl)-2-isopropyl-6-(2-methylphenyl)pyridine N-oxide, X-Am]* |

The following are the IUPAC names for the compounds described above:

16. (S)-4-[ [ [4-(4-Fluorophenyl)-5-methyl-2 -(1-methylethyl)-6-phenyl-3-pyridinyl]ethynyl] hydroxyphosphinyl]-3-hydroxybutanoic acid, disodium salt.
17. (S)-4-[ [ [4-Fluorophenyl)-2-(1-methylethyl)- 5H-indeno[ 1,2-b]pyridin-3-yl] ethynyl] hydroxyphosphinyl]- 3-hydroxybutanoic acid, disodium salt.
18. (S)-4-[ [ [4-(4-Fluoro-3-methylphenyl)-2 -(1-methylethyl)-6-phenyl-3-pyridinyl]ethynyl] -hydroxyphosphinyl-3-hydroxybutanoic acid, disodium salt.
19. (S)-4-[ [ [2-(1,1-Dimethylethyl)-4-(4 -fluorophenyl)-6-phenyl-3-pyridinyl]ethynyl]hydroxyphosphinyl] -3-hydroxybutanoic acid, disodium salt.
20. (S)-4-[ [ [4-(4-Fluorophenyl)-2-(1-methylethyl)- 6-(2-thienyl)-3-pyridinyl]ethynyl]hydroxyphosphinyl] -3-hydroxybutanoic acid, disodium salt.
21. (S)-4-[ [ [4-(4-Fluorophenyl)-5,6-dihydro- 2-(1-methylethyl)benzo[h]quinolin-3-yl]ethynyl] hydroxyphosphinyl]-3-hydroxybutanoic acid, disodium salt.
22. (S)-4-[ [ [6-(1,3-Benzodioxol-4-yl)-4-(4 -fluorophenyl)-2-(1-methylethyl)-3-pyridinyl] ethynyl]hydroxyphosphinyl]-3-hydroxybutanoic acid, disodium salt.
23. (S)-4-[ [ [4-(4-Fluorophenyl)-2-(1-methylethyl)- 5,6-diphenyl-3-pyridinyl]ethynyl]hydroxyphosphinyl] -3-hydroxybutanoic acid, disodium salt.
24. (S)-4-[ [ [4-(4-Fluorophenyl)-2-(1-methylethyl)- 6-(2-methylphenyl)-3-pyridinyl]ethynyl] hydroxyphosphinyl] -3-hydroxybutanoic acid, disodium salt.
25. (S)-4-[[[6-[[1,1'-Biphenyl]-3-yl]-4-(4 -fluorophenyl)-2-(1-methylethyl)-3-pyridinyl] ethynyl] hydroxyphosphinyl] -3-hydroxybutanoic acid, disodium salt.
26. (S)-4-[ [ [6-(1,3-Benzodioxol-5-yl)-4-(4 -fluorophenyl)-2-(1-methylethyl)-3-pyridinyl] ethynyl] hydroxyphosphinyl] -3-hydroxybutanoic acid, disodium salt.

27. (S)-4-[[[2-(1,1-Dimethylethyl)-1-(4-fluoro-3-methylphenyl)-6-phenyl-3-pyridinyl] ethynyl]hydroxyphosphinyl]-3-hydroxybutanoic acid, disodium salt.

28. (S)-4-[ [ [4-(4-Fluorophenyl)-6-methyl-2-(1-methylethyl)-3-pyridinyl]ethynyl]hydroxyphosphinyl] -3-hydroxybutanoic acid, 1-oxide, disodium salt.

29. (S)-4-[[[2-(1,1-Dimethylethyl)-4-(4-fluorophenyl)-6-(2-methylphenyl)-3-pyridinyl] ethynyl]hydroxyphosphinyl]-3-hydroxybutanoic acid, disodium salt.

30. (S)-4-[ [ [4-(4-Fluorophenyl)-2-(1-methylethyl)-6-phenyl-3-pyridinyl]ethynyl]hydroxyphosphinyl] -3-hydroxybutanoic acid, 1-oxide, disodium salt.

31. (S)-4-[ [ [4-(4-Fluorophenyl)-6,7-dihydro-2-(1-methylethyl)-5H-1-pyridin-3-yl] ethynyl] hydroxyphosphinyl] -3-hydroxybutanoic acid, disodium salt.

32. (S)-4-[ [ [4-(4-Fluorophenyl)-5,6,7,8-tetrahydro-2-(1-methylethyl)-3-quinolinyl] -ethynyl] hydroxyphosphinyl] -3-hydroxybutanoic acid, disodium salt.

33. (S)-4-[ [ [4-(4-Fluoro-3-methylphenyl)-2-(1-methylethyl)-3-quinolinyl]ethynyl]hydroxyphosphinyl] -3-hydroxybutanoic acid, 1-oxide, disodium salt.

34. (S)-4-[ [ [4-(1,1-Dimethylethyl)-2-(4-fluorophenyl)-3-quinolinyl] ethynyl] hydroxyphosphinyl] -3-hydroxybutanoic acid, disodium salt.

35. (S)-4-[ [ [2-(4-Fluoro-3-methylphenyl)-4-(1-methylethyl)-3-quinolinyl]-ethynyl]hydroxyphosphinyl] -3-hydroxybutanoic acid, sodium salt.

36. (S)-4-[ [ [4-(3,5-Dimethylphenyl)-2-(1-methylethyl)-6-phenyl-3-pyridinyl]ethynyl] hydroxyphosphinyl]-3-hydroxybutanoic acid, disodium salt.

37. (S)-4-[ [ [4-Fluorophenyl)-2-(1-methylethyl)-6-(2-pyridinyl)-3-pyridinyl]ethnyl]hydroxyphosphinyl] -3-hydroxybutanoic acid, disodium salt.

38. (S)-4-[ [ [4-Fluorophenyl)-6-(2-hydroxyphenyl)-2-(1-methylethyl)-3-pyridinyl]ethynyl] hydroxyphosphinyl] -3-hydroxybutanoic acid, disodium salt.

39. (S)-4-[ [ [4-(4-Fluorophenyl)-2-(1-methylethyl)-6-(2-methylphenyl)-3-pyridinyl]ethynyl] hydroxyphosphinyl] -3-hydroxybutanoic acid, 1-oxide, disodium salt.

40. (3R,5S,6E)-7-[4-(4-Fluoro-3-methylphenyl)-2-(1-methylethyl)-6-phenyl-3-pyridinyl] -3,5-dihydroxy-6-heptenoic acid, monosodium salt.

41. (3R,5S,6E)-7-[4-(3,5-Dimethylphenyl)-2-(1-methylethyl)-6-phenyl-3-pyridinyl] -3,5-dihydroxy-6-heptenoic acid, monosodium salt.

42. (3R,5S,6E)-7-[4-(4-Fluoro-2-methylphenyl)-2-(1-methylethyl)-6-phenyl-3-pyridinyl]-3,5-dihydroxy-6-heptanoic acid, monosodium salt.

43. (3R,5S,6E)-7-[4-(4-Fluorophenyl)-5-methyl-2-(1-methylethyl)-6-phenyl-3-pyridinyl] -3,5-dihydroxy-6-heptenoic acid, monosodium salt.

44. (3R,5S,6E)-7-[2-(4-Fluoro-methylphenyl)-4-(1-methylethyl)-6-phenyl-3-pyridinyl] -3,5-dihydroxy-6-heptenoic acid, monosodium salt.

45. (3R,5S,6E)-7-[4-(4-Fluorophenyl)-2-(1-methylethyl)-5,6-diphenyl-3-pyridinyl] -3,5-dihydroxy-6-heptenoic acid, monosodium salt.

46. (3R,5S,6E)-7-[4-(4-Fluorophenyl)-2-(1-methylethyl)-5H-indeno[1,2-b]-pyridin-3-yl] -3,5-dihydroxy-6-heptenoic acid, monosodium salt.

47. (3R,5S,6E)-7-[4-(4-Fluorophenyl)-5,6-dihydro-2-(1-methylethyl)benzo-[h]quinolin-3-yl]-3,5-dihydroxy-6-heptenoic acid, monosodium salt.

48. (3R,5S,6E)-7-[ 2-(1,1-Dimethylethyl)-4-(4-fluorophenyl)-6-phenyl-3-pyridinyl-3,5-dihydroxy-6-heptenoic acid, monosodium salt.

49. (3R,5S,6E)-7-[4-Fluoro-3-methylphenyl)-2-(1-methylethyl)-6-phenyl-3-pyridinyl]-3,5-dihydroxy-6-heptenoic acid, 1-oxide, monosodium salt.

50. (3R,5S,6E)-7-[4-(4-Fluorophenyl)-5-methyl-2-(1-methylethyl)-6-phenyl-3-pyridinyl] -3,5-dihydroxy-6-heptenoic acid, 1-oxide, monosodium salt.

51. (3R,5S,6E)-7-[4-(4-Fluorophenyl)-2-(1-methylethyl)-6-(2-methylphenyl)-3-pyridinyl-3,5 -dihydroxy-6-heptenoic acid, 1-oxide, monosodium salt.

Example 52

(S)-4-[ [ [ 4-(4-Fluoro-3-methylphenyl)-2-(1-methylethyl)-6-phenyl-3-pyridinyl] ethynyl] hydroxyphosphinyl] -3-hydroxybutanoic acid, dilithium salt A. 4-Fluoro-2-methylbenzaldehyde A −78° C. solution of 2-fluoro-5-bromotoluene (25.764 gm, 136.3 mmol) in THF (200 ml) was treated with n-BuLi (2.5M in hexane, 60 ml, 150 mmol) over a 12-minute period. After stirring for one hour, the cloudy white mixture was treated with neat dimethylformamide (30 ml, 28.3 gm, 387 mmol) over a two-minute period. Stirring continued for an additional hour. The mixture was then quenched with saturated $NH_4Cl$, warmed to room temperature, and made acidic with 10% HCl. The mixture was extracted with $Et_2O$ and the ether extract was washed with $H_2O$ and brine, then dried ($Na_2SO_4$), filtered, and stripped. The dark residue was distilled (bp 55° C. @ 1 mm) to give the title compound (16.286 gm, 86%).

TLC: $R_f$ 0.28 (20% EtOAc in hexane)

B. 3-(4-Fluoro-2-methylphenyl)-1-phenyl-2-propen-1-one

A mixture of the compound from part A (16.000 gm, 115.8 mmol) and acetophenone (13.920 gm, 115.8 mmol) in absolute EtOH (120 ml) was treated with a solution of EtONa in EtOH (21% solution, 4.3 ml, 11.6 mmol). A precipitate soon fell out of solution. After stirring at room temperature for 16 hours, the mixture was cooled to −10° C. and the precipitate was collected by filtration. The solid was washed with cold EtOH and dried in vacuo to yield the part B compound (23.560 gm, 85%) as a light yellow solid.

m.p. 100°–101° C. TLC: $R_f$ 0.42 (20% EtOAc in hexane)
Anal. Calc'd for $C_{16}H_{13}FO$: C 79.98 H 5.45 F 7.91 Found: C 79.80 H 5.35 F 8.03

C. β-(4-Fluoro-2-methylphenyl)-α-(2-methyl-1-oxopropyl)-Δ-oxobenzenepentanoic acid, ethyl ester A slurry of the part B compound (23.165 gm, 96.4 mmol) and ethyl isobutyrylacetate (22.88 gm, 144.6 mmol) in absolute EtOH (400 ml) was treated with a solution of EtONa in EtOH (21% by weight solution, 5.4 ml, 14.5 mmol). After stirring at room temperature for 4.5 hours, the solution was concentrated to 200 ml and partitioned between 50% saturated $NH_4Cl$ and EtOAc. The layers were separated and the EtOAc layer was washed with $H_2O$ (2×) and brine (2×), then dried ($Na_2SO_4$), filtered and stripped to yield an oil. The oil was taken up in hexane and cooled to produce a solid. The mixture was boiled and cooled to give the title compound a mixture of diastereomers, as a white amorphous solid (30.815 gm, 80%).

TLC: $R_f$ 0.34 and 0.30 (20% EtOAc in hexane)

D. 4-(4-Fluoro-2-methylphenyl)-2-(1-methylethyl)-6-phenyl-3-pyridinecarboxylic acid, ethyl ester A mixture of part C compound (30.395 gm, 76.3 mmol), $NH_4OAc$ (17.70 gm, 229.6 mmol), and $Cu(OAc)_2$ (38.062 gm, 190.6 mmol) in glacial HOAc (200 ml) was gently refluxed for three hours. The solution was cooled to room temperature and subsequently poured into an ice cold mixture of concentrated $NH_4OH$ (240 ml) in $H_2O$ (320 ml). The mixture was extracted with $Et_2O$ and the $Et_2O$ extract was washed with H$_2$O (2×) and brine, then dried (Na$_2$SO$_4$), filtered and stripped to yield the title compound as a crude yellow oil (28.460 gm, 99%). The crude material was used directly for the next reaction.

TLC: R$_f$ 0.51 (20% EtOAc in hexane)

E. 4-(4-Fluoro-2-methylphenyl)-2-(1-methylethyl)- 6-phenyl-3-pyridinemethanol

A cold (0° C.) solution of the crude part D compound (28.46 gm) in dry THF (350 ml) was treated with LiAlH$_4$ (9.20 gm, 242 mmol). Ten minutes after the addition, the cooling bath was removed and the mixture was stirred at room temperature for two hours. The dark solution was recooled to 0° C. and quenched with enough H$_2$O to form a thick aluminum salt paste. The solution was filtered and the salts were washed with EtOAc. The filtrate was washed with H$_2$O and brine, then dried (Na$_2$SO$_4$). Filtration and removal of the solvent afforded a solid. The solid was recrystallized from hot EtOAc/hexane to provide the title compound (19.152 gm, 75% from the part C compound) as a white solid.

m.p. 159°–160° C. TLC: R$_f$ 0.30 (20% EtOAc in hexane) Anal Calc'd for C$_{22}$H$_{22}$FNO: C 78.78 H 6.61 N 4.18 F 5.66 Found: C 78.65 H 6.71 N 4.01 F 5.67

F. 4-(4-Fluoro-2-methylphenyl)-2-(1-methylethyl)- 6-phenyl-3-pyridinecarboxaldehyde A −78° C. solution of oxalyl chloride (1.30 ml, 1.89 gm, 14.9 mmol) in CH$_2$Cl$_2$ (80 ml) was treated dropwise with a solution of dry DMSO (2.05 ml, 2.26 gm, 29 mmol) in CH$_2$Cl$_2$ (2 ml). After 15 minutes, a solution of the alcohol prepared in part E (4.000 gm, 11.93 mmol) in CH$_2$Cl$_2$ (13 ml) and THF (5 ml) was added dropwise to the above mixture. Twenty minutes after the addition, TEA (8.3 ml) was added and the mixture was stirred at −78° C. for 10 minutes and then warmed to room temperature. The mixture was diluted with Et$_2$O and washed twice with H$_2$O and once with brine. The organic layer was dried (Na$_2$SO$_4$), filtered, and stripped to yield a yellow solid. Recrystallization of the solid from hot hexane afforded the title compound as hard colorless crystals (3.684 gm, 93%).

m.p. 110.5°–112.5° C. TLC: R$_f$ 0.53 (20% EtOAc in hexane) Anal Calc'd for C$_{22}$H$_{20}$FNO: C 79.26 H 6.05 N 4.20 F 5.70 Found: C 79.10 H 5.98 N 4.11 F 5.58

G. 3-(2,2-Dibromoethenyl)-4-(4-fluoro-2 -methylphenyl)-2-(1-methylethyl-6-phenylpyridine A solution of carbon tetrabromide (5.39 gm, 16.3 mmol) in CH$_2$Cl$_2$ (15 ml) was added over a 5-minute period to a cold (0° C.) solution of the aldehyde prepared in part F (3.610 gm, 10.83 mmol) and triphenylphosphine (8.52 gm, 32.5 mmol) in CH$_2$Cl$_2$ (60 ml). After the addition was complete, the mixture was stirred at 0° C. for 20 minutes and then at room temperature for 10 minutes. The solution was quenched with saturated NaHCO$_3$ and extracted twice with CH$_2$Cl$_2$. The combined organic layers were dried (Na$_2$SO$_4$), filtered and concentrated. The concentrate was chromatographed (flash, Merck SiO$_2$, 30% CH$_2$Cl$_2$ in hexane) to give the title compound (5.076 gm, 96%) as a colorless oil which slowly solidified on standing.

m.p. 102.5°–104.5° C. TLC: R$_f$ 0.58 (20% EtOAc in hexane)

H. (S)-4-[[[4-(4-Fluoro-3-methylphenyl)-2 -(1-methylethyl)-6-phenyl-3-pyridinyl] ethynyl]methoxyphosphinyl]-3-[[(1,1 -dimethylethyl)diphenylsilyl]oxy]butanoic acid, methyl ester Meanwhile, a solution of the dibromide prepared in part G (3.000 gm, 6.13 mmol) in THF (15 ml) at −78° C. was treated with n-BuLi (2.5M in hexane, 4.9 ml, 12.25 mmol) over a 1-minute period and the resulting clear green-brown solution was stirred for 1 hour. The acetylenic anion solution was added dropwise via cannula over a 5-minute period to a −78° C. solution of the phosphonochloridate from Example 57, part G, in THF (20 ml). The resulting yellow-brown mixture was stirred at −78° C. for 30 minutes, then quenched with 75% saturated NH$_4$Cl. The solution was warmed to 0° C., diluted with H$_2$O, and poured into saturated NaHCO$_3$. The aqueous phase was extracted once with Et$_2$O. The Et$_2$O layer was washed with brine, dried (Na$_2$SO$_4$), filtered and stripped to give an orange oil. The residue was chromatographed (flash, Merck SiO$_2$, 40% EtOAc in hexane) to afford the title compound as a pale yellow foam (3.515 gm, 75%).

TLC: R$_f$ 0.31 (40% EtOAc in hexane)

I. (S)-4-[[[4-(4-Fluoro-3-methylphenyl)-2 -(1-methylethyl)-6-phenyl-3-pyridinyl] ethynyl]methoxyphosphinyl]-3-hydroxybutanoic acid, methyl ester A mixture of compound H (3.480 gm, 4.55 mmol), tetra-n-butylammonium fluoride (1.0M in THF, 13.6 ml, 13.6 mmol), and HOAc (1.31 ml, 1.37 gm, 22.9 mmol) in THF (25 ml) was stirred at room temperature for 16 hours. The solution was diluted with EtOAc and washed three times with 5% KHSO$_4$. The aqueous layers were back-extracted twice with EtOAc and the pooled EtOAc layers were dried (Na$_2$SO$_4$), filtered and stripped to afford a yellow oil. The oil was dissolved in Et$_2$O, cooled to 0° C. and treated with excess diazomethane for 20 minutes. The excess diazomethane was destroyed by the addition of HOAc and the solvent was removed in vacuo. The residue was chromatographed (flash, Merck SiO$_2$, 40% acetone in hexane followed by 1:1 acetone:hexane) to afford the title compound (1.949 gm, 82%) as a colorless oil.

TLC: R$_f$ 0.33 (1:1—acetone:hexane)

J. (S)-4-[ [ [4-(4-Fluoro-3-methylphenyl)-2 -(1-methylethyl)-6-phenyl-3-pyridinyl] ethynyl]hydroxyphosphinyl]-3-hydroxybutanoic acid, dilithium salt A solution of the compound (500 mg, 0.955 mmol) in dioxane (5 ml) was treated with 1N LiOH (3.3 ml, 3.3 mmol) at room temperature and the mixture was subsequently heated at 55° C. under argon for 1.5 hours. The solvent was evaporated and the residue was chromatographed on HP-20 eluting in succession with H$_2$O (200 ml), 25% MeOH in H$_2$O (100 ml), 50% MeOH in H$_2$O (200 ml), and 100% MeOH (100 ml). The desired fractions were pooled and evaporated and the residue was taken up in H$_2$O and lyophilized to give Example 52 (431 mg, 86%) as a white solid.

TLC: R$_f$ 0.45 (7:2:1—i-propanol:NH$_4$OH:H$_2$O) Anal Calc'd for C$_{27}$H$_{25}$FLi$_2$NO$_5$P * 1.11 H$_2$O: C 61.48 H 5.20 N 2.66 F 3.60 P 5.87 Found: C 61.51 H 5.31 N 2.63 F 3.78 P 5.85

Example 53

(S)-4-[ [
[4-(4-Fluorophenyl)-5-methyl-2-(1-methylethyl)-
6-phenyl-3-pyridinyl] ethynyl]hydroxyphosphinyl]
-3-hydroxybutanoic acid, dilithium salt A. 2-[(4-Fluorophenyl)methylene]-4-methyl- 3-oxopentanoic acid, ethyl ester A mixture of 4-fluorobenzaldehyde (3.00 gm, 24 mmol), ethyl isobutyrylacetate (3.82 gm, 24 mmol), piperdine (240 ul), and HOAc (42 ul) was refluxed in benzene (15 ml) with removal of water (Dean-Stark trap) for 22 hours. The cooled mixture was diluted with Et$_2$O and washed successively with 2% HCl, saturated NaHCO$_3$, H$_2$O, and brine, then dried ($Na_2SO_4$), filtered, and stripped to yield an oil. Distillation of the oil (bp 110°–113° C. at 0.25 mm) afforded the title compound (5.32 gm, 83%) as a pale yellow liquid. This reaction has been successfully scaled up to 300 mmol.

TLC: $R_f$ 0.35 (20% EtOAc in hexane) Micro Analyzed for $C_{15}H_{17}FO_3$: Calc'd: C 68.17 H 6.48 F 7.19 Found: C 68.06 H 6.65 F 7.35

B. β-(4-Fluorophenyl)-α-(2-methyl-1-oxopropyl)-Δ oxobenzenepentanoic acid, ethyl ester A –78° C. solution of LiN(TMS)$_2$ (1.0M in THF, 14.1 ml, 14.1 mmol) in dry THF (15 ml) was treated with a solution of propiophenone (1.900 gm, 14.2 mmol) in THF (1.5 ml) over a 5-minute period. After one hour, a solution of the part A compound (3.717 gm, 14.1 mmol) in THF (3 ml) was added dropwise to the above solution. After 1.5 hours, the mixture was quenched with saturated NH$_4$Cl and warmed to room temperature. The mixture was diluted with H$_2$O and subsequently extracted twice with Et$_2$O. The combined Et$_2$O extracts were washed with brine, dried (Na$_2$SO$_4$), filtered, and stripped to give an oil. Flash chromatography (Merck SiO$_2$, 15% EtOAc in hexane) afforded the title compound (4.755 gm, 85%) as a mixture of diastereomers.

TLC: $R_f$ 0.34 & 0.31 (20% EtOAc in hexane)

C. 4-(4-Fluorophenyl)-5-methyl-2-(1-methylethyl)-6-phenyl-3-pyridinecarboxylic acid, ethyl ester A mixture of the part B compound (4.730 gm, 11.87 mmol), NH$_4$OAc (2.745 gm, 35.6 mmol), and Cu(OAc)$_2$ (5.935 gm, 29.7 mmol) in glacial HOAc (30 ml) was gently refluxed for 24 hours. The solution was cooled to room temperature and subsequently poured into an ice cold mixture of concentrated NH$_4$OH (50 ml) in H$_2$O (100 ml). The mixture was extracted twice with Et$_2$O and the pooled Et$_2$O extracts were washed with H$_2$O and brine, then dried (Na$_2$SO$_4$), filtered and stripped to yield an oil. The oil was flashed (Merck SiO$_2$, 20% EtOAc in hexane) to give the title 3 as an oil (3.916 gm, 87%), which slowly solidified on standing.

m.p. 84°–88° C. TLC: $R_f$ 0.47 (20% EtOAc in hexane)

D. 4-(4-Fluorophenyl)-5-methyl-2-(1-methylethyl)- 6-phenyl-3-pyridine methanol

A cold (0° C.) solution of the ester from part C (4.571 gm, 12.11 mmol) in dry THF (60 ml) was treated with LiAlH$_4$ (1.49 gm, 39.3 mmol). Ten minutes after the addition, the cooling bath was removed and the mixture was stirred at room temperature for 4 hours. An additional 500 mg of LiAlH$_4$ was added and stirring was continued for two more hours. The solution was recooled to 0° C. and quenched in succession with H$_2$O (2 ml), 10% NaOH (2.5 ml), and H$_2$O (6 ml). The solution was filtered and the salts were washed with EtOAc. The filtrate was washed with H$_2$O and brine, then dried (Na$_2$SO$_4$). Filtration and removal of the solvent afforded a solid. The solid was recrystallized from hot EtOAc/hexane to provide the title compound (3.729 gm, 92%) as white crystals.

m.p. 182°–184° C. TLC: $R_f$ 0.20 (20% EtOAc in hexane) Microanalysis for $C_{22}H_{22}FNO$: Calc'd: C 78.78 H 6.61 N 4.18 F 5.66 Found: C 78.76 H 6.44 N 4.15 F 5.53

E. 4-(4-Fluorophenyl)-5-methyl-2-(1-methylethyl)- 6-phenyl-3-pyridine carboxaldehyde A –78° C. solution of oxalyl chloride (1.20 ml, 1.75 gm, 13.7 mmol) in CH$_2$Cl$_2$ (60 ml) was treated dropwise with a solution of dry DMSO (2.20 ml, 2.42 gm, 31 mmol) in CH$_2$Cl$_2$ (2 ml). After 15 minutes, a solution of the alcohol from part D (3.625 gm, 10.81 mmol) in CH$_2$Cl$_2$ (10 ml) and THF (10 ml) was added dropwise to the above mixture. Twenty-five minutes after the addition, TEA (8.5 ml) was added and the mixture was stirred at –78° C. for 10 minutes and then warmed to room temperature. The mixture was diluted with Et$_2$O and washed twice with H$_2$O and once with brine. The organic layer was dried (Na$_2$SO$_4$), filtered, and stripped. The residue was triturated with Et$_2$O to give a solid/liquid mixture. The mixture was taken up in hot hexane and cooled to give the aldehyde title compound (3.282 gm, 91%) as white needles.

m.p. 111°–112° C. TLC: $R_f$ 0.51 (20% EtOAc in hexane) Microanalysis for $C_{22}H_{20}FNO$: Calc'd: C 79.25 H 6.05 N 4.20 F 5.70 Found: C 79.28 H 6.10 N 4.13 F 5.63

F. 3-(2,2-Dibromoethenyl)-4-(4-fluorophenyl)- 5-methyl-2-(1-methylethyl)-6 -phenylpyridine A solution of carbon tetrabromide (4.785 gm, 14.4 mmol) in CH$_2$Cl$_2$ (10 ml) was added over a 8-minute period to a cold (0° C.) solution of the aldehyde from part E (3.174 gm, 9.52 mmol) and triphenylphosphine (7.556 gm,, 28.8 mmol) in CH$_2$Cl$_2$ (60 ml). After the addition was complete, the cooling bath was removed and the mixture was stirred for 20 minutes. The solution was quenched with saturated NaHCO$_3$ and extracted twice with CH$_2$Cl$_2$. The combined organic layers were dried (Na$_2$SO$_4$), filtered and concentrated. The concentrate was chromatographed (flash, Merck SiO$_2$, 30% CH$_2$Cl$_2$ in hexane) to give the dibromide title compound as a white solid. The solid was recrystallized from hot hexane to give the product (4.345 gm, 93%) as white crystals.

m.p. 169°–170° C. TLC: $R_f$ 0.58 (20% EtOAc in hexane) Microanalysis for $C_{23}H_{20}Br_2FN$: Calc'd: C 56.47 H 4.12 N 2.86 F 3.88 Br 32.67 Found: C 56.54 H 4.18 N 2.79 F 3.71 Br 32.22

G. (S)-4-[[[4-(4-Fluorophenyl)-5-methyl-2 -(1-methylethyl)-6-phenyl-3-pyridinyl] ethynyl]methoxyphosphinyl]-3-[[(1,1 -dimethylethyl)diphenylsilyl]oxy]butanoic acid, methyl ester A solution of the dibromide from part F (2.000 gm, 4.09 mmol) in THF (10 ml) at –78° C. was treated with n-BuLi (2.5M in hexane, 3.3 ml, 8.25 mmol) over a 1.5-minute period and the resulting clear yellow solution was stirred for 1 hour. The acetylenic anion solution was added dropwise via cannula over a 5-minute period to a –78° C. solution of the phosphonochloridate prepared in Example 57, part G in THF (14 ml). The resulting mixture was stirred at –78° C. for 30 minutes, then quenched with 50% saturated NH$_4$Cl. The solution was warmed to 0° C., diluted with H$_2$O, and poured into saturated NaHCO$_3$. The aqueous phase was extracted once with Et$_2$O. The Et$_2$O layer was washed with brine, dried (Na$_2$SO$_4$), filtered and stripped to give an orange oil. The residue was chromatographed (flash, Merck SiO$_2$, 40% EtOAc in hexane followed by 1:1 EtOAc:hexane) to afford the title compound as a colorless foam (2.169 gm, 69%).

TLC: $R_f$ 0.24 (40% EtOAc in hexane)

H. (S)-4-[[[4-(4-Fluorophenyl)-5-methyl-2 -(1-methylethyl)-6-phenyl-3-pyridinyl] ethynyl]methoxyphosphinyl] -3-hydroxy butanoic acid, methyl ester A mixture of the part G compound (2.136 gm, 2.80 mmol), tetra-n-butylammonium fluoride (1.0M in THF, 8.4 ml, 8.4 mmol), and HOAc (800 ul, 839 mg, 14 mmol) in THF (15 ml) was stirred at room temperature for 18 hours. The solution was diluted with EtOAc and washed three times with 5% KHSO$_4$. The aqueous layers were back-extracted once with EtOAc and the pooled EtOAc layers were dried (Na$_2$SO$_4$), filtered and stripped to afford a yellow oil. The oil was dissolved in Et$_2$O, cooled to 0° C. and treated with excess diazomethane for 20 minutes. The excess diazomethane was destroyed by the addition of HOAc and the solvent was removed in vacuo. The residue was chromatographed (flash, Merck SiO$_2$, 40% acetone in hexane followed by 1:1 acetone:hexane) to afford the title compound (1.200 gm, 82%) as a colorless oil.

TLC: R$_f$ 0.34 (1:1—acetone:hexane)

I. (S)-4-[ [ [4-(4-Fluorophenyl)-5-methyl-2 -(1-methylethyl)-6-phenyl-3-pyridinyl] ethynyl] hydroxyphosphinyl] -3-hydroxybutanoic acid, dilithium salt A solution of the title compound (482 mg, 0.92 mmol) in dioxane (5 ml) was treated with 1N LiOH (3.2 ml, 3.2 mmol) at room temperature and the mixture was subsequently heated at 55° C. under argon for 1.5 hours. The solvent was evaporated and the residue was chromatographed on HP-20, eluting in succession with H$_2$O (200 ml), 25% MeOH in H$_2$O (100 ml), and 50% MeOH in H$_2$O (200 ml). The desired fractions were pooled and evaporated and the residue was taken up in H$_2$O and lyophilized to give Example 53 (392 mg, 81%) as a white solid.

TLC: R$_f$ 0.50 (7:2:1—i-propanol:NH$_4$OH:H$_2$O) Anal. Calc'd for C$_{27}$H$_{25}$FLi$_2$NO$_5$P * 1.06 H$_2$O: C 61.59 H 5.19 N 2.66 F 3.61 P 5.88 Found: C 61.54 H 5.40 N 2.71 F 3.65 P 5.92

Example 54

(S)-4-[ [ [ 2-(1,1-Dimethylethyl)-4-(4-fluorophenyl)- 6-phenyl-3-pyridinyl] ethynyl] hydroxyphosphinyl] -3 -hydroxybutanoic acid, dilithium salt A. 3-(4-Fluorophenyl)-1-phenyl-2-propen-1-one A mixture of acetophenone (7.02 gm, 58.4 mmol), p-fluorobenzaldehyde (7.24 gm, 58.4 mmol) and concentrated H$_2$SO$_4$ (10 ml) in glacial HOAc (116 ml) was stirred at room temperature for 2 days. The solution was poured into H$_2$O (250 ml) and neutralized with 10% NaOH (200 ml). The aqueous layer was extracted once with Et$_2$O and the Et$_2$O layer was washed successively with H$_2$O, saturated NaHCO$_3$ (twice) and brine, then dried (magnesium sulfate). Filtration and removal of the solvent afforded a yellow solid, which was recrystallized from hot hexane to give the title compound (7.94 gm, 60%) as light yellow needles.

m.p. 86°–88° C. TLC: R$_f$= 0.36 (20% EtOAc in hexane) Anal. Calc'd for C$_{15}$H$_{11}$FO: C 79.63 H 4.90 F 8.40 Found: C 79.76 H 4.95 F 8.50

B. β-(4-Fluorophenyl-α-(2,2-dimethyl-1-oxopropyl)-Δ-oxobenzenepentanoic acid, ethyl ester A mixture of compound A (5.157 gm, 22.8 mmol) and ethyl pivaloylacetate (5.100 gm, 29.6 mmol) in absolute EtOH (100 ml) was treated with a solution of EtONa in EtOH (21% by weight solution, 1.28 ml, 3.4 mmol). After stirring at room temperature for 22 hours, a thick precipitate had formed. The mixture was diluted with EtOAc and poured into 50% saturated NH$_4$Cl. The EtOAc layer was washed with H$_2$O twice and brine, then dried (Na$_2$SO$_4$), filtered and stripped to yield a solid. The solid was recrystallized from hot EtOAc/hexane to afford the title compound, a mixture of diastereomers, as a white amorphous solid (8.673 gm, 95%).

TLC: R$_f$ 0.26 and 0.23 (20% EtOAc in hexane)

C. 2-(1,1-Dimethylethyl)-4-(4-fluorophenyl)- 6-phenyl-3-pyridinecarboxylic acid, ethyl ester A mixture of the compound of part B (8.440 gm, 21.2 mmol), NH$_4$OAc (4.92 gm, 63.8 mmol), and Cu(OAc)$_2$ (10.50 gm, 52.6 mmol) in glacial HOAc (55 ml) was gently refluxed for six hours. The solution was cooled to room temperature and subsequently poured into an ice cold mixture of concentrated NH$_4$OH (91 ml) in H$_2$O (180 ml). The mixture was extracted with Et$_2$O and the Et$_2$O extract was washed with H$_2$O and brine, then dried (Na$_2$SO$_4$), filtered and stripped to yield a dark red oil. The oil was flashed (Merck SiO$_2$, 5% EtOAc in hexane) to afford ester C (5.347 gm, 67%) as a red oil which slowly solidified on standing.

TLC: R$_f$ 0.55 (20% EtOAc in hexane)

D. 2-(1,1-Dimethylethyl)-4-(4-fluorophenyl)- 6-phenyl-3-pyridine methanol

A solution of the ester prepared in part C (5.319 gm, 14.1 mmol) in THF (100 ml) was treated with LiAlH$_4$ (2.58 gm, 68 mmol) and subsequently stirred at room temperature for two days. TLC analysis showed essentially no reaction. The mixture was refluxed for 9 hours and then stirred at room temperature for an additional 13 hours. The cooled (0° C.) reaction mixture was quenched successively with H$_2$O (2.6 ml), 10% NaOH (2.6 ml), and H$_2$O (8 ml). The solids were removed by filtration and the aluminum salts were washed with EtOAc. The filtrate was stripped and the resulting orange oil was flashed (Merck SiO$_2$, 20% EtOAc in hexane) to obtain a mixture of pure and impure product. The impure fractions were rechromatographed (Merck SiO$_2$, 20% EtOAc in hexane) and the pure fractions were pooled with the above to yield the title compound (1.478 gm, 31%) as a yellow oily foam.

TLC: R$_f$ 0.40 (20% EtOAc in hexane)

E. 2-(1,1-Dimethylethyl)-4-(4-fluorophenyl)- 6-phenyl-3-pyridine carboxaldehyde

A −78° C. solution of oxalyl chloride (580 ul, 844 mg, 6.65 mmol) in CH$_2$Cl$_2$ (23 ml) was treated dropwise with a solution of dry DMSO (950 ul, 1.05 gm, 13.4 mmol) in CH$_2$Cl$_2$ (1.5 ml). After 20 minutes, a solution of alcohol D (1.459 gm, 4.35 mmol) in CH$_2$Cl$_2$ (4 ml) was addded dropwise to the above mixture. Thirty minutes after the addition, TEA (4.0 ml) was added and the mixture was stirred at −78° C. for 15 minutes and then warmed to room temperature. The mixture was diluted with Et$_2$O and washed twice with H$_2$O and once with brine. The organic layer was dried (Na$_2$SO$_4$), filtered, and stripped to yield an oil. The oil was purified by flash chromatography (Merck SiO$_2$, 5% EtOAc in hexane) to give slightly impure aldehyde (title compound) as an oil which solidified on standing. Recrystallization of the solid from hot hexane afforded the title compound as a pale yellow solid (1.125 gm, 78%).

m.p. 101°–102° C. TLC: R$_f$ 0.52 (20% EtOAc in hexane) Microanalysis for C$_{22}$H$_{20}$FNO: Calc'd: C 79.25 H 6.05 N 4.20 F 5.70 Found: C 78.99 H 6.13 N 4.27 F 5.77

F. 3-(2,2-Dibromoethenyl)-2-(1,1-dimethylethyl)- 4-(4-fluorophenyl)-6-phenyl pyridine A cold (−7° C.) solution of the aldehyde from part E (729 mg, 2.19 mmol) and triphenylphosphine (2.248 gm, 8.6 mmol) in CH$_3$CN (15 ml) and CH$_2$Cl$_2$ (4 ml) was treated with a solution of CBr$_4$ (1.632 gm, 4.92 mmol) in CH$_3$CN (4 ml) over a 10-minute period. The cooling was removed and the mixture was stirred at room temperature for 24 hours. The solution was quenched with saturated NaHCO$_3$ and extracted twice with CH$_2$Cl$_2$. The combined organic layers were dried (Na$_2$SO$_4$), filtered and concentrated. The concentrate was chromatographed (flash, Merck SiO$_2$, 20% CH$_2$Cl$_2$ in hexane) to give the dibromide (title compound) (810 mg, 75%) as a colorless oil.

TLC: R$_f$ 0.53 (10% EtOAc in hexane)

G. (S)-4-[[[2-(1,1-Dimethylethyl)-4-(4 -fluorophenyl)-6-phenyl-3-pyridinyl] ethynyl]methoxyphosphinyl]-3-[[(1,1 -dimethylethyl)diphenylsilyl]oxy]butanoic acid, methyl ester A solution of the dibromide of part F (1.262 gm, 2.58 mmol) in THF (8 ml) at −78° C. was treated with n-BuLi (2.5M in hexane, 2.2 ml, 5.5 mmol) over a 1-minute period and the resulting dark blue-green solution was stirred for 1 hour. The acetylenic anion solution was added dropwise via cannula over a 4-minute period to a −78° C. solution of the phosphonochloridate of Example 57, part G, in THF (12 ml). The resulting mixture was stirred at −78° C. for 45 minutes, then quenched with 50% saturated NH$_4$Cl. The solution was warmed to room temperature, diluted with H$_2$O, and poured into saturated NaHCO$_3$. The aqueous phase was extracted once with Et$_2$O. The Et$_2$O layer was washed with brine, dried (Na$_2$SO$_4$), filtered and stripped to give an orange oil. The residue was chromatographed (flash, Merck SiO$_2$, 40% EtOAc in hexane) to afford the title compound as an off-white foam (698 mg, 35%).

TLC: R$_f$ 0.30 (40% EtOAc in hexane)

H. (S)-4-[[[2-(1,1-Dimethylethyl)-4-(4 -fluorophenyl)-6-phenyl-3-pyridinyl] ethynyl]methoxyphosphinyl]-3-hydroxy butanoic acid, methyl ester A mixture of the compound of part G (689 mg, 0.902 mmol), tetra-n-butylammonium fluoride (1.0M in THF, 2.7 ml, 2.7 mmol), and HOAc (280 ul, 294 mg, 4.9 mmol) in THF (10 ml) was stirred at room temperature for 16 hours. An additional 900 µl of TBAF solution was added to the mixture and stirring was continued for two more hours. The solution was poured into saturated NaHCO$_3$ and extracted with EtOAc. The EtOAc layer was washed with brine, dried (Na$_2$SO$_4$), filtered and stripped to afford a yellow oil. The residue was chromatographed (flash, Merck SiO$_2$, 40% acetone in hexane) to afford the title compound (273 mg, 58%) as a colorless oil.

TLC: R$_f$ 0.37 (1:1—acetone:hexane)

I. (S)-4-[[[2-(1,1-Dimethylethyl)-4-(4 -fluorophenyl)-6-phenyl-3-pyridinyl] ethynyl]hydroxyphosphinyl]-3-hydroxybutanoic acid, dilithium salt A solution of compound H (254 mg, 0.485 mmol) in dioxane (3 ml) was treated with 1N LiOH (1.8 ml, 1.8 mmol) at room temperature and the mixture was subsequently heated at 55° C. under argon for 1.5 hours. The solvent was evaporated and the residue was chromatographed on HP-20 eluting in succession with H$_2$O (150 ml), 25% MeOH in H$_2$O (100 ml), and 50% MeOH in H$_2$O (200 ml). The desired fractions were pooled and evaporated and the residue was taken up in H$_2$O and lyophilized to give Example 54 (210 mg, 82%) as a white solid.

TLC: R$_f$ 0.50 (7:2:1—i-propanol:NH$_4$OH:H$_2$O) Anal. Calc'd for C$_{27}$H$_{25}$FLi$_2$NO$_5$P * 1.01 H$_2$O: C 61.69 H 5.18 N 2.67 F 3.61 P 5.89 Found: C 61.74 H 5.16 N 2.62 F 3.55 P 5.82

Example 55

(S)-4-[[[4-(4-Fluorophenyl)-2-(1-methylethyl)-5H-indeno[1,2-b]pyridin-3-yl]ethynyl]hydroxyphosphinyl]-3-hydroxybutanoic acid, dilithium salt A. β-(4-Fluorophenyl)-2,3-dihydro-α-(2 -methyl-1-oxopropyl)-1-oxo-1H-indene-2 -propanoic acid, ethyl ester A −78° C. solution of LiN(TMS)$_2$ (1.0M in THF, 19 ml, 19 mmol) in dry THF (25 ml) was treated with a solution of 1-indanone (2.50 gm, 19 mmol) in THF (3 ml) over a 2-minute period. After 50 minutes, a solution of the compound prepared in part A of Example 53 (5.00 gm, 19 mmol) in THF (5 ml) was added dropwise to the above solution. After one hour, the mixture was quenched with saturated NH$_4$Cl and warmed to room temperature. The mixture was diluted with H$_2$O and subsequently extracted twice with Et$_2$O. The combined Et$_2$O extracts were washed with brine, dried (Na$_2$SO$_4$), filtered, and stripped to yield a brown cloudy oil. Flash chromatography (Merck SiO$_2$, 20% EtOAc in hexane) afforded the impure title compound (4.671 gm, oil/solid) as a complex material of diastereomers. The material was used directly in the next reaction.

TLC: R$_f$ 0.30, 0.24, & 0.20 (20% EtOAc in hexane)

B. 4-(4-Fluorophenyl)-2-(1-methylethyl)-5H-indeno[1,2-b]pyridine-3-carboxylic acid, ethyl ester A mixture of the crude compound of part A (4.671 gm), NH$_4$OAc (2.74 gm, 35.5 mmol), and Cu(OAc)$_2$ (5.88 gm, 29.5 mmol) in glacial HOAc (30 ml) was gently refluxed for 6 hours. The solution was cooled to room temperature and subsequently poured into an ice cold mixture of concentrated NH$_4$OH (50 ml) in H$_2$O (100 ml). The mixture was extracted once with Et$_2$O and once with EtOAc and the pooled organic extracts were washed with H$_2$O and brine, then dried (Na$_2$SO$_4$), filtered and stripped to yield a dark brown oil. TLC showed the reaction had not gone to completion. The oil was flashed (Merck SiO$_2$, 10% EtOAc in hexane) to give the title compound as a pinkish oil (1.416 gm, 20% from compound 1).

TLC: R$_f$ 0.48 (20% EtOAc in hexane)

C. 4-(4-Fluorophenyl)-2-(1-methylethyl)-5H-indeno[1,2-b]pyridine-3-methanol

A solution of the ester from part B (1.410 gm, 3.76 mmol) in dry THF (50 ml) was treated with LiAlH$_4$ (740 mg, 19.5 mmol). The deep purple reaction mixture was stirred at room temperature for 7.5 hours. The solution was then cooled to 0° C. and quenched in succession with H$_2$O (1 ml), 10% NaOH (1 ml), and H$_2$O (3 ml). The solution was filtered and the salts were washed with EtOAc and Et$_2$O. The filtrate was dried (Na$_2$SO$_4$), filtered and stripped of solvent to afford an oil. The oil was flashed (Merck SiO$_2$, 20% EtOAc in hexane) to provide the desired alcohol title compound (791 mg, 63%, 93% based on recovered ester) as a white solid and unreacted ester (454 mg). Analytically pure material was obtained by recrystallization from hot EtOAc/hexane.

m.p. 165.5°–167° C. TLC: R$_f$ 0.25 (20% EtOAc in hexane) Microanalysis for C$_{22}$H$_{20}$FNO * 0.12 H$_2$O: Calc'd: C 78.74 H 6.08 N 4.17 F 5.66 Found: C 78.74 H 6.15 N 4.17 F 5.64

D. 4-(4-Fluorophenyl)-2-(1-methylethyl)-5H-indeno[1,2-b]pyridine-3-carboxaldehyde A −78° C. solution of oxalyl chloride (280 ul, 407 mg, 3.21 mmol) in CH$_2$Cl$_2$ (10 ml) was treated dropwise with a solution of dry DMSO (455 ul, 501 mg, 6.4 mmol) in CH$_2$Cl$_2$ (1.5 ml). After 15 minutes, a solution of the alcohol from part C (764 mg, 2.29 mmol) in THF (3 ml) was added dropwise to the above mixture. Twenty minutes after the addition, TEA (2 ml) was added and the mixture was stirred at −78° C. for 5 minutes and then warmed to room temperature. The mixture was diluted with Et$_2$O and washed twice with H$_2$O and once with brine. The organic layer was dried (Na$_2$SO$_4$), filtered, and stripped to give a solid residue. The residue was flashed (Merck SiO$_2$, 10% EtOAc in hexane) providing the slightly impure aldehyde title compound (705 mg). The solid was recrystallized from hot hexane to give the title compound (637 mg, 84%) as white crystals.

m.p. 142.5°–143.7° C. TLC: R$_f$ 0.48 (20% EtOAc in hexane)

E. 3-(2,2-Dibromoethenyl)-4-(4-fluorophenyl)- 2-(1-methylethyl)-5H-indeno[1,2-b]pyridine A solution of carbon tetrabromide (940 mg, 2.83 mmol) in CH$_2$Cl$_2$ (2 ml) was added over a 4-minute period to a cold (−7° C.) solution of the aldehyde from part D (626 mg, 1.89 mmol) and triphenylphosphine (1.486 gm, 5.67 mmol) in CH$_2$Cl$_2$ (11 ml). After the addition was complete, the cooling bath was removed and the mixture was stirred at room temperature for 30 minutes. The solution was quenched with saturated NaHCO$_3$ and extracted twice with CH$_2$Cl$_2$. The combined organic layers were dried (Na$_2$SO$_4$), filtered and concentrated. The concentrate was chromatographed (flash, Merck SiO$_2$, 20% CH$_2$Cl$_2$ in hexane) to give the impure dibromide title compound. The product was rechromatographed to provide the title pure compound (632 mg, 69%) as a white foam.

TLC: R$_f$ 0.32 (10% EtOAc in hexane)

F. (S)-4-[[[4-(4-Fluorophenyl)-2-(1-methylethyl)- 5H-indeno[ 1,2-b]pyridin-3-yl] ethynyl]methoxyphosphinyl]-3-[ [ (1,1-dimethylethyl)diphenylsilyl]oxy]butanoic acid, methyl ester A solution of the dibromide from part E (622 mg, 1.28 mmol) in THF (8 ml) at −78° C. was treated with n-BuLi (2.5M in hexane, 1.2 ml, 3 mmol) over a 1-minute period and the resulting deep purple-blue solution was stirred at −78° C. for 1 hour. The acetylenic anion solution was added dropwise via cannula over a 2-minute period to a −78° C. solution of the phosphonochloridate from Example 57, part G in THF (8 ml). The resulting mixture was stirred at −78° C. for 30 minutes, then quenched with 50% saturated NH$_4$Cl. The solution was warmed to 0° C. and poured into saturated NaHCO$_3$. The aqueous phase was extracted once with Et$_2$O. The Et$_2$O layer was washed with brine, dried (Na$_2$SO$_4$), filtered and stripped to give an oil. The residue was chromatographed (flash, Merck SiO$_2$, 40% EtOAc in hexane) to afford the title compound as a colorless foam (305 mg, 31%).

TLC: R$_f$ 0.25 (40% EtOAc in hexane)

G. (S)-4-[[[4-(4-Fluorophenyl)-2-(1-methylethyl)- 5H-indeno[ 1,2-b]pyridin-3-yl] ethynyl]methoxyphosphinyl]-3-hydroxy butanoic acid, methyl ester A mixture of the compound of part F (304 mg, 0.40 mmol), tetra-n-butylammonium fluoride (1.0M in THF, 1.6 ml, 1.6 mmol), and HOAc (115 ul, 121 mg, 2 mmol) in THF (8 ml) was stirred at room temperature for 20 hours. The solution was diluted with EtOAc and washed three times with 5% KHSO$_4$. The aqueous layers were back-extracted once with EtOAc and the pooled EtOAc layers were dried (Na$_2$SO$_4$), filtered and stripped to afford a yellow oil. The oil was dissolved in Et$_2$O, cooled to 0° C. and treated with excess diazomethane for 10 minutes. The excess diazomethane was destroyed by the addition of HOAc and the solvent was removed in vacuo. The residue was chromatographed (flash, Merck SiO$_2$, 40% acetone in hexane) to afford the title compound (165 mg, 79%) as a yellow foam.

TLC: R$_f$ 0.31 (1:1—acetone:hexane)

H. (S)-4-[ [ [ 4-(4-Fluorophenyl)-2-(1-methylethyl)- 5H-indeno[1,2-b]pyridin-3-yl] ethynyl] hydroxyphosphinyl] -3-hydroxybutanoic acid, dilithium salt A solution of the compound of part G (164 mg, 0.314 mmol) in dioxane (3 ml) was treated with 1N LiOH (1.1 ml, 1.1 mmol) at room temperature and the mixture was subsequently heated at 65° C. under argon for 2 hours. The solvent was evaporated and the residue was chromatographed on HP-20, eluting in succession with H$_2$O (200 ml), 25% MeOH in H$_2$O (100 ml), and 50% MeOH in H$_2$O (200 ml). The desired fractions were pooled and evaporated and the residue was taken up in H$_2$O and lyophilized to give Example 55 (124 mg, 75%) as a pale yellow solid.

TLC: R$_f$ 0.40 (7:2:1—i-propanol:NH$_4$OH:H$_2$O) Anal. Calc'd for C$_{27}$H$_{23}$FLi$_2$NO$_5$P * 1.31 H$_2$O: C 61.30 H 4.88 N 2.65 F 3.59 P 5.85 Found: C 61.29 H 4.74 N 2.66 F 3.57 P 5.72

Example 56

(S)-4-[[[5,6-Diphenyl-4-(4-fluorophenyl)-2-(1-methylethyl)-3-pyridinyl]ethynyl]hydroxyphosphinyl] -3-hydroxybutanoic acid, disodium salt A. β-(4-Fluorophenyl)-α-(2-methyl-1-oxopropyl)-Δ-oxo-γ-phenylbenzenepentanoic acid, ethyl ester A −78° C. solution of LiN(TMS)$_2$ (1.0M in THF, 29 ml, 29 mmol) was treated with a solution of deoxybenzoin (5.684 gm, 29 mmol) in THF (10 ml) over a 2-minute period. After 20 minutes, a solution of the compound of part A in Example 53 (5.468 gm, 20.7 mmol) in THF (5 ml) was added dropwise to the above solution. The mixture was stirred at −78° C. for one hour and then warmed to 0° C. (the solution became clear orange). After 1.5 hours, the mixture was quenched with HOAc (3.3 ml), diluted with saturated NH$_4$Cl and H$_2$O and subsequently extracted with Et$_2$O. The Et$_2$O extract was washed with H$_2$O and brine, then dried (Na$_2$SO$_4$), filtered, and stripped to yield a solid/liquid mixture. The material was used directly in the next reaction.

TLC: R$_f$ 0.34, 0.28, & 0.24 (20% EtOAc in hexane)

B. 4-(4-Fluorophenyl)-2-(1-methylethyl)-5,6 -diphenyl-3-pyridinecarboxylic acid, ethyl ester The aforementioned crude mixture of the compound from part A, NH$_4$OAc (4.40 gm, 57.1 mmol), and Cu(OAc)$_2$ (12.5 gm, 62.6 mmol) in glacial HOAc (50 ml) was gently refluxed for 20 hours. The solution was cooled to room temperature and subsequently poured into an ice cold mixture of concentrated NH$_4$OH (60 ml) in H$_2$O (70 ml). The mixture was extracted once with Et$_2$O and the organic extract was washed with H$_2$O and brine, then dried (Na$_2$SO$_4$), filtered and stripped to yield an oil which solidified on standing. The solid was dissolved in EtOAc and was flashed (Merck SiO$_2$, 10% EtOAc in hexane) to give a mixture of the title compound and deoxybenzoin as a solid. The solid was recrystallized from hot EtOAc/hexane to provide pure ester 3 (5.473 gm, 60% from 1). The mother liquor contained solids (1.4 gm) which were comprised of a 1:1 mixture of the title compound and deoxybenzoin.

m.p. 135.2°–136.3° C. TLC: R$_f$ 0.51 (20% EtOAc in hexane) Microanalysis for C$_{29}$H$_{26}$FNO$_2$: Calc'd: C 79.25 H 5.96 N 3.19 F 4.32 Found: C 79.24 H 5.86 N 3.21 F 4.26

C. 4-(4-Fluorophenyl)-2-(1-methylethyl)-5,6 -diphenyl-3-pyridinemethanol

A cold (0° C.) solution of the ester from part B (5.490 gm, 12.5 mmol) in dry THF (120 ml) was treated with LiAlH$_4$ (1.916 gm, 50.5 mmol). The ice bath was removed and the mixture was stirred at room temperature for 1.75 hours. The solution was then cooled to 0° C. and quenched in succession with H$_2$O (2 ml), 10% NaOH (3 ml), and H$_2$O (6 ml). The solution was filtered and the salts were washed with EtOAc. The filtrate was stripped of solvent to afford a yellow solid. The residue was recrystallized from hot EtOAc/ hexane to provide the title compound (4.260 gm, 86%) as a white solid.

m.p. 169°–171° C. TLC: R$_f$ 0.17 (20% EtOAc in hexane) Microanalysis for C$_{27}$H$_{24}$FNO: Calc'd: C 81.58 H 6.09 N 3.52 F 4.78 Found: C 81.78 H 6.17 N 3.61 F 4.66

D. 4-(4-Fluorophenyl)-2-(1-methylethyl)-5,6 -diphenyl-3-pyridinecarboxaldehyde

A −78° C. solution of oxalyl chloride (790 μl, 1.15 gm, 9.1 mmol) in CH$_2$Cl$_2$ (30 ml) was treated dropwise with a solution of dry DMSO (1.30 ml, 1.43 gm, 18.3 mmol) in CH$_2$Cl$_2$ (2.5 ml). After 15 minutes, a solution of the alcohol from part C (3.000 gm, 7.55 mmol) in THF (9 ml) was added dropwise to the above mixture. Twenty five minutes after the addition, TEA (6 ml) was added and the mixture was stirred at −78° C. for 5 minutes and then warmed to room temperature. The mixture was diluted with Et$_2$O and washed twice with H$_2$O and once with brine. The organic layer was dried (Na$_2$SO$_4$), filtered, and stripped to give a solid residue. The solid was recrystallized from hot Et$_2$O/hexane to give the aldehyde title compound (2.621 gm, 88%) as white needles.

m.p. 136°–137.5° C. TLC: $R_f$ 0.50 (20% EtOAc in hexane)

E. 3-(2,2-Dibromoethenyl)-4-(4-fluorophenyl)- 2-(1-methylethyl)-5,6-diphenylpyridine A solution of carbon tetrabromide (3.354 gm, 10.1 mmol) in $CH_2Cl_2$ (10 ml) was added over a 5-minute period to a cold (–6° C.) solution of the aldehyde from part D (2.649 gm, 6.70 mmol) and triphenylphosphine (5.270 gm, 20.1 mmol) in $CH_2Cl_2$ (30 ml). After the addition was complete, the cooling bath was removed and the mixture stirred at room temperature for 40 minutes. The solution was quenched with saturated $NaHCO_3$ and extracted once with $CH_2Cl_2$. The organic layer was dried ($Na_2SO_4$), filtered and concentrated. The concentrate was chromatographed (flash, Merck $SiO_2$, 50% $CH_2Cl_2$ in hexane) to give dibromide title compound as a foam which solidified on standing. Recrystallization of the material provided the pure title compound (3.305 gm, 89%) as a white solid.

m.p. 154.5°–157.5° C. TLC: $R_f$ 0.56 (20% EtOAc in hexane)

F. (S)-4-[[[5,6-Diphenyl-4-(4-fluorophenyl)- 2-(1-methylethyl)-3-pyridinyl] ethynyl]methoxyphosphinyl]-3-[[(1,1 -dimethylethyl)diphenylsilyl]oxy]butanoic acid, methylester A solution of the dibromide from part E (2.500 gm, 4.53 mmol) in THF (12 ml) at –78° C. was treated with n-BuLi (2.5M in hexane, 3.90 ml, 9.7 mmol) over a 1-minute period and the resulting clear brown solution was stirred at –78° C. for 1 hour. The acetylenic anion solution was added dropwise via cannula over a 3-minute period to a –78° C. solution of the phosphonochloridate from Example 57, part G in THF (15 ml). The resulting mixture was stirred at –78° C. for 30 minutes, then quenched with 50% saturated $NH_4Cl$. The solution was warmed to 0° C. and poured into saturated $NaHCO_3$. The aqueous phase was extracted once with $Et_2O$. The $Et_2O$ layer was washed with brine, dried ($Na_2SO_4$), filtered and stripped to give an orange oil. The residue was chromatographed (flash, Merck $SiO_2$, 40% EtOAc in hexane) to afford the title compound as a colorless foam (2.670 gm, 71%).

TLC: $R_f$ 0.25 (40% EtOAc in hexane)

G. (S)-4-[[[5,6-Diphenyl-4-(4-fluorophenyl)- 2-(1-methylethyl)-3-pyridinyl] ethynyl]methoxyphosphinyl]-3-hydroxybutanoic acid, methylester A mixture of the compound of part F (2.617 gm, 3.17 mmol), tetra-n-butylammonium fluoride (1.0 M in THF, 9.5 ml, 9.5 mmol), and HOAc (725 ul, 760 mg, 12.7 mmol) in THF (20 ml) was stirred at room temperature for 17 hours. The solution was diluted with EtOAc and washed twice with 5% $KHSO_4$. The aqueous layers were back-extracted once with EtOAc and the pooled EtOAc layers were dried ($Na_2SO_4$), filtered and stripped to afford a yellow oil. The oil was dissolved in $Et_2O$, cooled to 0° C. and treated with excess diazomethane for 10 minutes. The excess diazomethane was destroyed by the addition of HOAc and the solvent was removed in vacuo. The residue was chromatographed (flash, Merck $SiO_2$, 40% acetone in hexane followed by 1:1 acetone:hexane) to afford the title compound (1.408 gm, 76%) as a white solid.

m.p. 143°–145.5° C. TLC: $R_f$ 0.36 (1:1—acetone:hexane)

H. (S)-4-[ [ [5,6-Diphenyl-4-(4-fluorophenyl)- 2-(1-methylethyl)-3-pyridinyl] ethynyl] hydroxyphosphinyl] -3-hydroxybutanoic acid, disodium salt A solution of the compound from part G (498 mg, 0.85 mmol) in dioxane (6 ml) was treated with 1 N NaOH (3.0 ml, 3.0 mmol) at room temperature and the mixture was subsequently heated at 60° C. under argon for 1.5 hours. The solvent was evaporated and the residue was chromatographed on HP-20 eluting in succession with $H_2O$ (200 ml), 25% MeOH in $H_2O$ (100 ml), and 50% MeOH in $H_2O$ (200 ml). The desired fractions were pooled and evaporated and the residue was taken up in $H_2O$ and lyophilized to give Example 56 (480 mg, 91%) as a white solid.

TLC: $R_f$ 0.18 (8:1:1—$CH_2Cl_2$:HOAc:MeOH) Anal. Calc'd for $C_{32}H_{27}FNNa_2O_5P$ * 1.22 $H_2O$: C 61.64 H 4.76 N 2.25 F 3.05 P 4.97 Found: C 61.66 H 4.95 N 2.30 F 3.14 P 4.88

Example 57

(S)-4-[ [ [ 4-(4-Fluorophenyl)-2-(1-methylethyl)- 6-(2-methylphenyl)-3-pyridinyl] ethynyl] hydroxyphosphinyl] -3-hydroxybutanoic acid, dilithium salt A. 3-(4-Fluorophenyl)-1-(2-methylphenyl)- 2-propen-1-one A mixture of 4-fluorobenzaldehyde (12.13 ml, 110 mmol, from Aldrich) and 2'-methylacetophenone (14.4 ml, 110 mmol, Aldrich) in absolute ethanol (120 ml) was treated with a solution of sodium ethoxide in ethanol (21% by weight solution; 4.1 ml, 11 mmol). The clear, dark reaction mixture was stirred at room temperature under argon for 24 hours. The reaction mixture was concentrated to ⅓ volume, and partitioned between 50% saturated $NH_4Cl$ and EtOAc. The layers were separated and the organic layer washed twice with $H_2O$ and brine, then dried ($Na_2SO_4$) and concentrated under reduced pressure. The product was obtained as a yellow oil (26.0 g, 100.0%) and used without further purification.

$R_f$ 0.54 (30% EtOAc/hexane), UV

B. β-(4-Fluorophenyl)-2-methyl-α-(2-methyl- 1-oxopropyl)-Δ-oxobenzenepentanoic acid, ethyl ester A mixture of the part A compound (15.18 g, 63.2 mmol) and ethyl isobutyrylacetate (10,0 g, 63.2 mmol) in absolute ethanol (150 ml) was treated with a solution of sodium ethoxide in ethanol (21% by weight solution, 2.43 ml, 6.32 mmol). A precipitate soon fell out of solution. After stirring at room temperature for 16 hours, the mixture was cooled to –10° C. and the precipitate was collected by filtration (15.17 g, white solids). The filtrate was concentrated to ⅓ volume, partitioned between 50% saturated $NH_4Cl$ and EtOAC. The layers were separated and the organic layer was washed with $H_2O$ (twice) and brine, then dried ($Na_2SO_4$) and concentrated under reduced pressure. The obtained oil was dissolved in hot hexane and cooled to produce a solid (6.0 g). Both crops were combined and recrystallized from hot hexane, yielding the title compound as a white solid (21.07 g, 84.0%; mixture of diastereomers).

m.p. 105°–106° C. $R_f$ 0.42 (30% EtOAc/hexane), UV Analysis for $C_{24}H_{27}FO_4$: Calc'd: C, 72.34; H, 6.83; F, 4.77 Found: C, 72,12; H, 6.89; F, 4.72

C. 4-(4-Fluorophenyl)-2-(1-methylethyl)-6 -(2-methylphenyl)-3-pyridinecarboxylic acid, ethyl ester A mixture of the part B compound (21.0 g, 52.70 mmol), ammonium acetate (12.18 g, 158.3 mmol) and copper (II) acetate (25.9 g, 131.75 mmol) in glacial acetic acid (150 ml) was heated at 110° C. for 20 hours (TLC indicated only a trace of starting material). The solution was cooled to room temperature and poured into an ice cold mixture of concentrated $NH_4OH$ (180 ml) and $H_2O$ (240 ml). The mixture was extracted with ether and the ether extract was washed with $H_2O$ (twice) and brine, then dried ($MgSO_4$), filtered and concentrated to yield the title compound as a yellow oil (19.9 g, 100.0%). The crude material was used directly in the next reaction.

R$_f$ 0.58 (30% EtOAc/hexane), UV

D. 4-(4-Fluorophenyl)-2-(1-methylethyl)-6-(2-methylphenyl)-3-pyridinemethanol

A cold (0° C.) solution of the crude ester from part C (19.9 g, 52.7 mmol) in dry THF (250 ml) was treated with LiAlH$_4$ (6.00 g, 158 mmol). Ten minutes after the addition, the cooling bath was removed and the reaction mixture was stirred at room temperature for 2 hours (TLC indicated the absence of starting material). The dark solution was cooled to 0° C. and, while stirring, carefully quenched first by dropwise addition of 6.0 ml of H$_2$O in THF (50 ml), then with 6.0 ml 15% NaOH, and finally with 12.0 ml H$_2$O. The precipitated aluminum salts were filtered and washed with EtOAc and ether. The filtrate was washed with H$_2$O and brine, dried (Na$_2$SO$_4$) filtered and concentrated under reduced pressure. The solid residue was recrystallized from hot EtOAc/hexane, yielding the compound as a white solid (13.5 g, 76.7%, from the part C compound).

m.p. 114°–115° C. R$_f$ 0.51 (30% EtOAc/hexane), UV

Analysis for C$_{22}$H$_{22}$NFO×0.22 H$_2$O: Calc'd: C, 77.84; H, 6.67; N,4.13; F, 5.60 Found: C, 78.20; H, 6.80; N,3.77; F, 5.64

E. 4-(4-Fluorophenyl)-2-(1-methylethyl)-6-(2-methylphenyl)-3-pyridinecarboxaldehyde A −78° C. solution of oxalyl chloride (1.25 ml, 14.3 mmol) in CH$_2$Cl$_2$ (80 ml) was treated dropwise with a solution of dry DMSO (2.03 ml, 28.6 mmol) in CH$_2$Cl$_2$ (2 ml). After 15 minutes, a solution of the alcohol from part D (4.0 g, 11.93 mmol) in CH$_2$Cl$_2$ (15 ml) was added dropwise to the above solution. After 20 minutes, triethylamine (9.9 ml, 71.58 mmol) was added and the mixture was stirred at −78° C. for 20 minutes and then warmed to room temperature. The mixture was diluted with ether and washed with H$_2$O (twice) and brine, then dried (MgSO$_4$), filtered and concentrated under reduced pressure. The yellow solid residue (4.0 g) was recrystallized from hot hexane. The title compound was obtained as a white crystalline material (3.0 g, 75.6%).

m.p. 138°–140° C. R$_f$ 0.57 (30% EtOAc/hexane), UV

Analysis for C$_{22}$H$_{20}$NFO: Calc'd: C, 79.25; H, 6.05; N,4.20; F, 5.70 Found: C, 79.13; H, 6.08; N,4.19; F, 5.53

F. 3-(2,2-Dibromoethenyl)-4-(4-fluorophenyl)-2-(1-methylethyl)-6-(2-methylphenyl)pyridine A solution of carbon tetrabromide (4.47 g, 13.5 mmol) in CH$_2$Cl$_2$ (15 ml) was added dropwise over a 5-minute period to a cold (0° C.) solution of the aldehyde from part E (3.0 g, 9.0 mmol) and triphenylphosphine (7.08 g, 127.0 mmol) in CH$_2$Cl$_2$ (60 ml). The mixture was stirred at 0° C. for 10 minutes and then at room temperature for 10 minutes. The solution was quenched with saturated NaHCO$_3$ and extracted twice with CH$_2$Cl$_2$. The combined organic layers were dried (Na$_2$SO$_4$), filtered, concentrated to half volume and applied on Merck silica gel column (50% CH$_2$Cl$_2$/hexane). Flash chromatography afforded the title compound as a colorless viscous oil that slowly solidified on standing (4.0 g, 90.0%).

m.p. 108°–110° C. R$_f$ 0.62 (20% EtOAc/hexane), UV

Analysis for C$_{23}$H$_{20}$NFBr$_2$: Calc'd: C, 56.47; H, 4.12; N, 2.86; F, 3.88 Found: C, 56,38; H, 4.04; N, 2.90; F, 3.71

G. (S)-4-Chloromethoxyphosphonyl-3-[[(1,1-dimethylethyl)diphenylsilyl]oxy] butanoic acid, methyl ester The title compound was prepared as described in Example 4, part C, first paragraph, except as described below. (S)-4-(Hydroxymethoxyphosphinyl)- 3-[[(1,1-dimethylethyl)diphenylsilyl]oxy] butanoic acid, methyl ester, dicyclohexylamine (1:1) salt (3.88 g, 6.15 mmol was partitioned between EtOAc and 5% KHSO$_4$. The EtOAc layer was washed (3× 5% KHSO$_4$, then with brine), dried (Na$_2$SO$_4$), filtered and concentrated under reduced pressure to afford the phosphinic acid monomethyl ester as a colorless oil. The oil was dissolved in dry CH$_2$Cl$_2$ (15 ml) and treated with N,N-diethyltrimethylsilylamine (2.33 ml, 12.3 mmol). After stirring at room temperature for 1 hour, the solvent was removed in vacuo and the residue was azeotroped with dry benzene (30 ml). The residue was redissolved in dry CH$_2$Cl$_2$ (15 ml), cooled to 0° C. and treated with 2 drops of DMF and oxalyl chloride (610 ul, 7.0 mmol). After 15 minutes, the solution was warmed to room temperature and stirred for an additional 60 minutes. The solvent was removed under reduced pressure and the yellow residue (the phosphonochloridate compound G) was azeotroped with dry benzene and dried in vacuo for 1 hour.

H. (S)-4-[[[4-(4-Fluorophenyl)-2-(1-methylethyl)- 6-(2-methylphenyl)-3-pyridinyl] ethynyl]methoxyphosphinyl]-3-[[(1,1-dimethylethyl)diphenylsilyl]oxy]butanoic acid, methyl ester A solution of the dibromide from part F (2.0 g, 4.1 mmol) in THF (10 ml) at −78° C. was treated with n-BuLi (2.5M in hexane, 3.3 ml, 8.2 mmol) over a 1-minute period. The dark-green reaction mixture was stirred for 1 hour at −78° C. and then transferred via cannula to a −78° C. solution of the phosphonochloridate from part G in THF (10 ml). The green-brown reaction mixture was stirred at −78° C. for 30 minutes and quenched with 50% saturated NH$_4$Cl. After warming to room temperature, the solution was diluted with H$_2$O and poured into saturated NaHCO$_3$. The layers were separated and the aqueous portion was back-extracted once with ether. The combined organic layers were washed with brine, dried (Na$_2$SO$_4$), filtered and concentrated under reduced pressure. The orange oily residue was purified by flash chromatography (Merck silica gel, 30% EtOAc/hexane) to afford the title compound as a pale yellow foam (1.9 g, 60.7%).

R$_f$ 0.31 (40% EtOAc/hexane), UV

I. (S)-4-[ [ [4-(4-Fluorophenyl)-2-(1-methylethyl)- 6-(2-methylphenyl)-3-pyridinyl] ethynyl]methoxyphosphinyl]-3-hydroxybutanoic acid, methyl ester To a solution of the acetylinic phosphonate from part H (1.85 g, 2.42 mmol) in THF (15 ml) was added HOAc (0.55 ml, 9.68 mmol) followed by tetra-n-butylammonium fluoride (1.0M in THF, 7.26 mmol, 7.26 ml). The reaction mixture was stirred at room temperature under argon for 20 hours. The solution was diluted with EtOAc and washed three times with 5% KHSO$_4$. The aqueous layer was back-extracted with EtOAc (twice) and the combined organic extracts were dried (Na$_2$SO$_4$), filtered and concentrated under reduced pressure. The yellow-orange oil was dissolved in ether, cooled to 0° C. and treated with excess diazomethane for 30 minutes. The excess diazomethane was destroyed by the addition of HOAc. Solvent removal gave an oily orange residue, which was purified by flash chromatography (Merck silica gel, 40% EtOAc/hexane). The title compound was obtained as a pale yellow oil (0.51 g, 41.0%).

R$_f$ 0.44 (50% acetone/hexane), UV

J. (S)-4-[[[4-(4-Fluorophenyl)-2-(1-methylethyl)- 6-(2-methylphenyl)-3-pyridinyl] ethynyl]hydroxyphosphinyl]-3-hydroxybutanoic acid, dilithium salt The diester from part I (0.50 g, 0.95 mmol) in dioxane (5 ml) was treated with 1N LiOH (3.3 ml, 3.3 mmol) at room temperature and then heated at 50° C. for 2.5 hours and at 60° C. for 1 hour (TLC indicated the absence of starting material). The solvent was evaporated and the residue was dissolved in $H_2O$ and chromatographed on HP-20 resin eluting first with $H_2O$ (200 ml), followed by 25% MeOH/$H_2O$ (100 ml), 50% MeOH/$H_2O$ (250 ml) and finally MeOH (100ml). The collected product fractions were evaporated, dissolved in $H_2O$, filtered, frozen and lyophilized to afford Example 57 as a white lyophilate (0.25 g, 60.7%).

$R_f$ 0.50 (8:1:1—$CHCl_2$:$CH_3OH$:HOAc), UV Analysis for $C_{24}H_{27}FLi_2NO_5P \times 1.1 H_2O$: Calc'd: C 61.28 H 5.56 N 2.65 F 3.59 P 5.82 Found: C 61.23 H 5.28 N 2.94 F 3.44 P 6.02

Example 58

(S)-4-[ [ [ 6-(1,3-Benzodioxol-4-yl )-4-(4-fluorophenyl)- 2-(1-methylethyl)-3-pyridinyl]ethynyl]- hydroxyphosphinyl] -3-hydroxybutanoic acid, dilithium salt A. 1,3-Benzodioxole-4-carboxaldehyde A mixture of 2,3-dihydroxybenzaldehyde (25.0 g, 180 mmol; from Aldrich Chemical Co.) and potassium fluoride (49.3 g, 830 mmol) in DMF (500 ml) was heated at 50° C. for 20 minutes. The reaction mixture was cooled to room temperature and dibromomethane (44.5 g, 250 mmol) was added and the dark reaction mixture was heated at 120° C. for 3 hours. After filtration of the cooled mixture, the filtrate was poured into 1 liter $H_2O$ and extracted with ether (2×200 ml). The combined ether extracts were washed with $H_2O$ (2×200 ml), 0.5N NaOH (2×200 ml) and brine, then dried ($MgSO_4$) and concentrated, yielding the title compound I as a yellow oil (19.8 g, 73.0%).

$R_f$ 0.56 (40% EtOAc/hexane), UV

B. α-Methyl-1,3-benzodioxole-4-methanol

A −78° C. solution of the compound of part A (19.0 g, 126.6 mmol) in ether (400 ml) was treated with methylmagnesium bromide (3M in ether, 55.0 ml, 165 mmol; from Aldrich Chemical Co.) over a 30-minute period using a syringe pump. After stirring for 1 hour the reaction mixture (heavy suspension) was carefully poured into saturated $NH_4Cl$ (250 ml). The layers were separated and the aqueous layer was extracted with ether (three times). The combined ether extracts were washed with $H_2O$ and brine, then dried ($MgSO_4$) and concentrated. The oily residue was purified by flash chromatography (Merck Silica gel, 10% EtOAc/hexane). The title compound was obtained as a colorless oil which slowly solidified on standing (13.3 g, 63.6%).

m.p. 45°–46° C. $R_f$ 0.39 (40% EtOAc/hexane), UV Anal. Calc'd for $C_9H_{10}O_3$: Calc'd: C, 65.05; H, 6.07; Found: C, 64.71; H, 6.00

C. 1-(1,3-Benzodioxol-4-yl-1-ethanone

A −78° C. solution of oxalyl chloride (8.68 ml, 99.6 mmol) in $CH_2Cl_2$ (120 ml) was treated dropwise with a solution of dry DMSO (14.2 ml, 199.2 mmol) in $CH_2Cl_2$ (20 ml). After 15 minutes, a solution of the alcohol from part B (13.5 g, 83.0 mmol) in $CH_2Cl_2$ (25 ml) was added dropwise to the above solution. After 20 minutes, triethylamine (34.7 ml) was added and the mixture was stirred at −78° C. for 20 minutes and then warmed to room temperature. The mixture was diluted with ether and washed twice with $H_2O$ and brine, then dried ($MgSO_4$), filtered and concentrated under reduced pressure. The solid residue was recrystallized from hot hexane. The title compound was obtained as white crystals (13.5 g, 82.8%).

m.p. 94°–95° C. $R_f$ 0.49 (30% EtOAc/hexane), UV Anal. Calc'd for $C_9H_8O$: Calc'd: C, 65.87; H, 4.91; Found: C, 65.54; H, 4.75

D. 1-(1,3-Benzodioxol-4-yl)-3-(4-fluorophenyl)- 2-propen-1-one

A mixture of 4-fluorobenzaldehyde (8.78 ml, 81.8 mmol, from Aldrich Chemical Co.) and the compound of part C (13.4 g, 81.8 mmol) in absolute ethanol (110 ml) was treated with a solution of sodium ethoxide in ethanol (21% by weight solution; 3.10 ml, 8.18 mmol). A precipitate soon fell out of solution. After stirring at room temperature for 18 hours, the mixture was cooled to −10° C. and the precipitate was collected by filtration. The solid was washed with cold ethanol and dried in vacuo and recrystallized from hot hexane. The title compound was obtained as a light yellow solid (12.5 g, 56.6%).

m.p. 248°–250° C. $R_f$ 0.68 (30% EtOAc/hexane), UV Anal. Calc'd for $C_{16}H_{11}FO_3 \times 0.18 H_2O$: Calc'd: C, 70.27; H, 4.19; F, 6.95; Found: C, 70.27; H, 3.87; F, 6.65

E. β-(4-Fluorophenyl)-α-(2-methyl-1-oxopropyl)-Δ -oxo-1, 3-benzodioxol-4-yl pentanoic acid, ethyl ester A slurry of the compound of part D (12.5 g, 46.25 mmol) and ethyl isobutyrylacetate (7.46 ml, 46.25 mmol) in absolute ethanol (120 ml) was treated with a solution of sodium ethoxide in absolute EtOH (21% by weight solution, 1.70 ml, 4.62 mmol). A white precipitate soon fell out of solution. After stirring at room temperature overnight, the mixture was cooled to −10° C. and the precipitate was collected by filtration. The solid was washed with cold ethanol, dried in vacuo and recrystallized from hot hexane. The title compound was obtained as a white solid (14.6 g, 75.0%).

m.p. 109°–110° C. $R_f$ 0.56 (30% EtOAc/hexane), UV Anal. Calc'd for $C_{24}H_{25}FO_6 \times 0.19 H_2O$: Calc'd: C, 66.75; H, 5.92; F, 4.40; Found: C, 66.75; H, 5.65; F, 4.36

F. 6-(1,3-Benzodioxol-4-yl)-4-(4-fluorophenyl)- 2-(1-methylethyl)-3-pyridinecarboxylic acid, ethyl ester A mixture of the compound of part E (13.5 g, 31.5 mmol), ammonium acetate (7.28 g, 94.5 mmol) and copper (II) acetate (15.70 g, 78.75 mmol) in glacial acetic acid (90 ml) was heated at 110° C. for 18 hours (TLC indicated the absence of starting material). The solution was cooled to room temperature and poured into an ice cold mixture of concentrated $NH_4OH$ (110 ml) and $H_2O$ (150 ml). The mixture was extracted with ether and the ether extract was washed twice with $H_2O$ and brine, then dried ($MgSO_4$), filtered and concentrated to yield a yellow solid residue. The crude material was recrystallized from hot hexane, yielding the title compound as a pale yellow solid (7.52 g, 58.3%).

m.p. 148°–150° C. $R_f$ 0.62 (30% EtOAc/hexane), UV Anal. Calc'd for $C_{24}H_{22}NFO_4$: Calc'd: C, 70.75; H, 5.44; N, 3.44; F, 4.66; Found: C, 70.92; H, 5.53; N, 3.49; F, 4.62

G. 6-(1,3-Benzodioxol-4-yl)-4-(4-fluorophenyl)- 2-(1-methylethyl)-3-pyridinemethanol A cold (0° C.) solution of the ester from part F (7.0 g, 17.05 mmol) in dry THF (85 ml) was treated with $LiAlH_4$ (1.94 g, 51.15 mmol). Ten minutes after the addition, cooling bath was removed and the reaction mixture was stirred at room temperature for 3 hours (TLC indicated the absence of starting material). The dark mixture was cooled to 0° C. and, while stirring, carefully quenched first by a dropwise addition of 1.94 ml of $H_2O$ in THF (15 ml), then 1.94 ml 15% NaOH and finally 4.0 ml $H_2O$. The precipitated aluminum salts were filtered and washed with EtOAc and ether. The filtrate was washed with $H_2O$ and brine, dried ($Na_2SO_4$) filtered and concentrated under reduced pressure. The solid residue was recrystallized from hot EtOAc/hexane, yielding the title compound as an off-white solid (6.0 g, 96.7%).

m.p. 114°–115° C. $R_f$ 0.44 (30% EtOAc/hexane), UV Anal. Calc'd for $C_{22}H_{20}NFO_3$: Calc'd: C, 72.31; H, 5.52; N, 3.83; F, 5.20; Found: C, 72.14; H, 5.40; N, 3.83; F, 5.07

H. 6-(1,3-Benzodioxol-4-yl)-4-(4-fluorophenyl)- 2-(1-methylethyl)-3-pyridinecarboxaldehyde A −78° C. solution of oxalyl chloride (0.57 ml, 6.57 mmol) in $CH_2Cl_2$ (80 ml) was treated dropwise with a solution of dry DMSO (0.93 ml, 13.12 mmol) in $CH_2Cl_2$ (2 ml). After 15 minutes, a solution of the alcohol from part G (2.0 g, 5.47 mmol) in $CH_2Cl_2$ (15 ml) was added dropwise to the above solution. After 20 minutes, triethylamine (4.57 ml) was added and the mixture was stirred at −78° C. for 20 minutes and then warmed to room temperature. The mixture was diluted with ether and washed twice with $H_2O$ and brine, dried ($MgSO_4$), filtered and concentrated under reduced pressure. The yellow solid residue was recrystallized from hot hexane. The title compound (two crops) was obtained as a pale yellow solid (1.65 g, 83.3%).

m.p. 121°–122° C. $R_f$ 0.57 (30% EtOAc/hexane), UV Anal. Calc'd for $C_{22}H_{18}NFO_3$: Calc'd: C, 72.71; H, 4.99; N, 3.86; F, 5.23; Found: C, 72.40; H, 5.05; N, 3.73; F, 5.33

I. 6-(1,3-Benzodioxol-4-yl)-3-(2,2-dibromoethenyl)- 4-(4-fluorophenyl)-2-(1-methylethyl)pyridine A solution of carbon tetrabromide (3.28 g, 6.6 mmol) in $CH_2Cl_2$ (15 ml) was added dropwise over a 5-minute period to a cold (0° C.) solution of the aldehyde from part H (1.60 g, 4.4 mmol) and triphenylphosphine (3.46 g, 13.2 mmol) in $CH_2Cl_2$ (60 ml). The mixture was stirred at 0° C. for 10 minutes and then at room temperature for 10 minutes. The solution was quenched with saturated $NaHCO_3$ and extracted twice with $CH_2Cl_2$. The combined organic layers were dried ($Na_2SO_4$), filtered, concentrated to half volume and applied on Merck silica gel column (50% $CH_2Cl_2$/hexane). Flash chromatography afforded the title compound as a colorless viscous oil which slowly solidified on standing (1.65 g, 89.0%).

m.p. 129°–131° C. $R_f$ 0.63 (30% EtOAc/hexane), UV Anal. Calc'd for $C_{23}H_{18}NO_2FBr_2$ Calc'd: C, 53.20; H, 3.49; N, 2.70; F, 3.66; Br, 30.78; Found: C, 53.14; H, 3.45; N, 2.66; F, 3.49; Br, 30,47

J. (S)-4-[[[6-(1,3-Benzodioxol-4-yl)-4-(4-fluorophenyl)-2-(1-methylethyl)-3 -pyridinyl]ethynyl]methoxyphosphinyl] -3 -[[(1,1-dimethylethyl)diphenylsilyl]oxy] butanoic acid, methylester A solution of the dibromide of part I (1.68 g, 3.17 mmol) in THF (10 ml) at −78° C. was treated with n-BuLi (2.5M in hexane, 2.53 ml, 6.34 mmol) over a 1-minute period. The dark-green reaction mixture was stirred for 1 hour at −78° C. and then transferred via cannula to a −78° C. solution of the phosphonochloridate prepared in Example 57, part G in THF (10 ml). The green-brown reaction mixture was stirred at −78° C. for 30 minutes and quenched with 50% saturated $NH_4Cl$. After warming to room temperature, the solution was diluted with $H_2O$ and poured into saturated $NaHCO_3$. The layers were separated and the aqueous layer was extracted once with ether. The combined organic layers were washed with brine, dried ($Na_2SO_4$), filtered and concentrated under reduced pressure. The orange oily residue was purified by flash chromatography (Merck silica gel, 25% EtOAc/hexane) to afford the title compound as a pale yellow foam (0.68 g, 27%).

$R_f$ 0.31 (40% EtOAc/hexane), UV

K. (S)-4-[[[6-(1,3-Benzodioxol-4-yl)-4-(4 -fluorophenyl)-2-(1-methylethyl)-3 -pyridinyl]ethynyl]methoxyphosphinyl] -3 -hydroxybutanoic acid, methylester To a solution of the acetylinic phosphonate of part J (0.94 g, 1.18 mmol) in THF (15 m) was added HOAc (0.27 ml, 4.72 mmol), followed by tetra-n-butylammonium fluoride (1.0M in THF, 3.54 ml, 3.54 mmol). The reaction mixture was stirred at room temperature under argon for 20 hours. The solution was diluted with EtOAc and washed 3× 5% $KHSO_4$. The aqueous layer was back-extracted twice with EtOAc and the combined organic extracts were dried ($Na_2SO_4$), filtered and concentrated under reduced pressure. The yellow-orange oil was dissolved in ether (a few drops of THF were added to obtain a clear solution), cooled to 0° C. and treated with excess diazomethane for 30 minutes. The excess diazomethane was destroyed by the addition of HOAc. Solvent removal gave an orange oily residue, which was purified by flash chromatography (Merck silica gel, 40% acetone/hexane). The title compound was obtained as a colorless oil (0.24 g, 37.0%).

$R_f$ 0.30 (50% acetone/hexane) UV

L. (S)-4-[[[6-(1,3-Benzodioxol-4-yl)-4-(4 -fluorophenyl)-2-(1-methylethyl)-3 -pyridinyl]ethynyl]hydroxyphosphinyl]-3 -hydroxybutanoic acid, dilithium salt The diester from part K (0.24 g, 0.43 mmol) in dioxane (5 ml) was treated with 1N LiOH (1.51 ml, 1.51 mmol) at room temperature and then heated at 50° C. for 2.5 hours (TLC indicated the absence of starting material). The solvent was evaporated and the residue was chromatographed on HP-20 resin eluting first with $H_2O$ (200 ml), followed by 25% MeOH/$H_2O$ (200 ml), 50% MeOH/$H_2O$ (250 ml) and finally MeOH (100 ml). The collected product fractions were evaporated, dissolved in $H_2O$, filtered, frozen and lyophilized to give Example 58 as a white lyophilate (0.22 g, 95.0%).

$R_f$ 0.55 (8:1:1—$CH_2Cl_2$:$CH_3OH$:HOAc), UV Anal. Calc'd for $C_{27}H_{23}FLi_2NO_7$×1.24 $H_2O$ Calc'd: C, 57.65; H, 4.62; N, 2.49; F, 3.38; P, 5.51; Found: C, 57.34; H, 4.50; N, 2.89; F, 3.30; P, 5.41.

Example 59

(S)-4-[ [ [5-Ethyl-4-(4-fluorophenyl)-2-(1-methylethyl)-6-phenyl-3-pyridinyl] ethynyl] hydroxyphosphinyl] -3-hydroxybutanoic acid, disodium salt A. γ-Ethyl-β-(4-fluorophenyl)-α-(2-methyl- 1-oxopropyl)-Δ-oxobenzenepentanoic acid, ethyl ester A −78° C. solution of LiN(TMS)$_2$ (1.0M in THF, 23 ml, 23 mmol) and THF (15 ml) was treated with a solution of butyrophenone (3.365 gm, 22.7 mmol) in THF (2 ml) over a 1-minute period. After 60 minutes, a solution of the compound prepared in Example 53, part A (5.000 gm, 18.9 mmol) in THF (5 ml) was added dropwise to the above solution. The mixture was stirred at −78° C. for 45 minutes and then warmed to 0° C. After 25 minutes, the mixture was quenched with HOAc (1.3 ml), diluted with saturated $NH_4Cl$ and $H_2O$ and subsequently extracted with $Et_2O$. The. $Et_2O$ extract was washed with brine, then dried ($Na_2SO_4$), filtered, and stripped to yield a yellow oil. The material was used directly in the next reaction.

TLC: $R_f$ 0.43, 0.33, & 0.30 (20% EtOAc in hexane)

B. 5-Ethyl-4-(4-fluorophenyl)-2-(1-methylethyl)- 6-phenyl-3-pyridinecarboxylic acid, ethyl ester The aforementioned crude mixture of the compound of part A, $NH_4OAc$ (4.455 gm, 58 mmol), and $Cu(OAc)_2$ (9.92 gm, 49.7 mmol) in glacial HOAc (50 ml) were gently refluxed for 25 hours. The solution was cooled to room temperature and subsequently poured into an ice cold mixture of concentrated $NH_4OH$ (78 ml) in $H_2O$ (150 ml). The mixture was extracted once with $Et_2O$ the organic extract was washed with $H_2O$ and brine, then dried ($Na_2SO_4$), filtered and stripped to yield a brown oil. The residue was flashed (Merck $SiO_2$, 10% EtOAc in hexane) to give the title compound as an oil (5.350 gm) which was contaminated with butyrophenone.

TLC: $R_f$ 0.48 (20% EtOAc in hexane)

C. 5-Ethyl-4-(4-fluorophenyl)-2-(1-methylethyl)- 6-phenyl-3-pyridinemethanol

A cold (0° C.) solution of the impure ester from part B (5.335 gm) in dry THF (150 ml) was treated with LiAlH$_4$ (1.645 gm, 43.3 mmol). The ice bath was removed and the mixture was stirred at room temperature for 4 hours. The solution was then cooled to 0° C. and quenched in succession with H$_2$O (1.5 ml), 10% NaOH (2 ml), and H$_2$O (3.5 ml). The solution was filtered and the salts were washed with EtOAc and THF. The filtrate was stripped of solvent to afford a solid. The residue was recrystallized from hot EtOAc/hexane to provide the title compound (3.540 gm, 53% from the compound from Example 53, part A as a white solid.

m.p. 228.5°–230° C. TLC: $R_f$ 0.16 (20% EtOAc in hexane) Microanalysis for $C_{23}H_{24}FNO$: Calc'd: C 79.05 H 6.92 N 4.01 F 5.44 Found: C 78.98 H 6.87 N 4.08 F 5.28

D. 5-Ethyl-4-(4-fluorophenyl)-2-(1-methylethyl)- 6-phenyl-3-pyridinecarboxaldehyde A –78° C. solution of oxalyl chloride (600 µl, 873 mg, 6.9 mmol) in CH$_2$Cl$_2$ (30 ml) was treated dropwise with a solution of dry DMSO (1.00 ml, 1.10 gm, 14.1 mmol) in CH$_2$Cl$_2$ (1 ml). After 15 minutes, a solution of the alcohol from part C (2.000 gm, 5.7 mmol) in THF (15 ml) was added dropwise to the above mixture. Fifteen minutes after the addition, TEA (4.5 ml) was added and the mixture was stirred at –78° C. for 3 minutes and then warmed to room temperature. The mixture was diluted with Et$_2$O and washed twice with H$_2$O and once with brine. The organic layer was dried (Na$_2$SO$_4$), filtered, and stripped to give a solid residue. The residue was flashed (LPS-1, CH$_2$Cl$_2$) to obtain a solid which was recrystallized from hot hexane to give the aldehyde title compound (1.715 gm, 86%) as an amorphous white solid.

m.p. 122°–123.8° C. TLC: $R_f$ 0.51 (20% EtOAc in hexane) Microanalysis for $C_{23}H_{22}FNO$: Calc'd: C 79.51 H 6.38 N 4.03 F 5.47 Found: C 79.35 H 6.40 N 4.12 F 5.36

E. 3-(2,2-Dibromoethenyl)-5-ethyl-4-(4 -fluorophenyl)-2-(1-methylethyl)-6 -phenylpyridine A solution of carbon tetrabromide (2.35 gm, 7.1 mmol) in CH$_2$Cl$_2$ (8 ml) was added over a 7-minute period to a cold (–5° C.) solution of the aldehyde from part D (1.630, 4.7 mmol) and triphenylphosphine (3.750 gm, 14.3 mmol) in CH$_2$Cl$_2$ (20 ml). After the addition was complete, the cooling bath was removed and the mixture was stirred at room temperature for 25 minutes. The solution was quenched with saturated NaHCO$_3$ and extracted twice with CH$_2$Cl$_2$. The organic layers were dried (Na$_2$SO$_4$), filtered and concentrated. The concentrate was chromatographed (flash, Merck SiO$_2$, 30% CH$_2$Cl$_2$ in hexane followed by 30% hexane in CH$_2$Cl$_2$) to give the dibromide title compound as a foam, which solidified on standing. Recrystallization of the material from CH$_2$Cl$_2$/hexane provided the pure title compound (2.237 gm, 95%) as white needles.

m.p. 155.5°–157° C. TLC: $R_f$ 0.40 (10% EtOAc in hexane) Microanalysis for $C_{24}H_{22}Br_2FN$: Calc'd: C 57.28 H 4.41 N 2.78 F 3.78 Br 31.76 Found: C 57.19 H 4.20 N 2.75 F 3.77 Br 31.99

F. (S)-4-[[[5-Ethyl-4-(4-fluorophenyl)-2 -(1-methylethyl)-6-phenyl-3-pyridinyl] -ethynyl]methoxyphosphinyl]-3-[[(1,1 -dimethylethyl)diphenylsilyl]oxy] butanoic acid, methylester A solution of the dibromide from part E (1.500 gm, 3.0 mmol) in THF (8 ml) at –78° C. was treated with n-BuLi (2.5M in hexane, 2.5 ml, 6.3 mmol) over a 1-minute period and the resulting clear brown solution was stirred at –78° C. for 50 minutes. The acetylenic anion solution was added dropwise via cannula over a 5-minute period to a –78° C. solution of the phosphonochloridate from Example 57, part G, in THF (12 ml). The resulting mixture was stirred at –78° C. for 35 minutes, then quenched with 50% saturated NH$_4$Cl. The solution was warmed to 0° C. and poured into saturated NaHCO$_3$. The aqueous phase was extracted once with Et$_2$O. The Et$_2$O layer was washed with brine, dried (Na$_2$SO$_4$), filtered and stripped to give an orange oil. The residue was chromatographed (flash, Merck SiO$_2$, 40% EtOAc in hexane) to afford the title compound as a colorless foam (1.726 gm, 74%).

TLC: $R_f$ 0.28 (40% EtOAc in hexane)

G. (S)-4-[[[5-Ethyl-4-(4-fluorophenyl)-2 -(1-methylethyl)-6-phenyl-3-pyridinyl] ethynyl]methoxyphosphinyl]-3-hydroxybutanoic acid, methylester A mixture of the part F compound (1.709 gm, 2.20 mmol), tetra-n-butylammonium fluoride (1.0M in THF, 6.6 ml, 6.6 mmol), and HOAc (500 µl, 525 mg, 8.7 mmol) in THF (10 ml) was stirred at room temperature for 18 hours. The solution was diluted with EtOAc and washed three times with 5% KHSO$_4$. The aqueous layers were back-extracted once with EtOAc and the pooled EtOAc layers were dried (Na$_2$SO$_4$), filtered and stripped to afford a yellow oil. The oil was dissolved in Et$_2$O, cooled to 0° C. and treated with excess diazomethane for 15 minutes. The excess diazomethane was destroyed by the addition of HOAc and the solvent was removed in vacuo. The residue was chromatographed (flash, Merck SiO$_2$, 40% acetone in hexane followed by 7:3 acetone:hexane) to afford the title compound (1.060 gm, 90%) as a colorless oil.

TLC: $R_f$ 0.34 (1:1—acetone:hexane)

H. (S)-4-[[[5-Ethyl-4-(4-fluorophenyl)-2 -(1-methylethyl)-6-phenyl-3-pyridinyl] ethynyl]hydroxyphosphinyl]-3-hydroxybutanoic acid, disodium salt A solution of the part G compound (1.039 gm, 1.93 mmol) in dioxane (8 ml) was treated with 1N NaOH (7.0 ml, 7.0 mmol) at room temperature and the mixture was subsequently heated at 65° C. under argon for 1.5 hours. The solvent was evaporated and the residue was chromatographed on HP-20 resin, eluting in succession with H$_2$O (200 ml), 50% MeOH in H$_2$O (200 ml), and MeOH (200 ml). The desired fractions were pooled and evaporated and the residue was taken up in H$_2$O and lyophilized to give Example 59 (910 mg, 80%) as a white solid.

TLC: $R_f$ 0.15 (8:1:1—CH$_2$Cl$_2$:HOAc:MeOH) Analysis for $C_{28}H_{27}FNNa_2O_5P$ 1.89 H$_2$O: Calc'd: C 57.24 H 5.28 N 2.38 F 3.23 P 5.27 Found: C 57.17 H 4.99 N 2.45 F 3.25 P 5.51

Example 60

(S)-4-[ [ [ 6-(Diphenylmethyl)-4-(4-fluorophenyl)-2 -(1-methylethyl)-3-pyridinyl] ethynyl] hydroxyphosphinyl] -3-hydroxybutanoic acid, disodium salt A. 4-(4-Fluorophenyl)-1,1-diphenyl-3 -buten-2-one A mixture of 4-fluorobenzaldehyde (3.54 gm, 28.5 mmol) and 1,1-diphenylacetone (5.000 gm, 23.8 mmol) in absolute EtOH (50 ml) was treated with a solution of EtONa in EtOH (21% solution, 900 µl, 2.4 mmol). After stirring at room temperature for 22 hours, the mixture was concentrated to 35 ml and the solution was treated with HOAc (200 mg). The solution was cooled to 0° C. and the precipitate that had formed was collected by filtration and washed with cold EtOH. The title compound was obtained as a pale yellow solid (5.787 gm, 77%).

m.p. 122°–124° C. TLC: $R_f$ 0.32 (20% EtOAc in hexane)

B. β-(4-Fluorophenyl)-α-(2-methyl-1-oxopropyl)-Δ -oxo- epsilonphenylbenzenehexanoic acid, ethyl ester A slurry of the part A compound (5.531 gm, 17.5 mmol) and ethyl isobutyrylacetate (4.220 gm, 26.7 mmol) in absolute EtOH (100 ml) was treated with a solution of EtONa in EtOH (21% by weight solution, 980 μl, 2.6 mmol). After stirring at room temperature for 4 hours, an additional 3.0 ml of EtONa solution was added. After stirring at room temperature for 28 hours, the mixture was treated with HOAc (1.14 gm), cooled to 0° C. and the precipitate was collected by filtration. The solid was washed with cold EtOH and hexane, then dried to give the title compound (5.858 gm, 71%) as a single diastereomer.

m.p. 130°–131° C. TLC: $R_f$ 0.20 (20% EtOAc in hexane)

C. 4-(4-Fluorophenyl)-2-(1-methylethyl)-6 -(diphenylmethyl)-3-pyridinecarboxylic acid, ethyl ester A mixture of the part B compound (5.590 gm, 11.8 mmol), $NH_4OAc$ (2.724 gm, 35.3 mmol), and $Cu(OAc)_2$ (5.89 gm, 29.5 mmol) in glacial HOAc (32 ml) was gently refluxed for 18 hours. The solution was cooled to room temperature and subsequently poured into an ice cold mixture of concentrated $NH_4OH$ (50 ml) in $H_2O$ (100 ml). The mixture was extracted with $Et_2O$ and the $Et_2O$ extract was washed with $H_2O$ (twice) and brine, then dried ($Na_2SO_4$), filtered and stripped to yield a cloudy orange-brown oil. The oil was chromatographed (flash, Merck $SiO_2$, 10% EtOAc in hexane) to afford the title compound (3.600 gm, 71%) as a yellow oil.

TLC: $R_f$ 0.49 (20% EtOAc in hexane)

D. 4-(4-Fluorophenyl)-2-(1-methylethyl)-6 -(diphenylmethyl)-3-pyridinemethanol

A cold (0° C.) solution of the ester from part C (3.562 gm) in dry THF (100 ml) was treated with $LiAlH_4$ (950 mg, 25 mmol). Ten minutes after the addition, the cooling bath was removed and the mixture was stirred at room temperature for two hours. Additional $LiAlH_4$ (390 mg, 10.3 mmol) was added and the mixture was stirred for one more hour. The dark solution was recooled to 0° C. and quenched in succession with $H_2O$ (1.5 ml), 10% NaOH (1.5 ml), and $H_2O$ (4.5 ml). The solution was filtered and the salts were washed with EtOAc. Removal of the solvent afforded an oil, which was chromatographed (flash, Merck $SiO_2$, 10% EtOAc in hexane) to give recovered starting material (1.319 gm) and the crude alcohol title compound (1.4 gm). The crude alcohol (an oil) was triturated with hexane to give a solid. Recrystallization from hot $Et_2O$/hexane provided the title compound (895 mg, 26%) as a pale yellow solid.

m.p. 138.5°–140° C. TLC: $R_f$ 0.26 (20% EtOAc in hexane)

E. 4-(4-Fluorophenyl)-2-(1-methylethyl)-6-(diphenylmethyl)-3-pyridinecarboxaldehyde A −78° C. solution of oxalyl chloride (230 ul, 335 mg, 2.6 mmol) in $CH_2Cl_2$ (10 ml) was treated dropwise with a solution of dry DMSO (400 μl, 440 mg, 5.6 mmol) in $CH_2Cl_2$ (1 ml). After 12 minutes, a solution of alcohol from part D (851 mg, 2.07 mmol) in $CH_2Cl_2$ (3 ml) was added dropwise to the above mixture. Twenty minutes after the addition, TEA (1.5 ml) was added and the mixture was stirred at −78° C. for 10 minutes and then warmed to room temperature. The mixture was diluted with $Et_2O$ and washed twice with $H_2O$ and once with brine. The organic layer was dried ($Na_2SO_4$), filtered, and stripped to yield a liquid/solid mixture. The residue was flashed (Merck $SiO_2$, 10% EtOAc in hexane) affording an oily solid that was recrystallized from hot hexane. The aldehyde title compound was obtained as a pale yellow solid (810 mg, 96%).

m.p. 101°–102° C. TLC: $R_f$ 0.50 (20% EtOAc in hexane)

F. 3-(2,2-Dibromoethenyl)-4-(4-Fluorophenyl)- 2-(1-methylethyl)-6-(diphenylethyl)pyridine A solution of carbon tetrabromide (1.039 gm, 3.13 mmol) in $CH_2Cl_2$ (3 ml) was added over a 5-minute period to a cold (−5° C.) solution of the aldehyde from part E (802 mg, 1.96 mmol) and triphenylphosphine (1.636 gm, 6.24 mmol) in $CH_2Cl_2$ (10 ml). After the addition was complete, the mixture was stirred at room temperature for 30 minutes. The solution was quenched with saturated $NaHCO_3$ and extracted twice with $CH_2Cl_2$. The combined organic layers were dried ($Na_2SO_4$), filtered and concentrated. The concentrate was chromatographed (flash, Merck $SiO_2$, 30% $CH_2Cl_2$ in hexane followed by $CH_2Cl_2$) to give the dibromide title compound as a solid. Recrystallization of the solid from hot $CH_2Cl_2$/hexane gave the product (1.000 gm, 90%) as white needles.

mp 141°–142° C. TLC: $R_f$ 0.42 (10% EtOAc in hexane)

Microanalysis for $C_{29}H_{24}Br_2FN$: Calc'd: C 61.61 H 4.28 N 2.48 Found C 61.65 H 4.25 N 2.51

G. 3-(1-Ethynyl)-4-(4-Fluorophenyl)-2-(1 -methylethyl)-6-(diphenylmethyl)pyridine A −78° C. solution of the dibromide from part F (981 mg, 1.74 mmol) in THF (8 ml) was treated rapidly with a solution of n-BuLi (2.5M in hexanes, 2.15 ml, 5.4 mmol). A very dark black-red solution developed. After 45 minutes, the solution was quenched with saturated $NH_4Cl$ (solution turned yellow), warmed to room temperature, and extracted with $Et_2O$. The $Et_2O$ extract was washed with brine, dried ($Na_2SO_4$), filtered and stripped to give an oil. The oil was flashed twice (Merck $SiO_2$, first in 2.5% EtOAc in hexane and then in 1% EtOAc in hexane) to yield a foam, which was triturated with hexane to give a solid. The solid was recrystallized from hot hexane to afford the title compound (450 mg, 64%) as an off-white solid.

m.p. 106.5°–107.5° C. TLC: Rf 0.36 (10% EtOAc in hexane)

H. (S)-4-[[[6-(Diphenylmethyl)-4-(4-fluorophenyl)- 2-(1-methylethyl)-3-pyridinyl] ethynyl]methoxyphosphinyl] -3-[ [ (1,1 -dimethylethyl)diphenylsilyl]oxy]butanoic acid, methylester Meanwhile, a solution of the acetylene from part G (445 mg, 1.1 mmol) in THF (8 ml) at −78° C. was treated with n-BuLi (1.6M in hexane, 760 μl, 1.22 mmol) over a 1-minute period. The acetylenic anion solution was added dropwise via cannula over a 5-minute period to a −78° C. solution of the phosphonochloridate from Example 57, part G, in THF (6 ml). The resulting mixture was stirred at −78° C. for 30 minutes then quenched with 50% saturated $NH_4Cl$. The solution was warmed to 0° C., diluted with $H_2O$, and poured into saturated $NaHCO_3$. The aqueous phase was extracted once with $Et_2O$. The $Et_2O$ layer was washed with brine, dried ($Na_2SO_4$), filtered and stripped to give a yellow oil. The residue was chromatographed (flash, Merck $SiO_2$, 40% EtOAc in hexane) to afford the title compound as an oily foam (329 mg, 36%).

TLC: $R_f$ 0.26 (40% EtOAc in hexane)

I. (S)-4-[[[6-(Diphenylmethyl)-4-(4-fluorophenyl)- 2-(1-methylethyl)-3-pyridinyl] ethynyl]methoxyphosphinyl]-3-hydroxybutanoic acid, methylester A mixture of the part H compound (314 mg, 0.38 mmol), tetra-n-butylammonium fluoride (1.0M in THF, 1.10 ml, 1.10 mmol), and HOAc (86 ul, 95 mg, 1.6 mmol) in THF (4 ml) was stirred at room temperature for 17 hours. The solution was diluted with EtOAc and washed three times with 5% KHSO$_4$. The EtOAc layer was washed with brine, dried (Na$_2$SO$_4$), filtered and stripped to afford a yellow oil. The oil was dissolved in Et$_2$O, cooled to 0° C. and treated with excess diazomethane for 20 minutes. The excess diazomethane was destroyed by the addition of HOAc and the solvent was removed vacuo. The residue was chromatographed (flash, Merck SiO$_2$, 40% acetone in hexane followed by 1:1 acetone:hexane) to afford the title compound (189 mg, 84%) as a colorless oil.

TLC: R$_f$ 0.34 (1:1—acetone:hexane)

J. (S)-4-[ [ [ 6-(Diphenylmethyl)-4-(4-fluorophenyl)- 2-(1-methylethyl)-3-pyridinyl] ethynyl] hydroxyphosphinyl] -3-hydroxybutanoic acid, disodium salt A solution of the part I compound (178 mg, 0.30 mmol) in dioxane (3.5 ml) was treated with 1 N NaOH (1.1 ml, 1.1 mmol) at room temperature and the mixture was subsequently heated at 58° C. under argon for 1.5 hours. The solvent was evaporated and the residue was chromatographed on HP-20 resin, eluting in succession with H$_2$O (150 ml), 50% MeOH in H$_2$O (200 ml), and 100% MeOH (100 ml). The desired fractions were pooled and evaporated and the residue was taken up in H$_2$O and lyophilized to give Example 60 (171 mg, 88%) as a white solid.

TLC: R$_f$ 0.16 (8:1:1—CH$_2$Cl$_2$:HOAc:MeOH) Analysis for C$_{33}$H$_{29}$FNNa$_2$O$_5$P * 2.0 H$_2$O: Calc'd: C 60.83 H 5.11N 2.15 F 2.92 P 4.75 Found: C 60.80 H 4.82 N 2.09 F 2.93 P 4.56

Example 61

(S)-4-[ [ 6-(1,1-Dimethylethyl)-4-(4-fluorophenyl)- 2-(1-methylethyl)-3-pyridinyl] ethynyl] hydroxyphosphinyl] -3-hydroxybutanoic acid, disodium salt A. 1-(4-Fluorophenyl)-4,4-dimethyl-1 -penten-3-one A mixture of 4-fluorobenzaldehyde (12.13 ml, 110 mmol, Aldrich) and pinacolone (12.48 ml, 100 mmol, Aldrich) in absolute ethanol (120 ml) was treated with a solution of sodium ethoxide in ethanol (21% by weight solution; 3.72 ml, 10 mmol). The clear yellow reaction mixture was stirred at room temperature under argon for 24 hours. The reaction mixture was concentrated to ⅓ volume and partitioned between 50% saturated NH$_4$Cl and EtOAc. The layers were separated and the organic layer was washed twice with H$_2$O and brine, then dried (Na$_2$SO$_4$) and concentrated under reduced pressure. The oily residue was purified by flash chromatography (Merck Silica gel, 10% EtOAc/hexane), yielding the title compound as a colorless oil that slowly solidified. The white solid was recrystallized from hexane, yielding the title compound as white crystals (13.9 g, 67.5%).

R$_f$ 0.62 (30% EtOAc/hexane), UV Analysis for C$_{13}$H$_{15}$FO: Calc'd: C, 75,70; H, 7.33 Found: C, 75.46; H, 7.23

B. 3-(4-Fluorophenyl)-6,6-dimethyl-2-(2 -methyl-1-oxopropyl)-5-oxoheptanoic acid, ethyl ester A mixture of the part A compound (13.02 g, 63.2 mmol) and ethyl isobutyrylacetate (10.00 g, 63.2 mmol) in absolute ethanol (150 ml) was treated with a solution of sodium ethoxide in ethanol (21% by weight solution, 2.43 ml, 6.32 mmol). After 6 hours, additional sodium ethoxide (0.2 equiv) was added and the reaction mixture was stirred overnight. The reaction mixture was concentrated to ⅓ volume and partitioned between 50% saturated NH$_4$Cl and EtOAc. The layers were separated and the organic layer was washed twice with H$_2$O and brine, dried (Na$_2$SO$_4$) and concentrated under reduced pressure. The oily residue was dissolved in hot hexane and cooled. The precipitated material was collected by filtration (17.1 g, 74.0%; mixture of diastereomers) to afford the title compound as a white solid.

m.p. 80°–89° C. R$_f$ 0.44+ 0.40 (20% EtOAc/hexane), UV Analysis for C$_{21}$H$_{29}$FO$_4$: Calc'd: C, 69.21; H, 8.02; F, 5.21 Found: C, 69.12; H, 8.06; F, 5.03

C. 6-(1,1-Dimethylethyl)-4-(4-fluorophenyl)- 2-(1-methylethyl)-3-pyridinecarboxylic acid, ethyl ester A mixture of the part B compound (17.0 g, 46.65 mmol), ammonium acetate (10.78 g, 139.95 mmol) and copper (II) acetate (23.28 g, 116.62 mmol) in glacial acetic acid (125 ml) was heated at 110° C. for 16 hours. The solution was cooled to room temperature and poured into an ice cold mixture of concentrated NH$_4$OH (150 ml) and H$_2$O (200 ml). The mixture was extracted with ether (twice) and the ether extracts were washed with H$_2$O (twice) and brine, then dried (MgSO$_4$), filtered and concentrated to give an oily residue. Purification by flash chromatography (Merck Silica gel, 5% EtOAc/hexane) afforded the title compound as a colorless oil (12.5 g, 78.0%).

R$_f$ 0.72 (15% EtOAc/hexane), UV

D. 6-(1,1-Dimethylethyl)-4-(4-fluorophenyl)- 2-(1-methylethyl)-3-pyridinemethanol A cold (0° C.) solution of the ester prepared in part C (12.5 g, 36.39 mmol) in dry THF (200 ml) was treated with LiAlH$_4$ (4.14 g, 109.17 mmol). Ten minutes after the addition the cooling bath was removed and the reaction mixture was stirred at room temperature for 2 hours. The reaction mixture was cooled to 0° C. and carefully quenched by dropwise addition of 4.2 ml of H$_2$O in THF (25 ml), then 4.2 ml 15% NaOH and finally 8.0 ml H$_2$O. The precipitated aluminum salts were filtered and washed with EtOAc and ether. The filtrate was washed with H$_2$O and brine, dried (Na$_2$SO$_4$), filtered and concentrated under reduced pressure. The solid residue was recrystallized from hexane, yielding the title compound as a white solid (9.3 g, 85.0%).

m.p. 112°–113° C. R$_f$ 0.47 (15% EtOAc/hexane), UV Analysis for C$_{19}$H$_{24}$NFO: Calc'd: C, 75.71; H, 8.03; N, 4.65; F, 6.30 Found: C, 75.77; H, 8.01; N, 4.63; F, 6.08

E. 6-(1,1-Dimethylethyl)-4-(4-fluorophenyl)- 2-(1-methylethyl)-3-pyridinecarboxaldehyde A –78° C. solution of oxalyl chloride (3.10 ml, 35.78 mmol) in CH$_2$Cl$_2$ (100 ml) was treated dropwise with a solution of dry DMSO (5.08 ml, 71.56 mmol) in CH$_2$Cl$_2$ (10 ml). After 15 minutes, a solution of the alcohol from part D (9.0 g, 29.82 mmol) in CH$_2$Cl$_2$ (50 ml) was added dropwise to the above solution. After 20 minutes, triethylamine (25.0 ml, 179.0 mmol) was added and the mixture was stirred at –78° C. for 20 minutes and then warmed to room temperature. After 1 hour, the reaction was quenched with H$_2$O and diluted with ether. The layers were separated and the aqueous layer was extracted with ether (twice). The combined organic solutions were washed with H$_2$O (twice) and brine, dried (MgSO$_4$), filtered and concentrated under reduced pressure. The dark oily residue was purified by flash chromatography (5% EtOAc/hexane) yielding the title compound as a colorless oil (6.95 g, 78.0%).

R$_f$ 0.60 (20% EtOAc/hexane), UV

F. 3-(2,2-Dibromoethenyl)-6-(1,1-dimethylethyl)- 4-(4-fluorophenyl)-2-(1-methylethyl)pyridine A solution of carbon tetrabromide (4.97 g, 15.0 mmol) in CH$_2$Cl$_2$ (15 ml) was added dropwise over a 5-minute period to a cold (0° C.) solution of the aldehyde from part E (3.00 g, 10.0 mmol) and triphenylphosphine (7.08 g, 127 mmol) in CH$_2$Cl$_2$ (60 ml). The mixture was stirred at 0° C. for 10 minutes and then at room temperature for 30 minutes. The solution was quenched with saturated NaHCO$_3$ and extracted twice with CH$_2$Cl$_2$. The combined organic layers were dried (Na$_2$SO$_4$), filtered, concentrated to ⅓ volume and applied on Merck silica gel column (50% CH$_2$Cl$_2$/hexane). Flash chromatography afforded the product as a colorless viscous oil which slowly solidified into an off-white solid. Recrystallization from hot hexane afforded the dibromide title compound as a white solid (3.95 g, 86.8%).

m.p. 98°–100° C. R$_f$ 0.56 (15% EtOAc/hexane), UV

G. (S)-4-[[6-(1,1-Dimethylethyl)-4-(4 -fluorophenyl)-2-(1-methylethyl)-3 -pyridinyl]ethynyl]methoxyphosphinyl]-3 -[[(1,1-dimethylethyl)diphenylsilyl]oxy] butanoic acid, methylester A solution of the dibromide from part F (3.80 g, 8.34 mmol) in THF (10 ml) at –78° C. was treated with n-BuLi (2.5M in hexane, 7.00 ml, 17.51 mmol) over a 1-minute period. The dark-blue reaction mixture was stirred for 1 hour at –78° C. and then transferred via cannula to a –78° C. solution of the phosphonochloridate from Example 57, part G, in THF (10 ml). The green-brown reaction mixture was stirred at –78° C. for 30 minutes and quenched with 50% saturated NH$_4$Cl. After warming to room temperature, the solution was diluted with H$_2$O and poured into saturated NaHCO$_3$. The layers were separated and the aqueous layer was extracted once with ether. The combined organic layers were washed with brine, dried (Na$_2$SO$_4$), filtered and concentrated under reduced pressure. The dark oily residue was purified by flash chromatography (Merck silica gel, 30% EtOAc/hexane) to afford the title compound as a pale yellow foam (3.85 g, 64.2%).

R$_f$ 0.20 (30% EtOAc/hexane), UV

H. (S)-4-[[6-(1,1-Dimethylethyl)-4-(4 -fluorophenyl)-2-(1-methylethyl)-3 -pyridinyl] ethynyl] methoxyphosphinyl] -3 -hydroxybutanoic acid, methylester To a solution of the acetylinic phosphonate of part G (3.75 g, 5.13 mmol) in THF (25 ml) was added HOAc (1.17 ml, 20.52 mmol), followed by tetra-n-butylammonium fluoride (1.0M in THF, 15.39 ml, 15.39 mmol). The reaction mixture was stirred at room temperature under argon for 24 hours. The solution was diluted with EtOAc and washed three times with 5% KHSO$_4$. The aqueous layer was back-extracted twice with EtOAc and the combined organic extracts were dried (Na$_2$SO$_4$), filtered and concentrated under reduced pressure. The yellow-orange oil was dissolved in ether (with a few drops of THF added to obtain a clear solution), cooled to 0° C. and treated with excess diazomethane for 30 minutes. The excess diazomethane was destroyed by the addition of HOAc. Solvent removal gave a dark oily residue, which was purified by flash chromatography (Merck silica gel, 40% EtOAc/hexane). The title compound was obtained as a colorless oil (0.24 g, 37.0%).

R$_f$ 0.41 (50% acetone/hexane) UV

I. (S)-4-[[6-(1,1-Dimethylethyl)-4-(4 -fluorophenyl)-2-(1-methylethyl)-3 -pyridinyl]ethynyl]hydroxyphosphinyl]-3 -hydroxybutanoic acid, disodium salt The diester from part H (1.50 g, 3.06 mmol) in dioxane (5 ml) was treated with 1N NaOH (10.70 ml, 10.7 mmol) at room temperature and then heated at 50° C. for 2.5 hours. The solvent was evaporated and the residue was chromatographed on HP-20 resin, eluting first with H$_2$O (200 ml), followed by 25% MeOH/H$_2$O (300 ml), 50% MeOH/H$_2$O (500 ml) and finally MeOH (100ml). The collected product fractions were evaporated, dissolved in H$_2$O, filtered, frozen and lyophilized to give Example 61 as a white lyophilate (0.22 g, 80.5%).

R$_f$ 0.25 (8:1:1—CH$_2$Cl$_2$:CH$_3$OH:HOAc), UV Analysis for C$_{24}$H$_{27}$NFPO$_5$Na$_2$×1.17 H$_2$O: Calc'd: C, 54,76; H, 5.62; N, 2.66; F, 3.61; P, 5.88 Found: C, 54.69; H, 5.69; N, 2.73; F, 3.44; P, 5.59

Example 62

(S)-4-[ [ [4-(4-Fluorophenyl)-6-(1-naphthalenyl)-2-(1-methylethyl)-3-pyridinyl] ethynyl] hydroxyphosphinyl] -3-hydroxybutanoic acid, disodium salt A. 3-(4-Fluorophenyl)-1-(1-naphthalenyl)- 2-propen-1-one A mixture of 4-fluorobenzaldehyde (6.40 ml, 60.0 mmol, Aldrich) and 1'-acetonaphtone (10.21 g, 60.0 mmol, Aldrich) in glacial HOAc (100 ml) and concentrated H$_2$SO$_4$ (8.75 ml) was stirred under argon at room temperature for 2 days. The dark yellow-red reaction mixture was cooled to 0° C. and poured into an ice cold mixture of concentrated NH$_4$OH/H$_2$O (150/225 ml). The mixture was extracted with ether (3×200 ml) and the combined ether extracts were washed with H$_2$O (three times), saturated NaHCO$_3$ (twice), and brine, then dried (Na$_2$SO$_4$), filtered and concentrated. The dark oily residue was distilled (0.5 mm Hg, bp 30° C.) to remove unreacted 4-fluorobenzaldehyde. The pot residue was purified by flash chromatography (Merck silica gel, 1% ether/toluene). The product was obtained as a dark yellow oil (18.0 g) which by NMR showed about 30% contamination with acetonaphtone.

R$_f$ 0.27 (20% EtOAc/hexane), UV, visually yellow

B. β-(4-Fluorophenyl)-α-(2-methyl-1-oxopropyl)-Δ -oxo-1-naphthalenepentanoic acid, ethyl ester A mixture of the part A compound (9.80 g, 35.67 mmol) and ethyl isobutyrylacetate (8.63 ml, 53.51 mmol) in absolute ethanol (120 ml) was treated with a solution of sodium ethoxide in ethanol (21% by weight solution, 1.97 ml, 5.35 mmol). The reaction mixture was stirred for 12 hours then concentrated to ⅓ volume and partitioned between 50% saturated NH$_4$Cl and EtOAc. The layers were separated and the organic layer was washed twice with H$_2$O and brine, then dried (Na$_2$SO$_4$) and concentrated under reduced pressure. The oily residue was dissolved in hot hexane and cooled. The precipitate was collected by filtration to give the title compound as a white solid (6.9 g, 47.0%; mixture of diastereomers).

m.p. 103°–105° C. R$_f$ 0.34+ 0.39 (20% EtOAc/hexane), UV Analysis for C$_{27}$H$_{27}$FO$_4$: Calc'd: C, 74.63; H, 6.26; F, 4.37 Found: C, 74.70; H, 6.26; F, 4.25

C. 4-(4-Fluorophenyl)-2-(1-methylethyl)-6 -(1-naphthalenyl)-3-pyridinecarboxylic acid, ethyl ester A mixture of the part B compound (7.50 g, 17.29 mmol), ammonium acetate (4.00 g, 51.87 mmol) and copper (II) acetate (8.62 g, 43.22 mmol) in glacial acetic acid (50 ml) was heated at 110° C. for 12 hours. The solution was cooled to room temperature and poured into an ice cold mixture of concentrated NH$_4$OH (70 ml) and H$_2$O (100 ml). The mixture was extracted with ether (twice) and the ether extracts were washed with H$_2$O (twice) and brine, then dried (MgSO$_4$), filtered and concentrated to give a yellow oily residue. Purification by flash chromatography (Merck Silica gel, 15% EtOAc/hexane) afforded the title compound as a pale yellow oil which solidified on standing under high vacuum (5.1 g, 71.8%). An analytical sample was recrystallized from hexane, yielding the product as a white crystalline material.

m.p. 113°–115° C. R$_f$ 0.42 (15% EtOAc/hexane), UV Analysis for C$_{27}$H$_{24}$NFO$_2$: Calc'd: C, 78.34; H, 5.85; N, 3.39; F, 4.59 Found: C, 78.50; H, 5.85; N, 3.33; F, 4.54

D. 4-(4-Fluorophenyl)-2-(1-methylethyl)-6-(1-naphthalenyl)-3-pyridinemethanol

A cold (0° C.) solution of the ester from part C (4.90 g, 11.85 mmol) in dry THF (60 ml) was treated with LiAlH$_4$ (1.35 g, 35.55 mmol). Ten minutes after the addition, the cooling bath was removed and the reaction mixture was stirred at room temperature for 1.5 hours. The reaction mixture was cooled to 0° C. and quenched by dropwise addition of 1.35 ml of H$_2$O in THF (15 ml), then 1.35 ml 15% NaOH, and finally 2.7 ml H$_2$O. The precipitated aluminum salts were filtered and washed with EtOAc and ether. The filtrate was washed with H$_2$O and brine, then dried (Na$_2$SO$_4$), filtered and concentrated under reduced pressure. The solid residue was recrystallized from hexane yielding the title compound as a white solid (3.9 g, 88.6%).

m.p. 73°–75° C. $R_f$ 0.34 (20% EtOAc/hexane), UV Analysis for C$_{25}$H$_{22}$NFO: Calc'd: C, 80.84; H, 5.97; N, 3.77; F, 5.11 Found: C, 80.74; H, 6.07; N, 3.55; F, 4.96

E. 4-(4-Fluorophenyl)-2-(1-methylethyl)-6 -(1-naphthalenyl)-3-pyridinecarboxaldehyde A −78° C. solution of oxalyl chloride (1.05 ml, 12.00 mmol) in CH$_2$Cl$_2$ (60 ml) was treated dropwise with a solution of dry DMSO (1.70 ml, 24.00 mmol) in CH$_2$Cl$_2$ (5 ml). After 15 minutes, a solution of the alcohol from part D (3.71 g, 10.00 mmol) in CH$_2$Cl$_2$ (25 ml) was added dropwise to the above solution. After 20 minutes, triethylamine (8.36 ml, 60.00 mmol) was added and the mixture was stirred at −78° C. for 20 minutes and then warmed to room temperature. After 1 hour, the reaction was quenched with H$_2$O and diluted with ether. The layers were separated and aqueous layer was extracted with ether (twice). The combined organic solutions were washed with H$_2$O (twice) and brine, dried (MgSO$_4$), filtered and concentrated under reduced pressure. The off-white solid residue was recrystallized from EtOAc/hexane yielding the title compound as an off-white solid (2.9 g, 78.0%).

m.p. 128°–129° C. $R_f$ 0.52 (20% EtOAc/hexane), UV Analysis for C$_{25}$H$_{20}$NFO: Calc'd: C, 81.28; H, 5.46; N, 3.79; F, 5.14 Found: C, 79.92; H, 5.71; N, 3.98; F, 5.01

F. 3-(2,2-Dibromoethenyl)-4-(4-fluorophenyl)- 2-(1-methylethyl)-6-(1 -naphthalenyl)-3-pyridine A solution of carbon tetrabromide (3.90 g, 11.75 mmol) in CH$_2$Cl$_2$ (10 ml) was added dropwise over a 5-minute period to a cold (0° C.) solution of the aldehyde from part E (2.90 g, 7.85 mmol) and triphenylphosphine (6.17 g, 23.55 mmol) in CH$_2$Cl$_2$ (60 ml). The mixture was stirred at 0° C. for 10 minutes and then at room temperature for 30 minutes. The solution was quenched with saturated NaHCO$_3$ and extracted twice with CH$_2$Cl$_2$. The combined organic layers were dried (Na$_2$SO$_4$), filtered, concentrated to ⅓ volume and applied on Merck silica gel column (50% CH$_2$Cl$_2$/hexane). Flash chromatography afforded the title compound as a colorless viscous oil which became a foam upon drying in vacuo (3.90 g, 95.1%).

$R_f$ 0.58 (15% EtOAc/hexane), UV

G. (S)-4-[ [ [ 4-(4-Fluorophenyl)-6-(1-naphthalenyl)- 2-(1-methylethyl)-3 -pyridinyl] ethynyl] methoxyphosphinyl] -3 -[ [ (1,1-dimethylethyl)diphenylsilyl]oxy] butanoic acid, methyl ester A solution of the dibromide from part F (3.80 g, 7.23 mmol) in THF (10 ml) at −78° C. was treated with n-BuLi (2.5M in hexane, 6.07 ml, 15.18 mmol) over a 1-minute period. The dark-blue reaction mixture was stirred for 1 hour at −78° C. and then transferred via cannula to a −78° C. solution of the phosphonochloridate from Example 57, part G, in THF (10 ml). The green-brown reaction mixture was stirred at −78° C. for 30 minutes and quenched with 50% saturated NH$_4$Cl. After warming to room temperature, the solution was diluted with H$_2$O and poured into saturated NaHCO$_3$. The layers were separated and the aqueous was extracted once with ether. The combined organic layers were washed with brine, dried (Na$_2$SO$_4$), filtered and concentrated under reduced pressure. The dark oily residue was purified by flash chromatography (Merck silica gel, 30% EtOAc/hexane) to afford the title compound as a pale yellow foam (2.65 g, 62.1%).

$R_f$ 0.13 (30% EtOAc/hexane), UV

H. (S)-4-[[[4-(4-Fluorophenyl)-6-(1-naphthalenyl)- 2-(1-methylethyl)-3 -pyridinyl]ethynyl]methoxyphosphinyl]-3 -hydroxybutanoic acid, methyl ester To a solution of the acetylinic phosphonate from part G (2.50 g, 3.12 mmol) in THF (25 ml) was added HOAc (0.72 ml, 12.48 mmol), followed by tetra-n-butylammonium fluoride (1.0M in THF, 9.37 ml, 9.37 mmol). The reaction mixture was stirred at room temperature under argon for 24 hours. The solution was diluted with EtOAc and washed three times with 5% KHSO$_4$. The aqueous layer was back-extracted twice with EtOAc and the combined organic extracts were dried (Na$_2$SO$_4$), filtered and concentrated under reduced pressure. The yellow-orange oil was dissolved in ether (with a few drops of THF to obtain a clear solution), cooled to 0° C. and treated with excess diazomethane for 20 minutes. The excess diazomethane was destroyed by the addition of HOAc. Solvent removal gave a dark oily residue, which was purified by flash chromatography (Merck silica gel, 40% acetone/hexane). The title compound was obtained as a pale yellow oil (1.08 g, 62.1%).

$R_f$ 0.32 (50% acetone/hexane) UV

I. (S)-4-[[[4-(4-Fluorophenyl)-6-(1-naphthalenyl)- 2-(1-methylethyl)-3 -pyridinyl]ethynyl]hydroxyphosphinyl]-3 -hydroxybutanoic acid, disodium salt The diester from part H (1.00 g, 1.78 mmol) in dioxane (5 ml) was treated with 1N NaOH (6.25 ml, 6.25 mmol) at room temperature and then heated at 50° C. for 2.5 hours. The solvent was evaporated and the residue was chromatographed on HP-20 resin, eluting first with H$_2$O (200 ml), followed by 25% MeOH/H$_2$O (250 ml), 50% MeOH/H$_2$O (250 ml) and finally with MeOH (100 ml). The collected product fractions were evaporated, dissolved in H$_2$O, filtered, frozen and lyophilized to give Example 62 as a white lyophilate (0.84 g, 82.3%).

$R_f$ 0.27 (8:1:1—CH$_2$Cl$_2$:CH$_3$OH:HOAc), UV Analysis for C$_{30}$H$_{25}$NFPO$_5$Na$_2$×1.22 H$_2$O: Calc'd: C, 60.31; H, 4.63; N, 2.34; F, 3.18; P, 5.18 Found: C, 60.22; H, 4.78; N, 2.43; F, 3.15; P, 4.98

Example 63

(S)-4-[ [ [4-(4-Fluorophenyl)-2-(1-methylethyl)benzo[ 6,7] cyclohepta[ 1,2-b]pyridin-3-yl] ethynyl] hydroxyphosphinyl]-3-hydroxybutanoic acid, disodium salt A. β-(4-Fluorophenyl)-6,7,8,9-tetrahydro-α -(2-methyl-1-oxopropyl)-5-oxo-5H-benzocycloheptene- 6-propanoic acid, ethyl ester A −78° C. solution of LiN(TMS)$_2$ (1.0M in THF, 27.5 ml, 27.5 mmol) and THF (15 ml) was treated with a solution of benzosuberone (6.000 gm, 22.7 mmol) in THF (3 ml) over a 1-minute period. After 60 minutes, a solution of the compound from Example 53, part A (4.08 gm, 15.4 mmol) in THF (3 ml) was added dropwise to the above solution. The mixture was stirred at −78° C. for 30 minutes and then warmed to 0° C. After 20 minutes, the mixture was quenched with HOAc (3.4 ml), diluted with saturated NH₄Cl and H₂O and subsequently extracted with Et₂O. The Et₂O extract was washed with brine, then dried (Na₂SO₄), filtered, and stripped to yield a viscous pale yellow gum. The material was used directly in the next reaction.

B. 4-(4-Fluorophenyl)-6,7-dihydro-2-(1 -methylethyl)-benzo[ 6,7] cyclohepta[ 1,2 -b]pyridine-3-carboxylic acid, ethyl ester The aforementioned crude mixture of the compound of part A, NH₄OAc (5.25 gm, 68.1 mmol), and Cu(OAc)₂ (11.33 gm, 57 mmol) in glacial HOAc (60 ml) was gently refluxed for 19 hours. The solution was cooled to room temperature and subsequently poured into an ice cold mixture of concentrated NH₄OH (100 ml) in H₂O (200 ml). The mixture was extracted once with Et₂O the organic extract was washed with H₂O and brine, then dried (Na₂SO₄), filtered and stripped to yield a dark red-purple oil. The residue was flashed (Merck SiO₂, 10% EtOAc in hexane) to give the impure title compound as an oil (6.707 gm, estimated purity of 90%).

TLC: $R_f$ 0.53 (20% EtOAc in hexane)

C. 4-(4-Fluorophenyl)-6,7-dihydro-2-(1 -methylethyl)-benzo[6,7]cyclohepta[1,2 -b]pyridine-3-methanol A cold (0° C.) solution of the impure ester of part B (6.692 gm) in dry THF (200 ml) was treated with LiAlH₄ (1.910 gm, 50 mmol). The ice bath was removed and the mixture was stirred at room temperature for 3.5 hours. The solution was then cooled to 0° C. and quenched in succession with H₂O (2 ml), 10% NaOH (2 ml), and H₂O (6 ml). The solution was filtered and the salts were washed with EtOAc and Et₂O. The filtrate was stripped of solvent to afford a gum, which was triturated with hexane to produce a solid. The solid was recrystallized twice from hot EtOAc/hexane to provide the title compound (3.800 gm, 68% from compound A from Example 53) as a white solid.

m.p. 160.5°–161.8° C. TLC: $R_f$ 0.24 (20% EtOAc in hexane)

D. 4-(4-Fluorophenyl)-6,7-dihydro-2-(1 -methylethyl)-benzo[6,7]cyclohepta[1,2 -b]pyridine-3-carboxaldehyde A –78° C. solution of oxalyl chloride (630 ul, 917 mg, 7.2 mmol) in CH₂Cl₂ (40 ml) was treated dropwise with a solution of dry DMSO (1.10 ml, 1.21 gm, 15.5 mmol) in CH₂Cl₂ (1 ml). After 10 minutes, a solution of the alcohol from part C (2.000 gm, 5.5 mmol) in THF (5 ml) was added dropwise to the above mixture. Fifteen minutes after the addition, TEA (4.6 ml) was added and the mixture was stirred at –78° C. for 5 minutes and then warmed to room temperature. The mixture was diluted with Et₂O and washed twice with H₂O and once with brine. The organic layer was dried (Na₂SO₄), filtered, and stripped to give a yellow oil, which solidified upon cooling to –78° C. in hexane. The mixture was then crystallized from hot hexane to give the aldehyde title compound (1.775 gm, 89%) as white needles.

m.p. 132°–134° C. TLC: $R_f$ 0.54 (20% EtOAc in hexane)

E. (3-(2,2-Dibromoethenyl)-4-(4-Fluorophenyl)- 6,7-dihydro-2-(1-methylethyl)benzo[ 6,7]cyclohepta[1,2-b]pyridine A solution of carbon tetrabromide (2.336 gm, 7.0 mmol) in CH₂Cl₂ (6 ml) was added over a 7-minute period to a cold (0° C.) solution of the aldehyde from part D (1.688, 4.7 mmol) and triphenylphosphine (3.698 gm, 14.1 mmol) in CH₂Cl₂ (20 ml). After the addition was complete, the cooling bath was removed and the mixture was stirred at room temperature for 25 minutes. The solution was quenched with saturated NaHCO₃ and extracted twice with CH₂Cl₂. The organic layers were dried (Na₂SO₄), filtered and concentrated. The concentrate was chromatographed (flash, Merck SiO₂, 40% CH₂Cl₂ in hexane) to give the dibromide title compound as a solid. Recrystallization of the material from hot EtOAc/hexane provided the pure title compound (2.257 gm, 93%) as a white solid.

m.p. 173°–175° C. TLC: $R_f$ 0.44 (10% EtOAc in hexane) Microanalysis for $C_{25}H_{22}Br_2FN$: Calc'd: C 58.27 H 4.30 N 2.72 F 3.69 Br 31.02 Found: C 58.27 H 4.29 N 2.69 F 3.62 Br 31.35

F. (S)-4-[ [ [4-(4-fluorophenyl)-2-(1-methylethyl)-benzo[ 6,7]cyclohepta[1,2-b] -pyridin-3-yl] ethynyl] methoxyphosphinyl] -3-[ [ (1,1-dimethylethyl)diphenylsilyl] oxy]butanoic acid, methyl ester Meanwhile, a solution of the dibromide from part E (2.000 gm, 3.88 mmol) in THF (10 ml) at –78° C. was treated with n-BuLi (2.5M in hexane, 3.3 ml, 8.2 mmol) over a 1-minute period, and the resulting clear green solution was stirred at –78 ° C. for 50 minutes. The acetylenic anion solution was added dropwise via cannula over a 10-minute period to a –78° C. solution of the phosphonochloridate from Example 57, part G in THF (12 ml). The resulting mixture was stirred at –78° C. for 30 minutes, then quenched with 50% saturated NH₄Cl. The solution was warmed to 0° C. and poured into saturated NaHCO₃. The aqueous phase was extracted once with Et₂O. The Et₂O layer was washed with brine, dried (Na₂SO₄), filtered and stripped to give an oil. The residue was chromatographed (flash, Merck SiO₂, 40% EtOAc in hexane) to afford the title compound as a colorless foam (2.517 gm, 82%).

TLC: $R_f$ 0.31 (40% EtOAc in hexane)

G. (S)-4-[[[4-(4-fluorophenyl)-2-(1-methylethyl)-benzo[ 6,7]cyclohepta[1,2-b] -pyridin-3-yl]ethynyl]methoxyphosphinyl] -3-hydroxybutanoic acid, methyl ester A mixture of the part F compound (2.487 gm, 3.15 mmol), tetra-n-butylammonium fluoride (1.0M in THF, 11.0 ml, 11.0 mmol), and HOAc (810 ul, 850 mg, 14.1 mmol) in THF (40 ml) was stirred at room temperature for 18 hours. The solution was diluted with EtOAc and washed three times with 5% KHSO₄ and once with brine. The EtOAc layer was dried (Na₂SO₄), filtered and stripped to afford a yellow oil. The oil was dissolved in Et₂O, cooled to 0° C. and treated with excess diazomethane for 10 minutes. The excess diazomethane was destroyed by the addition of HOAc and the solvent was removed in vacuo. The residue was chromatographed (flash, Merck SiO₂, 40% acetone in hexane) to afford the title compound (1.534 gm, 89%) as a colorless foam.

TLC: $R_f$ 0.38 (1:1—acetone:hexane)

H. (S)-4-[[[4-(4-Fluorophenyl)-2-(1-methylethyl)-benzo[ 6,7]cyclohepta[1,2-b] -pyridin-3-yl]ethynyl]hydroxyphosphinyl] -3-hydroxybutanoic acid, disodium salt A solution of the part G compound (780 mg, 1.42 mmol) in dioxane (7 ml) was treated with 1N NaOH (5.0 ml, 5.0 mmol) and the mixture was stirred at room temperature for 18 hours. The solvent was evaporated and the residue was chromatographed on HP-20, eluting in succession with H₂O (200 ml), 50% MeOH in H₂O (200 ml), and MeOH (100 ml). The desired fractions were pooled and evaporated and the residue was taken up in H₂O and lyophilized to give Example 63 (744 mg, 90%) as a white solid.

TLC: $R_f$ 0.17 (8:1:1—CH₂ Cl₂:HOAc:MeOH) Analysis for $C_{29}H_{27}FNNa_2O_5P\times0.80 H_2O$: C 60.06 H 4.97 N 2.42 F 3.28 P 5.34 Found: C 59.98 H 5.02 N 2.50 F 3.52 P 5.55

Example 64

(S)-4-[ [ [4-(4-Fluorophenyl)-2-(1-methylethyl)-6 -[2-(phenylmethyl)phenyl] -3-pyridinyl] ethynyl] hydroxyphosphinyl] -3-hydroxybutanoic acid, disodium salt A. 2'-(Phenylmethyl)acetophenone Oxalyl chloride (4.1 ml, 47 mmol) was added to a solution of 2-(phenylmethyl)benzoic acid (from Aldrich) in methylene chloride (100 ml) over 5 minutes at room temperature.

The solution was allowed to stir at room temperature for 2 hours. The solution was concentrated and the resultant orange gum azeotroped with benzene (twice) and placed under high vacuum for 1 hour. In a separate flask, methyl lithium (1.4M in THF, 100 ml, 140 mmol) was added over 10 minutes to a slurry of $CuI_2$ (13.432 gm, 42.3 mmole) in ether (125 ml). The slurry was allowed to stir for 2 minutes. The above-prepared acid chloride in ether (50 ml) at −78° C. was cannulated over 20 minutes into the dimethyl lithium-cuprate solution, which was also cooled to −78° C. The solution stirred for an additional 20 minutes, then was quenched with methanol (30 ml) and warmed to room temperature. The solution was then added to saturated $NH_4Cl$ (200 ml), and the aqueous layer was extracted with ether (twice). The organic layers were combined and washed with brine, then dried over $MgSO_4$, filtered and concentrated to afford an orange oil. The crude oil was purified by flash chromatography on Merck silica gel in 5% EtOAc in hexane. The fractions containing the product were combined and concentrated to afford the title compound as a pale yellow solid (3.090 gm, 63%).

m.p. 42°–43° C. TLC: Rf 0.39 (5% EtOAc in hexane)

B. 3-(4-Fluorophenyl)-1-[2-(phenylmethyl)phenyl- 2-propen-1-one

A solution of sodium ethoxide (21% by weight in EtOH, 0.100 gm, 1.47 mmol) was added to a solution of compound 2 (3.090 gm, 14.7 mmol) and 4 -fluorobenzaldehyde (2.00 gm, 16.2 mmol) in ethanol (100 ml), which was stirring under argon at room temperature. The solution was allowed to stir 18 hours and then was concentrated to afford an orange oil. The crude oil was dissolved in hexane and ether and, upon cooling, afforded the title compound as a yellow crystalline solid (2.30 gm, 86%).

m.p. 76°–78° C. TLC: Rf 0.24 (5% EtOAc in hexane) Elemental Analysis for $C_{22}H_{17}FO*$ 0.11 $H_2O$: Calc'd: C 83.02 H 5.45 F 5.97 Found: C 83.02 H 5.42 F 5.78

C. β-(4-Fluorophenyl-α-(2-methyl-1-oxopropyl)-γ -oxo-2-(phenylmethyl)benzenepentanoic acid, ethyl ester A solution of sodium ethoxide (21% by weight in EtOH, 0.192 gm, 2.8 mmol) was added to a slurry of the ethyl isobutyrylacetate from part B (4.480 gm, 28 mmol) and the enone from part B (6.015 gm, 19 mmol) in ethanol (100 ml), which was stirring under argon at room temperature. The slurry was allowed to stir 16 hours. Then, ethanol (30 ml) was added to the flask to make a slurry of the reaction mixture, which had partially solidified. Then, acetic acid (0.343 gm, 5.71 mmol) was added to the reaction mixture, and a white solid was filtered out of solution. The solid was dried under high vacuum for 2 hours to afford the title compound as a pure, white solid (8.220 gm, 92%).

m.p. 120°–122° C. TLC: Rf 0.49 (20% EtOAc in hexane) Elemental Analysis for $C_{30}H_{31}FO*$ 2.89 $H_2O$: Calc'd: C 75.28 H 7.75 F 3.97 Found: C 75.28 H 6.69 F 3.98

D. 4-(4-Fluorophenyl)-2-(1-methylethyl)-6 -[2-(phenylmethyl)phenyl]-3-pyridinecarboxylic acid, ethyl ester $NH_4OAc$ (4.00 gm, 52 mmol) and $Cu(OAc)_2$ (3.63 gm, 43.25 mmol) were added to an acetic acid solution (50 ml) of the 1,5 diketone from part C (8.220 gm, 17.3 mmol). The solution was allowed to reflux for 18 hours under argon. The solution was then poured into an ice-cold solution of $NH_4OH/H_2O$ (100 ml/100 ml). The mixture was extracted with ether (twice), washed with water and saturated NaCl, then dried over $Na_2SO_4$ and concentrated to afford an orange oil, which solidified upon standing. The orange solid was purified by flash chromatography on Merck silica gel in 15% EtOAc in hexane. Those fractions containing the product were pooled and evaporated to give the title compound as a slightly orange solid (5.220 gm, 67%).

m.p. 94°–97° C. TLC: Rf 0.64 (20% EtOAc in hexane) Elemental analysis for $C_{30}H_{28}NFO$: Calc'd: C 79.44 H 6.22 N 3.09 F 4.19 Found: C 79.45 H 6.01 N 3.02 F 4.27

E. 4-(4-Fluorophenyl)-2-(1-methylethyl)-6 -[ 2-(phenylmethyl)phenyl]-3-pyridinemethanol A THF solution (50 ml) of the ester from part D (5.220 gm, 11.5 mmol) was cooled to 0° C. and treated with $LiAlH_4$ (1.31 gm, 34.5 mmol). The solution stirred 17 hours, then was cooled to 0° C. and quenched by dropwise addition of 1.3 ml of water followed by 1.3 ml of 15% NaOH, then 3.9 ml water. The aluminum paste was filtered out of solution and the filtrate concentrated to give a yellowish solid. The solid was recrystallized from EtOAc and hexane to afford the title compound as large clear crystals (3.043 gm, 65%).

m.p. 122°–124° C. TLC: Rf 0.08 (10% EtOAc in hexane) Elemental Analysis for $C_{28}H_{24}NFO*$ 0.78 $H_2O$: Calc'd: C 79.41 H 6.08 N 3.30 F 4.49 Found: C 79.42 H 6.03 N 3.30 F 4.48

F. 4-(4-Fluorophenyl)-2-(1-methylethyl)-6 -[ 2-(phenylmethyl)phenyl]-3-pyridinecarboxaldehyde A solution of DMSO (0.993 gm, 12.71 mmol) in THF (5 ml) was added to oxalyl chloride (0.807 gm, 6.36 mmol) in THF (35 ml) at −78° C. under argon. The solution stirred 20 minutes, then the alcohol from part E (2.000 gm, 4.89 mmol) was added dropwise as a THF (10 ml) solution. Twenty-five minutes later, triethyl amine (3.65 ml, 26 mmol) was added to the reaction mixture. The solution was stirred for 20 minutes and then was warmed to room temperature. The solution was diluted with ether and washed with water and brine, then dried over $Na_2SO_4$, filtered and concentrated to afford a yellowish solid. The solid was purified by flash chromatography on Merck silica gel in 3–5% EtOAc in hexane. Fractions containing the product were combined and concentrated. The resultant white solid was recrystallized from hexane to give the title compound as white crystals (1.380 gm, 69%).

m.p. 205°–207° C. TLC: Rf 0.53 (20% EtOAc in hexane)

G. 3-(2,2-Dibromoethenyl)-4-(4-fluorophenyl)- 2-(1-methylethyl)-6-[ 2-(phenylmethyl)phenyl] -3-pyridine A solution of $CBr_4$ (1.68 gm, 5.06 mmol) in methylene chloride solution (25 ml) was added over 20 minutes to a solution of triphenyl phosphine (2.83 gm, 10.78 mmol) and the aldehyde from part F (1.38 gm, 3.37 mmol) in methylene chloride (25 ml), which was stirring under argon at 0° C. The solution stirred for an additional 45 minutes. Then, saturated $NaHCO_3$ (15 ml) was added to quench the reaction. The solution was then allowed to warm to room temperature. The aqueous layer was extracted with methylene chloride (twice) and the organic layers combined and washed with brine, then dried over $Na_2SO_4$, filtered concentrated to about 10 ml. The solution was subjected to flash chromatography on Merck silica gel in 20% methylene chloride in hexane. Pure fractions were pooled and concentrated to afford the title compound as a white foam (1.71 gm, 90%).

TLC: Rf 0.73 (10% EtOAc in hexane)

H. (S)-4-[[[4-(4-Fluorophenyl)-2-(1-methylethyl)- 6-[2-(phenylmethyl)phenyl]-3 -pyridinyl]ethynyl]-methoxyphosphinyl] -3-[[(1,1-dimethylethyl)diphenylsilyl] oxy]butanoic acid, methylester n-BuLi (2.5M in hexane, 2.3 ml, 5.66 mmol) was added dropwise to a solution of the dibromide from part G (1.60 gm, 2.83 mmol) in THF (20 ml) at −78° C. under argon. The solution was allowed to stir 1 hour at −78° C., then cannulated into a THF solution (15 ml) of the chloridate from Example 57, part G, which had also been cooled to −78° C. The resultant orange solution was stirred for 30 minutes, then quenched with saturated $NH_4Cl$ (15 ml) and warmed to 0° C. Saturated NaHCO₃ was then added to the solution. After warming to room temperature, the mixture was diluted with ether. The organic layer was washed with brine, dried over Na₂SO₄, filtered and concentrated to give an orange oil. The oil was purified by flash chromatography on Merck silica gel in 40% EtOAc in hexane. Pure product fractions were combined and evaporated to afford the title compound as a beige foam (1.37 gm, 58%).

TLC: Rf 0.53 (50% ETOAc in hexane)

I. (S)-4-[[[4-(4-Fluorophenyl)-2-(1-methylethyl)- 6-[2-(phenylmethyl)phenyl]-3 -pyridinyl]ethynyl]-methoxyphosphinyl] -3-hydroxybutanoic acid, methylester (Bu)₄NF (1.0M in THF, 4.8 ml, 4.8 mmol) was added to a solution of the silyl ether from part H (1.375 gm, 1.60 mmol) and acetic acid (0.387 gm, 6.4 mmol) in THF (10 ml) and allowed to stir 25 hours at room temperature. The solution was diluted with EtOAc (20 ml) and washed with 5% KHSO₄ (three times). The aqueous layers were extracted with EtOAc (twice). The organic layers were pooled and washed with brine, then dried over Na₂SO₄, filtered and concentrated to afford a pale yellow oil. The oil was dissolved in ether (15 ml) and treated with excess CH₂ N₂. Excess CH₂ N₂ was removed with a stream of argon, and the solution was concentrated to a yellow oil. The oil was purified by flash chromatography on Merck silica gel in 40% acetone in hexane. Pure product fractions were pooled and concentrated to afford the title compound as a beige foam (0.735 gm, 78%).

TLC: Rf 0.34 (40% acetone in hexane)

J. (S)-4-[[[4-(4-Fluorophenyl)-2-(1-methylethyl)- 6-[2-(phenylmethyl)phenyl]-3 -pyridinyl]ethynyl]-hydroxyphosphinyl]-3 -hydroxybutanoic acid, disodium salt The part I (0.545 gm, 0.93 mmol) was dissolved in dioxane (10 ml) and treated with NaOH (1M in water, 2.31 ml, 2.3 mmol). The solution was then heated to 55° C. for 1 hour. The mixture was concentrated to a yellowish solid. The solid was dissolved in water and chromatographed on HP-20 resin, eluting first with water (200 ml) and then with 50% MeOH in water (400 ml). The desired fractions were pooled and concentrated and the resultant residue was taken up in water and lyophilized to give Example 64 as a fluffy white solid (0.550 gm, 99%).

TLC: Rf 0.62 (6:3:1, n-propanol:NH₄OH:water) Elemental Analysis for $C_{33}H_{29}NFNa_2PO_5$* 1.24 H₂O: Calc'd: C 62.14 H 4.97 N 2.20 F 2.98 Found: C 62.02 H 5.05 N 2.32 F 3.02

Example 65

(S)-4-[ [
[4-(4-Fluorophenyl)-2,5-bis(1-methylethyl)-
6-phenyl-3-pyridinyl] ethynyl] hydroxyphosphinyl]
-3-hydroxybutanoic acid, disodium salt A. (3-Methyl-1-methylenebutyl)benzene Chloro-(2-methylpropyl)magnesium (150 ml, 0.300 mol, from Aldrich) was added over 20 minutes to a solution of benzonitrile (10.21 ml, 0.100 mol, from Aldrich) in ether (150 ml), stirring under argon at room temperature. The solution was allowed to stir under argon at room temperature for 18 hours. The reaction mixture was then cooled to 0° C. and 1.2N HCl (125 ml) was added. The aqueous layer was extracted with ether (twice), and the organic layers were combined and washed with brine and dried over MgSO₄, filtered and concentrated to a yellow oil. The oil was purified by flash chromatography on Merck silica gel in 2% EtOAc in hexane. Fractions containing the product were combined and concentrated to afford the title compound as a yellow oil (13.305 gm, 83%).

TLC: Rf 055 (5% EtOAc in hexane)

B. β-(4-Fluorophenyl)-γ-(1-methylethyl)-α -(2-methyl-1-oxopropyl)-Δ-oxobenzenepentanoic acid, ethyl ester A THF solution (3 ml) of the ketone from part A (5.0 gm, 0.031 mol) was added over 5 minutes to a solution of LiN(TMS)₂ (30.9 ml, 0.031 ml) in THF (17 ml), which was stirring under argon at −78° C. The solution was allowed to stir 1 hour and 45 minutes at −78° C. A solution of the β-keto ester from Example 53, part A (6.79 gm, 0.257 mol) in THF (5 ml) was then added over 5 minutes. The solution was warmed to 0° C. and stirred for 1 hour and 30 minutes. The reaction mixture was quenched with acetic acid. Then saturated NH₄Cl (100 ml) was added to the solution. The aqueous layer was extracted with ether (twice), the organic layers were combined and washed with brine, then dried over Na₂SO₄, filtered and concentrated to give a yellow oil. Purification of the oil was achieved by flash chromatography on Merck silica gel in 5% EtOAc in hexane. Fractions containing the product were combined and concentrated to afford the title compound as a clear oil (7.760 gm, 57%).

TLC: Rf 0.20 and 0.23 (20% EtOAc in hexane)

C. 4-(4-Fluorophenyl)-2,5-bis(1-methylethyl)- 6-phenyl-3-pyridinecarboxylic acid, ethyl ester NH₄OAc (4.202 gm, 54.5 mmol) and Cu(OAc)₂ (8.635 g, 43.25 mmol) were added to an acetic acid solution (50 ml) of 1,5 diketone B (7.760 gm, 18.2 mmol). The solution was allowed to reflux 18 hours under argon. The solution was then poured into an ice-cold solution of NH₄OH/H₂O (100 ml/100 ml). The mixture was extracted with ether (twice), washed with water and saturated NaCl, then dried over Na₂SO₄, and concentrated to afford an orange oil which solidified upon standing. The solid was purified by flash chromatography on Merck silica in 15% EtOAc in hexane. Fractions containing the pure product were pooled and concentrated. The resultant white solid was recrystallized from EtOAc and hexane to afford the title compound as fine white needles (3.341 gm, 45%).

m.p. 138°–140° C. TLC: Rf 0.55 (10% EtOAc in hexane) Elemental analysis for $C_{26}H_{32}NFO_2$: Calc'd: C 76.25 H 7.88 N 3.42 F 4.64 Found: C 76.90 H 6.98 N 3.53 F 4.74

D. 4-(4-Fluorophenyl)-2,5-bis(1-methylethyl)- 6-phenyl-3-pyridinemethanol

A THF solution (50 ml) of the ester from part C (3.214, 7.9 mmol) was cooled to 0° C. and treated with LiAlH₄ (0.902 gm, 23.77 mmol). The solution was allowed to stir 18 hours. The solution was then cooled to 0° C. and quenched by dropwise addition of 0.9 ml of water followed by 0.9 ml of 15% NaOH, then 2.7 ml water. The aluminum paste was filtered out of solution and the filtrate concentrated to a white solid. Recrystallization of the solid from EtOAc and hexane afforded the title compound as fluffy white needles (2.277 gm, 79%).

m.p. 244°–246° C. TLC: Rf 0.13 (20% EtOAc in hexane) Elemental Analysis for $C_{24}H_{28}NFO$* 0.14 H₂O: Calc'd: C 78.33 H 7.75 N 3.81 F 5.16 Found: C 78.29 H 7.10 N 3.85 F 5.16

E. 4-(4-Fluorophenyl)-2,5-bis(1-methylethyl)- 6-phenyl-3-pyridinecarboxaldehyde

A solution of DMSO (0.84 gm, 10.68 mmol) in CH₂ Cl₂ (1 ml) was added to a solution of oxalyl chloride (0.321 ml, 3.68 mmol) in CH₂ Cl₂ (35 ml) cooled to −78° C. under argon. After stirring 15 minutes, the alcohol from part D (1.025 gm, 2.83 mmol) was added dropwise to the flask as a THF/CH₂ Cl₂ (9 ml/5 ml) solution. Twenty-five minutes later, triethyl amine (2.9 ml, 21 mmol) was added to the reaction mixture. The solution stirred for 20 minutes and then was warmed to room temperature. The solution was diluted with ether and washed with water and brine, then dried over $Na_2SO_4$, filtered and concentrated to afford a white solid. The white solid was recrystallized from hexane to give the title compound as white, lumpy crystals (0.866 gm, 85%).

m.p. 159°–160° C. TLC: Rf 0.53 (20% EtOAc in hexane) Elemental Analysis for $C_{24}H_{24}NFO \times 0.07$ $H_2O$: Calc'd: C 79.48 H 6.71 N 3.86 F 5.24 Found: C 79.68 H 6.58 N 3.68 F 5.33

F. 3-(2,2-Dibromoethenyl)-4-(4-fluorophenyl)- 2,5-bis(1-methylethyl)-6 -phenylpyridine A solution of $CBr_4$ (1.185 gm, 3.57 mmol) in methylene chloride (7 ml) was added over 20 minutes to a solution of triphenylphosphine (1.87 gm, 7.14 mmol) and the aldehyde from part E (0.866 gm, 2.38 mmol) in methylene chloride (20 ml), which was stirring under argon at 0° C. The solution stirred for an additional twenty minutes, at 0° C., then was warmed to room temperature and stirred 30 minutes. The reaction was then quenched with saturated $NaHCO_3$. The aqueous layer was extracted with methylene chloride (twice), the organic layers were combined and washed with brine, then dried over $Na_2SO_4$, filtered and concentrated to about 5 ml. The solution was purified by flash chromatography on Merck silica gel in 30% methylene chloride in hexane. Pure fractions were pooled and concentrated to afford the title compound as a white foam (1.178 gm, 97.5%).

TLC: Rf 0.69 (20% EtOAc in hexane)

G. (S)-4-[[[4-(4-Fluorophenyl)-2,5-bis(1 -methylethyl)-6-phenyl-3-pyridinyl] ethynyl]methoxyphosphinyl]-3-[[(1,1-dimethylethyl)diphenylsilyl]oxy]butanoic acid, methyl ester N-BuLi (2.5M in hexane, 1.84 ml, 4.6 mmol) was added dropwise to a solution of the dibromide from part F (1.178 gm, 2.3 mmol) in THF (20 ml) at −78° C. under argon. The solution was allowed to stir 1 hour at −78° C., then cannulated into a THF solution (30 ml) of the chloridate from Example 57, part G which had also been cooled to −78° C. The resultant orange solution was stirred 1 hour, then quenched with saturated $NH_4Cl$ (15 ml). The solution was warmed to 0° C. and then saturated $NaHCO_3$ was added to the flask. The mixture was extracted with ether (three times), the organic layers were pooled and washed with brine, then dried over $Na_2SO_4$, filtered and concentrated to an amber oil. The oil was purified by flash chromatography on Merck silica gel in 40% EtOAc in hexane. Pure product fractions were combined and evaporated to afford the title compound as a beige foam (0.950 gm, 52%).

TLC: Rf 0.53 (50% ETOAc in hexane)

H. (S)-4-[[[4-(4-Fluorophenyl)-2,5-bis(1 -methylethyl)-6-phenyl-3-pyridinyl] ethynyl]methoxyphosphinyl]-3-hydroxybutanoic acid, methyl ester $(Bu)_4NF$ (1M in THF, 3.55 ml, 3.55 mmol) was added to the silyl ether from part G (0.948 gm, 1.194 mmol) and acetic acid (0.284 gm, 4.73 mmol) in THF (10 ml). The solution was allowed to stir 19 hours at room temperature. Additional $(Bu)_4NF$ (1M in THF, 236 ml, 2.36 mmol) and HOAc (0.19 gm, 3.16 mmol) was added to the solution which was allowed to stir 2 more hours. The mixture was diluted with EtOAc and washed with 5% $KHSO_4$ (three times). The aqueous layers were extracted with EtOAc (twice), the organic layers were combined and washed with brine, then dried over $Na_2SO_4$, filtered and concentrated to give an orange oil. The oil was dissolved in ether and treated with excess $CH_2 N_2$. Excess $CH_2 N_2$ was removed by bubbling argon through the solution. The solution was concentrated to give a yellow oil. The oil was purified by flash chromatography on Merck silica gel in 40% acetone in hexane. Fractions containing the product were combined and concentrated to afford the title compound as a white foam (0.496 gm, 81%).

TLC: Rf 0.22 (40% acetone in hexane)

I. (S)-4-[[[4-(4-Fluorophenyl)-2,5-bis(1 -methylethyl)-6-phenyl-3-pyridinyl] ethynyl]hydroxyphosphinyl]-3-hydroxybutanoic acid, disodium salt The alcohol from part H was dissolved in dioxane (10 ml) and treated with a solution of NaOH (1M in water, 2.31 ml, 2.3 mmol). The solution was heated to 55° C. for 1.5 hours. Additional NaOH (1M in water, 1.0 ml, 1.0 mmol) was added to the solution which was allowed to stir one more hour at 55° C. The solution was then concentrated to a yellowish solid which was dissolved in water and chromatographed on HP-20 resin, eluting first with water (200 ml) and then with 50% MeOH in water (400 ml). The desired fractions were pooled and concentrated. The resultant residue was taken up in water and lyophilized to give Example 65 as a fluffy white solid (0.310 gm, 94%).

TLC: Rf 0.62 (6:3:1, n-propanol:$NH_4OH$:water) Elemental Analysis for $C_{29}H_{29}NFNa_2PO_5$* 2.78 $H_2O$: Calc'd: C 56.40 H 5.64 N 2.27 F 3.08 Found: C 56.44 H 5.72 N 2.23 F 3.16

Example 66

(S)-4-[ [ [ 6-(1-Adamantyl)-4-(4-fluorophenyl)-2-(1-methylethyl)-3-pyridinyl] ethynyl]hydroxyphosphinyl] -3-hydroxybutanoic acid, disodium salt A. 1-(1-Adamantyl)-3-(4-fluorophenyl)- 2-propen-1-one A mixture of 4-fluorobenzaldehyde (6.01 ml, 56.10 mmol, Aldrich) and 1-adamantyl methyl ketone (10.00 g, 56.10 mmol) in absolute ethanol (100 ml) was treated with a solution of sodium ethoxide in ethanol (21% by weight solution; 2.08 ml, 5.61 mmol). A precipitate soon fell out of solution. After stirring at room temperature for 48 hours, the mixture was cooled to −10° C. and the precipitate was collected by filtration. The solid was washed with cold ethanol, dried in vacuo and recrystallized from hexane. The title compound was obtained as an off-white solid (9.20 g, 57.8%).

m.p. 126°–127° C. $R_f$ 0.55 (25% EtOAc/hexane), UV Analysis for $C_{19}H_{21}FO$: Calc'd C, 80.25; H, 7.44; F, 6.68 Found C, 79.43; H, 7.54; F, 6.94

B. (4-Fluorophenyl)-α-(2-methyl-1-oxopropyl)-Δ -oxo-1-adamantanepentanoic acid, ethyl ester A mixture of the part A compound (9.10 g, 32.00 mmol) and ethyl isobutyrylacetate (7.75 ml, 48.00 mmol) in absolute ethanol (120 ml) was treated with a solution of sodium ethoxide in ethanol (21% by weight solution, 5.95 ml, 16.00 mmol). The reaction mixture was stirred for 48 hours. The obtained heavy suspension was cooled to −10° C., filtered and the off-white solids were washed with cold EtOH. The crude product was recrystallized from hot hexane, affording the title compound as an off-white solid (10.6 g, 74.8%, mixture of diastereomers).

m.p. 104°–105° C. $R_f$ 0.42+ 0.44 (20% EtOAc/hexane), UV Analysis for $C_{27} H_{35} FO_4$: Calc'd C, 73.27; H,7.97; F, 4.29 Found C, 72.87; H,7.93; F, 4.25

C. 1-(1-Adamantyl)-4-(4-fluorophenyl)-2 -(1-methylethyl)-3-pyridinecarboxylic acid, ethyl ester A mixture of the part B compound (10.50 g, 23.70 mmol), ammonium acetate (5.48 g, 71.10 mmol) and copper (II) acetate (11.83 g, 59.25 mmol) in glacial acetic acid (75 ml) was heated at 110° C. for 16 hours. The solution was cooled to room temperature and poured into an ice cold mixture of concentrated $NH_4OH$ (100 ml) and $H_2O$ (150 ml). The mixture was extracted with ether (twice) and the ether extracts were washed with $H_2O$ (twice) and brine, then dried ($MgSO_4$), filtered and concentrated into an oily residue that became a white hard foam upon drying in vacuo (high) (10.0 g, 100.0%). The crude title compound was used directly for the next reaction.

$R_f$ 0.61 (20% EtOAc/hexane), UV

D. 1-(1-Adamantyl)-4-(4-fluorophenyl)-2 -(1-methylethyl)-3-pyridinemethanol

A cold (0° C.) solution of the ester from part C (10.0 g, 23.70 mmol) in dry THF (100 ml) was treated with $LiAlH_4$ (2.70 g, 71.17 mmol). Ten minutes after the addition the cooling bath was removed and the reaction mixture stirred at room temperature for 2.5 hours. The reaction mixture was cooled to 0° C. and while stirring, carefully quenched by the dropwise addition of 2.7 ml of $H_2O$ in THF (15 ml), then 2.7 ml of 15% NaOH and finally 5.4 ml $H_2O$. The precipitated aluminum salts were filtered and washed with EtOAc and ether. The filtrate was washed with $H_2O$ and brine, dried ($Na_2SO_4$), filtered and concentrated under reduced pressure to give an oily residue. Purification by flash chromatography (Merck silica gel, 5% EtOAc/hexane) yielded the title compound as a white solid, which was recrystallized from hot hexane (6.7 g, 74.6%).

m.p. 143°–145° C. $R_f$ 0.34 (20% EtOAc/hexane), UV Analysis for $C_{25}H_{30}NFO$: Calc'd C, 79.12; H, 7.97; N, 3.69; F, 5.01 Found C, 79.03; H, 8.25; N, 3.77; F, 4.90

E. 1-(1-Adamantyl)-4-(4-fluorophenyl)-2 -(1-methylethyl)-3-pyridinecarboxaldehyde A –78° C. solution of oxalyl chloride (1.85 ml, 21.21 mmol) in $CH_2Cl_2$ (150 ml) was treated dropwise with a solution of dry DMSO (3.01 ml, 42.40 mmol) in $CH_2Cl_2$ (25 ml). After 15 minutes, a solution of the alcohol from part D (6.70 g, 17.67 mmol) in $CH_2Cl_2$ (50 ml) was added dropwise to the above solution. After 20 minutes, triethylamine (14.78 ml, 106.02 mmol) was added and the mixture was stirred at –78° C. for 20 minutes and then warmed to room temperature. After 1.5 hours, the reaction was quenched with $H_2O$ and diluted with ether. The layers were separated and aqueous layer was extracted with ether (twice). The combined organic extracts were washed with $H_2O$ (twice) and brine, dried ($MgSO_4$), filtered and concentrated under reduced pressure. The oily residue was purified by flash chromatography (Merck silica gel, 5% EtOAc/hexane) to give the aldehyde title compound as a white solid. The solid was recrystallized from hexane yielding the title compound as white crystals (5.5 g, 83.5%).

m.p. 109°–110° C. $R_f$ 0.66 (20% EtOAc/hexane), UV Analysis for $C_{25}H_{28}NFO$: Calc'd C, 79.54; H, 7.48; N, 3.71; F, 5.03 Found C, 79.25; H, 7.32; N, 3.61; F, 4.80

F. 1-(1-Adamantyl)-3-(2,2-dibromoethenyl)-2-(1-methylethyl)pyridine

A solution of carbon tetrabromide (2.63 g, 7.95 mmol) in $CH_2Cl_2$ (10 ml) was added dropwise over a 5-minute period to a cold (0° C.) solution of the aldehyde from part E (2.00 g, 5.30 mmol) and triphenylphosphine (4.17 g, 15.90 mmol) in $CH_2Cl_2$ (60 ml). The mixture was stirred at 0° C. for 10 minutes and then at room temperature for 30 minutes. The solution was quenched with saturated $NaHCO_3$ and extracted twice with $CH_2Cl_2$. The combined organic layers were dried ($Na_2SO_4$), filtered, concentrated to ⅓ volume and applied on Merck silica gel column (50% $CH_2Cl_2$/hexane). Flash chromatography afforded the title compound as a white solid, which was recrystallized from hexane (2.3 g, 82.1%).

m.p. 176°–177° C. $R_f$ 0.65 (15% EtOAc/hexane), UV

G. (S)-4-[[[6-(1-Adamantyl)-4-(4-fluorophenyl)- 2-(1-methylethyl)-3-pyridinyl] ethynyl]methoxyphosphinyl]-3-[[(1,1-dimethylethyl)diphenylsilyl]oxy]butanoic acid, methyl ester A solution of the dibromide from part F (2.2 g, 4.13 mmol) in THF (18 ml) at –78° C. was treated with n-BuLi (2.5M in hexane, 3.46 ml, 8.67 mmol) over a minute period. The green-blue reaction mixture was stirred for 45 minutes at –78° C. and then transferred via cannula to –78° C. solution of the phosphonochloridate from Example 57, part G, in THF (10 ml). The green-brown reaction mixture was stirred at –78° C. for 30 minutes and quenched with 50% saturated $NH_4Cl$. After warming to room temperature, the solution was diluted with $H_2O$ and poured into saturated $NaHCO_3$. The layers were separated and the aqueous layer was extracted once with ether. The combined organic layers were washed with brine, dried ($Na_2SO_4$), filtered and concentrated under reduced pressure. The dark oily residue was purified by flash chromatography (Merck silica gel, 15% EtOAc/hexane) to afford the title compound as a colorless oil (1.95 g, 59.0%).

$R_f$ 0.36 (30% EtOAc/hexane), UV

H. (S)-4-[[[6-(1-Adamantyl)-4-(4-fluorophenyl)- 2-(1-methylethyl)-3-pyridinyl] ethynyl]methoxyphosphinyl]-3-hydroxybutanoic acid, methyl ester To a solution of the acetylinic phosphonate of part G (1.9 g, 2.36 mmol) in THF (15 mmol) was added HOAc (0.53 ml, 9.44 mmol), followed by tetra-n-butylammonium fluoride (1.0M in THF, 7.08 ml, 7.08 mmol). The reaction mixture was stirred at room temperature under argon for 24 hours. The solution was diluted with EtOAc and washed three times with 5% $KHSO_4$. The aqueous layer was back-extracted twice with EtOAc and the combined organic extracts were dried ($Na_2SO_4$), filtered and concentrated under reduced pressure. The yellow-orange oil was dissolved in ether (added a few drops of THF to obtain a clear solution), cooled to 0° C. and treated with excess diazomethane in ether for 20 minutes. The excess diazomethane was destroyed by the addition of HOAc. Solvent removal gave a dark oily residue, which was purified by flash chromatography (Merck silica gel, 20% acetone/hexane). The title compound was obtained as a colorless oil (0.69 g, 60.0%).

$R_f$ 0.59 (40% acetone/hexane) UV

I. (S)-4-[[[6-(1-Adamantyl)-4-(4-fluorophenyl)- 2-(1-methylethyl)-3-pyridinyl] ethynyl]hydroxyphosphinyl]-3-hydroxybutanoic acid, disodium salt The diester from part H (0.69 g, 1.21 mmol) in dioxane (15 ml) was treated with 1N NaOH (4.23 ml, 4.23 mmol) at room temperature and then heated at 50° C. for 2.5 hours. The reaction mixture became opaque and dioxane was added until a clear solution was obtained (30 ml). After heating for an additional 16 hours the reaction mixture again became opaque with oily droplets present. To obtain a clear solution, MeOH (15 ml) was added and the solution was treated with additional 1N NaOH (1.21ml) and heated for 4 hours. Solvent was evaporated and the residue was chromatographed on HP-20 resin, eluting first with $H_2O$ (300 ml), followed by 25% MeOH/$H_2O$ (300 ml), 50% MeOH/$H_2O$ (300 ml) and finally MeOH (100 ml). The collected product fractions were evaporated, dissolved in $H_2O$, filtered, frozen and lyophilized to yield Example 66 as a white lyophilate (0.30 g, 48.0%).

$R_f$ 0.45 (8:1:1—$CH_2Cl_2$:$CH_3OH$:HOAc), UV Analysis for $C_{30}H_{33}NFPO_5Na_2 \times 2.0\ H_2O$: Calc'd C, 58.15; H, 6.02; N, 2.26; F, 3.07; P, 5.00 Found C, 58.24; H, 5.77; N, 2.11; F, 3.04; P, 4.79

Example 67

(S)-4-[ [ [ 5-Fluoro-4-(4-fluorophenyl)-2-(1-methylethyl))-6-phenyl-3-pyridinyl]ethynyl]hydroxyphosphinyl] -3-hydroxybutanoic acid, disodium salt A. 2-Fluoroacetophenone A mixture of 2-bromoacetophenone (20.00 gm, 100 mmol) and KF (8.82 gm, 152 mmol) in dry DMF (35 ml) was heated at 100° C. for 1 hour. Additional KF (2.26 gm) was added and heating of the mixture continued for 4 more hours. The dark-red solution was cooled, poured into $Et_2O$ and washed with $H_2O$ (twice) and brine. The ethereal solution was dried ($Na_2SO_4$), filtered, and stripped to yield a dark red oil. The oil was distilled to collect a fraction boiling between 62°–64° C. at 1 mm Hg which was 91 molar percent the title compound and 9 molar percent acetophenone (6.00 gm). Flash chromatography (Merck $SiO_2$, 10% EtOAc in hexane) afforded the pure title compound (5.50 gm, 45%) as a liquid that solidifies near room temperature.

TLC $R_f$ 0.28 (20% EtOAc in hexane)

B. $\Delta$-Fluoro-$\beta$-(4-fluorophenyl)-$\alpha$-(2-methyl-1-oxopropyl)-$\Delta$-oxobenzenepentanoic acid, ethyl ester A $-78°$ C. solution of LiN(TMS)$_2$ (1.0M in THF, 28.7 ml, 28.7 mmol) in dry THF (17 ml) was treated with a solution of 2-fluoroacetophenone (A) (3.500 gm, 28.65 mmol) in THF (3 ml). After 30 minutes, a solution of title compound from Example 53, part A, (6.310 gm, 23.9 mmol) in THF (4 ml) was added dropwise to the above solution. After 1.25 hours, the red-orange mixture was quenched with saturated $NH_4Cl$ and warmed to room temperature. The mixture was diluted with $H_2O$ and subsequently extracted with $Et_2O$. The $Et_2O$ extract was washed with brine, dried ($Na_2SO_4$), filtered, and stripped to give a yellow oil containing the title compound in crude form.

C. 5-Fluoro-4-(4-fluorophenyl)-2-(1-methylethyl)- 6-phenyl-3-pyridinecarboxylic acid, ethyl ester A mixture of the above crude oil, $NH_4OAc$ (5.52 gm, 71.6 mmol), and Cu(OAc)$_2$ (16.77 gm, 84 mmol) in glacial HOAc (80 ml) was heated at 100° C. for 2 hours. Additional $NH_4OAc$ (2.5 gm) was added and the temperature of the reaction mixture was raised to 110° C. and heating continued for 16 hours. The solution was cooled to room temperature and subsequently poured into an ice cold mixture of concentrated $NH_4OH$ (90 ml) in $H_2O$ (120 ml). The mixture was extracted with $Et_2O$ and the $Et_2O$ extract was washed with $H_2O$ and brine, then dried ($Na_2SO_4$), filtered and stripped to yield a brown oil. The oil was flashed (Merck $SiO_2$, 5% EtOAc in hexane) to give the title compound as a colorless oil (1.190 gm, approx. 11%), which was contaminated with an undetermined amount of the non-5-fluorinated pyridine ester 4-(4-fluorophenyl)-2-(1-methylethyl)- 6-phenyl-3-pyridinecarboxylic acid, ethyl ester.

TLC $R_f$ 0.49 (20% EtOAc in hexane)

D. 5-Fluoro-4-(4-fluorophenyl)-2-(1-methylethyl)- 6-phenyl-3-pyridinemethanol

A cold (0° C.) solution of the ester from part C (purity uncertain, 2.875 gm, assume 7.5 mmol) in dry THF (80 ml) was treated with LiAlH$_4$ (990 mg, 26 mmol). After the addition, the temperature of the reaction was raised to 25° C. and stirring of the mixture continued for 2 hours. The solution was recooled to 0° C. and quenched in succession with $H_2O$ (1 ml), 10% NaOH (1.5 ml), and $H_2O$ (3 ml). The solution was filtered and the salts were washed with EtOAc. The filtrate was stripped to yield a mixture of the title compound and the non-fluorinated pyridine alcohol (the title compound where F on the pyridine ring is replaced with H) as a solid that could not be purified by recrystallization. The solid was dissolved in warm 40% EtOAc in hexane and flashed twice (Merck $SiO_2$, 20% EtOAc in hexane) to give the title compound (approx. 90% purity, 800 mg) and impure title compound (approx. 60% purity, 682 mg) as solids.

m.p. 163.5°–165° C. TLC $R_f$ 0.19 (20% EtOAc in hexane)

E. 5-Fluoro-4-(4-fluorophenyl)-2-(1-methylethyl)- 6-phenyl-3-pyridinecarboxaldehyde A $-78°$ C. solution of oxalyl chloride (435 µl, 633 mg, 5.0 mmol) in $CH_2Cl_2$ (15 ml) was treated dropwise with a solution of dry DMSO (710 µl, 782 mg, 10.0 mmol) in $CH_2Cl_2$ (1 ml). After 15 minutes, a solution of the alcohol from part D (91% purity, 1.300 gm, assume 3.83 mmol) in $CH_2Cl_2$ (5 ml) and THF (2 ml) was added dropwise to the above mixture. Twenty minutes after the addition, TEA (3.4 ml) was added and the mixture was stirred at $-78°$ C. for 5 minutes and then warmed to room temperature. The mixture was diluted with $Et_2O$ and washed twice with $H_2O$ and once with brine. The organic layer was dried ($Na_2SO_4$), filtered, and stripped to yield a solid. The solid was dissolved in $CH_2Cl_2$ and flashed (Merck $SiO_2$, 5% EtOAc in hexane) to give the desired product in approximately 92% purity. Recrystallization from hexane gave in two crops the title compound (1.153 gm, 89%) which was pure by NMR analysis.

m.p. 135.5°–137.2° C. TLC $R_f$ 0.45 (20% EtOAc in hexane)

F. 3-(2,2-Dibromoethenyl)-5-fluoro-4-(4 -fluorophenyl)-2-(1-methylethyl)-6 -phenylpyridine A solution of carbon tetrabromide (1.579 gm, 4.8 mmol) in $CH_2Cl_2$ (6 ml) was added over a 10-minute period to a cold (0° C.) solution of the aldehyde from part E (1.070 gm, 3.17 mmol) and triphenylphosphine (2.500 gm, 9.5 mmol) in $CH_2Cl_2$ (15 ml). After the addition was complete, the cooling bath was removed and the mixture was stirred for 30 minutes. The solution was quenched with saturated $NaHCO_3$ and extracted twice with $CH_2Cl_2$. The combined organic layers were dried ($Na_2SO_4$), filtered and concentrated. The concentrate was chromatographed (flash, Merck $SiO_2$, 30% $CH_2Cl_2$ in hexane) to give the dibromide title compound as a white foam that solidified. Recrystallization from hexane gave the title compound (1.321 gm, 84%) as a white solid.

m.p. 104.5°–107.0° C. TLC $R_f$ 0.54 (20% EtOAc in hexane)

G. (S)-4-[[[5-Fluoro-4-(4-fluorophenyl)-2 -(1-methylethyl)-6-phenyl-3-pyridinyl] ethynyl]methoxyphosphinyl]-3-[[(1 -dimethylethyl)diphenylsilyl]oxy]butanoic acid, methyl ester A solution of the dibromide from part F (1.230 gm, 2.49 mmol) in THF (8 ml) at $-78°$ C. was treated with n-BuLi (2.5M in hexane, 2.5 ml, 6.25 mmol) over a 15-second period and the resulting dark brown-red solution was stirred for 40 minutes. The acetylenic anion solution was added dropwise via cannula over a 10-minute period to a $-78°$ C. solution of the phosphonochloridate from Example 57, part G in THF (12 ml). The resulting mixture was stirred at $-78°$ C. for 30 minutes, then quenched with 50% saturated $NH_4Cl$. The solution was warmed to 0° C., diluted with $H_2O$, and poured into saturated $NaHCO_3$. The aqueous phase was extracted once with $Et_2O$. The $Et_2O$ layer was washed with brine, dried ($Na_2SO_4$), filtered and stripped to give an orange oil. The residue was chromatographed (flash, Merck SiO$_2$, 40% EtOAc in hexane) to afford the title compound as a yellow foam (1.254 gm, 66%).

TLC R$_f$ 0.29 (40% EtOAc in hexane)

H. (S)-4-[[[5-Fluoro-4-(4-fluorophenyl)-2 -(1-methylethyl)-6-phenyl-3-pyridinyl] ethynyl]methoxyphosphinyl]-3-hydroxybutanoic acid, methyl ester A mixture of the part G compound (1.227 gm, 1.60 mmol), tetra-n-butylammonium fluoride (1.0M in THF, 6.4 ml, 6.4 mmol), and HOAc (400 ul, 420 mg, 7 mmol) in THF (14 ml) was stirred at room temperature for 16 hours. The solution was diluted with EtOAc and washed 3 times with 5% KHSO$_4$. The EtOAc layer was dried (Na$_2$SO$_4$), filtered and stripped to afford an oil. The oil was dissolved in Et$_2$O, cooled to 0° C. and treated with excess diazomethane for 5 minutes. The excess diazomethane was destroyed by the addition of HOAc and the solvent was removed in vacuo. The residue was chromatographed (flash, Merck SiO$_2$, 30% acetone in hexane followed by 40% acetone in hexane) to afford the title compound (669 mg, 79%) as a colorless oil.

TLC R$_f$ 0.38 (1:1—acetone:hexane)

I. (S)-4-[[[5-Fluoro-4-(4-fluorophenyl)-2 -(1-methylethyl)-6-phenyl-3-pyridinyl] ethynyl]hydroxyphosphinyl]-3-hydroxybutanoic acid, disodium salt A solution of the part H compound (412 mg, 0.78 mmol) in dioxane (5 ml) was treated with 1N NaOH (2.8 ml, 2.8 mmol) at room temperature and the mixture was subsequently heated at 60° C. under argon for 1.5 hours. The solvent was evaporated and the residue was chromatographed on HP-20 resin, eluting in succession with H$_2$O (200 ml), 50% MeOH in H$_2$O (200 ml), and MeOH (100 ml). The desired fractions were pooled and evaporated and the residue was taken up in H$_2$O and lyophilized to give Example 67 (343 mg, 76%) as a white solid.

TLC R$_f$ 0.13 (8:1:1—CH$_2$Cl$_2$:HOAc:MeOH) Analysis for C$_{26}$H$_{22}$F$_2$Na$_2$NO$_5$P×1.79 H$_2$O: C, 54.25; H, 4.48; N, 2.43; F, 6.60; P, 5.38 Found: C, 54.23; H, 4.04; N, 2.45; F, 6.28; P, 5.33

Example 68

(S)-4-[ [ [ 4-(4-Fluorophenyl)-2,6-bis (1-methylethyl)-3-pyridinyl]ethynyl]hydroxyphosphinyl]-3-hydroxybutanoic acid, disodium salt A. 1-(4-Fluorophenyl)-4-methyl-1 -penten-3-one A sodium ethoxide solution (21% by weight in EtOH, 4.86 gm, 15 mmol) was added to a mixture of methylisopropylketone (8.61 gm, 100 mmol, from Aldrich) and 4-fluorobenzaldehyde (12.411 gm, 100 mmol, from Aldrich) in ethanol (150 ml). The solution was allowed to stir at room temperature for 3 hours. The solvent was evaporated to afford an orange oil. The oil was dissolved in ether, washed with saturated NH$_4$Cl and brine, then dried over Na$_2$SO$_4$, filtered and concentrated to give an orange oil. The oil was purified by distillation (bp= 106° C. at 1.3 mm Hg) to afford the title compound as a pale yellow oil (10.118 gm, 53%).

TLC: Rf 0.32 (5% EtOAc in hexane)

B. 3-(4-Fluorophenyl)-6-methyl-2-(2-methyl- 1-oxopropyl)-5-oxoheptanoic acid, ethyl ester A sodium ethoxide solution (21% by weight in EtOH, 3.27 gm, 10.1 mmol) was added to a mixture of ethyl isobutyrylacetate (16.03 gm, 101.1 mmol) and the enone of part A (12.944 gm, 67.4 mmol) in ethanol (200 ml). The solution was allowed to stir 66 hours under argon at room temperature. The solution was then concentrated to an orange oil and partitioned between saturated NH$_4$Cl and EtOAc. The organic layer was washed with water and brine, dried over Na$_2$SO$_4$, filtered and concentrated to give a pale yellow oil. The oil was dissolved in boiling hexane and cooled to 0° C. The title compound was obtained as fine white needles (18.352 gm, 78%).

m.p. 57°–60° C. TLC: Rf 0.20 (5% EtOAc in hexane) Elemental Analysis for C$_{20}$H$_{27}$FO$_4$: Calculated C, 68.55; H, 7.77; F, 5.42 Found C, 68.63; H, 7.96; F, 5.35

C. 4-(4-Fluorophenyl)-2,6-bis(1-methylethyl)- 3-pyridinecarboxylic acid, ethyl ester NH$_4$OAc (10.52, 136.5 mmol) and Cu(OAc)$_2$ (22.71 gm, 113.75 mmol)) were added to an acetic acid solution (100 ml) of the 1,5 diketone of part B (15.97 gm, 45.5 mmol). The solution was allowed to reflux 18 hours under argon, then cooled to room temperature and poured into an ice-cold solution of NH$_4$OH/H$_2$O (150 ml/200 ml). The mixture was extracted with ether (twice), the organic layers were pooled and washed with water and saturated NaCl, then dried over Na$_2$SO$_4$ and concentrated to afford a yellow oil which was used directly in the next reaction.

TLC: Rf 0.16 (10% EtOAc in hexane)

D. 4-(4-Fluorophenyl)-2,6-bis(1-methylethyl)- 3-pyridinemethanol

A THF solution (150 ml) of the crude ester from part C (14.900 gm, 45 mmol) was cooled to 0° C. and treated with LiAlH$_4$ (5.42 gm, 143 mmol). The solution was allowed to stir twenty minutes at 0° C. and then warmed to room temperature and stirred 3.5 hours. The solution was then cooled to 0° C. and quenched by dropwise addition of 5.4 ml of water, followed by 5.4 ml of 15% NaOH, then 16.2 ml water. The aluminum paste was filtered out of solution and the filtrate concentrated to give a yellow solid. The solid was recrystallized from hexane to afford the title compound as hard yellow crystals (9.429 gm, 73% from the part B compound).

m.p. 88°–90° C. TLC: Rf 0.125 (10% EtOAc in hexane) Elemental Analysis for C$_{18}$H$_{22}$NFO*0.08 H$_2$O: Calculated C, 74.85; H, 7.73; N, 4.85; F, 6.58 Found C, 75.01; H, 7.85; N, 4.69; F, 6.34

E. 4-(4-Fluorophenyl)-2,6-bis(1-methylethyl)- 3-pyridinecarboxaldehyde

A solution of DMSO (5.22 gm, 66.8 mmol) in methylene chloride (20 ml) was added to a solution of oxalyl chloride (4.24 gm, 33.4 mmol) in methylene chloride (125 ml) which had been cooled to −78° C. The alcohol from part D (7.350 gm, 26 mmol) was then added dropwise to the flask as a methylene chloride (25 ml) solution. Methylene chloride (25 ml) was added to the solution slowly in order to make a slurry out of the reaction mixture, which had solidified. Triethylamine (18.4 ml, 13.8 mmol) was added 20 minutes later, and the solution was stirred for an additional 10 minutes, then warmed to room temperature. The solution was diluted with ether, washed with water and brine, dried over Na$_2$SO$_4$, filtered and concentrated to afford a yellow solid. The solid was dissolved in hot hexane, and cooled, to give the title compound as hard yellowish crystals (5.839 gm, 79%).

m.p. 72°–75° C. TLC: Rf 0.21 (10% EtOAc in hexane)

F. 3-(2,2-Dibromoethenyl)-4-(4-fluorophenyl)- 2,6-bis(1-methylethyl)pyridine

A solution of CBr$_4$ (10.30 gm, 30.5 mmol) in methylene chloride (100 ml) was added over 15 minutes to a solution of triphenylphosphine (17.140 gm, 65.3 mmol) and the aldehyde from part E (5.800 g, 20.4 mmol) in methylene chloride (150 ml), which was stirring under argon at 0° C. The solution stirred for an additional 45 minutes at 0° C., then at room temperature for 1 hour. Saturated NaHCO$_3$ (70 ml) was then added to quench the reaction. The aqueous layer was extracted with methylene chloride (3 times), the organic layers were combined and washed with brine, then dried over Na$_2$SO$_4$, filtered, and concentrated to about 50 ml. The viscous solution was subjected to flash chromatography on Merck silica gel in 30% methylene chloride in hexane. The desired fractions were pooled and concentrated to give a clear oil, which solidified upon standing overnight. The white solid was recrystallized from hexane to afford the vinyl dibromide title compound as hard, white crystals (5.010 gm, 56%).

m.p. 52°–53° C. TLC: Rf 0.57 (5% EtOAc in hexane) Elemental Analysis for C$_{19}$H$_{20}$NBr$_2$F: Calculated C, 51.73; H, 4.57; N, 3.18; Br, 36.22; F, 4.31 Found C, 51.79; H, 4.52; N, 3.08; Br, 36.30; F, 4.21

G. (S)-4-[ [ [ 4-(4-Fluorophenyl)-2,6-bis (1 -methylethyl)-3-pyridinyl]ethynyl]methoxyphosphinyl] -3-[ [ (1,1-dimethylethyl)diphenylsilyl] oxy]butanoic acid, methyl ester n-BuLi (2.5M in hexane, 6.54 ml, 16.36 mmol) was added dropwise to a solution of the dibromide from part F (2.000 gm, 4.54 mmol) in THF (20 ml), stirring under argon at −78° C. The solution was allowed to stir 1 hour at −78° C., then cannulated into a THF solution (20 ml) of the chloridate from Example 57, part G which had also been cooled to −78° C. The solution was stirred at−78° C. for 45 minutes, then quenched with saturated NH$_4$Cl. The solution was warmed to 0° C., and saturated NaHCO$_3$ was added. The mixture was diluted with ether and the organic layer was washed with brine, dried over Na$_2$SO$_4$, filtered and concentrated to an orange oil. The oil was purified by flash. chromatography on Merck silica gel in 40% EtOAc in hexane. Pure product fractions were combined and evaporated to afford 0.660 gm of a yellow oil. Impure fractions were pooled, concentrated and purified again by flash chromatography in 35% EtOAc in hexane on Merck silica gel to afford an additional 0.360 gm of the title compound as a yellow oil (total yield, 1.020 gm, 33%).

TLC: Rf 0.64 (50% ETOAc in hexane) (For optimal results, the amount of 2.5M n-BuLi should be 3.80 ml, 9.53 mmol.)

H. (S)-4-[[[4-(4-Fluorophenyl)-2,6-bis(1 -methylethyl)-3-pyridinyl]ethynyl]methoxyphosphinyl] -3-hydroxybutanoic acid, methyl ester (Bu)$_4$NF (1.0M in THF, 4.47 ml, 4.47 mmol) was added to a solution of the silyl ether from part G (1.020 gm, 1.49 mmol) and acetic acid (0.45 gm, 7.45 mmol) in THF (20 ml) under argon. The solution was allowed to stir 17 hours at room temperature, then diluted with EtOAc (to 50 ml) and washed with 5% KHSO$_4$ (3 times). The aqueous layers were extracted with EtOAc (3 times). The organic layers were pooled and washed with brine, then dried over Na$_2$SO$_4$, filtered and concentrated to afford an orange oil. The oil was dissolved in ether and treated with excess CH$_2$N$_2$. Excess CH$_2$N$_2$ was removed with a stream of argon, and the solution was concentrated to give a yellow oil. The oil was purified by flash chromatography on Merck silica gel in 35% acetone in hexane. The desired fractions were pooled and concentrated to afford the title compound as a yellow oil (0.424 gm, 60%).

TLC: Rf 0.65 (50% acetone in hexane)

I. (S)-4-[[[4-(4-Fluorophenyl)-2,6-bis(1-methylethyl)-3-pyridinyl]ethynyl]hydroxyphosphinyl] -3-hydroxybutanoic acid, disodium salt NaOH (1M in water, 2.68 ml, 2.68 mmol) was added to a solution of the alcohol from part H (0.424 gm, 0.892 mmol) in dioxane (10 ml), which was stirring under argon at room temperature. The solution was then heated to 55° C. and allowed to stir 45 minutes. Additional NaOH (1M in water, 2.0 ml, 2.0 mmol) was added to the solution. The solution was allowed to stir 3.5 hours at 55° C. After cooling to room temperature, the solution was concentrated to a white solid. The solid was then chromatographed on HP-20 resin, eluting first with water (200 ml) and then a linear gradient from 100% H$_2$O (400 ml) to 100% MeOH (425 ml). The desired fractions were pooled, the solvent removed on the rotovap, the residue taken up in water and lyophilized to give Example 68 as a fluffy white solid (0.355 gm, 81%).

TLC: Rf 0.74 (6:3:1, n-propanol:NH$_4$OH:H$_2$O) Elemental Analysis for C$_{23}$H$_{25}$NFPNa$_2$O$_5$* 1.40 H$_2$O: Analysis: C, 53.47; H, 5.42; N, 2.71; F, 3.63; P, 5.99 Found: C, 53.49; H, 5.11; N, 2.69; F, 3.51; P, 6.24

Example 69

(S)-4-[ [ [ 6-Cyclohexyl-4-(4-fluorophenyl)-2-(1 -methylethyl)-3-pyridinyl]ethynyl]hydroxyphosphinyl] -3-hydroxybutanoic acid, disodium salt A. 1-Cyclohexyl-3-(4-fluorophenyl)-2 -propen-1-one A sodium ethoxide solution (21% by weight in ethanol, 6.805 gm, 21 mmol) was added to a mixture of 1-cyclohexyl-1-ethanone (18.749 g, 140 mmol, from Aldrich) and 4-fluorobenzaldehyde (17.37 g, 140 mmol, from Aldrich) in ethanol (100 ml), stirring under argon. The solution was allowed to stir 1.5 hours. The reaction mixture was then concentrated to afford an orange oil. The oil was dissolved in ether, washed with saturated NH$_4$Cl and brine, then dried over Na$_2$SO$_4$, filtered and concentrated to an orange oil. The oil was purified by distillation (bp= 143° C. at 1.3 mm Hg). The resultant yellowish oil slowly solidified to afford the title compound as hard yellow crystals (22.640 gm, 65%).

m.p. 44°–46° C. TLC: Rf 0.43 (5% EtOAc in hexane) Elemental Analysis for C$_{15}$H$_{17}$FO: Calculated: C, 77.56; H, 7.38; F, 8.18 Found: C, 77.57; H, 7.58; F, 7.99

B. β-(4-Fluoro-2-phenyl)-α-(2-methyl-1-oxopropyl)-Δ-oxocyclohexanepentanoic acid, ethyl ester A sodium ethoxide solution (21% by weight in ethanol, 0.530 gm, 7.79 mmol) was added to a mixture of the enone from part A (12.930, 52 mmol) and ethyl isobutyrylacetate (12.32 gm, 77.9 mmol) in ethanol (200 ml). The solution was allowed to stir under argon at room temperature for 16 hours. Additional ethanol (30 ml) was added to the flask to make a slurry of the partially solidified reaction mixture. A white solid was then filtered out of solution and recrystallized from hot hexane to afford the title compound as a waxy white solid (19.574 gm, 92%).

m.p. 75°–77° C. TLC: Rf 0.26 (10% EtOAc in hexane) Elemental Analysis for C$_{23}$H$_{31}$FO$_4$: Calculated: C, 70.74; H, 8.00; F, 4.87 Found: C, 70.82; H, 8.21; F, 4.82

C. 6-Cyclohexyl-4-(4-fluorophenyl)-2-(1 -methylethyl)-3-pyridinecarboxylic acid, ethyl ester NH$_4$OAc (7.46 gm, 96.8 mmol) and Cu(OAc)$_2$ (14.49 gm, 72.6 mmol) were added to an acetic acid solution (100 ml) of the 1,5 diketone from part B (9.850 gm, 24.2 mmol). The solution was allowed to reflux 18 hours under argon. The solution was then poured into an ice-cold solution of NH$_4$OH/H$_2$O (150 ml/200 ml). The mixture was extracted with ether (twice). The organic layers were combined and washed with water and brine, then dried over Na$_2$SO$_4$, and concentrated to afford a yellow oil. The oil was dissolved in hot hexane and cooled to afford the ester title compound as large yellowish crystals (4.300 gm, 48%).

m.p. 68°–70° C. TLC: Rf (10% EtOAc in hexane) Elemental Analysis for $C_{23}H_{27}NFO_2$: Calculated: C, 73.86; H, 7.44; N, 3.75; F, 5.08 Found: C, 74.08; H, 7.52; N, 3.53; F, 5.00

D. 6-Cyclohexyl-4-(4-fluorophenyl)-2-(1-methylethyl)-3-pyridinemethanol

A THF solution (20 ml) of the ester from part C (4.000 gm, 10.8 mmol) was cooled to 0° C. and treated with $LiAlH_4$ (1.23 gm, 55.7 mmol). The solution was allowed to stir 20 minutes at 0° C., then warmed to room temperature and stirred for 2 hours. Additional $LiAlH_4$ (0.885 gm, 23 mmol) was added to the solution at room temperature. The solution stirred 20 minutes. The solution was then cooled to 0° C. and quenched by dropwise addition of 2.1 ml of water, followed by 2.1 ml of 15% NaOH, and then 6.3 ml water. The aluminum paste was filtered out of solution and the filtrate concentrated to afford a yellow oil. The oil was dissolved in hot hexane and the resultant solution cooled to give the title compound as fine white needles (3.077 gm, 87%).

m.p. 101°–104° C. TLC: Rf 0.16 (5% EtOAc in hexane) Elemental Analysis for $C_{21}H_{25}NFO*0.27\ H_2O$: Calculated: C, 76.15; H, 7.77; N, 4.23; F, 5.74 Found: C, 76.43; H, 8.08; N, 3.95; F, 5.61

E. 6-Cyclohexyl-4-(4-fluorophenyl)-2-(1-methylethyl)-3-pyridinecarboxaldehyde

DMSO (0.929 gm, 11.9 mmol) was added to a solution of oxalyl chloride (0.756 gm, 5.95 mmol) in methylene chloride (40 ml), which was cooled to −78° C. under argon. The solution was allowed to stir 10 minutes. Then, the alcohol from part D (1.50 gm, 4.58 mmol) was added to the flask as a methylene chloride (10 ml) solution. Gentle heating was required to get the alcohol into solution. Triethylamine (3.65 ml) was added twenty minutes later. The solution was stirred for an additional 10 minutes, then was warmed to room temperature. The solution was diluted with ether, washed with water and brine, then dried over $Na_2SO_4$, filtered and concentrated to afford a yellow-brown oil. The compound was purified by flash chromatography on Merck silica gel in 5% EtOAc in hexane. Fractions containing pure product were combined and concentrated. The resulting yellowish solid was recrystallized from hexane to give the title compound as hard, white crystals (1.239 gm, 83%).

m.p. 59°–61° C. TLC: Rf 0.33 (10% EtOAc in hexane) Elemental Analysis for $C_{21}H_{23}NFO*0.21\ H_2O$: Calculated: C, 76.87; H, 7.19; N, 4.27; F, 5.79 Found: C, 77.06; H, 7.56; N, 4.08; F, 5.78

F. 3-(2,2-Dibromoethenyl)-6-Cyclohexyl-4-(4-fluorophenyl)-2-(1-methylethyl)pyridine $CBr_4$ (1.55 gm, 4.60 mmol) was added as a methylene chloride solution (10 ml) over 5 minutes to a mixture of triphenylphosphine (2.58, 9.85 mmol) and the aldehyde from part E (1.230 gm, 3.07 mmol) in methylene chloride (50 ml) that had been cooled to 0° C. The solution was stirred for an additional 30 minutes. The reaction was quenched with saturated $NaHCO_3$ and the solution allowed to warm to room temperature. The aqueous layer was extracted with methylene chloride (twice) and the organic layers were combined and washed with brine, then dried over $Na_2SO_4$, filtered and concentrated to about 10 ml. The solution was subjected to flash chromatography on Merck silica gel in 30% methylene chloride in hexane. The desired fractions were pooled and concentrated to afford a clear oil, which solidified upon standing overnight. The white solid was recrystallized from hexane to afford the title compound as hard, white crystals (1.220 gm, 85%).

m.p. 98°–100° C. TLC: Rf 0.89 (5% EtOAc in hexane) Elemental Analysis for $C_{20}H_{16}NBr_2FS$: Calculated: C, 49.92; H, 3.35; N, 2.91; Br, 33.21; F, 3.95; S, 6.66 Found: C, 50.43; H, 3.25; N, 2.67; Br, 33.43; F, 3.95; S, 6.96

G. (S)-4-[[[6-Cyclohexyl-4-(4-fluorophenyl)-2-(1-methylethyl)-3-pyridinyl]ethynyl] methoxyphosphinyl]-3[[(1,1-dimethylethyl)diphenylsilyl] oxy]butanoic acid, methyl ester 2.5M n-BuLi (1.68 ml, 4.2 mmol) was added dropwise to a solution of the dibromide from part F (3.976 gm, 2.10 mmol) in THF (15 ml) at −78° C. under argon. The solution was allowed to stir 1 hour at −78° C., then cannulated into a THF solution (15 ml) of the chloridate from Example 57, part G which had also been cooled to −78° C. The resultant red-amber solution was stirred for 45 minutes, then quenched with saturated $NH_4Cl$ (15 ml) and warmed to 0° C. Then, saturated $NaHCO_3$ was added to the solution, which was subsequently warmed to room temperature. The mixture was diluted with ether and the organic layer was washed with brine, dried over $Na_2SO_4$, filtered and concentrated to give an orange oil. The oil was purified by flash chromatography on Merck silica gel in 40% EtOAc in hexane. The desired fractions were combined and evaporated to afford the title compound as a beige foam (1.018 gm, 68%).

TLC: Rf 0.35 (40% EtOAc in hexane)

H. (S)-4-[[[6-Cyclohexyl-4-(4-fluorophenyl)- 2-(1-methylethyl)-3-pyridinyl] ethynyl]methoxyphosphinyl]-3-hydroxy] butanoic acid, methyl ester $(Bu)_4NF$ (1.0M in THF, 4.26 ml, 4.26 mmol) was added to a mixture of silyl ether from part G (1.018 gm, 1.42 mmol) and acetic acid (0.42 gm, 7.20 mmol) in THF (10 ml). The solution was allowed to stir 18 hours at room temperature under argon. The solution was diluted with EtOAc (20 ml) and then washed with 5% $KHSO_4$ (3×20 ml). The aqueous layers were back-extracted with EtOAc (3 times). The organic layers were pooled and washed with brine, then dried over $Na_2SO_4$, filtered and concentrated to afford a brown oil. The oil was dissolved in ether (15 ml) and treated with excess $CH_2N_2$. Excess $CH_2N_2$ was removed with a stream of argon, and the solution was concentrated to a brown oil. The oil was purified by flash chromatography on Merck silica gel in 35% acetone in hexane. The desired fractions were pooled and concentrated to afford the title compound as a beige foam (0.370 gm, 51%).

TLC: Rf 0.49 (40% acetone in hexane)

I. (S)-4-[[[6-Cyclohexyl-4-(4-fluorophenyl)- 2-(1-methylethyl)-3-pyridinyl] ethynyl]hydroxyphosphinyl]-3-hydroxybutanoic acid, disodium salt NaOH (1M in water, 2.10 ml, 2.10 mmol) was added to a solution of the part H compound (0.370 gm, 0.72 mmol) in dioxane (10 ml). The solution was then heated to 55° C., allowed to stir 45 minutes and then concentrated to a white solid. The residue was dissolved in water and chromatographed on HP-20 resin, eluting first with water (200 ml), then with 50% MeOH in water (400 ml), then with MeOH (200 mol). The desired fractions were pooled and concentrated. The residue was taken up in water and lyophilized to give Example 69 as a fluffy white solid (0.374 gm, 98%).

TLC: Rf 0.67 (6:3:1, n-propanol:$NH_4OH$:$H_2O$) Elemental Analysis for $C_{26}H_{29}NFNa_2PO_5*1.60\ H_2O$: Calculated: C, 55.74; H, 5.79; N, 2.50; F, 3.39; P, 5.53 Found: C, 55.74; H, 5.64; N, 2.66; F, 3.22; P 5.63

Example 70

(S)-4-[ [ [4-(4-Fluorophenyl)-2-(1-methylethyl)-6-(2-thienyl)-3-pyridinyl]ethynyl]hydroxyphosphinyl] -3-hydroxybutanoic acid, disodium salt A. 3-(4-Fluorophenyl)-1-(2-thienyl)-2-propen-1-one A solution of sodium ethoxide (21% by weight in EtOH, 0.68 gm, 10 mmol) was added to a solution of 2-acetylthiophene (12.60 gm, 100 mmol, from Aldrich) and 4-fluorobenzaldehyde (12.41 gm, 100 mmol, from Aldrich) in EtOH (50 ml) and the mixture stirred under argon for 15 minutes. More EtOH (25 ml) was then added to make a slurry of the reaction mixture, which had partially solidified. Acetic acid (0.60 gm, 11 mmol) was added and a yellow solid filtered out of solution. The solid was recrystallized from EtOAc and hexane to afford the title compound as long, pale yellow needles (17.679 gm, 71%).

m.p. 117°–120° C. TLC: Rf 0.24 (10% EtOAc in hexane) Elemental Analysis for $C_{13}H_9FSO*0.21\ H_2O$: Calculated: C, 66.13; H, 4.02; F, 8.05; S, 13.58 Found: C, 66.14; H, 3.95; F, 8.05; S, 13.58

B. β-(4-Fluoro-2-phenyl)-α-(2-methyl-1 -oxopropyl)-Δ-oxo-2-thiophenepentanoic acid, ethyl ester A solution of sodium ethoxide (21% by weight in EtOH, 0.530 gm, 7.79 mmol) was added to a solution of ethyl isobutyrylacetate (16.1 gm, 101 mmol) and the enone from part A (16.975 gm, 67.9 mmol) in EtOH (300 ml) and the mixture stirred under argon at room temperature for 17 hours. Acetic acid (0.667 gm, 11 mmol) was added to quench the reaction, and the solution was concentrated. The oily, yellow solid was dissolved in EtOAc and washed with saturated $NH_4Cl$, $H_2O$, and brine, then dried over $MgSO_4$, filtered and concentrated to give an oily, yellow solid. The solid was recrystallized from hexane to afford the title compound as fine white needles (21.413 gm, 77%).

m.p. 92°–105° C. TLC: Rf 0.25 & 0.30 (20% EtOAc in hexane) Elemental Analysis for $C_{21}H_{23}FSO_4$: Calculated: C, 64.59; H, 5.94; F, 4.87; S, 8.21 Found: C, 64.68; H, 5.98; F, 5.03; S, 8.27

C. 4-(4-Fluorophenyl)-2-(1-methylethyl)-6 -(2-thienyl)-3-pyridinecarboxylic acid, ethyl ester $NH_4OAc$ (8.176 gm, 106 mmol) and $Cu(OAc)_2$ (15.57 gm, 78 mmol) were added to an acetic acid solution (150 ml) of the 1,5 diketone from part B (10.025 gm, 26.5 mmol) and the mixture was allowed to reflux 18 hours under argon. The solution was then poured into an ice-cold solution of $NH_4OH/H_2O$ (200 ml/250 ml). The mixture was extracted with ether and EtOAc, washed with water and saturated NaCl, then dried over $Na_2SO_4$, and concentrated to afford a yellow-brown oil. Flash chromatography was performed on the oil in 5% EtOAc in hexane on Merck silica gel. Product fractions were pooled and concentrated to a yellow solid. The solid was recrystallized from hexane to afford the title compound as hard yellow crystals (5.627 gm, 58%).

m.p. 114°–115° C. TLC: Rf 0.78 (20% EtOAc in hexane)

D. 4-(4-Fluorophenyl)-2-(1-methylethyl)-6 -(2-thienyl)-3-pyridinemethanol

A THF solution (20 ml) of the ester from part C (5.620 gm, 15.2 mmol) was cooled to 0° C. and treated with $LiAlH_4$ (1.730 gm, 72 mmol). The solution was allowed to stir twenty minutes at 0° C. and then was warmed to room temperature. Additional $LiAlH_4$ (1.000 gm, 26.3 mmol) was added to the solution. The solution was allowed to stir 30 minutes, then cooled to 0° C. and quenched by dropwise addition of 2.73 ml of water followed by 2.73 ml of 15% NaOH, then 8.20 ml of water. The aluminum paste was filtered out of solution and the filtrate was concentrated to a yellow solid. The solid was recrystallized from hexane to afford the title compound as hard yellow crystals (4.067 gm, 82%).

m.p. 151°–153° C. TLC: Rf 0.42 (20% EtOAc in hexane) Elemental Analysis for $C_{19}H_{18}NFSO*0.06\ H_2O$: Calculated: C, 69.47; H, 5.56; N, 4.26; F, 5.78; S, 9.76 Found: C, 69.77; H, 5.50; N, 3.96; F, 5.67; S, 9.63

E. 4-(4-Fluorophenyl)-2-(1-methylethyl)-6 -(2-thienyl)-3-pyridinecarboxaldehyde

DMSO (1.53 gm, 19.6 mmol) was added to a solution of oxalyl chloride (1.25 gm, 9.80 mmol) in methylene chloride (40 ml), which had been cooled to −78° C. under argon. The solution was allowed to stir 10 minutes, then the alcohol from part D (2.456 gm, 7.55 mmol) was added to the flask as a methylene chloride (20 ml) solution. Triethylamine (5.25 ml, 38 mmol) was added 20 minutes later and the solution stirred for an additional 10 minutes, then warmed to room temperature. The solution was diluted with ether and washed with water and brine, then dried over $Na_2SO_4$, filtered and concentrated to afford a yellow solid. The solid was recrystallized from hexane to afford the title compound as hard, yellow crystals (2.255 gm, 93%).

m.p. 123°–125° C. TLC: Rf 0.50 (20% EtOAc in hexane)

F. 3-(2,2-Dibromoethenyl)-4-(4-fluorophenyl)- 2-(1-methylethyl)-6-(2 -thienyl)pyridine A solution of $CBr_4$ (3.36 gm, 10 mmol) in methylene chloride (15 ml) was added over 15 minutes to a solution of triphenylphosphine (5.59 gm, 21.3 mmol) and the aldehyde from part E (2.155 gm, 6.67 mmol) in methylene chloride (60 ml), which was stirring under argon at 0° C. The solution stirred for an additional 20 minutes at 0° C., then was warmed to room temperature and stirred 45 minutes. Saturated $NaHCO_3$ (15 ml) was added to quench the reaction. The aqueous layer was extracted with methylene chloride (twice), the organic layers were combined and washed with brine, then dried over $Na_2SO_4$, filtered and concentrated to about 15 ml. The viscous solution was purified by flash chromatography on Merck silica gel in 40% methylene chloride in hexane. Pure fractions were pooled and concentrated to afford a white foam. The foam was dissolved in hexane, and the solution cooled to afford the title compound as pale yellow crystals (2.942 gm, 92%)

m.p. 107°–108° C. TLC: Rf 0.70 (10% EtOAc in hexane) Elemental Analysis for $C_{20}H_{16}NBr_2FS$: Calculated: C, 49.92; H, 2.91; N, 2.91; Br, 33.21; F, 3.95; S, 6.66 Found: C, 50.43; H, 3.25; N, 2.67; Br, 33.43; F, 3.95; S, 6.96

G. (S)-4-[ [ 4-(4-Fluorophenyl)-2-(1-methylethyl)- 6-(2-thienyl)-3-pyridinyl]ethynyl] methoxyphosphinyl]-3-[ [ (1,1-dimethylethyl)diphenylsilyl] oxy]butanoic acid, methyl ester n-BuLi (2.5M in hexane, 3.34 ml, 8.34 mmol) was added dropwise to a solution of the dibromide from part F (2.000 gm, 4.17 mmol) in THF (20 ml) at −78° C. under argon. The solution was allowed to stir 1 hour at −78° C., then cannulated into a THF solution (15 ml) of the phosphonochloridate from Example 57, part G, which had also been cooled to −78° C. The resultant red-amber solution was stirred for 45 minutes, then quenched with saturated $NH_4Cl$, warmed to 0° C. and then saturated $NaHCO_3$ was added to the solution. The mixture was diluted with ether, the organic layer was washed with brine, then dried over Na2SO4, filtered and concentrated to give an orange oil. The oil was purified by flash chromatography on Merck silica gel in 40% EtOAc in hexane. Pure product fractions were combined and concentrated to afford the title compound as a beige foam (1.018 gm, 68%).

TLC: Rf 0.35 (40% EtOAc in hexane)

H. (S)-4-[[[4-(4-Fluorophenyl)-2-(1-methylethyl)- 6-(2-thienyl)-3-pyridinyl]ethynyl] methoxyphosphinyl]-3-hydroxybutanoic acid, methyl ester A solution of $(Bu)_4NF$ (1M in THF, 6.8 ml, 6.8 mmol) was added to a solution of the silyl ether from part G (1.640 gm, 2.2 mmol) and acetic acid (0.66 gm, 11.0 mmol) in THF (15 ml) and the solution allowed to stir at room temperature 16 hours. The solution was diluted with EtOAc, then washed with 5% $KHSO_4$ (3 times). The aqueous layers were extracted with EtOAc (3 times). The organic layers were pooled and washed with brine, then dried over $Na_2SO_4$, filtered and concentrated to afford a yellow oil. The oil was dissolved in ether and treated with excess $CH_2N_2$. Excess $CH_2N_2$ was removed with a stream of argon, and the solution was concentrated to give a yellow oil. The oil was purified by flash chromatography on Merck silica gel in 35% acetone in hexane. Pure product fractions were pooled and concentrated to afford the title compound as a beige foam (0.870 gm, 75%).

TLC: Rf 0.63 (50% acetone in hexane)

I. (S)-4-[ [ [4-(4-Fluorophenyl)-2-(1-methylethyl)- 6-(2-thienyl)-3-pyridinyl] ethynyl] hydroxyphosphinyl]-3-hydroxybutanoic acid, disodium salt A solution of the part H compound (0.870 gm, 1.66 mmol) in dioxane (10 ml) was treated with a solution of NaOH (1M in water, 4.95 ml, 4.95 mmol). The solution was then heated to 55° C. and allowed to stir 1.5 hours. The mixture was concentrated to a white solid. The residue was chromatographed on HP-20 resin, eluting first with water (200 ml), then with 50% MeOH in water (400 ml), then with MeOH (200 ml). The desired fractions were pooled and concentrated, the residue taken up in water and lyophilized to give Example 70 as a fluffy white solid (0.807 gm, 92%).

TLC: Rf 0.70 (6:3:1, n-propanol:$NH_4OH$:$H_2O$) Elemental Analysis for $C_{24}H_{21}NFNa_2PSO_5$*1.55 $H_2O$: Calculated: C, 51.53; H, 4.34; N, 2.50; F, 3.40; P, 5.54 Found: C, 51.58; H, 4.25; N, 2.58; F, 3.72; P, 5.71

Example 71

(S)-4-[ [ [ 6-Cyclopropyl-4-(4-fluorophenyl)-2-(1-methylethyl)-3-pyridinyl] ethynyl] hydroxyphosphinyl] -3-hydroxybutanoic acid, disodium salt A. 1-Cyclopropyl-3-(4-fluorophenyl)-2 -propen-1-one A mixture of 4-fluorobenzaldehyde (9.30 g, 75.00 mmol, Aldrich) and cyclopropyl methyl ketone (6.30 g, 75.00 mmol) in absolute ethanol (100 ml) was treated with a solution of sodium ethoxide in ethanol (21% by weight solution; 2.79 ml, 7.50 mmol). After stirring for 2 hours at room temperature, additional 4-fluorobenzaldehyde was added (1.86 g, 15.00 mmol). The reaction mixture was stirred for 2 hours, concentrated to ⅓ volume and partitioned between 50% saturated $NH_4Cl$/EtOAc (100 ml/250 ml). The layers were separated and the aqueous portion was extracted with EtOAc (twice) and the combined organics were washed with $H_2O$ (twice) and brine, dried ($Na_2SO_4$) and concentrated. The yellow oily residue was distilled (Vigroux column, bp 115°–120° C., 0.6 mm Hg) to afford the title compound as a colorless oil (12.8 g, 89.7%).

$R_f$ 0.37 (15% EtOAc/hexane), UV

B. β-(4-Fluorophenyl)-α-(2-methyl-1-oxopropyl)-Δ -oxocyclopropylpentanoic acid, ethyl ester A mixture of the compound from part A (6.65 g, 35.00 mmol) and ethyl isobutyrylacetate (8.47 ml, 52.50 mmol) in absolute ethanol (50 ml) was treated with a solution of sodium ethoxide in ethanol (21% by weight solution, 6.51 ml, 17.00 mmol). The reaction mixture was stirred at room temperature for 48 hours, then concentrated to ⅓ volume and partitioned between 50% saturated $NH_4Cl$/EtOAc (100 ml/250 ml). The layers were separated and the aqueous portion was extracted with EtOAc (twice) and the combined organics were washed with $H_2O$ (twice) and brine, then dried ($Na_2SO_4$) and concentrated. The dark oily residue was purified by flash chromatography (Merck silica gel, 5% EtOAc/hexane) to afford the title compound as a colorless oil (9.0 g, 74.3%, mixture of diastereomers).

$R_f$ 0.29+ 0.31 (25% EtOAc/hexane), UV

C. 6-(Cyclopropyl-4-(4-fluorophenyl)-2-(1 -methylethyl)-3-pyridinecarboxylic acid, ethyl ester A mixture of the part B compound (9.00 g, 25.7 mmol), ammonium acetate (5.94 g, 77.10 mmol) and copper (II) acetate (12.82 g, 64.25 mmol) in glacial acetic acid (80 ml) was heated at 115° C. for 16 hours (TLC after 30 minutes indicated the presence of two products and almost no starting material). The reaction mixture was cooled and carefully poured into an ice cold mixture of concentrated $NH_4OH$ (100 ml) and $H_2O$ (200 ml). The mixture was extracted with ether (twice) and the ether extracts were washed with $H_2O$ (twice) and brine, then dried ($MgSO_4$), filtered and concentrated. The dark oily residue was purified by flash chromatography (10% EtOAc/hexane) to afford Compound III as a colorless oil (3.45 g, 41.0%).

$R_f$ 0.62 (20% EtOAc/hexane), UV

D. 6-(Cyclopropyl-4-(4-fluorophenyl)-2-(1 -methylethyl)-3-pyridinemethanol

A cold (0° C.) solution of the ester from part C (3.40 g, 11.03 mmol) in dry THF (50 ml) was treated with $LiAlH_4$ (1.25 g, 33.00 mmol). Ten minutes after the addition the cooling bath was removed and the reaction mixture stirred at room temperature for 3 hours and then refluxed for 24 hours. The reaction mixture was cooled to 0° C. and carefully quenched in succession with 1.25 ml of $H_2O$ in THF (10 ml), then 1.25 ml 15% NaOH and finally 3.0 ml $H_2O$. The precipitated aluminum salts were filtered and washed with EtOAc and ether. The filtrate was washed with $H_2O$ and brine, dried ($Na_2SO_4$), filtered and concentrated under reduced pressure to give an oily residue. Purification by flash chromatography (Merck silica gel, 5% EtOAc/hexane) yielded the title compound as a colorless oil which solidified on standing under high vacuum. Recrystallization from hot hexane afforded the title compound as a white solid (2.32 g, 79.3%).

m.p. 94°–95° C. $R_f$ 0.36 (20% EtOAc/hexane), UV Analysis for $C_{18}H_{20}NFO$: Calc'd: C, 75.76; H, 7.06; N, 4.91; F, 6,66 Found: C, 75.23; H, 7.13; N, 4.92; F, 6.71

E. 6-(Cyclopropyl-4-(4-fluorophenyl)-2-(1 -methylethyl)-3-pyridinecarboxaldehyde A −78° C. solution of oxalyl chloride (0.85 ml, 9.67 mmol) in $CH_2Cl_2$ (70 ml) was treated dropwise with a solution of dry DMSO (1.37 ml, 19.34 mmol) in $CH_2Cl_2$ (10 ml). After 15 minutes, a solution of the alcohol from part D (2.30 g, 8.06 mmol) in $CH_2Cl_2$ (10 ml) was added dropwise to the above solution. After 20 minutes, triethylamine (6.75 ml, 48.36 mmol) was added and the mixture was stirred at −78° C. for 20 minutes and then warmed to room temperature. After 1 hour, the reaction was quenched with $H_2O$ and diluted with ether. The layers were separated and aqueous layer was extracted with ether (twice). The combined organic solutions were washed with $H_2O$ (twice) and brine, then dried ($MgSO_4$), filtered and concentrated under reduced pressure. The oily residue was purified by flash chromatography (Merck silica gel, 10% EtOAc/hexane), affording the aldehyde title compound as a colorless oil, which solidified on standing under high vacuum (1.74 g, 76.3%).

m.p. 67°–68° C. $R_f$ 0.56 (20% EtOAc/hexane), UV Analysis for $C_{18}H_{18}NFO$: Calc'd: C, 76.30; H, 6.40; N, 4.94; F, 6.71 Found: C, 75.99; H, 6.43; N, 4.69; F, 6.66

F. 6-Cyclopropyl-3-(2,2-dibromoethenyl)-4 -(4-fluorophenyl)-2-(1-methylethyl)pyridine A solution of carbon tetrabromide (2.89 g, 8.73 mmol) in $CH_2Cl_2$ (10 ml) was added dropwise over a 5-minute period to a cold (0° C.) solution of the aldehyde from part E (1.65 g, 5.82 mmol) and triphenylphosphine (4.58 g, 17.46 mmol)

in $CH_2Cl_2$ (60 ml). The mixture was stirred at 0° C. for 10 minutes and then at room temperature for 1 hour. The solution was quenched with saturated $NaHCO_3$ and extracted twice with $CH_2Cl_2$. The combined organic layers were dried ($Na_2SO_4$), filtered, concentrated to ⅓ volume and applied on Merck silica gel column (50% $CH_2Cl_2$/hexane). Flash chromatography afforded the title compound as a colorless oil (2.36 g, 93.0%).

$R_f$ 0.58 (10% EtOAc/hexane), UV

G. (S)-4-[ [ [ 6-Cyclopropyl-4-(4-fluorophenyl)- 2-(1-methylethyl)-3-pyridinyl] ethynyl]methoxyphosphinyl] -3-[ [ (1,1-dimethylethyl)diphenylsilyl]oxy]butanoic acid, methyl ester A solution of the dibromide from part F (2.00 g, 4.56 mmol) in THF (15 ml) at −78° C. was treated with n-BuLi (2.5M in hexane, 3.82 ml, 9.57 mmol) over a 1-minute period. The brown-red reaction mixture was stirred for 30 minutes at −78° C. and then transferred via cannula to −78° C. solution of the phosphonochloridate from Example 57, part G in THF (15 ml). The dark-brown reaction mixture was stirred −78° C. for 45 minutes and then quenched with 50% saturated $NH_4Cl$. After warming to room temperature, the solution was diluted with $H_2O$ and poured into saturated $NaHCO_3$. The layers were separated and the aqueous layer was extracted once with ether. The combined organic layers were washed with brine, dried ($Na_2SO_4$), filtered and concentrated under reduced pressure. The dark oily residue was purified by flash chromatography (Merck silica gel, 20% EtOAc/hexane) to afford Compound G as a pale yellow oil (2.11 g, 65.0%).

$R_f$ 0.18 (30% EtOAc/hexane), UV

H. (S)-4-[[[6-Cyclopropyl-4-(4-fluorophenyl)- 2-(1-methylethyl)-3-pyridinyl] ethynyl]methoxyphosphinyl]-3-hydroxybutanoic acid, methyl ester To a solution of the acetylinic phosphonate from part G (2.10 g, 2.95 mmol) in THF (15 ml) was added HOAc (0.67 ml, 11.8 mmol), followed by tetra-n-butylammonium fluoride (1.0M in THF, 8.85 ml, 8.85 mmol). The reaction mixture was stirred at room temperature under argon for 24 hours. The solution was diluted with EtOAc and washed three times with 5% $KHSO_4$. The aqueous layer was back-extracted twice with EtOAc and the combined organic extracts were dried ($Na_2SO_4$), filtered and concentrated under reduced pressure. The dark oil was dissolved in ether (added a few drops of THF to obtain a clear solution), cooled to 0° C. and treated with excess diazomethane in ether for 20 minutes. The excess diazomethane was destroyed by the addition of HOAc. Solvent removal gave a dark oily residue, which was purified by flash chromatography (Merck silica gel, 30% acetone/hexane). The product was obtained as a colorless oil (0.77 g, 55.7%).

$R_f$ 0.30 (40% acetone/hexane) UV

I. (S)-4-[ [ [ 6-Cyclopropyl-4-(4-fluorophenyl)- 2-(1-methylethyl)-3-pyridinyl] ethynyl] hydroxyphosphinyl]-3-hydroxybutanoic acid, disodium salt The diester from part H (0.76 g, 1.60 mmol) in dioxane (15 ml) was treated with 1N NaOH (5.60 ml, 5.60 mmol) at room temperature and then heated at 50° C. for 2.5 hours. The reaction mixture was concentrated and the residue was chromatographed on HP-20 resin, eluting first with $H_2O$ (300 ml), followed by 25% MeOH/$H_2O$ (300 ml), 50% MeOH/$H_2O$ (300 ml) and finally MeOH (100ml). The collected product fractions were evaporated, dissolved in $H_2O$, filtered, frozen and lyophilized to give Example 71 as a white lyophilate (0.61 g, 78.2%).

$R_f$ 0.27 (8:1:1—$CH_2Cl_2$:$CH_3OH$:HOAc), UV Analysis for $C_{23}H_{23}NFPO_5Na_2 \times 2.67 H_2O$: Calc'd: C, 51.40; H, 5.31; N, 2.61; F, 3.54; P, 5.76 Found: C, 51.70; H, 5.13; N, 2.31; F, 3.39; P, 5.55

Example 72

(S)-4-[ [ [ 4-(4-Fluorophenyl)-2-(1-methylethyl)-6-(2,3,5,6-tetrafluorophenyl)-3-pyridinyl]ethynyl] hydroxyphosphinyl] -3-hydroxybutanoic acid, disodium salt A. 3-(4-Fluorophenyl)-1-(pentafluorophenyl)- 2-propen-1-one A solution of sodium ethoxide (21% in EtOH, 0.32 gm, 4.76 mmol) was added to a mixture of 1-(pentafluorophenyl)-1-ethanone (5.91 gm, 47.6 mmol, Aldrich) and 4-fluorobenzaldehyde (10.00 gm, 47.6 mmol) stirring in ethanol (100 ml) under argon. The solution was allowed to stir at room temperature for 18 hours, then EtOH was evaporated to afford a yellowish, oily solid. The solid was redissolved in ether, washed with water and brine, then dried over $MgSO_4$, filtered and concentrated to give a yellow residue. The residue was purified by flash chromatography on Merck silica gel in 5% EtOAc/hexane. Fractions containing the product were combined and concentrated to a yellow solid. The solid was recrystallized from hexane to afford the title compound as large yellow crystals (8.220 gm, 52%).

m.p. 80°–84° C. TLC: Rf 0.69 (10% EtOAc in hexane) Elemental Analysis for $C_{15}H_6F_6O$: Calc'd: C 56.98 H 1.91 F 36.05 Found: C 56.81 H 1.73 F 35.43

B. 2,3,4,5,6-Pentafluoro-β-(4-fluorophenyl)-α -(2-methyl-1-oxopropyl)-Δ-oxobenzenepropanoic acid, ethyl ester A solution of sodium ethoxide (21% by weight in EtOH, 0.530 gm, 7.79 mmol) was added to an EtOH solution (100 ml) of the enone from part A (7.220 gm, 21.6 mmol) and ethyl isobutyrylacetate (5.12 gm, 32.4 mmol) stirring under argon at room temperature. In less than 5 minutes, the reaction mixture partially solidified. Ethanol (75 ml) was added to the flask to make a slurry of the reaction mixture. Acetic acid (0.214 gm, 3.56 mmol) was then added to quench the reaction and a yellowish solid was filtered out of solution. The solid was recrystallized from EtOAc/hexane to afford the title compound as hard yellow crystals (8.737 gm, 98%).

m.p. 84° C. TLC: Rf 0.30 (15% EtOAc in hexane)

C. 4-(4-Fluorophenyl)-2-(1-methylethyl)-6 -pentafluorophenyl-3-pyridinecarboxylic acid, ethyl ester $NH_4OAc$ (3.20 gm, 41.78 mmol) and $Cu(OAc)_2$ (6.89 gm, 34.75 mmol) were added to an acetic acid solution (20 ml) of the 1,5 diketone from part B (6.600 gm, 13.9 mmol). The mixture was allowed to reflux 18 hours under argon, then cooled and poured into an ice-cold solution of $NH_4OH$/$H_2O$ (50 ml/75 ml). The mixture was extracted with ether and EtOAc, the organic layers were combined and washed with water and saturated NaCl, then dried over $Na_2SO_4$ and concentrated to afford an amber oil. Flash chromatography was performed on the oil in 5% EtOAc in hexane on Merck silica gel. Product fractions were pooled and concentrated to afford the title compound as a clear oil (4.890 gm, 78%).

TLC: Rf 0.75 (15% EtOAc in hexane)

D. 4-(4-Fluorophenyl)-2-(1-methylethyl)-6 -2,3,5,6-tetrafluorophenyl-3-pyridinemethanol A THF solution (20 ml) of the ester from part C (1.425 gm, 3.14 mmol) was cooled to 0° C. and treated with $LiAlH_4$ (0.358 gm, 9.4 mmol). The solution was allowed to stir 20 minutes at 0° C., then was warmed to room temperature and stirred for an additional 3 hours. The solution was then cooled to 0° C. and quenched by dropwise addition of 1.1 ml of water, followed by 1.1 ml of 15% NaOH, and then 3.3 ml water. The aluminum paste was filtered out of solution. The filtrate was concentrated to a yellow solid. The solid was recrystallized from hexane to afford the title compound as hard yellow crystals (1.014 gm, 80%).

m.p. 130°–132° C. Rf 0.26 (15% EtOAc in hexane)

E. 4-(4-Fluorophenyl)-2-(1-methylethyl)-6 -(2,3,5,6-tetrafluorophenyl)-3-pyridine carboxaldehyde DMSO (0.79 gm, 10.12 mmol) was added to a −78° C. solution of oxalyl chloride (0.64 gm, 5.06 mmol) in methylene chloride (40 ml). After the solution stirred 20 minutes, the part D compound (1.595 gm, 3.89 mmol) was added dropwise to the flask as a methylene chloride (40 ml) solution, and the solution stirred for 20 minutes. Triethylamine (2.71 ml) was added to the solution, which was stirred an additional 10 minutes cold and then at room temperature for 45 minutes. The solution was diluted with ether, washed with water (twice) and brine, then dried over $Na_2SO_4$, filtered and concentrated to afford a yellow solid. The solid was purified by flash chromatography on Merck silica gel in 5% EtOAc in hexane. Fractions containing the product were pooled and concentrated to a yellow solid. The solid was recrystallized from EtOAc/hexane to afford the title compound as yellowish crystals (1.25 gm, 80%).

TLC: Rf 0.39 (15% EtOAc in hexane)

F. 3-(2,2-Dibromoethenyl)-4-(4-fluorophenyl)- 2-(1-methylethyl)-6-(2,3,5,6 -tetrafluorophenyl)pyridine A $CH_2Cl_2$ solution (40 ml) of $CBr_4$ was added over 10 minutes to a 0° C. solution of triphenylphosphine (2.55 gm, 9.72 mmol) and the aldehyde from part E (1.24 gm, 3.04 mmol) in methylene chloride (40 ml). The solution stirred for 45 minutes, then was warmed to room temperature over 30 minutes and the reaction quenched with saturated $NaHCO_3$ (15 ml). The aqueous layer was back-extracted with methylene chloride (twice), the organic layers combined and washed with brine, then dried over $Na_2SO_4$, filtered concentrated to about 10 ml. The solution was purified by flash chromatography on Merck silica gel in 40% methylene chloride in hexane. The desired fractions were pooled and concentrated to a white solid. The solid was recrystallized from hot hexane to afford the title compound as hard white crystals (1.346 gm, 77%).

m.p. 77° C. TLC: Rf 0.73 (15% EtOAc in hexane)

G. (S)-4-[[[4-(4-Fluorophenyl)-2-(1-methylethyl)- 6-(2,3,5, 6-tetrafluorophenyl)-3 -pyridinyl]ethynyl]methoxyphosphinyl] -3 -[[(1,1-dimethylethyl)diphenylsilyl]oxy] acid, methyl ester 2.5M n-BuLi (1.92 ml, 4.8 mmol) was added dropwise to a −78° C. solution of the dibromide from part F (1.346 gm, 2.40 mmol) in THF (20 ml). The solution was allowed to stir 1 hour at −78° C. and then cannulated into a −78° C. THF solution (15 ml) of the phosphonochloridate from Example 57, part G. The resultant red-amber solution was stirred for 45 minutes, then was quenched with saturated $NH_4Cl$ (15 ml) and warmed to 0° C. Then, saturated $NaHCO_3$ was added to the solution. The aqueous layer was back-extracted with ether, the organic layers combined and washed with brine (1× 50 ml), then dried over $Na_2SO_4$, filtered and concentrated to give an orange oil. The oil was purified by flash chromatography on Merck silica gel in 40% EtOAc in hexane. Pure product fractions were combined and evaporated to afford the title compound as a beige foam (0.584 gm, 50%).

TLC: Rf 0.35 (40% EtOAc in hexane)

H. (S)-4-[[[4-(4-Fluorophenyl)-2-(1-methylethyl)- 6-(2,3,5, 6-tetrafluorophenyl)-3 -pyridinyl]ethynyl]methoxyphosphinyl] -3 -hydroxybutanoic acid, methyl ester To solution of $(Bu)_4NF$ (1.0M in THF, 3.57 ml, 3.57 mmol) was added a THF solution (15 ml) of the silyl ether from part G (0.584 gm, 0.696 mmol) and acetic acid. The solution was allowed to stir 16 hours at room temperature. The solution was diluted with EtOAc and washed with 5% $KHSO_4$ (three times). The aqueous layers were back-extracted with EtOAc (three times). The organic layers were pooled and washed with brine, then dried over $Na_2SO_4$, filtered and concentrated to afford a yellow oil. The oil was dissolved in ether (15 ml) and treated with excess $CH_2N_2$. Excess $CH_2N_2$ was removed with a stream of argon, and the solution was concentrated to a yellow oil. The oil was purified by flash chromatography on Merck silica gel in 40% acetone in hexane. The desired fractions were pooled and concentrated to afford the title compound as a beige foam (0.305 gm, 73%).

TLC: Rf 0.56 (50% acetone in hexane)

I. (S)-4-[[[4-(4-Fluorophenyl)-2-(1-methylethyl)- 6-(2,3,5, 6-tetrafluorophenyl)-3 -pyridinyl]ethynyl]hydroxyphosphinyl]-3 -hydroxybutanoic acid, disodium salt A solution of NaOH (1.0M in water, 1.53 ml, 1.53 mmol) was added to a dioxane solution (5 ml) of the part H compound (0.305 gm, 0.51 mmol). The solution was heated to 55° C. and allowed to stir 2 hours. Additional NaOH (1M in water, 1.0 ml, 1.0 mmol) was added to the solution which was allowed to stir another hour. The mixture was cooled to room temperature and concentrated to a white solid. The residue was chromatographed on HP-20 resin, eluting first with water (200 ml), then with 50% MeOH in water (400 ml), and finally with MeOH (200 ml). The desired fractions were pooled and concentrated, the residue taken up in water and lyophilized to give Example 72 as a fluffy white solid (0.807 gm, 92%).

TLC: Rf 0.59 (6:3:1, n-propanol:$NH_4OH$:$H_2O$) Elemental Analysis for $C_{26}H_{16}NF_5Na_2PO_5$* 4.60 $H_2O$: Calc'd: C 45.90 H 4.18 N 2.06 F 13.96 P 4.55 Found: C 45.66 H 3.68 N 2.16 F 13.66 P 4.43

Example 73

(S,E)-4-[ [ 2-[ 6-(1,1-Dimethylethyl)-4-(4-fluorophenyl)- 2-(1-methylethyl)-3-pyridinyl]ethenyl] hydroxyphosphinyl] -3-hydroxybutanoic acid, disodium salt A. 6-(1,1-Dimethylethyl)-3-(1-ethynyl)-4 -(4-fluorophenyl)-2-(1-methylethyl)pyridine To a solution of compound F from Example 61 (4.5 g, 9.88 mmol) in THF (20 ml) at −78° C. was added n-BuLi (2.5M in hexanes, 9.88 ml, 24.7 mmol). The resulting blue-green reaction mixture was stirred for 1.5 hours at −78° C. The mixture was quenched with saturated $NH_4Cl$, warmed to room temperature, diluted with ether and the layers were separated. The aqueous layer was extracted with ether (2×50 ml) and the combined organic layers were washed with brine, dried ($MgSO_4$), and concentrated. The yellow oily residue was purified by flash chromatography (Merck silica gel, 2.5% EtOAc/hexane) affording compound A as a colorless oil (2.75 g, 94.5%).

$R_f$ 0.62 (10% EtOAc/hexane), UV

B. 6-(1,1-Dimethylethyl)-4-(4-fluorophenyl)- 3-(2-iodoethenyl)-2-(1-methylethyl)-pyridine A mixture of the compound prepared in part A (2.57 g, 8.70 mmol), tributyltin hydride (4.68 ml, 17.40 mmol) and α,α-azoisobutyronitrile (18.5 mg) was heated at 140° C. in an oil bath. After 1.5 hours, an additional 34.6 mg of α,α-azoisobutyronitrile was added and heating continued for additional 1.5 hours. The reaction mixture was cooled to room temperature, diluted with ether (100 ml) and treated with 12 (4.5 g). After stirring for 3 hours, the reaction mixture was washed with 10% $Na_2S_2O_3 \times 5 H_2O$ (3×50 ml), 10% $NH_4OH$ (2×25 ml) and brine, then dried ($MgSO_4$) and concentrated. The yellow oily residue was purified by flash chromatography (Merck silica gel, 2% EtOAc/hexane), affording the product as a white solid. Recrystallization from hexane afforded compound B as white crystals (2.77 g, 83.7%).

m.p. 78.0°–80.0° C. Analysis for $C_{20}H_{23}NFI$: Calc'd: C, 56.75; H, 5.48; N, 3.31; F, 4.49 Found: C, 57.23; H, 5.34; N, 3.28; F, 4.43

C. (S,E)-4-[[2-[6-(1,1-Dimethylethyl)-4 -(4-fluorophenyl)-2-(1-methylethyl)-3 -pyridinyl]ethenyl]methoxyphosphinyl] -3-[[(1,1-dimethylethyl)diphenylsilyl] oxy]butanoic acid, methyl ester A solution of the part B vinyl iodide (2.77 g, 6.54 mmol) in THF (15 ml) was added to a −78° C. solution of t-BuLi (1.7M in hexanes, 8.08 ml, 13.74 mmol) in THF (20 ml) over a 4-minute period. The dark blue-green reaction mixture was stirred for 1.5 hours at −78° C., then cooled to −100° C. and and transferred via cannula to −100° C. solution of the phosphonochloridate from Example 57, part G in THF (20 ml). The yellow-orange reaction mixture was stirred at −100° C. for 45 minutes and then quenched with 50% saturated $NH_4Cl$. After warming to room temperature, the solution was diluted with $H_2O$ and poured into saturated $NaHCO_3$. The layers were separated and the aqueous layer was extracted once with ether. The combined organic layers were washed with brine, dried ($Na_2SO_4$), filtered and concentrated under reduced pressure. The dark oily residue was purified by flash chromatography (Merck silica gel, 40% EtOAc/hexane) to afford the title compound as a beige foam (2.20 g, 46.0%).

$R_f$ 0.23 (40 % EtOAc/hexane), UV

D. (S,E)-4-[[2-[6-(1,1-Dimethylethyl)-4 -(4-fluorophenyl)-2-(1-methylethyl)-3 -pyridinyl]ethenyl]methoxyphosphinyl] -3-hydroxybutanoic acid, methyl ester To a solution of the part C silyl ether (2.20 g, 3.00 mmol) in THF (15 ml) was added HOAc (0.68 ml, 9.00 mmol), followed by tetra-n-butylammonium fluoride (1.0M in THF, 9.00 ml, 9.00 mmol). The reaction mixture was stirred at room temperature under argon for 20 hours. The solution was diluted with ether (100 ml) and washed twice with saturated $NaHCO_3$ and brine, then dried ($MgSO_4$) and concentrated under reduced pressure. The oily residue was purified by flash chromatography (Merck silica gel, 25% acetone/hexane). Compound D was obtained as as a colorless oil (1.05 g, 67.0%).

$R_f$ 0.18 (40% acetone/hexane) UV

E. (S,E)-4-[[2-[6-(1,1-Dimethylethyl)-4 -(4-fluorophenyl)-2-(1-methylethyl)-3 -pyridinyl]ethenyl]hydroxyphosphinyl] -3 -hydroxybutanoic acid, disodium salt The part D diester (0.20 g, 0.40 mmol) in dioxane (15 ml) was treated with 1N NaOH (1.40 ml, 1.40 mmol) at room temperature and then heated at 50° C. for 2 hours. The solvent was evaporated and the residue was chromatographed on HP-20 resin, eluting first with $H_2O$ (300 ml), followed by 25% $MeOH/H_2O$ (300 ml), 50% $MeOH/H_2O$ (300 ml) and finally MeOH (100 ml). The collected product fractions were evaporated, dissolved in $H_2O$, filtered, frozen and lyophilized to give Example 73 as a white lyophilate (0.128 g, 63.3%).

$R_f$ 50 (8:1:1—$CH_2 Cl_2$:$CH_3OH$:HOAc), UV Analysis for $C_{24}H_{29}NFPO_5Na_2 \times 2.1 H_2O$: Calc'd: C, 52.87; H, 6,14; N, 2.57; F, 3.48; P, 5.68 Found: C, 52.94; H, 6.24; N, 2.50; F, 3.36; P, 5.63

Example 74

(S)-4-[ [ 2-[ 6-(1,1-Dimethylethyl)-4-(4-fluorophenyl)- 2-(1-methylethyl)-3-pyridinyl]ethyl]-hydroxyphosphinyl] -3-hydroxybutanoic acid, disodium salt A. (S)-4-[[2-[6-(1,1-Dimethylethyl)-4-(4 -fluorophenyl)-2-(1-methylethyl)-3 -pyridinyl]ethyl]methoxyphosphinyl]-3 -hydroxybutanoic acid, methyl ester The solution of compound D from Example 73 (0.40 g, 0.81 mmol) in $CH_3OH$ (50 ml) containing 10% Pt/C (150 mg) was hydrogenated at 50 psi for 3 days. The catalyst was filtered, washed with $CH_3OH$, and the filtrates combined and concentrated. The oily residue was purified by flash chromatography (Merck Silica gel, 25% acetone/hexane followed by 50% acetone/hexane). The product was obtained as a colorless oil (0.24g, 60.0%).

$R_f$ 0.35 (50% acetone/hexane) UV

B. (S)-4-[[2-[6-(1,1-Dimethylethyl)-4-(4 -fluorophenyl )-2-(1-methylethyl)-3-pyridinyl] ethyl]hydroxyphosphinyl]-3-hydroxybutanoic acid, disodium salt The diester from part A (0.22 g, 0.44 mmol) in dioxane (15 ml) was treated with 1N NaOH (1.54 ml, 1.54 mmol) at room temperature and then heated at 50° C. for 21 hours. The solvent was evaporated and the residue was chromatographed twice on HP-20 resin, eluting first with $H_2O$ (200 ml), followed by 25% $MeOH/H_2O$ (100 ml), 50% $MeOH/H_2O$ (150 ml) and finally MeOH (150ml). The collected product fractions were evaporated, dissolved in $H_2O$, filtered, frozen and lyophilized to give Example 74 as a white lyophilate (0.106 g, 47.0%).

$R_f$ 0.34 (8:1:1—$CH_2 Cl_2$:$CH_3OH$:HOAc), UV Analysis for $C_{24}H_{31}NFPO_5Na_2 \times 2.0 H_2O$: Calc'd C, 52.85; H, 6.47; N, 2.57; F, 3.48; P, 5.68 Found C, 52.73; H, 6.65; N, 2.38; F, 3.70; P, 5.30

Example 75

(S,E)-4-[ [ 2-[ 4-(4-Fluorophenyl)-6,7-dihydro-2-(1 -methylethyl)-5H-benzo[ 6,7]cyclohepta[ 1,2-b]pyridin- 3-yl]ethyl]hydroxyphosphinyl]-3-hydroxybutanoic acid, disodium salt A. 3-Ethynyl-4-(4-fluorophenyl)-6,7 -dihydro-2-(1-methylethyl)-5H-benzo[ 6,7]cyclohepta[1,2-b]pyridine The vinyl dibromide compound D from Example 63 (3.520 gm, 6.8 mmol) was added as a solution of THF (4 ml) over 2.5 minutes to a −78° C. solution of n-BuLi (2.5M in hexane, 5.46 ml, 13.66 mmol), in THF (20 ml). The solution was allowed to stir at −78° C. for 1.5 hours. Saturated $NH_4Cl$ was added to quench the reaction and the mixture warmed to 0° C. and saturated $NaHCO_3$ added. The mixture was then warmed to room temperature, diluted with ether and the aqueous layer back-extracted with ether (twice). The organic layers were combined and washed with brine, then dried over $MgSO_4$, filtered and concentrated to afford a yellow oil, The yellow oil was purified by flash chromatography on Merck silica gel in 1% EtOAc in hexane. Fractions containing the product were pooled and concentrated to give a white solid. The solid was recrystallized from hexane as hard white crystals (2.108 gm, 87%).

m.p. 131°–132° C. Rf 0.43 (1% EtOAc in hexane)

B. (E)-3-(2-Iodoethenyl)-4-(4-fluorophenyl)- 6,7-dihydro-2-(1-methylethyl)-5H-benzo-[ 6,7]cyclohepta[1,2-b]pyridine A mixture of the acetylene prepared in part A (2.108 gm, 6.68 mmol), Bu$_3$SnH (3.507 gm, 12.03 mmol), and AIBN (0.0408 gm) was heated to 140° C. for 1.5 hours. Ether (20 ml) was added to the mixture after it had cooled to room temperature. The solution was then treated with I$_2$ (3.49 gm) and stirred at room temperature for 18 hours. The solution was diluted with ether, washed with 10% Na$_2$SO$_4$ in saturated NaHCO$_3$ and brine, then dried over MgSO$_4$, filtered and concentrated to a yellow oil. The oil was purified by flash chromatography on Merck silica gel in 1% EtOAc in hexane. Fractions containing product compound B were pooled and concentrated to give a yellow solid. The solid was recrystallized from hexane to afford product compound B as yellow crystals (2.363 gm, 80%).

m.p. 169°–170° C. TLC: Rf 0.55 (2% EtOAc in hexane)

C. (S)-4-[[2-[6-(1,1-Dimethylethyl)-4-(4 -fluorophenyl)-2-(1-methylethyl)-3-pyridinyl] ethyl]methoxyphosphinyl]-3-[[(1,1 -dimethylethyl)diphenylsilyl]oxy]butanoic acid, methyl ester The vinyl iodide from part B (2.363 gm, 5.0 mmol) was added as a THF solution (5 ml) over 3 minutes to a solution of t-BuLi (1.7M in pentane, 5.90 ml, 10 mmol) in THF (10 ml) at −78° C. The solution was allowed to stir 1 hour at −78° C., then cooled to −100° C. and cannulated over 1.5 minutes into a THF solution (20 ml) of the Example 57, part G chloridate also cooled to −100° C. The resultant red-amber solution was stirred for 45 minutes, then quenched with saturated NH$_4$Cl (15 ml). The solution was warmed to 0° C. and saturated NaHCO$_3$ was added. The mixture was diluted with ether and the aqueous layer back-extracted with ether (twice). The organic layers were combined and washed with brine, then dried over Na$_2$SO$_4$, filtered and concentrated to give an orange oil. The oil was purified by flash chromatography on Merck silica gel in 40% EtOAc in hexane. Desired fractions were combined and evaporated to afford the product as a beige foam (1.408 gm, 39%).

TLC: Rf 0.36 (40% EtOAc in hexane)

D. (S)-4-[[2-[6-(1,1-Dimethylethyl)-4-(4 -fluorophenyl)-2-(1-methylethyl)-3-pyridinyl] ethyl]methoxyphosphinyl]-3-hydroxybutanoic acid, methyl ester A THF solution (20 ml) of compound C (1.408 gm, 1.88 mmol) was treated with acetic acid (0.45 gm, 7.55 mmol) and then (Bu)$_4$NF (1.0M in THF, 5.64 ml, 5.64 mmol) and allowed to stir 16 hours at room temperature. The solution was diluted with EtOAc, then washed with saturated NaHCO$_3$, water, 1.5M HCl, water, and brine, then dried over MgSO$_4$, filtered and concentrated to give a yellow oil. The oil was purified by flash chromatography on Merck silica gel in 50% acetone in hexane. Pure product fractions were pooled and concentrated to afford compound D as a beige foam (0.726 gm, 71%).

TLC: Rf 0.48 (50% acetone in hexane)

E. (S,E)-4-[[2-[4-(4-Fluorophenyl)-6,7 -dihydro-2-(1-methylethyl)-5H-benzo[6,7] cyclohepta[1,2-b]pyridin-3-yl] ethyl] hydroxyphosphinyl]-3-hydroxybutanoic acid, disodium salt A solution of NaOH (1.0M in water, 2.1 ml, 2.1 mmol) was added to a solution of compound D in dioxane (5 ml) and allowed to stir 19 hours at room temperature. The solution was then concentrated to a white solid. The solid was dissolved in water and chromatographed on HP-20 resin, eluting first with water (200 ml), then with 50% MeOH in water (400 ml), then with MeOH (200 mol). The desired fractions were pooled and concentrated. The residue was taken up in water and lyophilized to give Example 75 as a fluffy white solid (0.375 gm, 97%).

TLC: Rf 0.68 (6:3:1, n-propanol:NH$_4$OH:H$_2$O) Elemental Analysis for C$_{29}$H$_{29}$NFNa$_2$PO$_5$×2.50 H$_2$O: Calculated: C, 56.87; H, 5.59; N, 2.29; F, 3.10; P, 5.06 Found: C, 56.53; H, 5.48; N, 2.38; F, 3.40; P, 5.26

Example 76

(S)-4-[ [ 2-[ 4-(4-Fluorophenyl)-6,7-dihydro-2-(1 -methylethyl)-5H-benzo[ 6,7] cyclohepta[ 1,2-b] pyridin- 3-yl] ethyl] hydroxyphosphinyl] -3-hydroxybutanoid acid, disodium salt A. (S)-4-[[2-[4-(4-Fluorophenyl)-6,7-dihydro- 2-(1-methylethyl)-5H-benzo[6,7]-cyclohepta[1,2-b]pyridin-3-yl] ethyl] methoxyphosphinyl]-3-hydroxybutanoid acid, methyl ester A mixture of compound D from Example 75 (0.347 g, 0.63 mmol) and 10% Pd/C (0.067 g, 0.063 mmol) in MeOH (50 ml) was purged with argon for fifteen minutes, then placed under a hydrogen pressure of 50 psi on a Parr apparatus for 7 days. The solution was then filtered through a pad of Celite® which was washed repeatedly with MeOH. The solution was concentrated and the white residue purified by flash chromatography on Merck silica gel in 40% acetone in hexane. After combining and concentrating the desired fractions, the product A was obtained as a white foam (0.295 gm, 85%).

TLC: Rf 0.44 (50% acetone in hexane)

B. (S)-4-[[2-[4-(4-Fluorophenyl)-6,7-dihydro- 2-(1-methylethyl)-5H-benzo[6,7]cyclohepta[ 1,2-b]pyridin-3-yl]ethyl] hydroxyphosphinyl] -3-hydroxybutanoid acid, disodium salt A solution of the part A compound (0.295 g, 0.533 mmol) in dioxane (7 ml) was treated with a solution of NaOH (1.0M in water, 1.60 ml, 1.60 mmol) and allowed to stir at 50° C. for 3 hours. The solution was cooled to room temperature and concentrated to a white solid. The residue was dissolved in water and chromatographed on HP-20 resin, eluting first with water (200 ml), then with 50% MeOH in water (400 ml), and then with MeOH (200 mol). The desired fractions were pooled and concentrated, the residue was taken up in water and lyophilized to give Example 76 as a fluffy white solid (0.285 gm, 94%).

TLC: Rf 0.66 (6:3:1, n-propanol:NH$_4$OH:H$_2$O) Elemental Analysis for C$_{29}$H$_{31}$NFNa$_2$PO$_5$×2.04 H$_2$O: Calculated: C, 57.46: H, 5.83; N, 2.31; F, 3.13; P, 5.11 Found: C, 57.59; H, 6.16; N, 2.33; F, 3.18; P, 5.38

Example 77

(S)-4-[ [ [ 4-(4-Fluorophenyl)-2-(1-methylethyl)-5,6-diphenyl-3-pyridinyl]ethynyl]-hydroxyphosphinyl]-3 -hydroxybutanoic acid, methyl ester, monosodium salt A solution of compound G from Example 56 (510 mg, 0.87 mmol) in CH$_2$Cl$_2$ (6 ml) was treated with BSTFA (277 µl, 269 mg, 1.05 mmol). After stirring at room temperature for 1.5 hours, the solution was treated with TMSBr (161 µl, 187 mg, 1.22 mmol). After 45 minutes, the mixture was quenched by the addition of MeOH (500 µl) and the solution was stirred for 15 minutes, then treated with TEA (250 µl), poured into EtOAc and subsequently washed with 5% KHSO$_4$ (twice) and brine. The organic layer was dried (Na$_2$SO$_4$), filtered and stripped to yield an oil, which was dissolved in cold Et$_2$O (4 ml) and treated with a solution of adamantamine (147 mg, 0.97 mmol) in hexane (2 ml). The resulting white solid (607 mg, 97% yield of the adamantamine salt of Example 77) was collected by filtration and washed with cold Et$_2$O.

A slurry of the amine salt (585 mg, 0.81 mmol) in a mixture of EtOAc (50 ml) and H$_2$O (7 ml) was treated dropwise with 1N HCl (0.82 ml, 0.82 mmol) and the two clear layers were separated and the EtOAc layer was washed with additional 5% KHSO$_4$ and brine, then dried (Na$_2$SO$_4$), filtered and stripped. The residue (white foam) was dissolved in CH$_2$Cl$_2$ (4 ml) and treated with TEA (192 µl). After stirring at room temperature for 15 minutes, the solvent was stripped and the residue was azeotroped with toluene. The resulting oily foam was dissolved in warm H$_2$O (7 ml) and passed through an ion exchange column (Dowex AG-50-WX2 (Na$^+$ form), 23 ml wet), eluting with H$_2$O. The desired fractions were pooled and lyophilized to give Example 77 (450 mg, 88%, 85% overall from 1) as a white solid.

TLC R$_f$ 0.61 (8:1:1—CH$_2$Cl$_2$:HOAc:MeOH) Analysis for C$_{33}$H$_{30}$FNNaO$_5$P×2.24 H$_2$O: Calc'd C, 62.53; H, 5.48; N, 2.21; F, 3.00; P, 4.89 Found C, 62.57; H, 5.15; N, 2.17; F, 3.02; P, 5.17

Example 78

(S,E)-4-[ [ 2-[ 4-(4-Fluorophenyl)-2-(1-methylethyl)- 6-phenyl-3-pyridinyl]ethenyl]-hydroxyphosphinyl] -3-hydroxybutanoic acid, methyl ester, monosodium salt A solution of compound C from Example 7 (315 mg, 0.616 mmol) in CH$_2$Cl$_2$ (6 ml) was treated with BSTFA (200 µl, 194 mg, 0.75 mmol). After stirring at room temperature for 1.25 hours, the solution was treated with TMSBr (115 µl, 133 mg, 0.87 mmol). After 40 minutes, the mixture was quenched by the addition of MeOH (400 µl) and the solution was stirred for 15 minutes, then treated with TEA (172 µl), poured into 5% KHSO$_4$ and extracted with EtOAc (3 times). The organic extract was washed with brine, then dried (Na$_2$SO$_4$), filtered and stripped to yield a wet solid. The solid was slurried in cold Et$_2$O and collected to give 201 mg of the free acid of Example 78. An additional 86 mg was obtained from concentration of the filtrate (total solids, 287 mg, 94%).

A slurry of the above solid (287 mg, 0.58 mmol) in CH$_2$Cl$_2$ (8 ml) was treated with TEA (121 µl). After stirring at room temperature for 15 minutes, the colorless homogeneous solution was stripped and the residue was azeotroped with toluene. The resulting white foam was dissolved in H$_2$O and passed through an ion exchange column (Na$^+$ form, 7 ml wet), eluting with H$_2$O. The desired fractions were pooled and lyophilized to give Example 78 (300 mg, 89%, 84% overall from compound C from Example 7) as a white solid.

TLC R$_f$ 0.58 (8:1:1—CH$_2$Cl$_2$:HOAc:MeOH) Analysis for C$_{27}$H$_{28}$FNNaO$_5$P×2.0 H$_2$O: Calc'd C, 58.37; H, 5.81; N, 2.52; F, 3.42; P, 5.57 Found C, 58.20; H, 5.46; N, 2.56; F, 3.47; P, 5.82

Example 79

(S)-4-[[[4-(4-Fluorophenyl)-6-methyl-2-(1-methylethyl)- 3-pyridinyl]ethynyl]hydroxyphosphinyl]-3 -hydroxybutanoic acid, disodium salt A. 3-(4-Fluorophenyl)-1-methyl-2 -propen-1-one A mixture of 4-fluorobenzaldehyde (4.53 ml, 42.0 mmol; Aldrich) and 1-triphenylphosphoranylidene- 2-propanone (11.1 g, 35.0 mmol; Aldrich) in CH$_2$Cl$_2$ was refluxed for 48 hours. After cooling to room temperature, the reaction mixture was concentrated and purified by flash chromatography (Merck silica gel, 10% EtOAc/hexane) to afford compound A as a colorless oil (4.95 g, 78.4%).

R$_f$ 0.34 (20% EtOAc/hexane), UV

B. β-(4-Fluorophenyl)-α-(2-methyl-1-oxopropyl)-Δ -oxohexanoic acid, ethyl ester

A solution of compound A (5.3 g, 32.3 mmol) in ether (80 ml) was added dropwise to a mixture of ethyl isobutyrylacetate (10.42 ml, 64.6 mmol) and KOH (0.15 g, 2.7 mmol) in absolute ethanol (1.5 ml). The reaction mixture was stirred at room temperature for 24 hours, acidified to pH 5 with glacial HOAc, washed twice with H$_2$O, then saturated NaHCO$_3$, dried (MgSO$_4$) and concentrated. The yellow oily residue was purified by flash chromatography (Merck silica gel, 10% EtOAc/hexane) to afford compound B as a colorless oil (5.8 g, 56.0%, mixture of diastereomers).

R$_f$ 0.32+ 0.36 (25% EtOAc/hexane), UV

C. 4-(4-Fluorophenyl)-6-methyl-2-(1-methylethyl)- 3-pyridinecarboxylic acid, ethyl ester A mixture of compound B (5.8 g, 18.0 mmol), ammonium acetate (4.16 g, 54.0 mmol) and copper (II) acetate (8.98 g, 45.0 mmol) in glacial acetic acid (60 ml) was heated at 115° C. for 2.5 hours. The reaction mixture was cooled and carefully poured into an ice cold mixture of concentrated NH$_4$OH (80 ml) and H$_2$O (100 ml). The mixture was extracted with ether (twice) and the ether extracts were washed with H$_2$O (twice) and brine, then dried (MgSO$_4$), filtered and concentrated. The dark oily residue was purified by flash chromatography (10% EtOAc/hexane) to afford compound C as a colorless oil (2.5 g, 46.3%).

R$_f$ 0.54 (20% EtOAc/hexane), UV

D. 4-(4-Fluorophenyl)-6-methyl-2-(1-methylethyl)- 3-pyridinemethanol

A cold (0° C.) solution of ester (2.42 g, 8.03 mmol) in dry THF (55 ml) was treated with LiAlH$_4$ (0.91 g, 24.10 mmol). Ten minutes after the addition the cooling bath was removed and the reaction mixture was stirred at room temperature for 24 hours. The reaction mixture was cooled to 0° C. and carefully quenched in succession with 0.91 ml of H$_2$O in THF (10 ml), then 0.91 ml 15% NaOH and finally 2.0 ml H$_2$O. The precipitated aluminum salts were filtered and washed with EtOAc and ether. The filtrate was washed with H$_2$O and brine, dried (Na$_2$SO$_4$), filtered and concentrated under reduced pressure to give an off-white solid residue. Recrystallization from hexane afforded compound D as a white solid (1.80 g, 86.0%).

m.p. 154°–155° C. R$_f$ 0.4 (20% EtOAc/hexane), UV Anal. Calc'd for C$_{16}$H$_{18}$NFO: Calc'd C, 74.10; H, 7.00; N, 5.40; F, 7.33 Found C, 74.15; H, 7.14; N, 5.25; F, 7.30

E. 4-(4-Fluorophenyl)-6-methyl-2-(1-methylethyl)- 3-pyridinecarboxaldehyde

A −78° C. solution of oxalyl chloride (0.73 ml, 8.32 mmol) in CH$_2$Cl$_2$ (80 ml) was treated dropwise with a solution of dry DMSO (1.18 ml, 16.65 mmol) in CH$_2$Cl$_2$ (10 ml). After 15 minutes, a solution of alcohol D (1.80 g, 6.94 mmol) in CH$_2$Cl$_2$ (10 ml) was added dropwise to the above solution. After 20 minutes, triethylamine (5.80 ml, 41.64 mmol) was added and the mixture was stirred at −78° C. for 20 minutes and then warmed to room temperature. After 1 hour, the reaction was quenched with H$_2$O and diluted with ether. The layers were separated and aqueous layer was extracted with CH$_2$Cl$_2$ (twice). The combined organic solutions were washed with H$_2$O (twice) and brine, then dried (MgSO$_4$), filtered and concentrated under reduced pressure. The oily residue was purified by flash chromatography (Merck silica gel, 10% EtOAc/hexane), affording the aldehyde E as a colorless oil (1.68 g, 94.5%).

$R_f$ 0.65 (20% EtOAc/hexane), UV

F. 3-(2,2-Dibromoethenyl)-4-(4-fluorophenyl)- 6-methyl-2-(1-methylethyl)pyridine A solution of carbon tetrabromide (3.24 g, 9.79 mmol) in $CH_2Cl_2$ (10 ml) was added dropwise over a 5-minute period to a cold (0° C.) solution of aldehyde E (1.68 g, 6.52 mmol) and triphenylphosphine (5.13 g, 19.56 mmol) in $CH_2Cl_2$ (60 ml). The mixture was stirred at 0° C. for 20 minutes and then at room temperature for 1 hour. The solution was quenched with saturated $NaHCO_3$ and extracted twice with $CH_2Cl_2$. The combined organic layers were dried ($Na_2SO_4$), filtered, concentrated to ⅓ volume and applied on Merck silica gel column (50% $CH_2Cl_2$/hexane). Flash chromatography afforded compound F as a colorless oil (2.68 g, 100.0%).

$R_f$ 0.50 (10% EtOAc/hexane), UV

G. (S)-4-[[[4-(4-Fluorophenyl)-6-methyl-2 -(1-methylethyl)-3-pyridinyl]ethynyl] methoxyphosphinyl]-3-[[(1,1-dimethylethyl)diphenylsilyl] oxy]butanoic acid, methyl ester A solution of dibromide F (2.60 g, 6.31 mmol) in THF (20 ml) at −78° C. was treated with n-BuLi (2.5M in hexane, 5.30 ml, 13.25 mmol) over a 1-minute period. The dark blue reaction mixture was stirred for 30 minutes at −78° C. and then transferred via cannula to a −78° C. solution of the phosphonochloridate from Example 57, part G in THF (20 ml). The dark-brown reaction mixture was stirred at −78° C. for 30 minutes and then quenched with 50% saturated $NH_4Cl$. After warming to room temperature, the solution was diluted with $H_2O$ and poured into saturated $NaHCO_3$. The layers were separated and the aqueous layer was extracted once with ether. The combined organic layers were washed with brine, dried ($Na_2SO_4$), filtered and concentrated under reduced pressure. The dark oily residue was purified by flash chromatography (Merck silica gel, 30% EtOAc/hexane) to afford compound G as a pale yellow oil (2.58 g, 60.0%).

$R_f$ 0.19 (30% EtOAc/hexane), UV

H. (S)-4-[[[4-(4-Fluorophenyl)-6-methyl-2 -(1-methylethyl)-3-pyridinyl]ethynyl] methoxyphosphinyl]-3-hydroxybutanoic acid, methyl ester To a solution of acetylinic phosphonate G (2.50 g, 3.65 mmol) in THF (15 ml) was added HOAc (0.83 ml, 14.60 mmol), followed by tetra-n-butylammonium fluoride (1.0M in THF, 10.95 ml, 10.95 mmol). The reaction mixture was stirred at room temperature under argon for 24 hours. The solution was diluted with EtOAc and washed three times with 5% $KHSO_4$. The pooled aqueous layers were back-extracted twice with EtOAc and the combined organic extracts were dried ($Na_2SO_4$), filtered and concentrated under reduced pressure. The dark oily residue was dissolved in ether (a few drops of THF were added to obtain a clear solution), cooled to 0° C. and treated with excess diazomethane in ether for 20 minutes. The excess diazomethane was destroyed by the addition of HOAc. Solvent removal gave a dark oily residue, which was purified by flash chromatography (Merck silica gel, 30% acetone/hexane). The product H was obtained as as a colorless oil (0.68 g, 42.5%).

$R_f$ 0.22 (40% acetone/hexane) UV

I. (S)-4-[[[4-(4-Fluorophenyl)-6-methyl-2 -(1-methylethyl)-3-pyridinyl]ethynyl] hydroxyphosphinyl]-3-hydroxybutanoic acid, disodium salt The diester H (0.20 g, 0.44 mmol) in dioxane (5 ml) was treated with 1N NaOH (1.54 ml, 1.54 mmol) at room temperature and then heated at 50° C. for 4 hours. The reaction mixture was concentrated and the residue was chromatographed on HP-20 resin, eluting first with $H_2O$ (200 ml), followed by 25% MeOH/$H_2O$ (150 ml), 50% MeOH/$H_2O$ (200 ml) and finally MeOH (100 ml). The collected product fractions were evaporated, dissolved in $H_2O$, filtered, frozen and lyophilized to give Example 79 as a white lyophilate (0.17 g, 85.5%).

m.p. >165° C. (decomposition) $R_f$ 0.1 (8:1:1—$CH_2Cl_2$:$CH_3OH$:HOAc), UV Analysis for $C_{21}H_{21}NFPO_5Na_2 \times 3.0\ H_2O$: Calc'd C, 48.75; H, 5.26; N, 2.71; F, 3.67; P, 5.99; Found C, 48.66; H, 4.90; N, 2.46; F, 3.53; P, 5.67

Example 80

(S)-4-[ [ [ 4-(4-Fluorophenyl)-5-methyl-2-(1-methylethyl)- 6-phenyl-3-pyridinyl] ethynyl] hydroxyphosphinyl] -3-hydroxybutanoic acid, methyl ester, monosodium salt A solution of compound H from Example 53 (666 mg, 1.27 mmol) in $CH_2Cl_2$ (7 ml) was treated with BSTFA (380 μl, 368 mg, 1.43 mmol). After stirring at room temperature for 1.5 hours, the solution was treated with TMSBr (185 μl, 214.6 mg, 1.4 mmol). After 30 minutes, additional TMSBr (80 μl) was added and stirring was continued for 15 minutes. The mixture was quenched by the addition of MeOH (500 μl) and the solution was stirred for 15 minutes, then treated with TEA (300 μl), poured into EtOAc and subsequently washed with 5% $KHSO_4$ (twice) and brine. The organic layer was dried ($Na_2SO_4$), filtered and stripped to yield an oily foam which was dissolved in cold $Et_2O$ (8 ml) and treated with a solution of adamantamine (195 mg, 1.29 mmol) in hexane (4 ml). The resulting solid (776 mg, 92% yield of the adamantamine salt of Example 80, mp. 226°–228° C.) was collected by filtration and washed with cold $Et_2O$.

The amine salt (747 mg, 1.13 mmol) was slurried between 5% $KHSO_4$ (50 ml) and EtOAc (50 ml) and treated with 1N HCl (1.1 ml, 1.1 mmol) and the layers were separated and the EtOAc layer was washed with additional 5% $KHSO_4$ and filtered. The filtrate was washed with brine, then dried ($Na_2SO_4$), filtered and stripped. The residue (white foam) was dissolved in $CH_2Cl_2$ (8 ml) and treated with TEA (265 μl). After stirring at room temperature for 10 minutes, the solvent was stripped and the residue was azeotroped with toluene. The resulting oily foam was dissolved in $H_2O$ and passed through an ion exchange column (Dowex AG-50-WX2 ($Na^+$ form), 20 ml wet), eluting with $H_2O$. The desired fractions were pooled and lyophilized to give Example 80 (550 mg, 92%, 85% overall from compound H, Example 53) as a white solid.

TLC $R_f$ 0.27 (8:1:1—$CH_2Cl_2$:HOAc:MeOH) Analysis for $C_{28}H_{28}FNNaO_5P \times 2.40\ H_2O$: Calc'd C, 58.51; H, 5.75; N, 2.44; F, 3.31; P, 5.39 Found C, 58.60; H, 5.30; N, 2.30; F, 3.55; P, 5.09

Example 81

(S)-4-[[2-[4-(4-Fluorophenyl)-5-methyl-2-(1-methylethyl)- 6-phenyl-3-pyridinyl]ethenyl]-hydroxyphosphinyl] -3-hydroxybutanoic acid, methyl ester, monosodium salt A. 3-(1-Ethynyl)-4-(4-fluorophenyl)-5 -methyl-2-(1-methylethyl)-6-phenylpyridine To a solution of n-BuLi (2.5M in hexanes, 4.00 ml, 10.0 mmol) in dry THF (8 ml) at −78° C. was added a solution of compound F from Example 53 (2.267 gm, 4.63 mmol) in dry THF (8 ml) over a 5 -minute period. After stirring at −78° C. for one hour, the pale green solution was quenched with saturated $NH_4Cl$ and warmed to room temperature. The mixture was diluted with $H_2O$, extracted with $Et_2O$ and the $Et_2O$ extract was washed with brine, dried ($Na_2SO_4$), filtered and stripped to yield a solid. The residue was recrystallized from hot EtOAc/hexane to afford acetylene A (1.169 gm) as a white solid. An additional 251 mg of product was obtained by recrystallization of the mother liquor to give a total of 1.420 gm (93%) of analytically pure material.

m.p. 178.0°–178.5° C. TLC $R_f$ 0.43 (10% EtOAc in hexane) Analysis for $C_{23}H_{20}FN \times 0.11\ H_2O$: Calc'd C, 83.37; H, 6.15; N, 4.23; F, 5.73 Found C, 83.25; H, 5.98; N, 4.35; F, 5.89

B. 4-(4-Fluorophenyl)-3-(2-iodoethenyl)- 5-methyl-2-(1-methylethyl)-6-phenylpyridine A mixture of compound A (1.355 gm, 4.1 mmol) and AIBN (20 mg) in tri-n-butylstannyl hydride (2.0 ml) was rapidly heated to 120° C. After 4 minutes of heating, the mixture was treated with additional $Bu_3SnH$ (0.6 ml) and the temperature of the reaction was raised to 140° C. Approximately 20 mg of AIBN was added to the reaction mixture one and two hours after heating was initiated. After 3 hours, the mixture was cooled to room temperature, diluted with $Et_2O$ (50 ml) and treated with solid $I_2$ (3.50 gm, 13.8 mmol). The dark reaction mixture was stirred for 45 minutes, then poured into a 50% saturated $NaHCO_3$ solution containing 6.7 gm $Na_2S_2O_3$. The layers were shaken and separated. The ethereal layer was washed successively $H_2O$, 1.7M $NH_4OH$, and brine, then dried ($Na_2SO_4$), filtered and stripped to yield a wet solid. The solid was taken up in $Et_2O$, filtered through Celite® and stripped. The residue was recrystallized from hot hexane to give compound B (1.335 gm) as white crystals. The mother liquor was flashed (Merck $SiO_2$, 5% EtOAc in hexane) and the desired fractions were pooled, stripped, recrystallized, and pooled with the above solid to give a total of 1.637 gm (87%) of compound B.

m.p. 148.5°–150.0° C. TLC $R_f$ 0.13 (2% EtOAC in hexane)

C. (S)-4-[[2-[4-(4-Fluorophenyl)-5-methyl- 2-(1-methylethyl)-6-phenyl-3-pyridinyl] ethenyl]methoxyphosphinyl]- 3-[[(1,1 -dimethylethyl)diphenylsilyl]oxy]butanoic acid, methyl ester A solution of vinyl iodide B (1.500 gm, 3.28 mmol) in THF (6 ml) was added over a 4-minute period to a −78° C. solution of t-butyllithium (1.7M in pentane, 4.05 ml, 6.9 mmol) in THF (10 ml). The resulting solution was stirred for 25 minutes and then cooled to minus 100° C. The vinyl anion solution was added over a 30-second period to a −100° C. solution of the phosphonochloridate from Example 4, part C in THF (15 ml). The resulting orange mixture was stirred at −100° C. for 40 minutes, then quenched with 50% saturated $NH_4Cl$. The solution was warmed to room temperature, diluted with $H_2O$, and poured into saturated $NaHCO_3$. The aqueous phase was extracted twice with $Et_2O$. The combined $Et_2O$ layers were washed with brine, dried ($Na_2SO_4$), filtered and stripped. The resulting yellow oil was chromatographed (flash, Merck $SiO_2$, 50% EtOAc in hexane) to afford compound C as an off-white foam (778 mg, 31%).

TLC $R_f$ 0.18 (40% EtOAc in hexane)

D. (S)-4-[[2-[4-(4-Fluorophenyl)-5-methyl- 2-(1-methylethyl)-6-phenyl-3-pyridinyl] ethenyl]methoxyphosphinyl]-3-butanoic acid, methyl ester A solution of compound C (768 mg, 1.0 mmol) in THF (6 ml) was treated with HOAc (286 μl, 300 mg, 5.0 mmol) and tetra-n-butylammonium fluoride (1.0M in THF, 5.0 ml, 5.0 mmol). After stirring at room temperature for 22 hours, the solution was poured into saturated $NaHCO_3$ and extracted with EtOAc. The EtOAc extract was washed with brine, dried ($Na_2SO_4$), filtered, and stripped to give an oil, which was subsequently chromatographed (flash, Merck $SiO_2$, 50% acetone in hexane). Compound D (425 mg, 81%) was obtained as an oil.

TLC $R_f$ 0.34 (1:1 acetone:hexane)

E. (S)-4-[[2-[4-(4-Fluorophenyl)-5-methyl- 2-(1-methylethyl)-6-phenyl-3-pyridinyl] ethenyl]hydroxyphosphinyl]-3-hydroxybutanoic acid, methyl ester, monosodium salt A solution of compound D (420 mg, 0.80 mmol) in $CH_2Cl_2$ (6 ml) was treated with BSTFA (255 μl, 247 mg, 0.96 mmol). After stirring at room temperature for 1.5 hours, the solution was treated with TMSBr (158 μl, 183 mg, 1.2 mmol). After 45 minutes, MeOH (400 μl) was added, and stirring was continued for an additional 15 minutes. The solution was treated with TEA (180 μl), poured into EtOAc and subsequently washed with 5% $KHSO_4$ (twice) and brine. The organic layer was dried ($Na_2SO_4$), filtered and stripped to yield an oil, which was dissolved in cold $Et_2O$ (4 ml) and treated with a solution of adamantamine (127 mg, 0.84 mmol) in hexane (3 ml). The resulting solid (279 mg, 53% yield of salt) was collected by filtration and washed with cold $Et_2O$.

The salt was slurried in 5% $KHSO_4$ and EtOAc and treated with 1N HCl (0.40 ml) and the layers were separated and the EtOAc layer was washed with additional 5% $KHSO_4$ and brine, then dried ($Na_2SO_4$), filtered and stripped. The residue was dissolved in $CH_2Cl_2$ (3 ml) and treated with TEA (60 μl). After stirring at room temperature for 10 minutes, the solvent was stripped and the residue was azeotroped with toluene (3 ml). The resulting acid was dissolved in $H_2O$ and passed through an ion exchange column ($Na^+$ form, 10 ml wet), eluting with $H_2O$. The desired fractions were pooled and lyophilized to give Example 81 (136 mg, 30% overall) as a white solid.

TLC Rf 0.51 (8:1:1—$CH_2Cl_2$:HOAc:MeOH) Analysis for $C_{28}H_{30}FNNaO_5P \times 1.80\ H_2O$: Calc'd C, 59.42; H, 5.98; N, 2.48 Found C, 59.35; H, 5.67; N, 2.55

Example 82

(S)-4-[[2-[4-(4-Fluorophenyl)-5-methyl-2-(1-methylethyl)-6-phenyl-3-pyridinyl]ethenyl]-hydroxyphosphinyl] -3-hydroxybutanoic acid, disodium salt A solution of Example 81 (61.4 mg, 0.11 mmol) in $H_2O$ (6 ml) was treated with 1N NaOH (250 μl, 0.25 mmol) at room temperature for 30 minutes and the mixture was subsequently heated at 55° C. for 30 minutes. The solution was chromatographed directly on HP-20, eluting in succession with $H_2O$ (100 ml) and 50% MeOH in $H_2O$ (150 ml). The desired fractions were pooled and evaporated and the residue was taken up in $H_2O$ and lyophilized to give Example 82 (64 mg, 100%) as a white solid.

TLC $R_f$ 0.72 (7:2:1, i-PrOH, $NH_4OH$, $H_2O$) Analysis for $C_{27}H_{27}FNNa_2O_5P \times 2.45\ H_2O$: Calc'd: C 55.38 H 5.49 N 2.39 Found: C 55.40 H 5.49 N 2.15

Example 83

(S)-4-[ [ 2-[ 4-(4-Fluorophenyl)-5-methyl-2-(1-methylethyl)-6-phenyl-3-pyridinyl] ethyl] hydroxyphosphinyl] -3-hydroxybutanoic acid, disodium salt A. (S)-4-[[2-[4-(4-Fluorophenyl)-5-methyl- 2-(1-methylethyl)-6-phenyl-3-pyridinyl] ethyl]methoxyphosphinyl]-3-hydroxybutanoic acid, methyl ester A mixture of compound D from Example 81 (494 mg, 0.94 mmol) and Pd on carbon (10% Pd on C, 110 mg) in MeOH (20 ml) was shaken under 50 psi of $H_2$ for 3 days. The solution was filtered, stripped, and chromatographed (flash, Merck $SiO_2$, 50% acetone in hexane) to give compound A (419 mg, 85%) as a colorless oil.

TLC R$_f$ 0.36 (1:1—acetone:hexane)

B. (S)-4-[ [ 2-[4-(4-Fluorophenyl)-5-methyl- 2-(1-methylethyl)-6-phenyl-3-pyridinyl] ethyl] hydroxyphosphinyl] -3-hydroxybutanoic acid, disodium salt A solution of compound A (405 mg, 0.77 mmol) in dioxane (5 ml) was treated with 1N NaOH (2.7 ml, 2.7 mmol) and the mixture was stirred at 60° C. for 1.75 hours. The solvent was evaporated and the residue was chromatographed on HP-20, eluting in succession with H$_2$O and 50% MeOH in H$_2$O. The desired fractions were pooled and evaporated, and the residue was taken up in H$_2$O and lyophilized to give Example 78 (360 mg, 77%) as a white solid.

m.p. 293° C. (decomp.); [a]$_D$= + 0.8° (MeOH, c= 0.49) TLC R$_f$ 0.10 (8:1:1—CH$_2$ Cl$_2$:HOAc:MeOH) Microanalysis for C$_{27}$H$_{29}$FNNa$_2$O$_5$P×3.69 H$_2$O: Calc'd: C 53.17 H 6.01 N 2.30 F 3.11 P 5.08 Found: C 53.17 H 5.62 N 2.31 F 3.20 P 5.10

Example 84

(S)-4-[ [ [ 2-Ethyl-4-(4-fluorophenyl)-5-methyl-6-phenyl-3-pyridinyl]ethynyl]hydroxyphosphinyl]-3 -hydroxybutanoic acid, disodium salt A. 2-[(4-Fluorophenyl)methylene]-3-oxopentanoic acid, methyl ester A mixture of para-fluorobenzaldehyde (37.98 gm, 306 mmol), 3-oxopentanoic acid, methyl ester (39.78 gm, 306 mmol), piperidine (2.60 gm, 30.6 mmol) and HOAc (0.555 gm, 9.2 mmol) was allowed to reflux in benzene (150 ml) 7 hours under argon. The solution was cooled to room temperature, then diluted with ether and washed with 2% HCl, saturated NaHCO$_3$, water, and brine, then dried over MgSO$_4$, filtered and concentrated to give a yellow oil. The oil was purified by distillation (bp= 144° C. at 2.7 mm Hg) to give the title compound as a yellow oil (50.612 gm, 70%).

Microanalysis for C$_{13}$H$_{13}$FO$_3$: Calc'd: C 66.09 H 5.55 F 8.04 Found: C 66.45 H 5.59 F 7.79

B. β-(4-Fluorophenyl)-γ-methyl-α-(1-oxopropyl)-Δ -oxobenzenepentanoic acid, ethyl ester Propiophenone (5.68 gm, 42.37 mmol) was added dropwise to a solution of LiN(TMS)$_2$ (1M in THF, 42.37 ml, 42.37 mmol) cooled to −78° C. in THF (50 ml) and stirred 1 hour. Compound A (8.00 gm, 33.90 mmol) was then added dropwise as a solution in THF (5 ml) over two minutes. The solution was allowed to stir for one hour at −78° C., then warmed to 0° C. and stirred for an additional 30 minutes. The reaction was then quenched with NH$_4$Cl and warmed to room temperature. The solution was diluted with ether and EtOAc and the organic layer washed with water and brine, then dried over Na$_2$SO$_4$, filtered and concentrated to give a yellow oil. Excess propriophenone was removed by distillation under vacuum (104° C. at 1 mm Hg). The pot residue, compound B, was used directly in the next reaction.

C. 2-Ethyl-4-(4-fluorophenyl)-5-methyl-6 -phenyl-3-pyridinecarboxylic acid, ethyl ester NH$_4$OAc (7.84 gm, 102 mmol) and Cu(OAc)$_2$ (16.92 gm, 84.7 mmol) were added to an acetic acid solution (75 ml) of crude 1,5 diketone B (12.543 gm, 33.9 mmol) and the mixture allowed to reflux 16 hours while stirring under argon. The solution was then poured into an ice-cold solution of NH$_4$OH/H$_2$O (100 ml/150 ml). The mixture was extracted with ether and EtOAc and the organic layer washed with water and saturated NaCl, then dried over MgSO$_4$, filtered and concentrated to afford a brown oil. The oil was purified by flash chromatography on Merck silica in 10–15% EtOAc in hexane. The desired fractions were pooled and concentrated to give a red solid. Upon recrystallization of the solid from EtOAc/hexane, product C was obtained as hard reddish crystals (7.540 gm, 61%).

m.p. 84°–86° C. TLC: Rf 0.57 (15% EtOAc in hexane) Elemental Analysis for C$_{23}$H$_{22}$NFO: Calc'd: C 76.01 H 6.10 N 3.86 F 5.23 Found: C 75.63 H 5.78 N 3.97 F 5.38

D. 2-Ethyl-4-(4-Fluorophenyl)-5-methyl-6 -phenyl-3-pyridinemethanol

A THF solution (75 ml) of ester C (7.540 gm, 20.8 mmol) was cooled to 0° C. and treated with LiAlH$_4$ (2.36 gm, 62.3 mmol). After stirring 15 minutes at 0° C., the solution was warmed to room temperature and stirred for 16 hours. The solution was cooled to 0° C. and quenched by dropwise addition of 2.36 ml of water, followed by 2.36 ml of 15% NaOH, then 7.0 ml water. The aluminum paste was filtered out of solution and the filtrate was concentrated to afford alcohol D as a white solid (6.106 gm, 99.6%).

m.p. 180°–181° C. TLC: Rf 0.46 (40% EtOAc in hexane)

E. 2-Ethyl-4-(4-Fluorophenyl)-5-methyl-6 -phenyl-3-pyridinecarboxaldehyde

Tetrapropylammonium perruthenate (0.352 gm, 1.00 mmol) was added to a CH$_2$ Cl$_2$ solution (215 ml) of alcohol D (5.455 gm, 18.5 mmol) and 4-Methylmorpholine-N-oxide (4.01 g, 34.2 mmol), stirring over 4 angstrom sieves (10.85 gm) at room temperature. Forty-five minutes later, the reaction mixture was diluted with ether and filtered through a Celite® pad. The pad was washed repeatedly with ether and EtOAc. The solution was concentrated to give a dark oil which was purified by flash chromatography on Merck silica gel in 5% EtOAc in hexane. The desired fractions were combined and concentrated to give a yellow solid. The solid was recrystallized from hexane to afford product E as pale yellow needles (4.393 gm, 81%).

m.p. 97°–98° C. Elemental Analysis for C$_{21}$H$_{18}$NFO: Calc'd: C 78.97 H 5.68 N 4.39 F 5.95 Found: C 79.03 H 5.52 N 4.35 F 5.82

F. 2-Ethyl-4-(4-Fluorophenyl)-5-methyl-6 -phenyl-3-pyridinecarboxaldehyde

A solution of CBr$_4$ (7.57 gm, 22.5 mmol) in methylene chloride solution (30 ml) was added dropwise over 30 minutes to a solution of the aldehyde E (4.393, 15 mmol) and triphenylphosphine (12.59, 48 mmol) in methylene chloride (100 ml), which was stirring under argon at 0° C. The solution was stirred at 0° C. for an additional 30 minutes, then warmed to room temperature. Saturated NaHCO$_3$ was then added to quench the reaction. The organic layer was washed with brine, then dried over Na$_2$SO$_4$, filtered and concentrated to about 20 ml. The solution was purified by flash chromatography on Merck silica gel in 15–25% EtOAc in hexane. The desired fractions were pooled and concentrated to afford a yellowish solid, which was recrystallized from boiling hexane to afford compound F as fine white needles (6.019 gm, 89%).

m.p. 137°–138° C. TLC: Rf 0.50 (5% EtOAc in hexane) Elemental Analysis for C$_{22}$H$_{18}$NBr$_2$F: Calc'd: C 55.61 H 3.82 N 2.95 Br 33.63 F 4.00 Found: C 55.89 H 3.59 N 2.93 Br 33.97 F 4.20

G. 2-Ethyl-3-ethynyl-4-(4-fluorophenyl)-5 -methyl-6-phenylpyridine

A solution of vinyl dibromide F (6.019 gm, 13.4 mmol) in THF (7 ml) was added dropwise to a solution of n-BuLi (2.5M in hexane, 11.2 ml, 28.1 mmol) in THF (40 ml), stirring at −78° C. under argon. The solution was allowed to stir 1 hour at −78° C., then quenched with saturated NH$_4$Cl and warmed to 0° C., after which saturated NaHCO$_3$ was added. The mixture was diluted with ether, the organic layer washed with brine, then dried over $Na_2SO_4$, filtered and concentrated to give a yellow oil. The oil was purified by flash chromatography on Merck silica gel in 1% EtOAc in hexane. Pure product fractions were combined and concentrated to afford compound G as a white solid (3.568 gm, 85%).

TLC: $R_f$ 0.48 (1% EtOSc in hexane) Elemental Analysis for $C_{22}H_{18}NF$: Calc'd: C 83.31 H 5.78 N 4.42 F 5.99 Found: C 83.40 H 5.65 N 4.33 F 5.96

H. (S)-4-[[[2-Ethyl-4-(4-fluorophenyl)-5 -methyl-6-phenyl-3-pyridinyl]ethynyl] methoxyphosphinyl]-3-[[(1,1-dimethylethyl)diphenylsilyl] oxy]butanoic acid, methyl ester A solution of acetylene G (0.500 gm, 1.52 mmol) in THF (10 ml) was added dropwise to a solution of n-BuLi (2.5M in hexane, 0.67 ml, 1.67 mmol) in THF (15 ml) stirring at −78° C. under argon. The solution was allowed to stir 45 minutes at −78° C., then cannulated into a THF solution (15 ml) of the chloridate from Example 57, part G, which had also been cooled to −78° C. The solution was stirred for 30 minutes at −78 ° C., then quenched with saturated $NH_4Cl$ and warmed to 0° C., after which saturated $NaHCO_3$ was added. The solution was diluted with ether and the organic layer was washed with brine, dried over $Na_2SO_4$, filtered and concentrated to give a dark orange oil. The oil was purified by flash chromatography on Merck silica gel in 40% EtOAc in hexane. The desired fractions were combined and concentrated to afford compound H as a yellowish oil (0.550 gm, 46%).

TLC: Rf 0.52 (50% acetone in hexane)

I. (S)-4-[[[2-Ethyl-4-(4-fluorophenyl)-5 -methyl-6-phenyl-3-pyridinyl]ethynyl] methoxyphosphinyl]-3-hydroxybutanoic acid, methyl ester $(Bu)_4NF$ (1M in THF, 2.21 ml, 2.21 mmol) was added to a solution of silyl ether H (0.550 gm, 0.736 mmol) and HOAc (0.176 gm, 2.94 mmol) in THF (20 ml) under argon and allowed to stir 19 hours at room temperature. The reaction mixture was diluted with EtOAc, then washed with 5% $KHSO_4$ (three times). The aqueous layers were extracted with EtOAc (three times). The organic layers were pooled and washed with brine, then dried over $Na_2SO_4$, filtered and concentrated to afford a brown oil. The oil was dissolved in ether (15 ml) and treated with excess $CH_2 N_2$. Excess $CH_2N_2$ was removed with a stream of argon, and the solution was concentrated to give a brown-yellow oil. The oil was purified by flash chromatography on Merck silica gel in 50% acetone in hexane. The desired fractions were pooled and concentrated to afford the title compound as a clear oil (0.200 gm, 53%).

TLC: Rf 0.52 (50% acetone in hexane)

J. (S)-4-[[[2-Ethyl-4-(4-fluorophenyl)-5 -methyl-6-phenyl-3-pyridinyl]ethynyl] hydroxyphosphinyl]-3-hydroxybutanoic acid, disodium salt Di-ester I (0.200 gm, 0.393 mmol) was dissolved in dioxane (10 ml) and treated with NaOH (1M in $H_2O$, 1.18 ml, 1.18 mmol). The solution was then heated to 55° C. and allowed to stir 2 hours and 15 minutes. The solution was concentrated to a yellowish solid. The solid was dissolved in water and chromatographed on HP-20 resin, eluting first with water (200 ml), then with 50% MeOH in water (400 ml), and finally MeOH (200 ml). The desired fractions were pooled and concentrated, and the resultant white solid was dissolved in water and lyophilized to give Example 84 as a fluffy, pale yellow solid (0.180 gm, 87%).

m.p. 310° C. (decomp) Elemental Analysis for $C_{26}H_{23}NFNa_2PO_5 \times 2.00 H_2O$: Calc'd: C 55.63 H 4.85 N 2.50 F 3.38 P 5.52 Found: C 55.52 H 4.67 N 2.55 F 3.33 P 5.45 Optical Rotation: $[a]_D = +8.1°$ (MeOH, c= 3.45 mg/ml)

Example 85

(S,E)-4-[ [ 2-[ 2-Ethyl-4-(4-fluorophenyl)-5-methyl-6-phenyl-3-pyridinyl] ethenyl] hydroxyphosphinyl] -3 -hydroxybutanoic acid, disodium salt A. 1-Ethyl-4-(4-fluorophenyl)-5-methyl-6 -phenyl-3-[2-(tributylstannyl)ethenyl] pyridine A mixture of tri-n-butyltin hydride (4.27 gm, 14.6 mmol), acetylene G from Example 84 (2.560 gm, 8.14 mmol) and AIBN (0.050 gm) was heated to 140° C. for 30 minutes. The solution was then cooled to room temperature and diluted with ether (30 ml). Iodine (4.25 gm, 16.73 mmol) was added and the solution allowed to stir 16 hours at room temperature. Additional iodine (2.00 gm, 7.87 mmol) was added to the solution, which stirred for 2 more hours. The solution was then quenched with 10% $Na_2S_2O_3$ in saturated $NaHCO_3$. The solution was diluted with ether, washed with 10% $Na_2S_2O_3$ in saturated $NaHCO_3$ (twice) and brine, then dried over $Na_2SO_4$, filtered and concentrated to give a dark brown residue. The oil was purified by flash chromatography on Merck silica gel in 60% $CH_2 Cl_2$ in hexane. The desired fractions were combined and concentrated to give a white solid. The white solid was recrystallized from hexane to afford product A as white crystals (2.565 gm, 73%).

m.p. 124°–126° C. TLC: Rf 0.27 (2% EtOAc in hexane) Elemental Analysis for $C_{22}H_{18}NF \times 0.10 H_2O$: Calc'd: C 83.31 H 5.78 N 4.42 F 5.99 Found: C 83.40 H 5.65 N 4.33 F 5.96

B. (S,E)-4-[[2-[2-Ethyl-4-(4-fluorophenyl)- 5-methyl-6-phenyl-3-pyridinyl] ethenyl]methoxyphosphinyl]-3-[[(1,1 -dimethylethyl)diphenylsilyl]oxy] butanoic acid, methyl ester A solution of vinyl iodide A (1.639 gm, 3.70 mmol) in THF (7 ml) was added dropwise over 5 minutes to a solution of n-BuLi (1.7M in pentane, 4.35 ml, 7.4 mmol) in THF (10 ml) cooled to −78° C. stirring under argon. The solution was allowed to stir 15 minutes at −78° C., then cooled to −100° C. and cannulated over 12 minutes into a THF solution (15 ml) of the chloridate from Example 57, part G, also cooled to −100° C. The solution was stirred 20 minutes at −100° C., then quenched with saturated $NH_4Cl$ and warmed to 0° C., and then saturated $NaHCO_3$ was added to the solution. The solution was diluted with ether and the organic layer was washed with brine, then dried over $Na_2SO_4$, filtered and concentrated to give a dark orange oil. The oil was purified by flash chromatography on Merck silica gel in 50% EtOAc in hexane. The desired fractions were combined and evaporated to afford compound B as a white, fluffy solid (0.985 gm, 36%).

TLC: $R_f$ 0.50 (45% EtOAc in hexane)

C. (S,E)-4-[[2-[2-Ethyl-4-(4-fluorophenyl)- 5-methyl-6-phenyl-3-pyridinyl] ethenyl]methoxyphosphinyl]-3-hydroxybutanoic acid, methyl ester $(Bu)_4NF$ (1M in THF, 3.94 ml, 3.94 mmol) was added to a solution of silyl ether B (0.985 gm, 1.31 mmol) and HOAc (0.315 gm, 5.24 mmol) in THF (20 ml) and allowed to stir 15 hours at room temperature. Additional TBAF (1.30 ml, 1.30 mmol) and HOAc (0.100 ml, 1.75 mmol) were added, and the reaction mixture was allowed to stir under argon for another 3 hours. The solution was diluted with EtOAc and washed with 5% $KHSO_4$ (three times). The aqueous layers were extracted with EtOAc (twice) and the organic layers were combined and washed with brine, then dried over $Na_2SO_4$, filtered and concentrated to give a yellow oil. The oil was purified by flash chromatography on Merck silica gel in 50% acetone in hexane. The desired fractions were pooled and concentrated to afford compound C as a clear oil (0.430 gm, 64%).

TLC: Rf 0.54 (50% acetone in hexane)

D. (S,E)-4-[ [2-[2-Ethyl-4-(4-fluorophenyl)- 5-methyl-6-phenyl-3-pyridinyl] ethenyl] hydroxyphosphinyl] -3-hydroxybutanoic acid, disodium salt NaOH (1M in $H_2O$, 1.29 ml, 1.29 mmol) was added dropwise to compound C (0.219 gm, 0.428 mmol) in dioxane (10 ml) and warmed to 60° C. and stirred 3 hours. Additional NaOH (1M in $H_2O$, 0.40 ml, 0.40 mmol) was added to the solution, which stirred for another hour at 60° C. The mixture was then concentrated to a white solid. The solid was dissolved in water and chromatographed on HP-20 resin, eluting first with water (200 ml), then with 50% MeOH in water (400 ml), and finally, MeOH (200 ml). The desired fractions were pooled, concentrated, and the resultant white solid dissolved in water and lyophilized to give Example 85 as a fluffy white solid (0.175 gm, 78%).

m.p. 305° C. (decomp) TLC: Rf 0.69 (6:3:1, n-propanol:$NH_4OH$:$H_2O$) Elemental Analysis for $C_{26}H_{25}NFNa_2PO_5 \times 1.75$ $H_2O$: Calc'd: C 55.86 H 5.01 N 2.51 F 3.40 P 5.54 Found: C 55.86 H 5.01 N 2.51 F 3.54 P 5.45 Optical Rotation: $[a]_D$= +1.8° (MeOH, c= 4.8 mg/ml)

Example 86

(S)-4-[ [ [ 4-(4-Fluorophenyl)-5,6-dihydro-2-(1-methylethyl)benzo[h] quinolin-3-yl] ethynyl] hydroxyphosphinyl] -3-hydroxybutanoic acid, disodium salt A. β-(4-Fluorophenyl)-1,2,3,4-tetrahydro-α -(2-methyl-1-oxopropyl)-1-oxo-2 -naphthalenepropanoic acid, ethyl ester A −78° C. solution of lithium bis(trimethylsilyl)amide (1M in THF, 33.5 ml, 33.6 mmol) in THF (70 ml) was treated dropwise with a solution of 3,4-dihydro-1(2H)-naphthalenone (4.46 ml, 33.6 mmol, Aldrich) in THF (10 ml). After one hour, a solution of the compound from Example 53, part A (6.96 gm, 28.0 mmol) in THF (5 ml) was added to the solution. The mixture was stirred at −78° C. for one hour, then at 0° C. for 1.5 hours. The reaction mixture was treated with glacial HOAc (8 ml), then quenched with 50% saturated $NH_4Cl$ and extracted with EtOAc. The aqueous layer was back-extracted with EtOAc. The organic layers were combined and washed with $H_2O$ and brine, then dried over $Na_2SO_4$, filtered and concentrated to afford a dark oily residue. The residue was dried under high vacuum and used in the next step without further purification.

B. 1-(4-Fluorophenyl)-9,10-dihydro-3-(1 -methylethyl)-2-phenanthrenecarboxylic acid, ethyl ester A mixture of crude 1,5 diketone A, ammonium acetate (6.47 gm, 84.0 mmol) and copper (II) acetate (13.97 gm, 70.0 mmol) in glacial acetic acid (75 ml) was allowed to reflux for 16 hours. The reaction mixture was then cooled and poured into an ice cold mixture of $NH_4OH$/$H_2O$ (120 ml/150 ml). The mixture was extracted with ether (twice) and the ether extracts were washed with water (twice) and brine, then dried over $MgSO_4$, filtered and concentrated. The dark oily residue was purified by flash chromatography (10% ether/hexane) to afford compound B as a pink solid (5.2 gm, 46% from the naphthalenone), which was contaminated with a higher Rf component.

TLC: Rf 0.5 (10% ether/hexane), UV+ Rf 0.62 (10% ether/hexane), UV, fluorescence C. 1-(4-Fluorophenyl)-9,10-dihydro-3-(1 -methylethyl)-2-phenanthrenemethanol A 0° C. solution of ester B in dry THF (60 ml) was treated with LAH (1.46 gm, 38.52 mmol). Ten minutes after the addition the solution was warmed to room temperature and stirred for two hours. The reaction mixture was then cooled to 0° C. and quenched by dropwise addition of 1.46 ml of $H_2O$ in THF (10 ml), then 1.46 ml 15% NaOH, and finally 3.0 ml $H_2O$. The precipitated aluminum salts were filtered out of solution and washed with EtOAc and ether. The filtrate and washings were combined and washed with water and brine, then dried over $Na_2SO_4$, filtered and concentrated to give an oily residue. Purification by flash chromatography (Merck silica gel, 10% ether/hexane, followed by 10% EtOAc/hexane) afforded a colorless oil which solidified on standing under high vacuum. Recrystallization of the solid from hexane afforded compound C as a white solid (4.0 gm, 89.8%).

m.p. 138°–139° C. Rf 0.42 (20% EtOAc/hexane), UV Analysis for $C_{23}H_{22}NFO*0.18$ $H_2O$: Calc'd: C 78,79 H 6.43 N 4.00 F 5.42 Found: C 78.80 H 6.45 N 3.99 F 5.24

D. 1-(4-Fluorophenyl)-9,10-dihydro-3-(1 -methylethyl)-2-phenanthrenecarboxaldehyde A solution of NMO (0.989 gm, 8.44 mmol) in $CH_2Cl_2$ (30 ml) was allowed to stir over $MgSO_4$ for 30 minutes before being added to a mixture of compound C (1.647 gm, 4.56 mmol) and 4 angstrom sieves (2.67 gm) in $CH_2Cl_2$ (20 ml). The mixture was allowed to stir 5 minutes at room temperature, then TPAP (0.087 gm, 0.25 mmol) was added to the flask and the solution stirred for an additional hour. The mixture was diluted with ether, then filtered through a Celite® pad and washed with ether and EtOAc. The filtrate and washings were combined and concentrated to a dark green solid. The solid was purified by flash chromatography on Merck silcia gel in 15% EtOAc in hexane. The desired fractions were combined and concentrated to a white solid. The white solid was recrystallized from hexane to afford compound D as hard white crystals (1.364 gm, 83%).

m.p. 129°–130° C. TLC: Rf 0.62 (25% EtOAc in hexane)

E. 2-(2,2-Dibromoethenyl)-1-(4-fluorophenyl)- 3-(1-methylethyl)phenanthrene

A solution of $CBr_4$ (0.281 gm, 0.836 mmol) in $CH_2Cl_2$ (5 ml) was added dropwise to a 0° C. solution of aldehyde D (0.200 gm, 0.557 mmol) and triphenylphosphine (0.470 gm, 1.78 mmol) in $CH_2Cl_2$ (20 ml). The solution was allowed to stir 30 minutes at 0° C., then warmed to room temperature over 15 minutes. The solution was then quenched with $NaHCO_3$ and diluted with EtOAc and ether. The organic layer was washed with brine, then dried over $Na_2SO_4$, filtered and concentrated to a yellow solid. The solid was purified by flash chromatography on Merck silica gel in 15% EtOAc in hexane. The desired fractions were combined and concentrated to a white solid. The solid was recrystallized from hexane to afford compound E as large clear crystals (0.254 gm, 88.5%).

m.p. 121°–122° C. Elemental Analysis dor $C_{24}H_{20}NBr_2F*0.18$ $H_2O$: Calc'd: C 57.14 H 4.07 N 2.78 Br 31.68 F 3.77 Found: C 57.53 H 3.92 N 2.72 Br 31.21 F 3.83

F. (S)-4-[[[4-(4-Fluorophenyl)-5,6-dihydro- 2-(1-methylethyl)benzo[h]quinolin-3-yl]ethynyl]methoxyphosphinyl]-3-[ [(1,1 -dimethylethyl)diphenylsilyl]oxy]butanoic acid, methyl ester N-BuLi (2.5M in hexane, 1.31 ml, 3.27 mmol) was added dropwise to a solution of vinyl dibromide E (0.780 gm, 1.56 mmol) in THF (10 ml) at −78° C. under argon. The solution was allowed to stir 1 hour at −78° C., then cannulated into a THF solution (15 ml) of the chloridate from Example 57, part G, which had also been cooled to −78° C. The solution was stirred 30 minutes at −78° C., then quenched with saturated $NH_4Cl$ and warmed to 0° C., and then saturated NaHCO$_3$ was added. The solution was diluted with ether and the organic layer was washed with brine, then dried over Na$_2$SO$_4$, filtered and concentrated to a dark orange oil. The oil was purified by flash chromatography on Merck silica gel in 45% EtOAc in hexane. The desired fractions were combined and concentrated to afford compound F as a brown oil (0.385 gm, 33%).

TLC: Rf 0.62 (1:1, EtOAc:hexane)

G. (S)-4-[[[4-(4-Fluorophenyl)-5,6-dihydro- 2-(1-methylethyl)benzo[h]quinolin-3-yl] ethynyl]methoxyphosphinyl]-3-hydroxybutanoic acid, methyl ester (Bu)$_4$NF (1M in THF, 1.55 ml, 1.55 mmol) was added to a solution of compound F (0.385 gm, 0.52 mmol) and HOAc (0.125 gm, 2.08 mmol) in THF (10 ml) under argon and allowed to stir 17 hours at room temperature. The reaction mixture was diluted with EtOAc, then washed with 5% KHSO$_4$ (three times). The aqueous layers were back-extracted with EtOAc (twice). The organic layers were pooled and washed with brine, then dried over Na$_2$SO$_4$, filtered and concentrated to afford an orange oil. The oil was dissolved in ether (10 ml) and treated with excess CH$_2$N$_2$. Excess CH$_2$N$_2$ was removed with a stream of argon, and the solution was concentrated to give an orange oil. The oil was purified by flash chromatography on Merck silica gel in 35% acetone in hexane. The desired fractions were pooled and concentrated to afford compound G as a clear oil (0.195 gm, 70%).

TLC: Rf 0.80 (8:1:1, CH$_2$Cl$_2$:MeOH:HOAc)

H. (S)-4-[[[4-(4-Fluorophenyl)-5,6-dihydro- 2-(1-methylethyl)benzo[h]quinolin-3-yl] ethynyl]hydroxyphosphinyl]-3-hydroxybutanoic acid, disodium salt A solution of compound G (0.190 gm, 0.357 mmol) in dioxane (10 ml) was treated with NaOH (1 M in H$_2$O, 1.10 ml 1.10 mmol), then heated to 55° C. and allowed to stir 3 hours. The solution was cooled to room temperature and concentrated to a white solid. The solid was dissolved in water and chromatographed on HP-20 resin, eluting first with water (200 ml), then with 50% MeOH in water (400 ml), and finally with MeOH (200 ml). The desired fractions were pooled and concentrated. The resultant white solid was dissolved in water and lyophilized to give Example 86 as a fluffy white solid (0.150 gm, 76%).

m.p. 282° C. (decomp) Elemental Analysis for C$_{28}$H$_{25}$FNO$_5$P*2 Na*2.25 H$_2$O: Calc'd: C 56.81 H 5.02 N 2.37 F 3.21 P 5.23 Found: C 56.84 H 4.83 N 2.48 F 3.44 P 4.84 Optical Rotation: [a]$_D$=+11.4° (MeOH, C= 4.0 mg/ml)

Example 87

(S,E)-4-[ [ 2-[5-Ethyl-4-(4-fluorophenyl)-2-(1-methylethyl)-6-phenyl-3-pyridinyl] ethenyl] hydroxyphosphinyl] -3-hydroxybutanoic acid, disodium salt A. 5-Ethyl-3-ethynyl-4-(4-fluorophenyl)-2 -(1-methylethyl)-6-phenylpyridine To a solution of compound E from Example 59 (2.001 gm, 4.0 mmol) in dry THF (15 ml) at –78° C. was added n-BuLi (2.5M in hexanes, 3.80 ml, 9.5 mmol) over a 1-minute period. After stirring at –78° C. for 50 minutes, the clear green solution was quenched with saturated NH$_4$Cl and warmed to room temperature. The mixture was diluted with H$_2$O, Et$_2$O, and EtOAc and the mixture was shaken in a separatory funnel. The organic layer contained a finely divided white solid. The organic layer was washed with brine and filtered to give approximately 1 gram of solid. Additional solid was obtained after evaporation of the organic filtrate. The pooled solids were refluxed in EtOAc/acetone, diluted with hexane, and cooled to give the acetylene title compound (1.253 gm, 91%) as a white solid that is poorly soluble in most common organic solvents.

m.p. 245° C. TLC R$_f$ 0.44 (10% EtOAc in hexane) Analysis for C$_{24}$H$_{22}$FN: Calc'd: C 83.93 H 6.46 N 4.08 F 5.53 Found: C 83.53 H 6.28 N 4.06 F 5.68

B. 5-Ethyl-4-(4-fluorophenyl)-3-(2-iodoethynyl)- 2-(1-methylethyl)-6-phenylpyridine A mixture of compound A (1.222 gm, 3.56 mmol) and AIBN (20 mg) in tri-n-butylstannyl hydride (2.3 ml) was rapidly heated to 140° C. by immersion in a pre-heated oil bath. Approximately 20 mg of AIBN was added to the reaction mixture one and two hours after heating was initiated. After 3 hours, the mixture was cooled to room temperature, diluted with Et$_2$O (40 ml) and treated with solid I$_2$ (3.40 gm, 13.4 mmol). The dark reaction mixture was stirred for 50 minutes, then poured into a 50% saturated NaHCO$_3$ solution containing 6.8 gm Na$_2$S$_2$O$_3$. The layers were shaken and separated. The ethereal layer was washed successively H$_2$O, 1.7M NH$_4$OH, H$_2$O, and brine, then dried (Na$_2$SO$_4$), filtered and stripped to yield an oil. The residue was subjected to flash chromatography (Merck SiO$_2$, 10% EtOAc in hexane) to afford the crude title compound as a solid. Recrystallization from hexane gave the title compound (1.389 gm, 87%) as pale yellow crystals.

m.p. 116.8°–118.8° C. TLC R$_f$ 0.36 (4% EtOAC in hexane) Microanalysis for C$_{24}$H$_{23}$FNI: Calc'd: C 61.15 H 4.92 N 2.97 F 4.03 I 26.92 Found: C 60.34 H 4.92 N 2.69 F NA I 26.53

C. (S,E)-4-[[2-[5-Ethyl-4-(4-fluorophenyl)- 2-(1-methylethyl)-6-phenyl-3 -pyridinyl]ethenyl]methoxyphosphinyl]-3 -[[(1,1-dimethylethyl)diphenylsilyl]oxy] butanoic acid, methyl ester A solution of the part B vinyl iodide (1.300 gm, 2.76 mol) in THF (8 ml) was added over a 5-minute period to a –100° C. solution of t-butyllithium (1.7M in pentane, 3.40 ml, 5.8 mmol) in THF (8 ml). The resulting solution was stirred for 15 minutes, then added over a 10-minute period to a –100° C. solution of the phosphonochloridate from Example 57, part G in THF (15 ml). The resulting yellow mixture was stirred at minus 100° C. for 10 minutes, then at –78° C. for 30 minutes, then quenched with 50% saturated NH$_4$Cl. The solution was warmed to room temperature, diluted with H$_2$O, and poured into saturated NaHCO$_3$. The aqueous phase was extracted with Et$_2$O. The Et$_2$O extract was washed with brine, dried (Na$_2$SO$_4$), filtered and stripped. The resulting yellow-orange oil was chromatographed (flash, LPS-1, 50% EtOAc in hexane) to afford the title compound as a tan foam (1.261 gm, 59%).

TLC R$_f$ 0.21 (40% EtOAc in hexane)

D. (S,E)-4-[[2-[5-Ethyl-4-(4-fluorophenyl)- 2-(1-methylethyl)-6-phenyl-3 -pyridinyl]ethenyl]methoxyphosphinyl]-3 -hydroxybutanoic acid, methyl ester A solution of the part C compound (1.241 gm, 1.59 mmol) in THF (15 ml) was treated with HOAc (470 ul, 493 mg, 8.2 mmol) and tetra-n-butyl-ammonium fluoride (1.0M in THF, 7.8 ml, 7.8 mmol). After stirring at room temperature for 16 hours, the solution was poured into saturated NaHCO$_3$ and extracted with EtOAc. The EtOAc extract was washed with brine, dried (Na$_2$SO$_4$), filtered, and stripped to give an oil, which was subsequently chromatographed (flash, Merck SiO$_2$, 40% acetone in hexane followed by 60% acetone in hexane). Compound D (770 mg, 90%) was obtained as a white foam.

TLC R$_f$ 0.40 (1:1 acetone:hexane)

E. (S,E)-4-[ [ 2-[ 5-Ethyl-4-(4-fluorophenyl)- 2-(1-methylethyl)-6-phenyl-3-pyridinyl] ethenyl] hydroxyphosphinyl] -3-hydroxybutanoic acid, disodium salt A solution of compound D (286 mg, 0.53 mmol) in dioxane (3 ml) was treated with 1N NaOH (1.9 ml, 1.9 mmol) and the mixture was stirred at 60° C. for 1 hour. The solvent was evaporated and the residue was taken up in H$_2$O and chromatographed on HP-20, eluting in succession with H$_2$O (150 ml) and 50% MeOH in H$_2$O (200 ml). The desired fractions were pooled and evaporated and the residue was taken up in H$_2$O and lyophilized to give Example 87 (270 mg, 82%) as a white solid.

m.p. 285° C. (decomp.); [a]$_D$= + 10.9° (MeOH, c= 0.52) TLC R$_f$ 0.12 (8:1:1—CH$_2$Cl$_2$:HOAc:MeOH) Microanalysis for C$_{28}$H$_{29}$FNNa$_2$O$_5$P×3.85 H$_2$O: Calc'd: C 53,83 H 5.92 N 2.24 F 3.04 P 4.96 Found: C 53.87 H 5.65 N 2.19 F 3.11 P 4.95

Example 88

(S)-4-[ [ 2-[ 5-Ethyl-4-(4-fluorophenyl)-2-(1-methylethyl)- 6-phenyl-3-pyridinyl]ethyl]-hydroxyphosphinyl] -3-hydroxybutanoic acid, disodium salt A. (S)-4-[[2-[5-Ethyl-4-(4-fluorophenyl)-2 -(1-methylethyl)-6-phenyl-3-pyridinyl] ethyl]methoxyphosphinyl]-3-hydroxybutanoic acid, methyl ester A mixture of compound C from Example 87 (467 mg, 0.865 mmol) and Pd on carbon (10% Pd on C, 100 mg) in MeOH (20 ml) was shaken under 50 psi of H$_2$ for 3 days. The solution was filtered, stripped, and chromatographed (flash, Merck SiO$_2$, 50% acetone in hexane) to give compound A (411 mg, 88%) as a colorless oil.

TLC R$_f$ 0.39 (1:1—acetone:hexane)

B. (S)-4-[[2-[5-Ethyl-4-(4-fluorophenyl)-2 -(1-methylethyl)-6-phenyl-3-pyridinyl] ethyl]hydroxyphosphinyl]-3-hydroxybutanoic acid, disodium salt A solution of compound A (393 mg, 0.725 mmol) in dioxane (5 ml) was treated with 1N NaOH (2.5 ml, 2.5 mmol) and the mixture was stirred at 60° C. for 2 hours. The solvent was evaporated and the residue was chromatographed on HP-20, eluting in succession with H$_2$O (150 ml) and 50% MeOH in H$_2$O (200 ml). The desired fractions were pooled and evaporated and the residue was taken up in H$_2$O and lyophilized to give Example 88 (346 mg, 77%) as a white solid.

m.p. 297° C. (decomp.); [a]$_D$= + 1.0° (MeOH, c= 0.48) TLC R$_f$ 0.11 (8:1:1—CH$_2$Cl$_2$:HOAc:MeOH) Microanalysis for C$_{28}$H$_{31}$FNNa$_2$O$_5$P×3.33 H$_2$O: Calc'd: C 54.46 H 6.15 N 2.27 F 3.08 P 5.02 Found: C 54.46 H 5.87 N 2.26 F 3.05 P 4.93

Example 89

(S)-4-[ [ [ 4-(4-Fluoro-2-methylphenyl)-2-(1-methylethyl)- 6-phenyl-3-pyridinyl] ethynyl] hydroxyphosphinyl] -3-hydroxybutanoic acid, disodium salt A. 4-Fluoro-2-methylbenzaldehyde n-BuLi (2.6M in hexane, 57 ml, 143 mmol) was added over 15 minutes to a THF solution (200 ml) of 2-methyl-4-fluorophenylbromide, cooled to −78° C. and allowed to stir 1 hour at −78° C. DMF (26.61 gm, 364 mmol) was then added over 2 minutes, and the solution was allowed to stir another hour. The reaction was quenched with NH$_4$Cl and warmed to room temperature. 10% HCl was added until the solution became acidic. The mixture was diluted with ether and the organic layer washed with water and brine, then dried over MgSO$_4$, filtered and concentrated to give an orange oil. The oil was purified by distillation (bp= 69° C. at 7 mm Hg) to afford aldehyde A as a clear liquid (13.284 gm, 74%).

TLC: Rf 0.30 (10% EtOAc in hexane)

B. 3-(4-Fluoro-2-methylphenyl)-1-phenyl- 2-propen-1-one

A solution of sodium ethoxide in ethanol (21% by weight, 3.08 gm, 9.50 mmol) was added to a mixture of aldehyde A (13.084 gm, 95 mmol) and acetophenone (11.38 gm, 95 mmol, from Aldrich) in ethanol (125 ml). After stirring at room temperature for 17 hours, the solution was concentrated to about 30 ml to give an orange oil. The oil was dissolved in ether and EtOAc, washed with water and brine, then dried over MgSO$_4$, filtered and concentrated to afford an orange oil. The oil was purified by flash chromatography on Merck silica gel in 5–10% EtOAc in hexane. Fractions containing product B, were pooled and concentrated to afford compound B as a pale yellow oil (17.285 gm, 76%).

TLC: Rf 0.39 (10% EtOAc in hexane)

C. β-(4-Fluoro-2-methylphenyl)-α-(2-methyl- 1-oxopropyl)-Δ-oxobenzenepentanoic acid, ethyl ester A solution of sodium ethoxide in ethanol (21% by weight, 3.49 gm, 10.8 mmol) was added to a mixture of enone B (17.280 gm, 72 mmol) and ethylisobutyrylacetate (17.086 gm, 108 mmol) in ethanol (300 ml) and stirred at room temperature for 6 hours, the solution was concentrated to about 50 ml, dissolved in ether and EtOAc, washed with saturated NH$_4$Cl, water and brine, then dried over MgSO$_4$, filtered and concentrated to afford an orange oil. The oil was purified by flash chromatography on Merck silica gel in 5–10% EtOAc in hexane. Fractions containing the product were pooled and concentrated to give compound C as a white, crystalline solid (23.905 gm, 87%).

m.p.= 73°–77° C. TLC: Rf 0.38, 0.43 (15% EtOAc in hexane)

D. 4-(4-Fluoro-2-methylphenyl)-2-(1-methylethyl)- 6-phenyl-3-pyridinecarboxylic acid, ethyl ester NH$_4$OAc (14.47 gm, 188 mmol) and Cu(OAc)$_2$ (31.23 gm, 156 mmol) were added to an acetic acid solution (100 ml) of 1,5 diketone C (23.905 gm, 62.6 mmol). The resulting mixture was allowed to reflux for 13 hours while stirring under argon. The solution was then poured into an ice-cold solution of NH$_4$OH/H$_2$O (125 ml/150 ml). The mixture was extracted with EtOAc (twice), washed with water and saturated NaCl, then dried over MgSO$_4$, filtered and concentrated to afford an orange oil. The oil was purified by flash chromatography on Merck silica in 5% EtOAc in hexane. Those fractions containing pure product D were pooled and concentrated to give a clear oil (19.140 gm, 81%).

TLC: Rf 0.63 (10% EtOAc in hexane)

E. 4-(4-Fluoro-2-methylphenyl)-2-(1-methylethyl)- 6-phenyl-3-pyridinemethanol

A THF solution (20 ml) of ester D (19.140 gm, 50.8 mmol) was cooled to 0° C. and treated with LiAlH$_4$ (5.78 gm, 152 mmol). After stirring 15 minutes at 0° C., the solution was warmed to room temperature and stirred for an additional 3 hours. The solution was cooled to 0° C. and quenched by dropwise addition of 5.8 ml of water followed by 5.8 ml of 15% NaOH, then 17.0 ml water. The aluminum paste was filtered out of solution and the filtrate concentrated to a white solid. Recrystallization of the solid from EtOAc/hexane gave compound E as hard, white crystals (15.072 gm, 94%).

m.p. 134°–135° C. TLC: Rf 0.62 (27% EtOAc in hexane) Elemental Analysis for C$_{22}$H$_{22}$NFO: Calc'd C, 78.78; H, 6.61; N, 4.18; F, 5.66 Found C, 78.85; H, 6.68; N, 4.18; F, 5.54

F. 4-(4-Fluoro-2-methylphenyl)-2-(1-methylethyl)- 6-phenyl-3-pyridinecarboxaldehyde DMSO (9.66 gm, 124 mmol) was added to a −78° C. solution of oxalyl chloride (7.85 gm, 61.9 mmol) in methylene chloride (200 ml). The mixture was allowed to stir 20 minutes at −78° C. under argon. Compound E (15.072 gm, 47.5 mmol) was then added dropwise to the flask as a methylene chloride (50 ml) solution. Twenty minutes later, triethyl amine (33 ml, 0.327 mmol) was added dropwise to the cloudy white solution, and the mixture was stirred for 20 minutes, then warmed to room temperature. The solution was diluted with ether and the organic layer washed with water and brine, then dried over $Na_2SO_4$, filtered and concentrated to afford a yellow oil. The compound was purified by flash chromatography on Merck silica gel in 10% EtOAc in hexane. The desired fractions were combined and concentrated to afford product F as a yellow, crystalline solid (13.70 gm, 92%).

m.p. 90°–93° C. TLC: Rf 0.62 (15% EtOAc in hexane) Elemental Analysis for $C_{22}H_{20}NFO$: Calc'd C, 79.26; H, 6.05; N, 4.20; F, 5.70 Found C, 79.27; H, 6.06; N, 4.20; F, 5.82

G. 3-(2,2-Dibromoethenyl)-4-(4-fluoro-2-methylphenyl)-2-(1-methylethyl)-6-phenylpyridine A solution of $CBr_4$ (21.95 gm, 65.2 mmol) in methylene chloride (75 ml) was added over 20 minutes to a 0° C. solution of aldehyde F (13.70 gm, 43.5 mmol) and triphenyl phosphine (36.51 gm, 139 mmol) in methylene chloride (250 ml). The solution stirred at 0° C. for an additional 30 minutes, then warmed to room temperature over 40 minutes. Saturated $NaHCO_3$ was then added to quench the reaction. The organic layer was washed with brine, then dried over $Na_2SO_4$, filtered and concentrated to about 100 ml. The solution was purified by flash chromatography on Merck silica gel in 15% EtOAc in hexane. The desired fractions were pooled and concentrated to afford a yellowish solid. The solid was recrystallized from hexane to afford product G as hard, clear crystals (16.560 gm, 81%).

m.p. 128°–129° C. TLC: Rf 0.37 (5% EtOAc in hexane) Elemental Analysis for $C_{23}H_{20}NBr_2F$: Calc'd C, 56.47; H, 4.12; N, 2.86; Br, 32.67; F, 3.88 Found C, 56.71; H, 4.00; N, 2.82; Br, 32.46; F, 3.86

H. 3-Ethynyl-4-(4-fluoro-2-methylphenyl)-2-(1-methylethyl)-6-phenylpyridine

A solution of vinyl dibromide G (8.280 gm, 17.6 mmol) in THF (10 ml) was added dropwise to a solution of n-BuLi (2.5M in hexane, 14.7 ml, 36.9 mmol) in THF (20 ml) stirring at −78° C. under argon. The solution was allowed to stir 1 hour at −78° C., then quenched with saturated $NH_4Cl$ and warmed to 0° C., then saturated $NaHCO_3$ was added to the solution. The mixture was diluted with ether, and the organic layer was washed with brine, dried over $Na_2SO_4$, filtered and concentrated to give yellow oil. The oil was purified by flash chromatography on Merck silica gel in 1% EtOAc in hexane. The desired fractions were combined and concentrated to afford compound H as a white solid (5.514 gm, 95%).

m.p. 72°–74° C. TLC: Rf 0.32 (1% EtOAc in hexane) Elemental Analysis for $C_{23}H_{20}NF$: Calc'd C, 83.86; H, 6.12; N, 4.25; F, 5.77 Found C, 83.72; H, 6.02; N, 4.21; F, 5.68

I. (S)-4-[[[4-(4-Fluoro-2-methylphenyl)-2-(1-methylethyl)-6-phenyl-3-pyridinyl] ethynyl]methoxyphosphinyl]-3-[[(1,1-dimethylethyl)diphenylsilyl]oxy]butanoic acid, methyl ester n-BuLi (2.5M in hexane, 0.67 ml, 1.67 mmol) was added dropwise to a solution of acetylene H (0.500 gm, 1.52 mmol) in THF (10 ml) at −78° C. under argon. The solution was allowed to stir 1 hour at −78° C., then cannulated into a THF solution (15 ml) of the chloridate from Example 57, part G, which had also been cooled to −78° C. The solution was stirred 30 minutes at −78° C., then quenched with saturated $NH_4Cl$ and warmed to 0° C., then saturated $NaHCO_3$ was added to the solution. The solution was diluted with ether and the organic layer was washed with brine, then dried over $Na_2SO_4$, filtered and concentrated to a dark orange oil. The oil was purified by flash chromatography on Merck silica gel in 45% EtOAc in hexane. The desired fractions were combined and concentrated to afford compound I as a beige foam (0.878 gm, 76%).

TLC: Rf 0.47 (40% EtOAc in hexane)

J. (S)-4-[[[4-(4-Fluoro-2-methylphenyl)-2-(1-methylethyl)-6-phenyl-3-pyridinyl]ethynyl]methoxyphosphinyl]-3-hydroxybutanoic acid, methyl ester $(Bu)_4NF$ (1M in THF, 3.86 ml, 3.86 mmol) was added to a solution of silyl ether I (0.878 gm, 1.28 mmol) and HOAc (0.307 gm, 5.12 mmol) in THF (20 ml) under argon and allowed to stir 16 hours at room temperature. The reaction mixture was diluted with EtOAc, then washed with 5% $KHSO_4$ (3 times). The aqueous layers were back-extracted with EtOAc (twice). The organic layers were pooled and washed with brine, then dried over $Na_2SO_4$, filtered and concentrated to afford a brown oil. The oil was dissolved in ether (15 ml) and treated with excess $CH_2N_2$. Excess $CH_2N_2$ was removed with a stream of argon, and the solution was concentrated to give a brown-yellow oil. The oil was purified by flash chromatography on Merck silica gel in 50% acetone in hexane. The desired fractions were pooled and concentrated to afford compound J as a clear oil (0.325 gm, 48%).

TLC: Rf 0.63 (50% acetone in hexane)

K. (S)-4-[[[4-(4-Fluoro-2-methylphenyl)-2-(1-methylethyl)-6-phenyl-3-pyridinyl] ethynyl]hydroxyphosphinyl]-3-hydroxybutanoic acid, disodium salt A solution of compound J (0.325 gm, 0.62 mmol) in dioxane (10 ml) was treated with NaOH (1M in $H_2O$, 2.20 ml, 2.20 mmol), then heated to 55° C. and allowed to stir 2 hours. The solution was then cooled to room temperature and concentrated to a white solid. The solid was dissolved in water and chromatographed on HP-20 resin, eluting first with water (200 ml), then with 50% MeOH in water (400 ml), and finally with MeOH (200 ml). The desired fractions were pooled and concentrated. The resultant white solid was dissolved in water and lyophilized to give Example 89 as a fluffy white solid (0.300 gm, 90%).

m.p. 305° C. (decomp). TLC: Rf 0.64 (6:3:1, n-propanol:$NH_4OH$:$H_2O$) Elemental Analysis for $C_{27}H_{25}NFNa_2PO_5$·3.0 $H_2O$: Calc'd C, 56.41; H, 5.06; N, 2.27; F, 3.08; P, 5.02 Found C, 56.37; H, 4.89; N, 2.30; F, 3.12; P, 5.36 Optical Rotation: $[a]_D = +8.8°$ (MeOH, c= 3.8 mg/ml)

Example 90

(S)-4-[ [ [ 2-Cyclopropyl-4-(4-fluorophenyl)-6-phenyl- 3-pyridinyl] ethynyl] hydroxyphosphinyl] -3-hydroxybutanoic acid, disodium salt A. 3-Cyclopropyl-3-oxopropanoic acid, ethyl ester To a slurry of NaH (60% in mineral oil, 19.200 gm, 0.48 mol) in dry diethyl carbonate (80 ml) was added a solution of methyl cyclopropyl ketone (23.5 ml, 20.00 gm, 0.238 mol) in $Et_2O$ (30 ml). After the addition of approximately 10% of the ketone solution, EtOH (0.25 ml) was added and addition of the ketone continued. Soon after the addition was complete, the reaction became quite exothermic with vigorous $H_2$ evolution. Periodic cooling with an ice bath was required. After one hour, $H_2$ evolution had ceased and the mixture was diluted with $Et_2O$ (200 ml) and hexane (185 ml). The solution was cooled in an ice bath and carefully treated with 5% HCl (10 ml), at which time a thick slurry developed. The solid was collected by filtration and washed with hexane. The solid was then partitioned between $Et_2O$ and 5% HCl until all of the solid had dissolved and the aqueous layer remained acidic. The organic layer was separated and washed with $H_2O$, saturated $NaHCO_3$, and brine, then dried ($MgSO_4$), filtered and stripped. The liquid residue was subjected to flash chromatography (Merck $SiO_2$, 20% EtOAc in hexane) to provide compound A (20.357 gm, 55%) as a yellow liquid.

TLC $R_f$ 0.24 (20% EtOAc in hexane)

B. 3-Fluorophenyl-1-phenyl-2-propen-1-one

A solution of benzaldehyde (19.220 gm, 181 mmol) and p-fluoroacetophenone (25.000 gm, 181 mmol) in ethanol (200 ml) was treated with sodium methoxide (1.972 gm, 36.5 mmol). A precipitate fell out of solution after 30 minutes. After stirring at room temperature for 15 hours, the solution was treated with 50 ml of $H_2O$, cooled in an ice bath, and filtered. The solid was rinsed with cold ethanol and dried under high vacuum to yield compound B (29.730 gm, 73%) as a yellow crystalline solid.

m.p. 76.3°–77.5° C. TLC $R_f$ 0.46 (20% EtOAc in hexane) Microanalysis for $C_{15}H_{11}FO$: Calc'd C, 79.63; H, 4.90; F, 8.40 Found C, 79.57; H, 4.77; F, 8.30

C. α-(2-Cyclopropyl-1-oxoethyl)-β-(4-fluorophenyl)-Δ-oxophenylpentanoic acid, ethyl ester A mixture of compound B (7.280 gm, 32.2 mmol) and compound A (6.00 gm, 38.4 mmol) in absolute EtOH (100 ml) was treated with a solution of EtONa in EtOH (21% by weight solution, 1.28 gm, 4.8 mmol). After stirring at room temperature for 30 minutes, a thick precipitate fell out of solution. Additional EtOH (40 ml) was added and stirring continued for an hour. The solution was treated with acetic acid (0.28 ml) and cooled to 0° C. The solid was collected by filtration, washed with cold EtOH and hexane, and dried in vacuo to give compound C, a mixture of diastereomers, as a white amorphous solid (10.295 gm, 84%).

m.p. 114°–117° C. TLC $R_f$ 0.21 (20% EtOAc in hexane)

D. 2-Cyclopropyl-4-(4-fluorophenyl)-6-phenyl-3-pyridinecarboxylic acid, ethyl ester A mixture of compound C (10.113 gm, 26.4 mmol), $NH_4OAc$ (6.142 gm, 79.7 mmol), and $Cu(OAc)_2$ (13.920 gm, 70.0 mmol) in glacial HOAc (70 ml) was heated at 110° C. for 0.5 hours. Additional $NH_4OAc$ (2.10 gm) was added and heating continued for four more hours. The solution was cooled to room temperature and subsequently poured into an ice cold mixture of concentrated $NH_4OH$ (85 ml) in $H_2O$ (150 ml). The mixture was extracted with $Et_2O$ and the $Et_2O$ extract was washed with $H_2O$ (twice) and brine, then dried ($Na_2SO_4$), filtered and stripped to yield a yellow oil that solidified on standing. Recrystallization from EtOAc/hexane afforded compound D as a pale yellow solid (7.810 gm). The mother liquor was flashed (Merck $SiO_2$, 10% EtOAc in hexane) to give additional product, which was recrystallized from hexane (477 mg). Total pooled solids were 8.287 gm, 87% yield.

m.p. 89.5°–92° C. TLC $R_f$ 0.50 (20% EtOAc in hexane) Microanalysis for $C_{23}H_{20}FNO_2$: Calc'd C, 76.43; H, 5.58; N, 3.88; F, 5.26 Found C, 76.40; H, 5.58; N, 3.70; F, 5.15

E. 2-Cyclopropyl-4-(4-fluorophenyl)-6-phenyl-3-pyridinemethanol

A cold (0° C.) solution of ester D (7.798 gm, 21.6 mmol) in dry THF (200 ml) was treated with $LiAlH_4$ (2.378 gm, 62.7 mmol). Ten minutes after the addition, the cooling bath was removed and the mixture was stirred at room temperature for one hour. The solution was recooled to 0° C. and quenched in succession with $H_2O$ (2.5 ml), 10% NaOH (4.0 ml), and $H_2O$ (7.5 ml). The solution was filtered and the salts were washed with EtOAc and $Et_2O$. Removal of the filtrate solvent afforded a solid. The solid was recrystallized from EtOAc/hexane to provide compound E (5.866 gm, 85%) as an amorphous white solid.

m.p. 176°–177° C. TLC $R_f$ 0.53 (40% EtOAc in hexane) Microanalysis for $C_{21}H_{18}FNO$: Calc'd C, 78.97; H, 5.68; N, 4.39; F, 5.95 Found C, 78.72; H, 5.67; N, 4.23; F, 5.67

F. 2-Cyclopropyl-4-(4-fluorophenyl)-6-phenyl-3-pyridinecarboxaldehyde

A solution of 4-methylmorpholine-N-oxide (2.982 gm, 25.5 mmol) in $CH_2Cl_2$ (80 ml) was dried over $MgSO_4$ for 15 minutes. The solution was filtered directly into a 500 ml flask, using approximately 20 ml $CH_2Cl_2$ to effect the transfer. The flask was then charged with dry 4 angstrom molecular sieves (10.4 gm), alcohol E (4.012 gm, 12.56 mmol), and tetrapropylammonium perruthenate (222 mg, 0.63 mmol). After stirring at room temperature for 40 minutes, the black solution was diluted with $Et_2O$ (120 ml), stirred for 5 minutes, then filtered through Celite®. The filtrate was stripped and the dark residue was dissolved in $CH_2Cl_2$ and flashed (Merck $SiO_2$, 20% EtOAc in hexane) to give the product as a solid. The solid was recrystallized from EtOAc/hexane (2 crops) to give compound F (3.115 gm, 78%) as a yellow solid.

m.p. 110°–113° C. TLC $R_f$ 0.52 (20% EtOAc in hexane)

G. 3-(2,2-Dibromoethenyl)-2-cyclopropyl-4-(4-fluorophenyl)-6-phenylpyridine

A solution of carbon tetrabromide (4.245 gm, 12.8 mmol) in $CH_2Cl_2$ (10 ml) was added over a 9-minute period to a cold (0° C.) solution of aldehyde F (2.725 gm, 8.6 mmol) and triphenylphosphine (6.761 gm, 25.8 mmol) in $CH_2Cl_2$ (35 ml). After the addition was complete, the cooling bath was removed and the mixture was stirred at room temperature for 25 minutes. The solution was quenched with saturated $NaHCO_3$ and extracted twice with $CH_2Cl_2$. The combined organic layers were dried ($Na_2SO_4$), filtered and concentrated. The concentrate was chromatographed (flash, Merck $SiO_2$, 35% $CH_2Cl_2$ in hexane) to give impure dibromide G as a solid. Recrystallization from EtOAc/hexane (2 crops) provided compound G (3.588 gm, 88%) as fine white needles.

m.p. 170°–172° C. TLC $R_f$ 0.58 (20% EtOAc in hexane) Microanalysis for $C_{22}H_{16}Br_2FN$: Calc'd C, 55.84; H, 3.41; N, 2.96; F, 4.02; Br, 33.77 Found C, 55.95; H, 3.20; N, 2.77; F, 4.21; Br, 33.59

H. (S)-4-[[[2-Cyclopropyl-4-(4-fluorophenyl)-6-phenyl-3-pyridinyl]ethynyl]methoxyphosphinyl]-3-[[(1,1-dimethylethyl)diphenylsilyl]oxy]butanoic acid, methyl ester A solution of dibromide G (1.000 gm, 2.11 mmol) in THF (7 ml) was added dropwise to a solution of n-BuLi (2.5M in hexane, 1.8 ml, 4.5 mmol) in THF (10 ml) at −78° C. over a 6-minute period. The resulting clear yellow solution was stirred at −78° C. for 40 minutes, then added dropwise via cannula over a 10-minute period to a −78° C. solution of the phosphonochloridate from Example 57, part G in THF (15 ml). The resulting greenish mixture was stirred at −78° C. for 20 minutes, then quenched with 50% saturated $NH_4Cl$. The solution was warmed to 0° C., diluted with $H_2O$, and poured into saturated $NaHCO_3$. The aqueous phase was extracted once with $Et_2O$. The $Et_2O$ layer was washed with brine, dried ($Na_2SO_4$), filtered and stripped to give a yellow oil. The residue was chromatographed (flash, Merck $SiO_2$, 40% EtOAc in hexane) to afford compound H as a white foam (1.270 gm, 81%).

TLC $R_f$ 0.25 (40% EtOAc in hexane)

I. (S)-4-[[[2-Cyclopropyl-4-(4-fluorophenyl)-6-phenyl-3-pyridinyl] ethynyl] methoxyphosphinyl]-3-hydroxybutanoic acid, methyl ester A mixture of compound H (1.255 gm, 1.68 mmol) and HOAc (490 μl, 514 mg, 8.6 mmol) in THF (25 ml) was treated with tetra-n-butylammonium fluoride (1.0 M in THF, 8.2 ml, 8.2 mmol). After stirring at room temperature for 16 hours, the solution was diluted with EtOAc and washed 3 times with 5% $KHSO_4$. The EtOAc layer was washed with brine, dried ($Na_2SO_4$), filtered and stripped to afford a yellow oil. The oil was dissolved in $Et_2O$, cooled to 0° C. and treated with excess diazomethane for 15 minutes. The excess diazomethane was destroyed by the addition of HOAc and the solvent was removed in vacuo. The residue was chromatographed (flash, Merck $SiO_2$, 1:1—acetone:hexane) to afford compound I (746 mg, 87%) as a white foam.

TLC $R_f$ 0.30 (1:1—acetone:hexane)

J. (S)-4-[[[2-Cyclopropyl-4-(4-fluorophenyl)- 6-phenyl-3-pyridinyl]ethynyl]hydroxyphosphinyl] -3-hydroxybutanoic acid, disodium salt A solution of compound I (730 mg, 1.44 mmol) in dioxane (6 ml) was treated with 1N NaOH (5.0 ml, 5.0 mmol) at room temperature and the mixture was subsequently heated at 60° C. under argon for 0.5 hour. The solvent was evaporated and the residue was chromatographed on HP-20 resin, eluting in succession with $H_2O$ (200 ml) and 50% MeOH in $H_2O$ (200 ml). The desired fractions were pooled and evaporated and the residue was taken up in $H_2O$ and lyophilized to give Example 90 (674 mg, 84%) as a white solid.

m.p. decomposition at 285° C. TLC $R_f$ 0.07 (8:1:1—$CH_2Cl_2$:HOAc:MeOH) Analysis for $C_{26}H_{21}FNNa_2O_5P \times 2.0$ $H_2O$: Calc'd C, 55.82; H, 4.51; N, 2.50; F, 3.40; P, 5.54 Found: C, 55.84; H, 4.28; N, 2.46; F, 3.33; P, 5.50 Rotation $[a]_D = +5.6°$ (MeOH, 9.8 mg in 1.21 ml)

Example 91

(S)-4-[ [ [2-Cyclopropyl-4-(4-fluorophenyl)- 5-methyl- 6-phenyl-3-pyridinyl] ethynyl] hydroxyphosphinyl] -3 -hydroxybutanoic acid, disodium salt A. 3-Cyclopropyl-2-[(4-fluorophenyl)methylene] -3-oxopropanoic acid, ethyl ester A mixture of 4-fluorobenzaldehyde (4.768 gm, 38.4 mmol), ethyl 3-cyclopropyl-3-oxopropionate from Example 88, part A (6.000 gm, 38.4 mmol), piperidine (380 μl), and HOAc (75 μl) was refluxed in benzene (40 ml) with removal of water (Dean-Stark trap) for 16 hours. The cooled mixture was diluted with $Et_2O$ and washed successively with 5% HCl, saturated $NaHCO_3$, $H_2O$, and brine, then dried ($Na_2SO_4$), filtered, and stripped to yield an oil. Distillation of the oil (bp 127°–135° C. at 0.2 mm Hg) afforded compound A (8.299 gm, 82%) as a pale yellow liquid.

TLC $R_f$ 0.31 (20% EtOAc in hexane) Microanalysis for $C_{15}H_{15}FO_3$: Calcd C, 68.69; H, 5.76; F, 7.24 Found C, 68.92; H, 5.90; F, 7.25

B. α-(1-Cyclopropyl-1-oxomethyl)-β-(4 -fluorophenyl)-γ-methyl-Δ-oxophenylpentanoic acid, ethyl ester A –78° C. solution of $LiN(TMS)_2$ (1.0M in THF, 38 ml, 38 mmol) in dry THF (40 ml) was treated with a solution of propiophenone (5.015 gm, 37.4 mmol) in THF (6 ml) over a 4-minute period. After 30 minutes, a solution of compound A (7.842 gm, 29.9 mmol) in THF (15 ml) was added dropwise to the above solution. After one hour, the mixture was quenched with acetic acid (2.5 ml) and saturated $NH_4Cl$ and warmed to room temperature. The mixture was diluted with $H_2O$ and subsequently extracted once with $Et_2O$. The $Et_2O$ extract was washed with brine, dried ($Na_2SO_4$), filtered, and stripped to give an oil. The oil was transferred to a round bottom flask which was fitted with a short path distillation apparatus and the oil was heated at 65° C. and 0.2 mm Hg to remove the volatiles and excess propiophenone. The pot residue, crude compound B, was used directly in the next reaction.

C. 2-Cyclopropyl-4-(4-fluorophenyl)-5 -methyl-6-phenyl-3-pyridinecarboxylic acid, ethyl ester A mixture of crude compound B, $NH_4OAc$ (9.210 gm, 119.5 mmol), and $Cu(OAc)_2$ (17.921 gm, 89.8 mmol) in glacial HOAc (80 ml) was heated at 110° C. for 21 hours. The solution was cooled to room temperature and subsequently poured into an ice cold mixture of concentrated $NH_4OH$ (100 ml) in $H_2O$ (200 ml). The mixture was extracted twice with $Et_2O$ and the pooled $Et_2O$ extracts were washed with $H_2O$ and brine, then dried ($Na_2SO_4$), filtered and stripped to yield a brown solid. The solid was dissolved in $CH_2Cl_2$ and flashed (Merck $SiO_2$, 20% EtOAc in hexane) to give compound C as a reddish oil which readily solidified. Recrystallization from EtOAc/hexane (2 crops) afforded compound C (9.615 gm, 86%) as white crystals.

m.p. 113°–114.5° C. TLC $R_f$ 0.46 (20% EtOAc in hexane) Microanalysis for $C_{24}H_{22}FNO_2$: Calc'd C, 76.78; H, 5.91; N, 3.73; F, 5.06 Found C, 76.68; H, 5.92; N, 3.63; F, 5.06

D. 2-Cyclopropyl-4-(4-fluorophenyl)-5 -methyl-6-phenyl-3-pyridinemethanol

A cold (0° C.) solution of ester C (8.942 gm, 23.8 mmol) in dry THF (200 ml) was treated with $LiAlH_4$ (2.701 gm, 71.2 mmol). Ten minutes after the addition, the cooling bath was removed and the mixture was stirred at room temperature for 1.5 hours. The solution was recooled to 0° C. and quenched in succession with $H_2O$ (3.0 ml), 10% NaOH (4.5 ml), and $H_2O$ (8.5 ml). The solution was filtered and the salts were washed with EtOAc and $Et_2O$. Removal of the filtrate solvent afforded an oily solid residue. The residue was dissolved in $Et_2O$, diluted with hexane, heated to remove the $Et_2O$, and cooled to provide compound D (6.548 gm, 83%) as an amorphous white solid.

m.p. 140.5°–142° C. TLC $R_f$ 0.18 (20% EtOAc in hexane) Microanalysis for $C_{22}H_{20}FNO$: Calc'd C 79.25 H 6.05 N 4.20 F 5.70 Found C 79.14 H 5.99 N 4.15 F 5.73

E. 2-Cyclopropyl-4-(4-fluorophenyl)-5-methyl- 6-phenyl-3-pyridinecarboxaldehyde

A solution of 4-methylmorpholine-N-oxide (4.002 gm, 34.2 mmol) in $CH_2Cl_2$ (130 ml) was dried over $MgSO_4$ for 15 minutes. The solution was filtered directly into a 500-ml flask, using approximately 30 ml $CH_2Cl_2$ to effect the transfer. The flask was then charged with dry 4 angstrom molecular sieves (16 gm), alcohol D (5.686 gm, 17.05 mmol), and tetrapropylammonium perruthenate (301 mg, 0.86 mmol). After stirring at room temperature for 30 minutes, the black solution was diluted with $Et_2O$ (200 ml), stirred for 5 minutes, then filtered through a plug of silica gel (Merck, 65×30 mm), washing with $Et_2O$. The filtrate was stripped to give a pale yellow solid. The solid was recrystallized from EtOAc/hexane to give compound E (3.982 gm) as white crystals. Flashing the mother liquor (Merck $SiO_2$, 20% EtOAc in hexane) gave additional product, which was recrystallized from hexane (499 mg). Total pooled solids were 4.481 gm (79%).

m.p. 137°–139° C. TLC $R_f$ 0.50 (20% EtOAc in hexane) Microanalysis for $C_{22}H_{18}FNO$: Calc'd C, 79.74; H, 5.47; N, 4.23; F, 5.73 Found C, 79.32; H, 5.49; N, 4.13; F, 5.65

F. 2-Cyclopropyl-3-(2,2-dibromoethenyl)- 4-(4-fluorophenyl)-5-methyl-6-phenylpyridine A solution of carbon tetrabromide (5.810 gm, 17.5 mmol) in $CH_2Cl_2$ (9 ml) was added over a 12 -minute period to a cold (0° C.) solution of aldehyde E (3.864 gm, 11.7 mmol)

and triphenylphosphine (9.191 gm, 35.0 mmol) in $CH_2Cl_2$ (60 ml). After the addition was complete, the cooling bath was removed and the mixture was stirred at room temperature for 20 minutes. The solution was quenched with saturated $NaHCO_3$ (40 ml) and extracted twice with $CH_2Cl_2$. The combined organic layers were dried ($Na_2SO_4$), filtered and concentrated. The concentrate was chromatographed (flash, Merck $SiO_2$, 40% $CH_2Cl_2$ in hexane) and the pure desired fractions were stripped to give a solid. Recrystallization from EtOAc/hexane (2 crops) provided compound F (5.432 gm, 96%) as white crystals.

m.p. 155°–157° C. TLC $R_f$ 0.58 (20% EtOAc in hexane) Microanalysis for $C_{23}H_{18}Br_2FN$: Calc'd C, 56.70; H, 3.72; N, 2.88; F, 3.90; Br, 32.80 Found C, 56.55; H, 3.68; N, 2.82; F, 3.89; Br, 32.72

G. (S)-4-[[[2-Cyclopropyl-4-(4-fluorophenyl)- 5-methyl-6-phenyl-3-pyridinyl]ethynyl] methoxyphosphinyl]-3-[[(1,1-dimethylethyl)diphenylsilyl] oxy]butanoic acid, methyl ester A solution of dibromide F (1.000 gm, 2.05 mmol) in THF (5 ml) was added dropwise to a solution of n-BuLi (2.5M in hexane, 1.73 ml, 4.3 mmol) in THF (10 ml) at −78° C. over a 10-minute period. The resulting pale yellow solution was stirred at −78° C. for one hour, then added dropwise via cannula over a 12-minute period to a −78° C. solution of the phosphonochloridate from Example 57, part G, in THF (15 ml). The resulting mixture was stirred at −78° C. for 30 minutes, then quenched with 50% saturated $NH_4Cl$. The solution was warmed to 0° C., diluted with $H_2O$, and poured into saturated $NaHCO_3$. The aqueous phase was extracted once with $Et_2O$. The $Et_2O$ layer was washed with brine, dried ($Na_2SO_4$), filtered and stripped to give an oil. The residue was chromatographed (flash, Merck $SiO_2$, 50% EtOAc in hexane) to afford compound G as a white foam (1.158 gm, 74%).

TLC $R_f$ 0.27 (40% EtOAc in hexane)

H. (S)-4-[[[2-Cyclopropyl-4-(4-fluorophenyl)- 5-methyl-6-phenyl-3-pyridinyl]ethynyl] methoxyphosphinyl]-3-hydroxybutanoic acid, methyl ester A mixture of compound G (1.148 gm, 1.51 mmol) and HOAc (460 μl, 482 mg, 8.0 mmol) in THF (25 ml) was treated with tetra-n-butylammonium fluoride (1.0M in THF, 7.6 ml, 7.6 mmol). After stirring at room temperature for 17 hours, the solution was diluted with EtOAc and washed 3 times with 5% $KHSO_4$. The pooled aqueous extracts were back-extracted once with EtOAc and the combined EtOAc layers were washed with brine, dried ($Na_2SO_4$), filtered and stripped to afford a yellow oil. The oil was dissolved in $Et_2O$, cooled to 0° C. and treated with excess diazomethane for 15 minutes. The excess diazomethane was destroyed by the addition of HOAc and the solvent was removed in vacuo. The residue was chromatographed (flash, Merck $SiO_2$, 40% acetone in hexane followed by 40% hexane in acetone) to afford compound H (684 mg, 87%) as a white foam.

TLC $R_f$ 0.37 (1:1—acetone:hexane)

I. (S)-4-[[[2-Cyclopropyl-4-(4-fluorophenyl)- 5-methyl-6-phenyl-3-pyridinyl]ethynyl] hydroxyphosphinyl]-3-hydroxybutanoic acid, disodium salt A solution of compound H (672 mg, 1.29 mmol) in dioxane (7 ml) was treated with 1N NaOH (4.5 ml, 4.5 mmol) at room temperature and the mixture was subsequently heated at 60° C. under argon for one hour. The solvent was evaporated and the solid residue was dissolved in warm $H_2O$ and chromatographed on HP-20, eluting in succession with $H_2O$ (150 ml) and 50% MeOH in $H_2O$ (200 ml). The desired fractions were pooled and evaporated and the residue was taken up in $H_2O$ and lyophilized to give Example 91 (640 mg, 89%) as a white solid.

m.p. decomposition at 295° C. TLC $R_f$ 0.07 (8:1:1—$CH_2Cl_2$:HOAc:MeOH) Calc'd for $C_{27}H_{23}FNNa_2O_5P \times 1.25 H_2O$: Calc'd C, 57.92; H, 4.59; N, 2.50; F, 3.39; P, 5.53 Found C, 58.05; H, 4.50; N, 2.35; F, 3.38; P, 5.72 Rotation [ a]$_D$= + 8.8° (MeOH, 7.6 mg in 1.22 ml)

Example 92

(S)-4-[ [ 2-[ 2-Ethyl-4-(4-fluorophenyl)-5-methyl-6 -phenyl-3-pyridinyl]ethyl]hydroxyphosphinyl]-3 -hydroxybutanoic acid, disodium salt A. (S)-4-[ [2-[2-Ethyl-4-(4-fluorophenyl)-5 -methyl-6-phenyl-3-pyridinyl] ethyl] methoxyphosphinyl]-3-hydroxybutanoic acid, methyl ester 10% Pd/C (0.044 gm, 0.041 mmol) was added to a Parr bottle containing an argon-purged, MeOH (50 ml) solution of compound C from Example 85 (0.211, 0.413 mmol). The bottle was then placed under 50 psi of hydrogen and shaken for 15 hours. The solution was then filtered through a Celite® pad, which was washed repeatedly with methanol and chloroform. The filtrate and washings were combined and concentrated to a yellowish oil. The oil was purified by flash chromatography on Merck silica gel in 50% acetone in hexane. After concentrating the desired fractions, product A was obtained as a white foam (0.160 gm, 75%).

TLC: Rf 0.52 (50% acetone in hexane)

B. (S)-4-[ [ 2-[ 2-Ethyl-4-(4-fluorophenyl)-5-methyl-6-phenyl-3-pyridinyl] ethyl] hydroxyphosphinyl] -3-hydroxybutanoic acid, disodium salt A dioxane solution (10 ml) of compound A (0.160 gm, 0.303 mmol) was treated with a solution of NaOH (1M in $H_2O$, 0.91 ml, 0.91 mmol) and then heated to 55° C. for 3 hours. Additional NaOH (1M in $H_2O$, 0.31 ml, 0.31 mmol) was added to the solution, which was allowed to stir another hour. The solution was then concentrated to a white solid. The solid was dissolved in water and chromatographed on HP-20 resin, eluting first with water (200 ml), then with 50% MeOH in water (400 ml), and finally, MeOH (200 ml). The desired fractions were pooled, concentrated, the resultant white solid dissolved in water and lyophilized to give Example 92 as a fluffy white solid (0.100 g, 61%).

m.p. 295° C. (decomp) TLC: Rf 0.69 (6:3:1, n-propanol:$NH_4OH$:$H_2O$) Elemental Analysis for $C_{26}H_{27}FNO_5P \times 2Na \times 1.25H_2O$: Calc'd: C 56.57 H 5.39 N 2.54 F 3.44 P 5.61 Found: C 56.53 H 5.02 N 2.24 F 3.47 P 5.51

Example 93

(S,E)-4-[[2-[4-(4-Fluoro-2-methylphenyl)-2-(1 -methylethyl)-6-phenyl-3-pyridinyl]ethenyl]-hydroxyphosphinyl] -3-hydroxybutanoic acid, disodium salt A. (E)-3-(2-Iodoethenyl)-4-fluoro-2-methylphenyl)- 2-(1-methylethyl)-6-phenylpyridine A mixture of (E)-3-[2-(Tributylstannyl)ethenyl] -4-(4-fluoro-2-methylphenyl)-2-(1-methylethyl)- 6-phenylpyridine (7.18 gm, 24.7 mmol), acetylene 1 (4.500 gm, 13.7 mmol) and AIBN (0.084 gm, 5.1 mmol) were heated at 140° C. for 1.5 hours. The solution was cooled to room temperature and diluted with ether (30 ml). Iodine (7.16 gm, 27.1 mmol) was added and an unexpectedly strong exothermic reaction occurred and approximately half the solution foamed out of the flask. The flask was recapped and allowed to stir 16 hours. The solution was then quenched with 10% $Na_2S_2O_3$ in saturated $NaHCO_3$. The solution was diluted with ether, washed with 10% Na$_2$S$_2$O$_3$ in saturated NaHCO$_3$ (twice) and brine, then dried over Na$_2$SO$_4$, filtered and concentrated to a yellow oil. The oil was purified by flash chromatography on Merck silica gel in 1% EtOAc in hexane. The desired fractions were combined and concentrated to afford a white solid, which was recrystallized from hexane to give product A as hard, off-white crystals (2.830 gm, 45%).

m.p. 115°–117° C. Elemental Analysis for C$_{23}$H$_{21}$FIO$_5$: Calc'd: C 60.4 H 4.63 N 3.06 F 4.15 I 27.75 Found: C 60.87 H 4.58 N 2.93 F 4.12 I 27.51

B. (S,E)-4-[ [2-[4-(4-Fluoro-2-methylphenyl)- 2-(1-methylethyl)-6-phenyl-3 -pyridinyl] ethenyl] methoxyphosphinyl] -3 -[ [ (1,1-dimethylethyl)diphenylsilyl]oxy] butanoic acid, methyl ester Vinyl iodide A (2.380 gm, 5.19 mmol) was added dropwise to a –78° C. solution of t-BuLi (1.7 M in pentane, 6.11 ml, 10.4 mmol) in THF (10 ml) stirring under argon. The solution was allowed to stir 15 minutes at –78° C., then cooled to –100° C. and cannulated into a THF solution (15 ml) of the chloridate from Example 57, part G, also cooled to –100° C. The solution was stirred 15 minutes at –100° C., quenched with saturated NH$_4$Cl and warmed to 0° C., after which saturated NaHCO$_3$ was added. The solution was diluted with ether and the organic layer washed with brine, dried over Na$_2$SO$_4$, filtered and concentrated to give a dark orange oil. The oil was purified by flash chromatography on Merck silica gel in 60% EtOAc in hexane. Pure product fractions were combined and evaporated to afford compound B as a white, fluffy foam (1.230 gm, 35%).

TLC: Rf 0.39 (40% EtOAc in hexane)

C. (S,E)-4-[[2-[4-(4-Fluoro-2-methylphenyl)- 2-(1-methylethyl)-6-phenyl-3 -pyridinyl]ethenyl]methoxyphosphinyl]-3 -hydroxybutanoic acid, methyl ester (Bu)$_4$NF (1M in THF, 5.40 ml, 5.40 mmol) was added to a solution of silyl ether B (1.230 gm, 1.80 mmol) and HOAc (0.54 ml, 9.43 mmol) in THF (20 ml) and allowed to stir 17 hours at room temperature. Additional TBAF (1.80 ml, 1.80 mmol) and HoAC (0.172 ml, 3.2 mmol) were added to the reaction mixture, which was allowed to stir under argon another 3 hours. The solution was diluted with EtOAc and washed with 5% KHSO$_4$ (three times). The aqueous layers were extracted with EtOAc (twice) and the organic layers were combined and washed with brine, then dried over Na$_2$SO$_4$, filtered and concentrated to give a clear oil. The oil was purified by flash chromatography on Merck silica gel in 35% acetone in hexane. Product fractions were pooled and concentrated to afford compound C as a clear oil (0.785 gm, 83%).

TLC: Rf 0.54 (50% acetone in hexane)

D. (S,E)-4-[[2-[4-(4-Fluoro-2-methylphenyl)- 2-(1-methylethyl)-6-phenyl-3-pyridinyl]ethenyl]hydroxyphosphinyl]-3-hydroxybutanoic acid, disodium salt NaOH (1M in H$_2$O, 2.26 ml, 2.26 mmol) was added dropwise to a solution of compound C (0.335 gm, 0.64 mmol) in dioxane (10 ml), allowed to stir at room temperature for 1.5 hours, and then heated to 60° C. and stirred for 1 hour. The mixture was then concentrated to a white solid. The solid was dissolved in water and chromatographed on HP-20 resin, eluting first with water (200 ml), then with 50% MeOH in water (400 ml), and finally with MeOH (200 ml). The desired fractions were pooled, concentrated, and the resultant white solid dissolved in water and lyophilized to give Example 93 as a fluffy white solid (0.300 gm, 90%).

m.p. 312° C. (decomp) TLC: Rf 0.61 (6:3:1, n-propanol:NH$_4$OH:H$_2$O) Elemental Analysis for C$_{27}$H$_{27}$NFPO$_5$Na$_2$×2.20 H$_2$O: Calc'd: C 55.81 H 5.45 N 2.41 F 3.27 P 5.33 Found: C 55.78 H 5.40 N 2.44 F 3.12 P 5.32 Optical Rotation: [a]$_D$= +1.6° (MeOH, c= 4.1 mg/ml)

Example 94

(S)-4-[ [ 2-[ 4-(4-Fluoro-2-methylphenyl)-2-(1 -methylethyl)-6-phenyl-3-pyridinyl]ethyl]hydroxyphosphinyl] -3-hydroxybutanoic acid, disodium salt A. (S)-4-[[2-[4-(4-Fluoro-2-methylphenyl)- 2-(1-methylethyl)-6-phenyl-3-pyridinyl] ethyl]methoxyphosphinyl]-3-hydroxybutanoic acid, methyl ester 10% Pd/C (0.185 gm, 0.174 mmol) was added to a Parr bottle containing an argon-purged, MeOH (50 ml) solution of compound C from Example 93 (0.450 gm, 0.854 mmol). The bottle was then placed under 50 psi of hydrogen and shaken for 3 hours. The solution was then filtered through a Celite® pad, which was washed repeatedly with methanol. The filtrate was concentrated to give a clear oil. The oil was purified by flash chromatography on Merck silica gel in 60% acetone in hexane. After concentrating the desired fractions, product A was obtained as a white foam (0.300 gm, 67%).

TLC: Rf 0.50 (50% acetone in hexane)

B. (S)-4-[ [ 2-[ 4-(4-Fluoro-2-methylphenyl)- 2-(1-methylethyl)-6-phenyl-3-pyridinyl] ethyl] hydroxyphosphinyl] -3-hydroxybutanoic acid, disodium salt Di-ester A (0.300 gm, 0.57 mmol) was dissolved in dioxane (10 ml) and treated with NaOH (1M in H$_2$O, 1.71 ml, 1.71 mmol). The solution was heated to 55° C. and allowed to stir 3 hours. The solution was concentrated to a white solid. The solid was dissolved in water and chromatographed on HP-20 resin, eluting first with water (200 ml), then with 50% MeOH in water (400 ml), and finally, MeOH (200 ml). The desired fractions were pooled and concentrated, and the resultant white solid was dissolved in water and lyophilized to give Example 94 as a fluffy white solid (0.290 gm, 94%).

m.p. 312° C. (decomp) TLC: Rf 0.67 (6:3:1, n-propanol:NH$_4$OH, H$_2$O) Elemental Analysis for C$_{27}$H$_{29}$NFNa$_2$PO$_5$*1.75 H$_2$O: Calc'd: C 56.39 H 5.70 N 2.44 F 3.30 P 5.39 Found: C 56.71 H 5.52 N 2.35 F 3.11 P 5.23 Optical Rotation: [a]$_D$ = –1.9° (MeOH, c= 4.3 mg/ml)

Example 95

(S)-4-[ [ [ 2-Cyclopropyl-4-(4-fluorophenyl)-6 -phenyl-3-pyridinyl] ethynyl] hydroxyphosphinyl] -3 -hydroxybutanoic acid, disodium salt A. 3-Cyclopropyl-3-oxopropanoic acid, ethyl ester To a slurry of NaH (60% in mineral oil, 19.200 g, 0.48 mol) in dry diethyl carbonate (80 ml) was added a solution of methyl cyclopropyl ketone (23.5 ml, 20.00 g, 0.238 mol) in Et$_2$O (30 ml). After the addition of approximately 10% of the ketone solution, EtOH (0.25 ml) was added and the addition of the ketone continued. Soon after the addition was complete, the reaction became quite exothermic with vigorous H$_2$ evolution. Periodic cooling with an ice bath was required. After one hour, H$_2$ evolution had ceased and the mixture was diluted with Et$_2$O (200 ml) and hexane (185 ml). The solution was cooled in an ice bath and carefully treated with 5% HCl (10 ml), at which time a thick slurry developed. The solid was collected by filtration and washed with hexane. The solid was then partitioned between Et$_2$O and 5% HCl until all of the solid had dissolved and the aqueous layer remained acidic. The organic layer was separated and washed with H$_2$O, saturated NaHCO$_3$, and brine, then dried (MgSO$_4$), filtered and stripped. The liquid residue was subjected to flash chromatography (Merck SiO$_2$, 20% EtOAc in hexane) to provide compound A (20.357 g, 55%) as a yellow liquid.

TLC: $R_f$= 0.24 (20% EtOAc in hexane).

B. 3-(4-Fluorophenyl)-1-phenyl-2-propen-1-one

A solution of benzaldehyde (19.220 g, 181 mmol) and p-fluoroacetophenone (25.000 g, 181 mmol) in ethanol (200 ml) was treated with sodium methoxide (1.972 g, 36.5 mmol). A precipitate fell out of solution after 30 minutes. After stirring at room temperature for 15 hours, the solution was treated with 50 ml of $H_2O$, cooled in an ice bath, and filtered. The solid was rinsed with cold ethanol and dried under high vacuum to yield compound B (29.730 g, 73%) as a yellow crystalline solid.

Melting point: 76.3°–77.5° TLC: $R_f$= 0.46 (20% EtOAc in hexane) Microanalysis for $C_{15}H_{11}FO$: Calc'd: C 79.63, H 4.90, F 8.40 Found: C 79.57, H 4.77, F 8.30

C. α-Cyclopropylcarbonyl-β-(4-fluorophenyl)-Δ -oxobenzenepentanoic acid, ethyl ester A mixture of compound B (7.280 g, 32.2 mmol) and compound A (6.00 g, 38.4 mmol) in absolute EtOH (100 ml) was treated with a solution of EtONa in EtOH (21% by weight solution, 1.28 g, 4.8 mmol). After stirring at room temperature for 30 minutes, a thick precipitate fell out of solution. Additional EtOH (40 ml) was added and stirring continued for an hour. The solution was treated with acetic acid (0.28 ml) and cooled to 0° C. The solid was collected by filtration, washed with cold EtOH and hexane, and dried in vacuo to give compound C, a mixture of diastereomers, as a white amorphous solid (10.295 g, 84%).

m.p. 114°–117° C. TLC: $R_f$ 0.21 (20% EtOAc in hexane)

D. 2-Cyclopropyl-4-(4-fluorophenyl)-6-phenyl- 3-pyridinecarboxylic acid, ethyl ester A mixture of compound C (10.113 g, 26.4 mmol), $NH_4OAC$ (6.142 g, 79.7 mmol) and $Cu(OAc)_2$ (13.920 g, 70.0 mmol) in glacial HOAc (70 ml) was heated at 110° C. for 0.5 hours. Additional $NH_4OAc$ (2.10 g) was added, and heating continued for four more hours. The solution was cooled to room temperature and subsequently poured into an ice cold mixture of concentrated $NH_4OH$ (85 ml) in $H_2O$ (150 ml). The mixture was extracted with $Et_2O$ and the $Et_2O$ extract was washed with $H_2O$ and brine, then dried ($Na_2SO_4$), filtered and stripped to yield a yellow oil which solidified on standing. Recrystallization from EtOAc/hexane afforded compound D as a pale yellow solid (7.810 g). The mother liquor was flashed (Merck $SiO_2$, 10% EtOAc in hexane) to five additional product, which was recrystallized from hexane (477 mg). Total pooled solids (8.287 g, 87%).

m.p. 89.5°–92° C. TLC: $R_f$ 0.50 (20% EtOAc in hexane) Microanalysis for $C_{23}H_{20}FNO_2$: Calc'd: C 76.43 H 5.58 N 3.88 F 5.26 C 76.40 H 5.58 N 3.70 F 5.15

E. 2-Cyclopropyl-4-(4-fluorophenyl)-6 -phenyl-3-pyridinemethanol

A cold (0° C.) solution of ester D (7.798 g, 21.6 mmol) in dry THF (200 ml) was treated with $LiAlH_4$ (2.378 g, 62.7 mmol). Ten minutes after the addition, the cooling bath was removed and the mixture was stirred at room temperature for one hour. The solution was recooled to 0° C. and quenched in succession with $H_2O$ (2.5 ml), 10% NaOH (4.0 ml), and $H_2O$ (7.5 ml). The solution was filtered and the salts were washed with EtOAc. Removal of the filtrate solvent afforded a solid. The solid was recrystallized from EtOAc and $Et_2O$. Removal of the filtrate solvent afforded a solid. The solid was recrystallized from EtOAc/hexane to provide compound E (5.866 g, 85%) as an amorphous white solid.

m.p. 176°–177° C. TLC: $R_f$ 0.53 (40% EtOAc in hexane) Microanalysis for $C_{21}H_{18}FNO$: Calc'd:C 78.97 H 5.68 N 4.39 F 5.95 Found: C 78.72 H 5.67 N 4.23 F 5.67

F. 2-Cyclopropyl-4-(4-fluorophenyl)-6-phenyl-3-pyridinecarboxaldehyde

A solution of 4-methylmorpholine N-oxide (2.982 g, 25.5 mmol) in $CH_2Cl_2$ (80 ml) was dried over $MgSO_4$ for 15 minutes. The solution was filtered directly into a 500 ml flask, using approximately 20 ml $CH_2Cl_2$ to effect transfer. The flask was then charged with dry 4A molecular sieves (10.4 g), alcohol E (4.012 g, 12.56 mmol), and tetrapropylammonium perruthenate (222 mg, 0.63 mmol). After stirring at room temperature for 40 minutes, the black solution was diluted with $Et_2O$ (120 ml), stirred for 5 minutes, then filtered through Celite®. The filtrate was stripped and the dark residue was dissolved in $CH_2Cl_2$ and flashed (Merck $SiO_2$, 20% EtOAc in hexane) to give the product as a solid. The solid was recrystallized from EtOAc/hexane (2 crops) to give compound F (3.115 g, 78%) as a yellow solid.

m.p. 110°–113° C. TLC: $R_f$ 0.52 (20% EtOAc in hexane)

G. 2-Cyclopropyl-3-(2,2-dibromoethenyl)-4 -(4-fluorophenyl)-6-phenylpyridine

A solution of carbon tetrabromide (4.245 g, 12.8 mmol) in $CH_2Cl_2$ (10 ml) was added over a 9 minute period to a cold (0° C.) solution of aldehyde F (2.725 g, 8.6 mmol) and triphenylphosphine (6.761 g, 25.8 mmol) in $CH_2Cl_2$ (35 ml). After the addition was complete, the cooling bath was removed and the mixture was stirred at room temperature for 25 minutes. The solution was quenched with saturated $NaHCO_3$ and extracted 2 times with $CH_2Cl_2$. The combined organic layers were dried ($Na_2SO_4$), filtered and concentrated. The concentrate was chromatographed (flash, Merck $SiO_2$, 35% $CH_2Cl_2$ in hexane) to give impure dibromide G as a solid. Recrystallization from EtOAc/hexane (2 crops) provided compound G (3.588 g, 88%) as fine white needles.

H. (S)-4-[[[2-Cyclopropyl-4-(4-fluorophenyl)- 6-phenyl-3-pyridinyl]ethynyl]methoxyphosphinyl] -3-[[(1,1-dimethylethyl)diphenylsilyl] oxy]butanoic acid, ethyl ester A solution of dibromide G (1.000 g, 2.11 mmol) in THF (7 ml) was added dropwise to a solution of n-BuLi (2.5M in hexane, 1.8 ml, 4.5 mmol) in THF (10 ml) at –78° C. over a 6-minute period. The resulting clear yellow solution was stirred at –78° C. for 40 minutes, then added dropwise via cannula over a 10-minute period to a –78° C. solution of the phosphonochloridate from Example 57, part G in THF (15 ml). The resulting greenish mixture was stirred at –78° C. for 20 minutes, then quenched with 50% saturated $NH_4Cl$. The solution was warmed to 0° C., diluted with $H_2O$, and poured into saturated $NaHCO_3$. The aqueous phase was extracted once with $Et_2O$. The $Et_2O$ layer was washed with brine, dried ($Na_2SO_4$), filtered and stripped to give a yellow oil. The residue was chromatographed (flash, Merck $SiO_2$, 40% EtOAc in hexane) to afford compound H as a white foam (1.270 g, 81%).

TLC: $R_f$= 0.25 (40% EtOAc in hexane).

I. (S)-4-[[[2-Cyclopropyl-4-(4-fluorophenyl)- 6-phenyl-3-pyridinyl]ethynyl]methoxyphosphinyl] -3-hydroxybutanoic acid, ethyl ester A mixture of compound H (1.255 g, 1.68 mmol) and HOAc (490 μl, 5.14 mg, 8.6 mmol) in THF (25 ml) was treated with tetra-n-butylammonium fluoride (1.0M in THF, 8.2 ml, 8.2 mmol). After stirring at room temperature for 16 hours, the solution was diluted with EtOAc and washed three times with 5% $KHSO_4$. The EtOAc layer was washed with brine, dried ($Na_2SO_4$), filtered and stripped to afford a yellow oil. The oil was dissolved in $Et_2O$, cooled to 0° C. and treated with excess diazomethane for 15 minutes. The excess diazomethane was destroyed by the addition of HOAc and the solvent was removed in vacuo. The residue was chromatographed (flash, Merck $SiO_2$, 1:1—acetone:hexane) to afford intermediate I (746 mg, 87%) as a white foam.

TLC: $R_f = 0.30$ (1:1—acetone:hexane)

J. (S)-4-[[[2-Cyclopropyl-4-(4-fluorophenyl)- 6-phenyl-3-pyridinyl]ethynyl]hydroxyphosphinyl] -3-hydroxybutanoic acid, disodium salt A solution of intermediate I (730 mg, 1.44 mmol) in dioxane (6 ml) was treated with 1N NaOH (5.0 ml, 5.0 mmol) at room temperature and the mixture was subsequently heated at 60° C. under argon for 0.5 hour. The solvent was evaporated and the residue was chromatographed on HP-20 eluting in succession with $H_2O$ (200 ml) and 50% MeOH in $H_2O$ (200 ml). The desired fractions were pooled and evaporated and the residue was taken up in $H_2O$ and lyophilized to give Example 95 (674 mg, 84%) as a white solid.

m.p. decomp. ≧285° C. TLC: $R_f = 0.07$ (8:1:1—$CH_2Cl_2$:HOAc:MeOH) Microanalysis for $C_{26}H_{21}FNNa_2O_5P$* 2.0 $H_2O$: Calc'd: C 55.82, H. 4.51; N 2.50; F 3.40; P 5.54 Found: C 55.84, H. 4.28; N 2.46; F 3.33; P 5.50 Rotation $[\alpha]_D = +5.6°$ (MeOH, 9.8 mg in 1.21 ml)

Example 96

(S)-4-[ [ [ 2-Cyclopropyl-4-(4-fluorophenyl)-5 -methyl-6-phenyl-3-pyridinyl] ethynyl] hydroxyphosphinyl] -3-hydroxybutanoic acid, disodium salt A. 2-Cyclopropylcarbonyl-3-(4-fluorophenyl)-2 -propenoic acid, ethyl ester A mixture of 4-fluorobenzaldehyde (4.768 g, 38.4 mmol), the compound from Example 95, part A (6.000 g, 38.4 mmol), piperidine (380 μl), and HOAc (75 μl) was refluxed in benzene (40 ml) with removal of water (Dean-Stark trap) for 16 hours. The cooled mixture was diluted with $Et_2O$ and washed successively with 5% HCl, saturated $NaHCO_3$, $H_2O$, and brine, then dried ($Na_2SO_4$), filtered, and stripped to yield an oil. Distillation of the oil (bp 127°–135° C. at 0.2 mm Hg) afforded compound A (9.299 g, 82%) as a pale yellow liquid.

TLC: $R_f = 0.31$ (20% EtOAc in hexane) Microanalysis for $C_{15}H_{15}FO_3$: Calc'd: C 68.69; H 5.76; F 7.24 Found: C 68.92; H 5.90; F 7.25

B. α-Cyclopropylcarbonyl-β -(4-fluorophenyl)-γ -methyl-Δ-oxobenzenepentanoic acid, ethyl ester A −78° C. solution of LiN(TMS)$_2$ (1.0M in THF, 38 ml, 38 mmol) in dry THF (40 ml) was treated with a solution of propiophenone (5.015 g, 37.4 mmol) in THF (6 ml) over a 4-minute period. After 30 minutes, a solution of compound A (7.842 g, 29.9 mmol) in THF (15 ml) was added dropwise to the above solution. After one hour, the mixture was quenched with acetic acid (2.5 ml) and saturated $NH_4Cl$ and warmed to room temperature. The mixture was diluted with $H_2O$ and subsequently extracted once with $Et_2O$. The $Et_2O$ extract was washed with brine, dried ($Na_2SO_4$), filtered and stripped to give an oil. The oil was transferred to a round bottom flask which was fitted with a short path distillation apparatus and the oil was heated at 65° C. at 0.2 mm Hg to remove the volatiles and excess propiophenone. The pot residue, crude compound B was used directly in the next reaction.

C. 2-Cyclopropyl-4-(4-fluorophenyl)-5-methyl- 6-phenyl-3-pyridinecarboxylic acid, ethyl ester A mixture of crude compound B, $NH_4OAc$ (9.210 g, 119.5 mmol), and Cu(OAc)$_2$ (17.921 g, 89.8 mmol) in glacial HOAc (80 ml) was heated at 110° C. for 21 hours. The solution was cooled to room temperature and subsequently poured into an ice cold mixture of concentrated $NH_4OH$ (100 ml) in $H_2O$ (200 ml). The mixture was extracted twice with $Et_2O$ and the pooled $Et_2O$ extracts were washed with $H_2O$ and brine, then dried ($Na_2SO_4$), filtered and stripped to yield a brown solid. The solid was dissolved in $CH_2Cl_2$ and flashed (Merck $SiO_2$, 20% EtOAc in hexane) to give compound C as a reddish oil which readily solidified. Recrystallization from EtOAc/hexane (2 crops) afforded ester compound C (9.615 g, 86%) as white crystals.

m.p. 113°–114.5° C. TLC: $R_f = 0.46$ (20% EtOAc in hexane) Microanalysis for $C_{24}H_{22}FNO_2$: Calc'd: C 76.78; H 5.91; N 3.73; F 5.06 Found: C 76.68; H 5.92; N 3.63; F 5.06

D. (S)-4-[ [ [ 2-Cyclopropyl-4-(4-fluorophenyl)- 5-methyl-6-phenyl-3-pyridinyl] ethynyl] hydroxyphosphinyl] -3-hydroxybutanoic acid, disodium salt A cold (0° C.) solution of ester C (8.942 g, 23.8 mmol) in dry THF (200 ml) was treated with LiAlH$_4$ (2.701 g, 71.2 mmol). Ten minutes after the addition, the cooling bath was removed and the mixture was stirred at room temperature for 1.5 hours. The solution was recooled to 0° C. and quenched in succession with $H_2O$ (3.0 ml), 10% NaOH (4.5 ml), and $H_2O$ (8.5 ml). The solution was filtered and the salts were washed with EtOAc and $Et_2O$. Removal of the filtrate solvent afforded an oily solid residue. The residue was dissolved in $Et_2O$, diluted with hexane, heated to remove the $Et_2O$, and cooled to provide compound D (6.548 g, 83%) as an amorphous white solid.

m.p. 140.5°–142° C. TLC: $R_f = 0.18$ (20% EtOAc in hexane) Microanalysis for $C_{22}H_{20}FNO$: Calc'd: C 79.25; H 6.05; N 4.20; F 5.70 Found: C 79.14; H 5.99; N 4.15; F 5.73

E. 2-Cyclopropyl-4-(4-fluorophenyl)-5-methyl- 6-phenyl-3-pyridinecarboxaldehyde

A solution of 4-methylmorpholine N-oxide (4.002 g, 34.2 mmol) in $CH_2Cl_2$ (130 ml) was dried over $MgSO_4$ for 15 minutes. The solution was filtered directly into a 500-ml flask, using approximately 30 ml $CH_2Cl_2$ to effect the transfer. The flask was then charged with dry 4A molecular sieves (16 g), alcohol D (5.686 g, 17.05 mmol), and tetrapropylammonium perruthenate (301 mg, 0.86 mmol). After stirring at room temperature for 30 minutes, the black solution was diluted with $Et_2O$ (200 ml), stirred for 5 minutes, then filtered through a plug of silica gel (Merck, 65×30 mm) washed with $Et_2O$. The filtrate was stripped to give a pale yellow solid. The solid was recrystallized from EtOAc/hexane to give compound E (3.982 g) as white crystals. Flashing the mother liquor (Merck $SiO_2$, 20% EtOAc in hexane) gave additional product, which was recrystallized from hexane (499 mg). Total pooled solids, 4.481 g (79%).

m.p. 137°–139° C. TLC: $R_f = 0.50$ (20% EtOAc in hexane) Microanalysis for $C_{22}H_{18}FNO$: Calc'd: C 79.74; H 5.47; N 4.23; F 5.73 Found: C 79.32; H 5.49; N 4.13; F 5.65

F. 2-cyclopropyl-3-(2,2-dibromoethenyl)-4 -(4-fluorophenyl)-5-methyl-6-phenylpyridine A solution of carbon tetrabromide (5.810 g, 17.5 mmol) in $CH_2Cl_2$ (9 ml) was added over a 12-minute period to a cold (0° C.) solution of aldehyde E (3.864 g, 11.7 mmol) and triphenylphosphine (9.191 g, 35.0 mmol) in $CH_2Cl_2$ (60 ml). After the addition was complete, the cooling bath was removed and the mixture was stirred at room temperature for 20 minutes. The solution was quenched with saturated $NaHCO_3$ (40 ml) and extracted twice with $CH_2Cl_2$. The combined organic layers were dried ($Na_2SO_4$), filtered and concentrated. The concentrate was chromatographed (flash, Merck $SiO_2$, 40% $CH_2Cl_2$ in hexane) and the pure desired fractions were stripped to give a solid. Recrystallization from EtOAc/hexane (2 crops) provided compound F (5.432 g, 96%) as white crystals.

m.p. 155°–157° C. TLC: $R_f$ = 0.58 (20% EtOAc in hexane). Microanalysis for $C_{23}H_{18}Br_2FN$: Calc'd: C 56.70; H 3.72; N 2.88; F 3.90; Br 32.80 Found: C 56.55; H 3.68; N 2.82; F 3.89; Br 32.72

G. (S)-4-[ [ [2-Cyclopropyl-4-(4-fluorophenyl)- 5-methyl-6-phenyl-3-pyridinyl] ethynyl] methoxyphosphinyl] -3-[ [ (1,1-dimethylethyl)diphenylsilyl] oxy]butanoic acid, ethyl ester A solution of dibromide F (1.000 g, 2.05 mmol) in THF (5 ml) was added dropwise to a solution of n-BuLi (2.5M in hexane, 1.73 ml, 4.3 mmol) in THF (10 ml) at −78° C. over a 10-minute period. The resulting pale yellow solution was stirred at −78° C. for one hour, then added dropwise via cannula over a 12-minute period to a −78° C. solution of the phosphonochloridate from Example 57, part G in THF (15 ml). The resulting mixture was stirred at −78° C. for 30 minutes, then quenched with 50% saturated $NH_4Cl$. The solution was warmed to 0° C., diluted with $H_2O$, and poured into saturated $NaHCO_3$. The aqueous phase was extracted once with $Et_2O$. The $Et_2O$ layer was washed with brine, dried ($Na_2SO_4$), filtered and stripped to give an oil. The residue was chromatographed (flash, Merck $SiO_2$, 50% EtOAc in hexane) to afford compound G as a white foam (1.158 g, 74%).

TLC: $R_f$ = 0.27 (40% EtOAc in hexane)

H. (S)-4-[ [ [2-Cyclopropyl-4-(4-fluorophenyl)- 5-methyl-6-phenyl-3-pyridinyl] ethynyl] methoxyphosphinyl] -3-hydroxybutanoic acid, ethyl ester A mixture of compound G (1.148 g, 1.51 mmol) and HOAc (460 μl, 482 mg, 8.0 mmol) in THF (25 ml) was treated with tetra-n-butylammonium fluoride (1.0M in THF, 7.6 ml, 7.6 mmol). After stirring at room temperature for 17 hours, the solution was diluted with EtOAc and washed three times with 5% $KHSO_4$. The pooled aqueous extracts were back-extracted once with EtOAc and the combined EtOAc layers were washed with brine, dried ($Na_2SO_4$), filtered and stripped to afford a yellow oil. The oil was dissolved in $Et_2O$, cooled to 0° C. and treated with excess diazomethane for 15 minutes. The excess diazomethane was destroyed by the addition of HOAc and the solvent was removed in vacuo. The residue was chromatographed (flash, Merck $SiO_2$, 40% acetone in hexane, followed by 40% hexane in acetone) to afford compound H (684 mg, 87% as a white foam.

TLC: $R_f$ = 0.37 (1:1—acetone:hexane)

I. (S)-4-[ [ [2-Cyclopropyl-4-(4-fluorophenyl)- 5-methyl-6-phenyl-3-pyridinyl] ethynyl] hydroxyphosphinyl] -3-hydroxybutanoic acid, disodium salt A solution of compound H (672 mg, 1.29 mmol) in dioxane (7 ml) was treated with 1N NaOH (4.5 ml, 4.5 mmol) at room temperature and the mixture was subsequently heated at 60° C. under argon for one hour. The solvent was evaporated and the solid residue was dissolved in warm $H_2O$ and chromatographed on HP-20, eluting in succession with $H_2O$ (150 ml) and 50% MeOH in $H_2O$ (200 ml). The desired fractions were pooled and evaporated and the residue was taken up in $H_2O$ and lyophilized to give Example 96 (640 mg, 89%) as a white solid.

m.p. decomp. ≥295° C. TLC: $R_f$ = 0.07 (8:1-1—$CH_2Cl_2$:HOAc:MeOH) Microanalysis for $C_{27}H_{23}FNNa_2O_5P$ * 1.25 $H_2O$ Calc'd: C 57.92; H 4.59; N 2.50; F 3.39; P 5.53 Found: C 58.05; H 4.50; N 2.35; F 3.38; P 5.72 Rotation: $[\alpha]_D$ = +8.8° (MeOH, 7.6 mg in 1.22 ml)

Example 97

(S,E)-4-[ [ 2-[ 2-Cyclopropyl-4-(4-fluorophenyl)-5-methyl-6-phenyl-3-pyridinyl] ethenyl] hydroxyphosphinyl] -3-hydroxybutanoic acid, disodium salt A. 2-Cyclopropyl-3-(2-ethynyl)-4-(4-fluorophenyl)-5-methyl-6-phenylpyridine The compound from Example 96, part F (4.000 g, 8.21 mmol) in dry THF (12 ml) was added to a solution of n-BuLi (2.5M in hexanes, 7.40 ml, 18.5 mmol) in THF (35 ml) over a 6-minute period. After stirring at −78° C. for 50 minutes, the lime-green solution was quenched with saturated $NH_4Cl$ and warmed to room temperature. The colorless mixture was diluted with $H_2O$ and extracted with $Et_2O$. The organic layer was washed with brine, dried ($Na_2SO_4$), filtered and stripped to give a white solid. The solid was recrystallized from hexane to give very pale lavender-colored needles (1st crop 2.062). From the mother liquor was obtained a second (392 mg) and third crop (151 mg) of pure product. Total pooled solids (compound A) were 2.064 g, 97%.

m.p.: 140°–142° C. TLC: $R_f$ = 0.55 (EtOAc in hexane) Analysis for $C_{23}H_{18}FN$: Calc'd: C 84,38; H 5.54; N 4.28; F 5.80 Found: C 84.42; H 5.45, N 4.44; F 5.88

B. 2-Cyclopropyl-3-(2-iodoethenyl)-4-(4 -fluorophenyl)-5-methyl-6-phenylpyridine A mixture of compound A (1.400 g, 4.28 mmol) and AIBN (20 mg) in tri-n-butylstannyl hydride (2.4 ml, 2.60 g, 8.9 mmol) was rapidly heated to 140° C. by immersion in a pre-heated oil bath. Approximately 20 mg of AIBN was added to the reaction mixture after 0.5 hour and again one hour after heating was initiated. After 1.5 hours, the dark orange mixture was cooled to room temperature, diluted with $Et_2O$ (40 ml) and treated with 2,6-lutidine (1.30 ml, 1.19 g, 11.2 mmol) followed by solid $I_2$ (3.27 g, 12.9 mmol). The dark reaction mixture was stirred for 60 minutes, then poured into a 50% saturated $NaHCO_3$ solution containing 3.6 g $Na_2S_2O_3$. The layers were shaken and separated. The ethereal layer was washed successively with $H_2O$, 4.5M $NH_4OH$, $H_2O$, and brine, then dried ($Na_2SO_4$), filtered and stripped to yield an oil. The residue was subjected to flash chromatography (Merck $SiO_2$, 10% EtOAc in hexane) to afford crude compound B as a solid. Recrystallization from hexane gave compound B (1.288 g) as a yellow solid. The mother liquor was flashed (Merck $SiO_2$, 5% EtOAc in hexane) and the desired fractions were pooled, stripped, and recrystallized from hexane to give additional product (235 mg). Total yield of pure compound C 1.523 g, 78%.

m.p.: 134°–136° C. TLC: $R_f$ = 0.45 (10% EtOAC in hexane) Microanalysis for $C_{23}H_{19}FIN$: Calc'd: C 60.67; H 4.21; N 3.08; F 4.17; I 27.87 Found: C 60.76; H 4.19; N 2.92; F 4.26; I 27.90

C. (S)-4-[ [ [ 2-Cyclopropyl-4-(4-fluorophenyl)- 5-methyl-6-phenyl-3-pyridinyl] ethenyl] methoxyphosphinyl]-3-[ [ (1,1-dimethylethyl)diphenylsilyl] oxy]butanoic acid, methyl ester A solution of the vinyl iodide from part B (1.300 g 2.85 mmol) in THF (6 ml) was added over a 5-minute period to a −100° C. solution of t-butyllithium (1.7M in pentane, 3.50 ml, 5.95 mmol) in THF (8 ml). The resulting deep muddy red solution was stirred for 20 minutes, then added over a 10-minute period to a −100° C. solution of the phosphonochloridate from Example 57, part G in THF (15 ml). The resulting yellow mixture was stirred at minus 100° C. for 30 minutes, then quenched with 50% saturated $NH_4Cl$. The solution was warmed to room temperature, diluted with H₂O, and poured into saturated NaHCO₃. The aqueous phase was extracted with Et₂O. The Et₂O extract was washed with brine, dried (Na₂SO₄), filtered and stripped. The resulting yellow oil was chromatographed (flash, Merck SiO₂, EtOAc in hexane) to afford compound C as an oily foam (1.056 g, 49%).

TLC: $R_f$= 0.19 & 0.14 (40% EtOAc in hexane)

D. (S)-4-[ [ [ 2-Cyclopropyl-4-(4-fluorophenyl)- 5-methyl-6-phenyl-3-pyridinyl] ethenyl] methoxyphosphinyl] -3-hydroxybutanoic acid, methyl ester A solution of compound C (1.030 g, 1.35 mmol) in THF (20 ml) was treated with HOAc (400 μl, 420 mg, 7.0 mmol) and tetra-n-butyl-ammonium fluoride (1.0M in THF, 6.7 mmol). After stirring at room temperature for 16 hours, the solution was poured into saturated NaHCO₃ and extracted with EtOAc. The EtOAc extracted with washed with brine, dried (Na₂SO₄), filtered, and stripped to give an oil, which was subsequently chromatographed (flash, Merck SiO₂, 1:1—acetone:hexane followed by 5:2—acetone:hexane). Compound D (647 mg, 92%) was obtained as an oily foam.

TLC: $R_f$ = 0.31 (1:1—acetone:hexane)

E. (S,E)-4-[ [2-[2-Cyclopropyl-4-(4-fluorophenyl)- 5-methyl-6-phenyl-3-pyridinyl] ethenyl] hydroxyphosphinyl] -3-hydroxybutanoic acid, disodium salt A solution of compound D (320 mg, 0.61 mmol) in dioxane (4.5 ml) was treated with 1 N NaOH (2.1 ml, 2.1 mmol) and the mixture was stirred at 50° C. for 1.75 hours. The solvent was evaporated and the residue was taken up in H₂O and chromatographed on HP-20, eluting in succession with H₂O (150 ml) and 50% MeOH in H₂O (200 ml). The desired fractions were pooled and evaporated and the residue was taken up in H₂O and lyophilized to give Example 97 (292 mg, 85%) as a white solid.

m.p.: 310° C. (decomp.); [α]$_D$= +6.7° (MeOH, 6.3 mg in 1.25 ml) TLC: $R_f$ = 0.08 (8:1:1—CH₂Cl₂:HOAc:MeOH) Microanalysis for C₂₇H₂₅FNNa₂O₅P * 1.33 H₂O: Calc'd: C 57.56; H 4.95; N 2.49; F 3.37; P 5.50 Found: C 57.54; H 4.99; N 2.51; F 3.54; P 5.70

Example 98

(S)-4-[ [ 2-[ 2-Cyclopropyl-4-(4-fluorophenyl)-5-methyl-6-phenyl-3-pyridinyl] ethyl] hydroxyphosphinyl[ -3-hydroxybutanoic acid, disodium salt A. (S)-4-[ [ [ 2-Cyclopropyl-4-(4-fluorophenyl)- 5-methyl-6-phenyl-3-pyridinyl] ethyl] hydroxyphosphinyl] -3-hydroxybutanoic acid, disodium salt A mixture of compound D from Example 96 (308 mg, 0.59 mmol) and Pd on carbon (10% Pd on C, 129 mg) in MeOH (20 ml) was shaken under 50 psi of H₂ for 7 hours. The solution was filtered, stripped, and chromatographed (flash, Merck SiO₂, 14:11—acetone hexane followed by 100% acetone) to give compound A (271 mg, 87%) as a colorless oil.

TLC: $R_f$= 0.29 (1:1—acetone:hexane)

B. (S)-4-[[2-[2-Cyclopropyl-4-(4-fluorophenyl)- 5-methyl-6-phenyl-3-pyridinyl] ethyl]hydroxyphosphinyl[-3-hydroxybutanoic acid, disodium salt A solution of compound A (260 mg, 0.495 mmol) in dioxane (3 ml) was treated with 1N NaOH (1.8 ml, 1.8 mmol) and the mixture was stirred at 50° C. for 2.5 hours. The solvent was evaporated and the residue was chromatographed on HP-20, eluting in succession with H₂O (150 ml) and 50% MeOH in H₂O (150 ml). The desired fractions were pooled and evaporated and the residue was taken up in H₂O and lyophilized to give Example 98 (242 mg, 87%) as a white solid.

m.p.: 300° C. (decomp.); [α]$_D$=–0.3° (MeOH, 4.0 mg in 1.25 ml) TLC: $R_f$= 0.09 (8:1:1—CH₂Cl₂:HOAc:MeOH) Microanalysis for C₂₇H₂₇FNNa₂O₅P * 1.25 H₂O: Calc'd: C 57.50; H 5.27; N 2.48; F 3.37; P 5.49 Found: C 57.46; H 5.23; N 2.38; F 3.38; P 5.61

Example 99

(S)-4-[ [ [4-(4-Fluorophenyl)-6,7-dihydro-2-(1 -methylethyl)-5H-benzo[ 6,7] cyclohepta[ 1,2-b] -pyridin-3-yl] methoxy] hydroxyphosphinyl] -3-hydroxybutanoic acid, disodium salt A. (S)-4-[[[4-(4-Fluorophenyl)-6,7-dihydro-2 -(1-methylethyl)-5H-benzo[6,7]cyclohepta[1,2 -b]pyridin-3-yl-)methoxy]methoxyphosphinyl] -3-[[(1,1-dimethylethyl-)diphenylsilyl] oxy]butanoic acid, methyl ester The phosphonochloridate from Example 57, part G (2.157 g, 3.41 mmol) was partitioned between EtOAc and 5% KHSO₄. The EtOAc layer was washed three times with 5% KHSO₄, then with brine, then dried (Na₂SO₄), filtered and stripped to give a colorless oil (phosphonic acid monomethyl ester). The oil was dissolved in dry CH₂Cl₂ (20 ml) and treated with N,N-diethyltrimethylsilylamine (0.992 g, 6.85 mmol). After stirring at room temperature for one hour, the solvent was removed in vacuo and the residue was azeotroped with dry toluene (20 ml). The residue was redissolved in dry CH₂Cl₂ (20 ml), cooled to 0° C. and treated with DMF (0.050 g, 0.68 mmol) and oxalyl chloride (0.52 g, 4.10 mmol). After 15 minutes, the solution was warmed to room temperature and stirred for an additional 45 minutes. The solvent was stripped and the yellow residue was azeotroped with toluene (20 ml) and dried in vacuo (oil pump) for 1 hour. The residue was then dissolved in pyridine (15 ml) and the temperature of the solution was lowered to 0° C. A pyridine solution (5 ml) of compound C from Example 63 (0.691 g, 1.91 mmol) was then added to the flask dropwise and the solution was allowed to stir 17 hours at 0° C. The reaction was then quenched with saturated NH₄Cl, and the mixture diluted with EtOAc (50 ml). The organic layer was washed with water and brine, then dried over Na₂SO₄, filtered and concentrated to an amber oil. The oil was purified by flash chromatography on Merck silica gel in 30% EtOAc in hexane. After combination and concentration of those fractions containing product, compound A was obtained as a yellow oil (0.604 g, 40%).

TLC: $R_f$= 0.53 (40% EtOAc in hexane).

B. (S)-4-[ [ [ 4-(4-Fluorophenyl)-6,7-dihydro-2 -(1-methylethyl)-5H-benzo[ 6,7] cyclohepta [ 1,2-b] pyridin-3-yl] methoxy] methoxyphosphinyl] -3-hydroxybutanoic acid, methyl ester TBAF (1M in THF, 2.25 ml, 2.25 mmol) was added to a THF (20 ml) solution of compound A (0.597 mmol) and acetic acid (0.180 g, 3.01 mmol), and the solution was allowed to stir at room temperature for 17 hours. More TBAF (1.0M in THF, 1.12 g, 1.12 mmol) and HOAc (0.090 g, 1.50 mmol) were added to the solution, which stirred another 3 hours. The solution was then diluted with EtOAc (50 ml), washed with saturated NaHCO₃, water and brine, dried over Na₂SO₄, and filtered and concentrated to an orange oil. The oil was purified by flash chromatography on Merck silica gel in 40% acetone in hexane. Product fractions were combined and concentrated to afford compound B as a clear oil (0.404 g, 97%).

TLC: $R_f$= 0.63 (50% acetone in hexane).

C. (S)-4-[ [ [4-(4-Fluorophenyl)-6,7-dihydro-2 -(1-methylethyl)-5H-benzo[6,7] cyclohepto [ 1,2-b] pyridin-3-yl] methoxy] hydroxyphosphinyl] -3-hydroxybutanoic acid, disodium salt An aqueous solution of NaOH (1M in $H_2O$, 1.99 ml, 1.99 mmol) was added to a solution of compound B (0.370 g, 0.67 mmol) in dioxane (10 ml). The mixture was stirred at 55° C. for 17 hours. The solution was then concentrated to a white solid. The solid was dissolved in hot $H_2O$ to form a white slurry. The slurry was applied to a column of HP20 gel, and the column was eluted first with 200 ml $H_2O$, then with 400 ml 30% MeOH in $H_2O$. Those fractions containing the product were combined and concentrated to a white solid. The solid was dissolved in water and lyophilized to afford Example 99 as a white, fluffy solid (0.280 g, 73%).

Melting point: 300° C. (decomp). Elemental analysis for $C_{28}H_{29}NFNa_2PO_6*2.00$ mole $H_2O$ Calc'd: C 55.36, H 5.47, N 2.31, F 3.13, P 5.10 Found: C 55.65, H 5.38, N 2.19, F 3.12, P 5.17 Optical rotation: $[a]_D= -0.3°$ (MeOH, c= 3.8 mg/ml).

Examples 100 to 104

These examples were prepared following the procedures of Example 99, substituting the appropriate pyridine methanol to form the product. The examples follow the formula

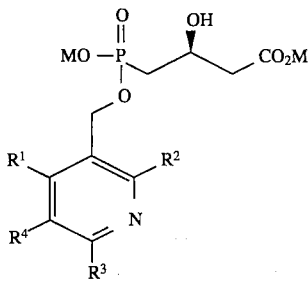

in which M is sodium and $R^1$ to $R^4$ are as defined in the table below.

| Example | $R^1$ | $R^2$ | $R^3$ | $R^4$ |
|---------|-------|-------|-------|-------|
| 100 | 4-F-$C_6H_4$ | i-$C_3H_7$ | $C_6H_5$ | H |
| 101 | 4-F-$C_6H_4$ | i-$C_3H_7$ | $C_6H_5$ | $CH_3$ |
| 102 | 4-F-$C_6H_4$ | i-$C_3H_7$ | $C_6H_5$ | $CH_2CH_3$ |
| 103 | 4-F-$C_6H_4$ | c-$C_3H_5$ | $C_6H_5$ | $CH_3$ |
| 104 | 4-F-$C_6H_4$ | $CH_2CH_3$ | $C_6H_5$ | $CH_3$ |

Example 105

This example embodies reaction scheme 9. All reactions were carried out under a static atmosphere of argon and stirred magnetically unless otherwise noted. All reagents used were of commercial quality and were obtained from Aldrich Chemical Co. Dry THF and $Et_2O$ were obtained by distillation from the sodium ketyl of benzophenone under nitrogen. Dry $CH_2Cl_2$ were obtained by distillation from $CaH_2$ under nitrogen. Pyridine and dioxane were obtained from American Burdick and Jackson and were stored over 4 angstrom molecular sieves. All flash chromatographic separations were performed using E. Merck silica gel (60, particle size, 0.040–0.063 mm). Reactions were monitored by TLC using 0.25 mm E. Merck silica gel plates (60 $F_{254}$).

A. 2-Methyl-1-(2aminophenyl)-1-propanone

A cold (0° C.) solution of anthranilonitrile (8.507 g, 72.0 mmol) in dry $Et_2O$ (30 ml) was treated dropwise with i-propylmagnesium chloride (2.0M in $Et_2O$, 100 ml, 200 mmol) over a 15-minute period. After the addition was complete, the mixture was warmed to room temperature and stirring continued for 4.5 hours. The solution was re-cooled to 0° C. and carefully quenched by the addition of 10% HCl (150 ml). The mixture was warmed to room temperature, stirred for 30 minutes, re-cooled to 0° C. and made basic by the addition of solid NaOH (25 g). The aqueous layer was extracted with $Et_2O$ (3×200 ml) and the combined ethereal extracts were washed with brine (150 ml) and dried ($Na_2SO_4$). The solution was evaporated and the crude product was flash chromatographed on a silica gel column (50 cm×200 cm) using 15% EtOAc in hexane as the eluting solvent mixture to afford compound A as a golden yellow oil (yield 10.916 g, 92%); $R_f$ 0.32 (20% EtOAc in hexane). Pure compound A may also be obtained in slightly diminished yield (75%) by direct distillation of the crude product (bp 86°–91° C./0.5 Torr).

Microanalysis for $C_{10}H_{13}NO$: Calc'd: C 73.58 H 8.03 N 8.58 Found: C 73.57 H 8.01 N 8.94

B. 3-[ [2-(2-Methyl-1-oxopropyl)phenyl] amino]-3-oxopropanoic acid, ethyl ester

A mixture of compound A (5.000 g, 30.6 mmol) and dry pyridine (7.4 ml), 7.2 g, 91.5 mmol) in dry $CH_2Cl_2$ (60 ml) at −78° C. was treated dropwise with a solution of ethyl malonyl chloride (Aldrich, tech. grade, 4.62 g, 30.7 mmol based on 100% purity) in $CH_2Cl_2$ (10 ml) over a 15-minute period. Thirty minutes after the addition, the reaction was quenched with $H_2O$ (50 ml) and warmed to room temperature. The mixture was extracted with $Et_2O$ (150 ml) and the organic extract is washed in succession with $H_2O$ (50 ml), 5% HCl (50 ml), $H_2O$ (50 ml), and brine (50 ml), then dried ($Na_2SO_4$), filtered, and concentrated affording a red-brown oil. Flash column chromatography (50 cm×230 cm) of the crude oil on silica gel using 25% EtOAc in hexane as the eluant provides compound B as a near-colorless oil; yield 5.620 g, (66%); $R_f$ 0.49 (40% EtOAc in hexane).

Microanalysis for $C_{15}H_{19}NO_4$: Calc'd: C 64.96 H 6.91 N 5.05 Found: C 64.94 H 6.80 N 6.40

C. 2-Hydroxy-4-(1-methylethyl)-3-quinolinecarboxylic acid, ethyl ester

A solution of compound B (4.555 g, 16.4 mmol) in absolute EtOH (65 ml) was treated with a solution of EtONa in EtOH (21% by weight, 1.8 g, 6.8 mmol) and the mixture was stirred at room temperature for 5 minutes, then at reflux for 5 minutes. The solution was cooled and partitioned between EtOAc (200 ml) and 50% saturated $NH_4Cl$ (150 ml). The layers were shaken and separated and the organic layer is washed with brine (2×75 ml) and dried ($Na_2SO_4$). Filtration and solvent removal afforded a solid, which was recrystallized from EtOAc/hexane giving compound C (2 crops) as fine white needles; yield 3.950 g, (93%); $R_f$ 0.16 (40% EtOAc in hexane).

m.p. 195.2°–196.8° C. Microanalysis for $C_{15}H_{17}NO_3$: Calc'd: C 69.48 H 6.61 N 5.40 Found: C 69.47 H 6.61 N 5.38

D. 3-(Hydroxymethyl)-4-(1-methylethyl)-2 -quinolinol

To a cold (0° C.) slurry of $LiAlH_4$ (1.624 g, 42.8 mmol) in dry THF (200 ml) was added compound C (10.000 g, 38.6 mmol) portionwise as a solid (Caution: vigorous $H_2$ evolution). After stirring at 0° C. for 45 minutes, the solution was carefully quenched by the successive addition of $H_2O$ (75 ml) and saturated $NH_4Cl$ (150 ml). The mixture was extracted with EtOAc (2×150 ml) and the pooled organic extracts were washed with brine (100 ml), dried ($Na_2SO_4$), filtered and evaporated to provide a yellow solid. The solid residue was recrystallized from EtOAc, giving compound D as a pale yellow amorphous solid (2 crops); yield 7.803 g, (93%); $R_f$ 0.18 (1:1 acetone:hexane).

m.p. 149.5°–152.0° C. Microanalysis for $C_{13}H_{15}NO_2$: Calc'd: C 71.86 H 6.96 N 6.45 Found: C 71.61 H 6.94 N 6.31

E. 2-Hydroxy-4-(1-methylethyl)-3-quinolinecarboxaldehyde

A mixture of compound D (3.000 g, 13.8 mmol) and $MnO_2$ (Aldrich, activated type, 4.02 g, 46.2 mmol) in $CH_2Cl_2$ (100 ml) was stirred at room temperature for 24 hours. The reaction was treated with additional $MnO_2$ (3.00 g, 34.5 mmol) and the mixture was subsequently refluxed for 3 days. After cooling to room temperature, the solution is filtered through a Celite® pad, which was washed with $CH_2Cl_2$. Evaporation of the filtrate solvent gives a greenish solid which is dissolved in acetone and filtered through a plug of silica gel (100 g), washing with 1:1 acetone:hexane. The filtrate is stripped and the residue is recrystallized from EtOAc/hexane affording compound E (two crops) as bright yellow crystals (2.512 g, 85% yield); $R_f$ 0.44 (1:1 acetone:hexane).

m.p. 177.0°–179.0° C. Microanalysis for $C_{13}H_{13}NO_2$: Calc'd: C 72.54 H 6.09 N 6.51 Found: C 72.42 H 6.03 N 6.32

F. 4-(1-Methylethyl)-2-[[(trifluoromethyl)sulfonyl] oxy]-3-quinolinecarboxaldehyde A bright yellow solution of compound E (1.961 g, 9.1 mmol) and dry pyridine (2.20 ml, 2.15 g, 27.2 mmol) in dry $CH_2Cl_2$ (33 ml) is cooled to 0° C. and subsequently treated dropwise with neat trifluoromethanesulfonic anhydride (1.80 ml, 3.02 g, 10.7 mmol) over a 5-minute period. After stirring for 1.75 hours at 0° C., the tan solution is partitioned between $Et_2O$ (100 ml) and saturated $NaHCO_3$ (60 ml). The layers are shaken and separated and the organic layer is washed with brine (50 ml), dried ($Na_2SO_4$), filtered, and stripped. The residue is flash chromatographed on a silica gel column (50 cm×160 cm) using 20% EtOAc in hexane as the eluting solvent mixture to afford compound F as a white solid. Recrystallization of the solid from hexane gives the product as cubic crystals; yield 2.836 g, (90%); $R_f$ 0.34 (20% EtOAc in hexane).

m.p. 69°–71° C. Microanalysis for $C_{14}H_{12}F_3NO_4S$: Calc'd: C 48.41 H 3.48 N 4.03 F 16.33 S 9.23 Found: C 48.40 H 3.26 N 3.79 F 16.04 S 9.18

G. 2-(4-Fluorophenyl)-4-(1-methylethyl)-3-quinolinecarboxaldehyde

A mixture of compound F (2.000 g, 5.76 mmol), (4-fluorophenyl)tributylstannane (2.400 g, 6.23 mmol) prepared by reaction of the corresponding lithium or Grignard reagent with tri-n-butyltin chloride in $Et_2O$ at −78° C.), anhydrous LiCl (832 mg, 19.6 mmol), and BHT (50 mg) in dry dioxane (35 ml) was treated with $(PPh_3)_4Pd$ (200 mg, 0.17 mmol) at room temperature. The temperature of the reaction was slowly raised to 100° C. over a 2-hour period and heating was continued for 13 hours. The dark mixture was cooled to room temperature and partitioned between $Et_2O$ (100 ml) and $H_2O$ (75 ml). The layers were shaken and separated and the organic layer is washed in succession with $H_2O$ (50 ml), 15% $NH_4OH$ (75 ml), $H_2O$ (50 ml), and brine (50 ml), then dried ($Na_2SO_4$), filtered, and stripped. The residual yellow oil was flash-chromatographed on a silica gel column (50 cm×150 cm) using 15% EtOAc in hexane as the eluting solvent mixture to afford the desired product as a pale yellow oil that solidified on standing. Recrystallization of the solid from hexane (2 crops) gave compound G as pale yellow needles; yield 1.597 g, (95%); $R_f$ 0.45 (20% EtOAc in hexane).

m.p. 69.3°–71.5° C. Microanalysis for $C_{19}H_{16}FNO$: Calc'd: C 77.79 H 5.50 N 4.78 F 6.48 Found: C 77.83 H 5.44 N 4.82 F 6.43

The abbreviations used herein have the following meanings:

| | |
|---|---|
| HOAc | Acetic Acid |
| $Et_2O$ | Diethyl Ether |
| THF | Tetrahydrofuran |
| EtOH | Ethanol |
| LAH | Lithium Aluminum Hydride |
| $LiAlH_4$ | Lithium Aluminum Hydride |
| DIBAL-H | Diisobutyl Aluminum Hydride |
| DMF | Dimethylformamide |
| DMSO | Dimethyl Sulfoxide |
| MeONa | Sodium Methoxide |
| EtONa | Sodium Ethoxide |
| $KOBu_t$ | Potassium t-butoxide |
| NaH | Sodium Hydride |
| LDA | Lithium Diisopropylamide |
| LiTMP | Lithium Tetramethylpiperidide |
| $LiN(TMS)_2$ | Lithium Bistrimethylsilylamide |
| $NH_2OH.HCl$ | Hydroxylamine Hydrochloride |
| $NH_4OAc$ | Ammonium Acetate |
| $Cu(OAc)_2$ | Copper (II) Acetate |
| MeOH | Methanol |
| Pd | Palladium |
| Pt | Platinum |
| Ru | Ruthenium |
| EtOAc | Ethyl Acetate |
| n-BuLi | n-Butyl Lithium |
| BSTFA | Bis(trimethylsilyl)-trifluoroacetamide |
| TMSBr | Trimethylsilyl bromide |
| NMO | 4-methyl morpholine N-oxide |
| TPAP | tetrapropylammonium perruthenate |
| Pd/C | Palladium on carbon |
| BHT | Butylated hydroxytoluene |
| $PPh_3$ | Triphenylphosphine |
| TBAF | Tetrabutyl Ammonium Fluoride |
| $(MeO)_2POCHN_2$ | Dimethyl Diazomethylphosphonate |
| $CHCl_3$ | Chloroform |
| $Bu_3SnH$ | Tri-n-butyl tin Hydride |
| $Bu_4NF$ | Tetrabutylammonium fluoride |
| AIBN | α,α'-Azaisobutyrylnitrile |
| TEA | Triethylamine |
| $ClSi(t-butyl)Ph_2$ | t-Butyldiphenylsilyl Chloride |
| $ClSi(t-butyl)Me_2$ | t-Butyldimethylsilyl Chloride |
| $ClSi Ph_3$ | Triphenylsilyl Chloride |
| HF | Hydrofluoric Acid |
| m-CPBA | meta-Chloroperoxybenzoic Acid |
| $CF_3CO_3H$ | Peroxytrifluoroacetic Acid |
| t-butylLi (or t-BuLi) | t-Butyl Lithium |
| EDTA | Ethylenediaminetetroacetic acid |

What is claimed is:
1. A compound of the formula

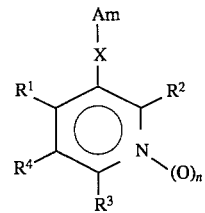

or a pharmaceutically acceptable salt thereof wherein:
Am is

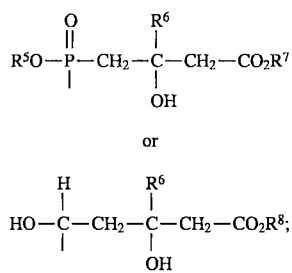

X is —(CH$_2$)$_a$—, —CH=CH—, —C≡C— or —CH$_2$O—;

R$^1$ and R$^2$ are the same or different and are each independently selected from
(i) hydrogen,
(ii) alkyl,
(iii) aryl,
(iv) cycloalkyl,
(v) aralkyl,
(vi) aralkoxy,
(vii) alkenyl, and
(viii) cycloalkenyl;

R$^3$ is selected from
(i) hydrogen,
(ii) lower alkyl,
(iii) aryl,
(iv) cycloalkyl,
(v) alkoxy,
(vi) aralkyl,
(vii) aralkoxy,
(viii) alkenyl,
(ix) cycloalkenyl,
(x) halo-substituted alkyl,
(xi) adamantyl and
(xii) thienyl, furyl, pyrrolyl, pyridyl, benzodioxolyl, imidazolyl, pyrrolidinyl, piperidinyl and indolyl;

R$^4$ is selected from
(i) hydrogen,
(ii) lower alkyl,
(iii) aryl,
(iv) cycloalkyl,
(v) alkoxy,
(vi) aralkyl,
(vii) aralkoxy,
(viii) alkenyl,
(ix) cycloalkenyl,
(x) adamantyl,
(xi) halogen,
(xii) halo-substituted alkyl and
(xiii) thienyl, furyl, pyrrolyl, pyridyl, benzodioxolyl, imidazolyl, pyrrolidinyl, piperidinyl and indolyl;

R$^5$ and R$^7$ are each independently selected form hydrogen, lower alkyl, alkali metal salt ion and alkaline earth metal salt ion;

R$^6$ is hydrogen or lower alkyl;

R$^8$ is hydrogen or lower alkyl in the free acid form or in the form of a physiologically acceptable and hydrolyzable ester or δ-lactone thereof, or an alkali metal salt ion or alkaline earth metal salt ion;

n is 0 or 1; and a is 1, 2 or 3, and wherein "aryl" by itself or as part of another group is a monocyclic or bicyclic aromatic group containing 6 to 10 carbons in the ring portion;

"alkyl" or "lower alkyl" by itself or as part of another group contains 1 to 12 carbons;

"cycloalkyl" by itself or as part of another group contains 3 to 12 carbons;

"cycloalkenyl" by itself or as part of another group contains 3 to 12 carbons.

2. A compound as defined in claim 1, wherein R$^1$ is aryl.

3. A compound as defined in claim 1, wherein R$^1$ is 4-fluorophenyl.

4. A compound as defined in claim 1, wherein R$^4$ is hydrogen or lower alkyl.

5. A compound as defined in claim 1, wherein R$^3$ is lower alkyl, aryl or cycloalkyl.

6. A compound as defined in claim 1, wherein R$^3$ is aryl.

7. A compound as defined in claim 1, wherein X is trans—CH=CH—.

8. A compound as defined in claim 1, wherein X is cis—CH=CH—.

9. A compound as defined in claim 1, selected from the group consisting of (3R*, 5S*, 6E)-7-[4-(4-Fluorophenyl)-2-(1-methylethyl)-6-phenyl-3-pyridinyl]-3,5-dihydroxy-6-heptenoic acid, (3R*, 5S*, 6E)-7-[4-(4-Fluorophenyl)-2-methyl-6-phenyl-3-pyridinyl]-3,5-dihydroxy-6-heptenoic acid, (3R*, 5S*, 6E)-7-[2-(4-Fluorophenyl)-4-(1-methylethyl)-6-phenyl-3-pyridinyl]-3,5-dihydroxy-6-heptenoic acid, (S)-4-[[[4-(4-Fluorophenyl)-2-(1-methylethyl)-6-phenyl-3-pyridinyl]ethynyl]hydroxyphosphinyl] -3-hydroxybutanoic acid, (S)-4-[[2-[4-(4-Fluorophenyl)-2-(1-methylethyl)-6-phenyl-3-pyridinyl]ethyl]hydroxyphosphinyl] -3-hydroxybutanoic acid, (S,E)-4-[[2-[4-(4-Fluorophenyl)-2-(1-methylethyl)-6-phenyl-3-pyridinyl]ethenyl]hydroxyphosphinyl] -3-hydroxybutanoic acid, (S)-4-[[[2-(4-Fluorophenyl)-4-(1-methylethyl)-6-phenyl-3-pyridinyl]ethynyl]hydroxyphosphinyl] -3-hydroxybutanoic acid,

[3S,4(E)]-4-[[2-[2-(4-Fluorophenyl)-4-(1-methylethyl)-6-phenyl-3-pyridinyl]ethenyl] hydroxyphosphinyl]-3-hydroxybutanoic acid, (S)-4-[[[4-(4-Fluorophenyl)-5-methyl-2-(1-methylethyl)-6-phenyl-3-pyridinyl]ethynyl] hydroxyphosphinyl]-3-hydroxybutanoic acid, (S)-4-[[[4-(4-Fluoro-3-methylphenyl)-2-(1-methylethyl)-6-phenyl-3-pyridinyl]ethynyl]hydroxyphosphinyl- 3-hydroxybutanoic acid, (S)-4-[[[2-(1,1-Dimethylethyl)-4-(4-fluorophenyl)-6-phenyl-3-pyridinyl]ethynyl]hydroxyphosphinyl] -3-hydroxybutanoic acid, (S)-4-[[[4-(4-Fluorophenyl)-2-(1-methylethyl)-6-(2-thienyl)-3-pyridinyl]ethynyl]hydroxyphosphinyl] -3-hydroxybutanoic acid, (S)-4-[ [ [ 6-(1,3-Benzodioxol-4-yl)-4-(4-fluorophenyl)-2-(1-methylethyl)-3-pyridinyl]ethynyl] hydroxyphosphinyl] -3-hydroxybutanoic acid, (S)-4-[[[4-(4-Fluorophenyl)-2-(1-methylethyl)-5,6-diphenyl-3-pyridinyl]ethynyl]hydroxyphosphinyl]-3-hydroxybutanoic acid, (S)-4-[[[4-(4-Fluorophenyl)-2-(1-methylethyl)-6-(2-methylphenyl)-3-pyridinyl]ethynyl]hydroxyphosphinyl] -3-hydroxybutanoic acid, (S)-4-[ [ 6-[ [1,1'-Biphenyl]-3-yl]-4-(4-fluorophenyl)-2-(1-methylethyl)-3-pyridinyl]ethynyl] hydroxyphosphinyl]-3-hydroxybutanoic acid, (S)-4-[ [ 6-(1,3-Benzodioxol-5-yl)-4-(4-fluorophenyl)-2-(1-methylethyl)-3-pyridinyl] ethynyl]hydroxyphosphinyl] -3-hydroxybutanoic acid, (S)-4-[ [ 2-(1,1-Dimethylethyl)-1-(4-fluoro- 3-methylphenyl)-6-phenyl-3-pyridinyl] ethynyl] hydroxyphosphinyl] -3-hydroxybutanoic acid, (S)-4-[[[4-(4-Fluorophenyl)-6-methyl-2-(1 -methylethyl)-3-pyridinyl]ethynyl]hydroxyphosphinyl] -3-hydroxybutanoic acid, 1-oxide, (S)-4-[[[2-(1,1-Dimethylethyl)-4-(4-fluorophenyl)- 6-(2-methylphenyl)-3-pyridinyl]ethynyl] hydroxyphosphinyl]-3-hydroxybutanoic acid, (S)-4-[ [ 4-(4-Fluorophenyl)-2-(1-methylethyl)- 6-phenyl-3-pyridinyl] ethynyl] hydroxyphosphinyl] -3 -hydroxybutanoic acid, 1-oxide, (S)-4-[ [ 4-(4-Fluorophenyl)-6,7-dihydro-2-(1 -methylethyl)-5H-1-pyridin-3-yl] ethynyl] hydroxyphosphinyl] -3-hydroxybutanoic acid, (S)-4-[[[4-(3,5-Dimethylphenyl)-2-(1 -methylethyl)-6-phenyl-3-pyridinyl]ethynyl] hydroxyphosphinyl]-3-hydroxybutanoic acid, (S)-4-[[[4-Fluorophenyl)-2-(1-methylethyl)- 6-(2-pyridinyl)-3-pyridinyl]ethynyl]hydroxyphosphinyl] -3-hydroxybutanoic acid, (S)-4-[[[4-Fluorophenyl)-6-(2-hydroxyphenyl)- 2-(1-methylethyl)-3-pyridinyl]ethynyl]hydroxyphosphinyl] -3-hydroxybutanoic acid, (S)-4-[[[4-(4-Fluorophenyl)-2-(1-methylethyl)- 6-(2-methylphenyl)-3-pyridinyl]ethynyl] hydroxyphosphinyl]-3-hydroxybutanoic acid, 1-oxide, (3R,5S,6E)-7-[4-(4-Fluoro-3-methylphenyl)-2 -(1-methylethyl)-6-phenyl-3-pyridinyl]-3,5-dihydroxy- 6-heptenoic acid, (3R,5S,6E)-7-[4-(3,5-Dimethylphenyl)-2-(1 -methylethyl)-6-phenyl-3-pyridinyl]-3,5-dihydroxy- 6-heptenoic acid, (3R,5S,6E)-7-[4-(4-Fluoro-2-methylphenyl)- 2-(1-methylethyl)-6-phenyl-3-pyridinyl]-3,5 -dihydroxy-6-heptanoic acid, (3R,5S,6E)-7-[4-(4-Fluorophenyl)-5-methyl- 2-(1-methylethyl)-6-phenyl-3-pyridinyl]-3,5 -dihydroxy-6-heptenoic acid, (3R,5S,6E)-7-[2-(4-Fluoro-methylphenyl)- 4-(1-methylethyl)-6-phenyl-3-pyridinyl] -3,5 -dihydroxy-6-heptenoic acid, (3R,5S,6E)-7-[4-(4-Fluorophenyl)-2-(1 -methylethyl)-5,6-diphenyl-3-pyridinyl]-3,5 -dihydroxy-6-heptenoic acid, (3R,5S,6E)-7-[2-(1,1-Dimethylethyl)-4-(4 -fluorophenyl)-6-phenyl-3-pyridinyl-3,5-dihydroxy- 6-heptenoic acid, (3R,5S,6E)-7-[4-Fluoro-3-methylphenyl)-2 -(1-methylethyl)-6-phenyl-3-pyridinyl]-3,5 -dihydroxy-6-heptenoic acid, 1-oxide, (3R,5S,6E)-7-[4-(4-Fluorophenyl)-5-methyl-2 -(1-methylethyl)-6-phenyl-3-pyridinyl]-3,5 -dihydroxy-6-heptenoic acid, 1-oxide, (3R,5S,6E)-7-[4-(4-Fluorophenyl)-2-(1 -methylethyl)-6-(2-methylphenyl)-3-pyridinyl-3,5 -dihydroxy-6-heptenoic acid, 1-oxide, (S)-4-[[[4-(4-Fluorophenyl)-2-(1-methylethyl)- 6-phenyl-3-pyridinyl]methoxy]hydroxyphosphinyl] -3-hydroxybutanoic acid, (S)-4-[ [ [4-(4-Fluorophenyl)-5-methyl-2-(1 -methylethyl)-6-phenyl-3-pyridinyl] methoxy] hydroxyphosphinyl] -3-hydroxybutanoic acid, (S)-4-[[[4-(4-Fluorophenyl)-5-ethyl-2-(1 -methylethyl)-6-phenyl-3-pyridinyl]methoxy]hydroxyphosphinyl] -3-hydroxybutanoic acid, (S)-4-[[[4-(4-Fluorophenyl)-5-methyl-2-(1 -methylethenyl)-6-phenyl-3-pyridinyl]methoxy]hydroxyphosphinyl] -3-hydroxybutanoic acid, and (S)-4-[[[4-(4-Fluorophenyl)-5-methyl-2-ethyl- 6-phenyl-3-pyridinyl]methoxy]hydroxyphosphinyl]-3 -hydroxybutanoic acid.

10. A hypocholesterolemic or hypolipidemic composition comprising a compound as defined in claim 1 and a pharmaceutically acceptable carrier therefor.

11. A method of inhibiting cholesterol biosynthesis which comprises administering to a mammal an effective amount of a compound as defined in claim 1.

12. A compound of the formula $$
\begin{array}{c}
\text{Am} \\
| \\
\text{X} \\
R^1 \diagup\!\!\!\diagdown R^2 \\
\phantom{xx}\bigcirc \\
R^4 \diagdown\!\!\!\diagup \text{N} \\
\phantom{xxxx} | \phantom{xx}(O)_n \\
R^3
\end{array}
$$

or a pharmaceutically acceptable salt thereof wherein:

Am is $$R^5O-\overset{O}{\underset{|}{P}}-CH_2-\overset{R^6}{\underset{|}{C}}-CH_2-CO_2R^7$$
$$\phantom{xxxxxxxx}OH$$

or $$HO-\overset{H}{\underset{|}{C}}-CH_2-\overset{R^6}{\underset{|}{C}}-CH_2-CO_2R^8;$$
$$\phantom{xxxxxxxx}OH$$

X is $-(CH_2)_a-$, $-CH=CH-$, $-C\equiv C-$ or $-CH_2O-$;

$R^1$ and $R^2$ are the same or different and are each independently selected from
(i) hydrogen,
(ii) alkyl,
(iii) aryl,
(iv) cycloalkyl and
(v) alkenyl, $R^3$ is selected from
(i) hydrogen,
(ii) lower alkyl,
(iii) aryl,
(iv) cycloalkyl,
(v) aralkyl,
(vi) alkenyl,
(vii) adamantyl and
(vii) thienyl, furyl, pyrrolyl, pyridyl, benzodioxoyl, imidazolyl, pyrrolidinyl, piperidinyl and indolyl;

$R^4$ is selected from (i) hydrogen,
(ii) lower alkyl,
(iii) aryl,
(iv) cycloalkyl,
(v) aralkyl,
(vi) alkenyl and
(vii) thienyl, furyl, pyrrolyl, pyridyl, benzodioxolyl, imidazolyl, pyrrolidinyl, piperidinyl and indolyl;

$R^5$ and $R^7$ are each independently selected form hydrogen, lower alkyl, alkali metal salt ion and alkaline earth metal salt ion;

$R^6$ is hydrogen or lower alkyl;

$R^8$ is hydrogen or lower alkyl in the free acid form or in the form of a physiologically acceptable and hydrolyzable ester or δ-lactone thereof, or an alkali metal salt ion or alkaline earth metal salt ion;

n is 0 or 1; and a is 1, 2 or 3 and wherein "aryl" by itself or as part of another group is a monocyclic or bicyclic aromatic group containing 6 to 10 carbons in the ring portion;

"alkyl" or "lower alkyl" by itself or as part of another group contains 1 to 12 carbons;

"cycloalkyl" by itself or as part of another group contains 3 to 12 carbons;

"cycloalkenyl" by itself or as part of another group contains 3 to 12 carbons.

13. A compound as defined in claim 12, wherein X is trans—CH=CH—.

14. A compound as defined in claim 12, wherein X is cis—CH=CH—.

15. A hypocholesterolemic or hypolipidemic composition comprising a compound as defined in claim 12 and a pharmaceutically acceptable carrier therefor.

16. A method of inhibiting cholesterol biosynthesis which comprises administering to a mammal an effective amount of a compound as defined in claim 12.

17. A compound as defined in claim 12, wherein $R^1$ is aryl.

18. A compound as defined in claim 12, wherein $R^1$ is 4-fluorophenyl.

19. A compound as defined in claim 12 wherein $R^4$ is hydrogen or lower alkyl.

20. A compound as defined in claim 12, wherein $R^3$ is lower alkyl, aryl or cycloalkyl.

21. A compound as defined in claim 12, wherein $R^3$ is aryl.

22. (S)-4-[ [2-[4-(4-Fluorophenyl)-5-methyl-2-(1-methylethyl)-6-phenyl-3-pyridinyl] ethenyl] hydroxyphosphinyl]-3-hydroxybutanoic acid.

* * * * *